United States Patent [19]
Klein et al.

[11] Patent Number: 5,958,954
[45] Date of Patent: *Sep. 28, 1999

[54] SYNTHESIS AND USE OF RETINOID COMPOUNDS HAVING NEGATIVE HORMONE AND/OR ANTAGONIST ACTIVITIES

[75] Inventors: Elliott S. Klein, Marina del Rey; Alan T. Johnson, Rancho Santa Margarita; Andrew M. Standeven, Ventura; Richard L. Beard, Newport Beach; Samuel J. Gillett, Albany; Tien T. Duong, Irvine; Sunil Nagpal, Lake Forest; Vidyasagar Vuligonda, Irvine; Min Teng, San Diego; Roshantha A. Chandraratna, Mission Viejo, all of Calif.

[73] Assignee: Allergan Sales, Inc., Irvine, Calif.

[*] Notice: This patent is subject to a terminal disclaimer.

[21] Appl. No.: 08/998,319

[22] Filed: Dec. 24, 1997

Related U.S. Application Data

[60] Continuation-in-part of application No. 08/871,093, Jun. 9, 1997, which is a division of application No. 08/613,863, Mar. 11, 1996, Pat. No. 5,776,699
[60] Provisional application No. 60/019,015, Sep. 1, 1995, provisional application No. 60/064,853, Sep. 1, 1995, and provisional application No. 60/020,501, Oct. 13, 1995.

[51] Int. Cl.[6] ............. C07D 311/58; C07D 335/06; C07D 405/06; A61K 31/35
[52] U.S. Cl. ............. 514/333; 514/337; 514/432; 514/456; 546/256; 546/280.1; 546/282.7; 549/49; 549/51; 549/396; 549/408
[58] Field of Search ............. 514/333, 337, 514/432, 456; 546/256, 280.1, 282.7; 549/49, 51, 396, 408

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |

(List continued on next page.)

FOREIGN PATENT DOCUMENTS

| | | | |
|---|---|---|---|
| 0098591 | 1/1984 | European Pat. Off. | C07D 333/54 |
| 0130795 | 1/1985 | European Pat. Off. | C07D 311/58 |
| 170105 | 2/1986 | European Pat. Off. | . |
| 0176032 | 4/1986 | European Pat. Off. | C07C 65/38 |
| 0176033 | 4/1986 | European Pat. Off. | C07D 261/18 |
| 0253302 | 1/1988 | European Pat. Off. | C07D 213/16 |
| 0272921 | 6/1988 | European Pat. Off. | C07D 213/80 |
| 0284261 | 9/1988 | European Pat. Off. | C07D 213/80 |
| 0284288 | 9/1988 | European Pat. Off. | C07D 401/04 |
| 0286364 | 10/1988 | European Pat. Off. | C07C 103/78 |
| 0303915 | 2/1989 | European Pat. Off. | A61K 31/255 |
| 0303186 | 3/1989 | European Pat. Off. | . |
| 176034 | 4/1989 | European Pat. Off. | C07C 63/66 |
| 0315071 | 5/1989 | European Pat. Off. | C07C 63/66 |

(List continued on next page.)

OTHER PUBLICATIONS

A General Synthesis of Terminal and Internal Arylalkynes by the Palladium–Catalyzed Reaction of Alkynylzinc Reagents with Aryl Halides by Anthony O. King and Ei–ichi, *J. Org. Chem.*, (1978) 43/2: p. 358.
Conversion of Methyl Ketones into Terminal Acetylenes and (E)–Tri–substituted Olefins of Terpenoid Origin by Ei–ichi, et al., *J. Org. Chem.*, (1980) 45/12: p. 2526.
Sporn et al. in *J. Amer. Acad. Derm.*, (1986) 15:756–764.
Teng et al., J. Med. Chem. 1997 40 2445–2451 Identification of High Potent Retinoic Acid Receptor α–Selective Antagonists.
"A Convenient Synthesis of Ethynylarenes and Diethynylarenes" by S. Takahashi et al. *Synthesis* (1980) pp. 627–630.
Shudo et al. *Chem. Phar. Bull.*, (1985) 33:404–407.
Kagechika et al. in *J. Med. Chem.*, (1988) 31:2182–2192.
Chemistry and Biology of Synthetic Retinoids by Marcia I. Dawson and William II. Okamura, published by CRC Press Inc., 1990, pp. 334–335, 354.
Synthesis of 2,2'–Diacyl–1,1'–Biaryls. Regiocontrolled Protection of . . . by Mervic, et al, *J. Org. Chem.*, (1980) No. 45, pp. 4720–4725.
A Dopamine Receptor Model and Its Application in the Design of a New Class of Rigid Pyrrolo [2,3–g]isoquinoline Antipsychotics, Gary L. Olson et al. *American Chemical Societe*, (1981) 24/9:1026–1031.
6.2.3 Conformational Restriction, Williams, et al., *Drug Discovery and Development*, The Humana Press, (1987) pp. 54–55.

(List continued on next page.)

*Primary Examiner*—Mukund J. Shah
*Assistant Examiner*—Deepak R. Rao
*Attorney, Agent, or Firm*—Gabor L. Szekeres; Robert J. Baran; Martin A. Voet

[57] ABSTRACT

2,2-Dialkyl-4-aryl-substituted benzopyran and benzothiopyran derivatives of the formula

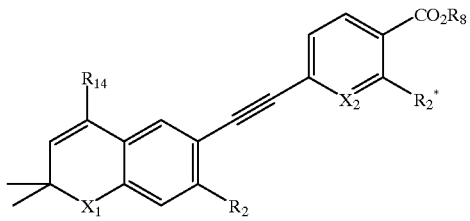

where the symbols have the meaning described in the specification, have retinoid negative hormone and/or antagonist-like biological activities. The invented RAR antagonists can be administered to mammals, including humans, for the purpose of preventing or diminishing action of RAR agonists on the bound receptor sites. Specifically, the RAR agonists are administered or coadministered with retinoid drugs to prevent or ameliorate toxicity or side effects caused by retinoids or vitamin A or vitamin A precursors. The retinoid negative hormones can be used to potentiate the activities of other retinoids and nuclear receptor agonists.

46 Claims, 20 Drawing Sheets

U.S. PATENT DOCUMENTS

| | | | |
|---|---|---|---|
| 4,391,731 | 7/1983 | Boller et al. | 252/299.26 |
| 4,485,252 | 11/1984 | Fuchs et al. | 560/8 |
| 4,539,154 | 9/1985 | Krebs | 260/410 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Shroot, et al. | 514/443 |
| 4,810,804 | 3/1989 | Chandrafatna | 514/311 |
| 4,826,969 | 5/1989 | Maignan et al. | 536/55.2 |
| 4,826,984 | 5/1989 | Berlin et al. | 546/134 |
| 4,833,240 | 5/1989 | Maignan et al. | 536/55.2 |
| 4,855,320 | 8/1989 | Chatterjee et al. | 514/473 |
| 4,895,868 | 1/1990 | Chandraratna | 514/432 |
| 4,923,884 | 5/1990 | Chandraratna | 514/354 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,310,662 | 5/1994 | Evans et al. | 435/64 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,354,776 | 10/1994 | Chandratatna | 514/461 |
| 5,380,877 | 1/1995 | Chandraratna | 549/60 |
| 5,391,753 | 2/1995 | Chandraratna | 546/323 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,420,145 | 5/1995 | Shudo | 514/352 |
| 5,426,118 | 6/1995 | Chandraratna | 514/337 |
| 5,434,173 | 7/1995 | Chandraratna | 514/354 |
| 5,451,605 | 9/1995 | Chandraratna et al. | 514/475 |
| 5,455,265 | 10/1995 | Chandraratna | 514/448 |
| 5,466,861 | 11/1995 | Dawson et al. | 560/100 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |
| 5,489,584 | 2/1996 | Vuligonda et al. | 514/188 |
| 5,498,755 | 3/1996 | Chandraratna | 564/272 |
| 5,498,795 | 3/1996 | Song et al. | 562/474 |
| 5,514,825 | 5/1996 | Vuligonda et al. | 558/462 |
| 5,516,904 | 5/1996 | Chandraratna | 514/269 |
| 5,523,457 | 6/1996 | Starrett, Jr. et al. | 560/24 |
| 5,534,516 | 7/1996 | Chandraratna | 514/253 |
| 5,534,641 | 7/1996 | Song et al. | 549/416 |
| 5,543,534 | 8/1996 | Vuligonda et al. | 549/421 |
| 5,556,996 | 9/1996 | Beard et al. | 549/407 |
| 5,559,248 | 9/1996 | Starrett, Jr. et al. | 549/79 |
| 5,563,292 | 10/1996 | Shih et al. | 560/255 |
| 5,571,696 | 11/1996 | Evans et al. | 435/69.1 |
| 5,578,483 | 11/1996 | Evans et al. | 435/240.2 |
| 5,591,858 | 1/1997 | Vuligonda et al. | 546/322 |
| 5,599,819 | 2/1997 | Chandraratna | 514/314 |
| 5,599,967 | 2/1997 | Vuligonda et al. | 560/48 |
| 5,602,130 | 2/1997 | Chandraratna | 514/247 |
| 5,602,135 | 2/1997 | Chandraratna | 514/252 |
| 5,605,915 | 2/1997 | Vuligond et al. | 514/356 |
| 5,616,597 | 4/1997 | Chandraratna | 514/365 |
| 5,616,712 | 4/1997 | Teng et al. | 546/158 |
| 5,618,836 | 4/1997 | Chandraratna et al. | 514/444 |
| 5,618,839 | 4/1997 | Starrett, Jr. et al. | 514/513 |
| 5,618,931 | 4/1997 | Beard et al. | 544/224 |
| 5,618,943 | 4/1997 | Vuligonda et al. | 546/342 |
| 5,648,385 | 7/1997 | Starrett, Jr. et al. | 514/513 |
| 5,648,503 | 7/1997 | Vuligonda et al. | 549/13 |
| 5,648,514 | 7/1997 | Johnson et al. | 560/102 |
| 5,654,469 | 8/1997 | Vuligonda et al. | 560/56 |
| 5,663,347 | 9/1997 | Chandraratna | 546/152 |
| 5,663,357 | 9/1997 | Teng et al. | 546/323 |
| 5,663,367 | 9/1997 | Vuligonda et al. | 549/4 |
| 5,672,710 | 9/1997 | Beard et al. | 548/188 |
| 5,675,024 | 10/1997 | Teng et al. | 549/405 |
| 5,675,033 | 10/1997 | Vuligonda et al. | 560/100 |
| 5,677,320 | 10/1997 | Chandraratna | 514/365 |
| 5,677,323 | 10/1997 | Chandraratna | 514/374 |
| 5,677,451 | 10/1997 | Chandraratna | 544/238 |
| 5,688,957 | 11/1997 | Teng et al. | 546/280.1 |
| 5,696,162 | 12/1997 | Chandraratna | 514/532 |
| 5,698,700 | 12/1997 | Song et al. | 546/282.1 |
| 5,717,094 | 2/1998 | Chandraratna | 544/238 |
| 5,723,620 | 3/1998 | Vuligonda et al. | 546/280.1 |
| 5,723,666 | 3/1998 | Vuligonda et al. | 564/253 |
| 5,728,846 | 3/1998 | Vuligonda et al. | 549/16 |
| 5,739,338 | 4/1998 | Beard et al. | 546/153 |

FOREIGN PATENT DOCUMENTS

| | | | |
|---|---|---|---|
| 0350846 | 7/1989 | European Pat. Off. | C07D 311/85 |
| 0412387 | 2/1991 | European Pat. Off. | C07C 317/14 |
| 0478787 | 10/1991 | European Pat. Off. | C07C 233/65 |
| 0514269 | 11/1992 | European Pat. Off. | C07C 257/08 |
| 0617020 | 9/1994 | European Pat. Off. | C07D 213/82 |
| 0619116 | 10/1994 | European Pat. Off. | A61K 31/19 |
| 0661259 | 5/1995 | European Pat. Off. | C07C 233/81 |
| 0661258 | 7/1995 | European Pat. Off. | C07D 65/19 |
| 0661261 | 7/1995 | European Pat. Off. | C07C 235/84 |
| 0718285 | 8/1996 | European Pat. Off. | C07C 403/20 |
| 3316932 | 11/1983 | Germany | C07C 63/66 |
| 3524199 | 1/1986 | Germany | C07C 63/66 |
| 3602473 | 7/1987 | Germany | C07C 43/215 |
| 3708060 | 9/1987 | Germany | C07D 311/04 |
| 3715955 | 11/1987 | Germany | C07C 15/58 |
| 2190378 | 11/1987 | United Kingdom | C07C 39/21 |
| 85/00806 | 2/1985 | WIPO | A61K 31/00 |
| 85/04652 | 10/1985 | WIPO | A61K 31/19 |
| 91/16051 | 10/1991 | WIPO | A61K 31/44 |
| 92/06948 | 4/1992 | WIPO | C07C 69/86 |
| 93/03713 | 3/1993 | WIPO | A61K 31/07 |
| 93/11755 | 6/1993 | WIPO | A61K 31/07 |
| 93/21146 | 10/1993 | WIPO | C07C 69/76 |
| 94/14777 | 7/1994 | WIPO | C07D 231/54 |
| 95/04036 | 2/1995 | WIPO | C07C 403/20 |
| 96/05165 | 2/1996 | WIPO | C07C 57/50 |

OTHER PUBLICATIONS

V. Retinoid Structure–Biological Activity Relationships, Chemistry and Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid and Acitretin on the Proliferation, Lipid Synthesis and Keratin Expression of Cultured Human Sebocytes in Vitro" C.C. Zouboulis, *The Journal of Investigative Dermatology*, (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology*, (1991) 96/3:.

"Synthesis and Evaluation of Stilbene and Dihydrostilbene Derivateives as Potential Anticancer Agents That Inhibit Tubulin Polymerization" by Cushman, Mark et al. *J. Med. Chem.*, (1991) 34:2579–2588.

"Synthesis and Evaluation of New Pretoein Tyrosine Kinase Inhibitors. Part 1. Pyridine–Containing Stilbenes and Amides" by Cushman, Mark et al. *Bioorganic & Medicinal Chemistry Letters*, (1991) 1/4:211–214.

"Di–and Tri–methoxystyryl Derivatives of Heterocyclic Nitrogen Compounds" by Bahner,C. T. et al. *Arzneim–Forsch./Drug Res.* (1981)31 (I), Nr. 3.

"Retinobenzoic acids. 3. Structure–Activity Relationships of Retinoidal Azobenzene–4–Carboxylic Acids and Stilbene–4–Carboxylic Acids" by H. Kagechika et al., *Journal of Medicinal Chemistry*, (1989), 32:1098–1108.

Eyrolles, L. et al. "Retinoid Antagonists: Molecular Design Based on the Ligand Superfamily Concept" *Med. Chem. Res.*, (1992) 2:361–367.

Liu S.S. et al. "Systemic Pharmacokinetics of Acetylenic Retinoids in Rats", *Drug Metabolism and Disposition*, (1990) 18/6: 1071–1077.

Chemical Abstracts, vol. 122, No. 13,Mar. 27, 1995 abstract No. 151372m, (S. Kaku et al.).

Chemical Abstracts, vol. 117, No. 13,Sep. 28, 1992 abstract No. 124091j, (S. Sun et al.).

European Journal of Biochemistry, vol. 212, No. 1, 1993, Berlin, pp. 13–26, XP000618300 (S. Keidel et al.).

Journal of Medicinal Chemistry, vol. 39, No. 16, Aug. 2, 1996, pp. 3035–3038, Min Teng et al.

Journal of Medicinal Chemistry, vol. 37, No. 10, May 13, 1994, pp. 1508–1517, Laurence Eyrolles.

Kagechira et al. Biochemical and Biophysical Research Communications, vol. 155, No. 1, 1988, pp. 503–508.

Chemical Abstracts, vol. 121, No. 9, 1994, 108128d, (Yu et al.).

Database WPI, Section CH, Week 9416, Derwent Publications Ltd. London, GB; Class B05, AN 94–128759 and JP 6078266A, see English language abstract in Derwent, 1994.

Yoshimura et al Journal of Medicinal Chemistry, vol. 38, No. 16, Aug. 4, 1995, pp. 3163–3173.

Weiner et al., "A phase I trial of topically applied trans–retinoic acid in cervical dysplasia–clinical efficacy", *Investigational New Drugs*, 4:241–244, 1996.

Jones et al., "A dose–response study of 13–cis–retinoic acid in acne vulgaris", *British Journal of Dermatology*, (1983) 108, 333–343.

Fekrat, et al., "The Effect of Oral 13–cis–retinoic Acid on Retinal Redetachment after Surgical Repair in Eyes with Proliferative Vitreoretinopathy", *Ophthalmology*, vol. 102, No. 3 (Mar. 1995), pp. 412–418.

Nagpal, et al., "Separation of Transactivation and AP1 Antagonism Functions of Retinoic Acid Receptor α", *The Journal of Biological Chemistry*, 270/2(1995):923–927.

Allegretto, et al., "Transactivation Properties of Retinoic Acid and Retinoid X Receptors in Mammalian Cells and Yeast", *The Journal of Biological Chemistry*, vol. 268, No. 35 (Dec. 15, 1993), pp. 26625–26633.

Gruapner, et al., "6'–Substituted Naphthalene–2–Carboxylic Acid Analogs, A New Class of Retinoic Acid Receptor Subtype–Specific Ligands," *Biochemical and Biophysical Communications*, vol. 179, No. 3, (Sep. 30, 1991), pp. 1554–1561.

Moore, et al., "Retinoic Acid and Interferon in Human Cancer: Mechanistic and Clinical Studies," *Seminars in Hematology*, 31/4, Suppl 5 (Oct. 1994), pp. 31–37.

Mangelesdorf, et al. "The Retinoid Receptors", *Biology, Chemistry and Medicine*, 2nd Ed. Chapter 8, pp. 319–349.

Nagpal, et al., *Cell Growth & Differentiation*, vol. 7 (Dec. 1996), pp. 1783–1791.

Horlein, et al. *Letters to Nature*, vol. 377 (Oct. 5, 1995), pp. 397–404.

Ishikawa, et al., "A Functional Retinoic Acid Receptor Encoded by the Gene on Human Chromosome 12", *Molecular Endocinology*, vol. 4, No. 6 (1990), pp. 837–844.

Campochiaro, et al., *Investigative Ophthalmology & Visual Science*, vol. 32, No. 1 (Jan. 1991), pp. 65–72.

Sen, et al., *Arch. Ophthalmol*, vol. 106 (Sep. 1988), pp. 1291–1294.

Peck, et al., *The New England Journal of Medicine*, vol. 300 No. 7 (Feb. 15, 1979), pp. 329–333.

Araiz, et al., *Investigative Ophthalmology & Visual Science* vol. 34, No. 3. (Mar. 1993), pp. 522–530).

Benbrook, et al., "A new retinoic acid receptor identified from a hepatocellular carcinoma", *Letters to Nature*, vol. 333, No. 16, (Jun. 1988), pp. 669–672.

de Wet, et al., "Firefly Luciferase Gene: Structure and Expression in Mammalian Cells", *Molecular and Cellular Biology*, vol. 7 No. 2 (Feb. 1987).

Matrisian, et al., *Molecular and Cellular Biology*, vol. 6, No. 5 (May 1986).

Madsen, et al., *The Journal of Investigative Dermatology*, vol. 99, No. 3 (Sep. 1992), pp. 299–305.

Fekrat, et al., *Ophthalmology*, vol. 102, No. 3 (Mar. 1995), pp. 412–418.

Mangelsdorf, et al., "Nuclear receptor that identifies a novel retinoic acid response pathway", *Nature*, vol. 345, 17 (May 1990), pp. 224–229.

Umesono, et al., "Retinoic acid and thyroid hormone induce gene expression through a common responsive element", *Nature*, vol. 336, 17 (Nov. 1988), pp. 262–265.

Ferrara, et al,. "Highly Potent Transcriptional Activation by 16–ene Derivatives of 1,25–Dihydroxyvitamin $D_3$," *The Journal of Biological Chemistry*, vol. 269, No. 4 (Jan. 28,.

Ellis, et al., *Cell*, vol. 45 (Jun. 6, 1986), pp. 721–732.

Klein–Hitpab, et al., *Cell*, vol. 46 (Sep. 26, 1986), pp. 1053–1061.

Hollenberg, et al., "Multiple and Cooperative Trans–Activation Domains of the Human Glucocorticoid Receptor," *Cell*, vol. 55 (Dec. 2, 1988), pp. 899–906.

Heyman et al., "9–Cis Retinoic Acid Is a High Affinity Ligand for the Retinoid X Receptor," *Cell,* vol. 68 (Jan. 24, 1992), pp. 397–406.

Nicholson, et al., *The EMBO Journal,* vol. 9, No. 13 (1990), pp. 4443–4454.

Nagpal, et al., *The EMBO Journal,* vol. 12, No. 6 (1993), pp. 2349–2360.

Pfahl, Magnus, "Nuclear Receptor/AP–1 Interaction," *Endocrine Reviews,* vol. 14, No. 5 (1993), pp. 651–658.

Wilkinson, et al., *Journal of Cell Science,* 91 (1988), pp. 221–230.

Andreatta–Van Leyen, et al., *Journal of Cellular Physiology,* 160:265–274 (1994).

Lippman, et al., vol. 84, No. 4 (Feb. 19, 1992), pp. 241–245.

Keidel, et al., *Molecular and Cellular Biology,* vol. 14, No. 1 (Jan. 1994), pp. 287–298.

Luckow, et al., *Nucleic Acids Research,* vol. 15, No. 13 (1987), p. 5490.

Chen et al., *Nature,* vol. 377,5 (Oct. 1995), pp. 454–457.

Felgner et al., "Lipofection: A highly efficient, lipid–mediated DNA–transfection procedure," *Proc. Natl. Acad. Sci. USA,* vol. 84 (Nov. 1987), pp. 7413–7417.

Graham, et al., *The Western Journal of Medicine,* vol. 145, No. 2 (Aug. 1986), pp. 192–195.

Kurlandsky, et al., *The Journal of Investigative Dermatology,* vol. 102, No. 4 (Apr. 1994), SID Abstracts, 611, p. 625.

Tahcher, et al., *The Journal of Investigative Dermatology,* vol. 104 (Apr. 1995), Abstracts, 237, p. 594.

Cheng, et al., Reaction, *Biochemical Pharmacology,* vol. 22, pp. 3099–3108, 1973.

Agarwal, et al., *Cancer Research,* 51, pp. 3982–3989, 1991.

Agarwal, et al., *Cancer Research,* 54, pp. 2108–2112, 1994.

Hembree, et al., *Cancer Research,* 54, pp. 3160–3166, 1994.

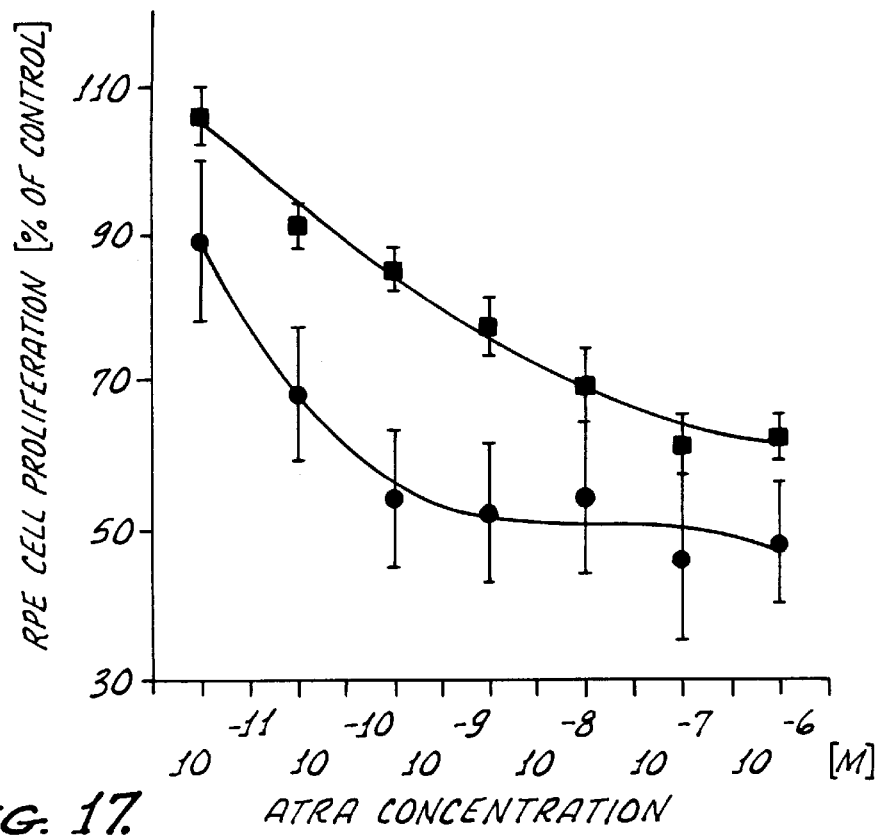
FIG. 17. ATRA CONCENTRATION
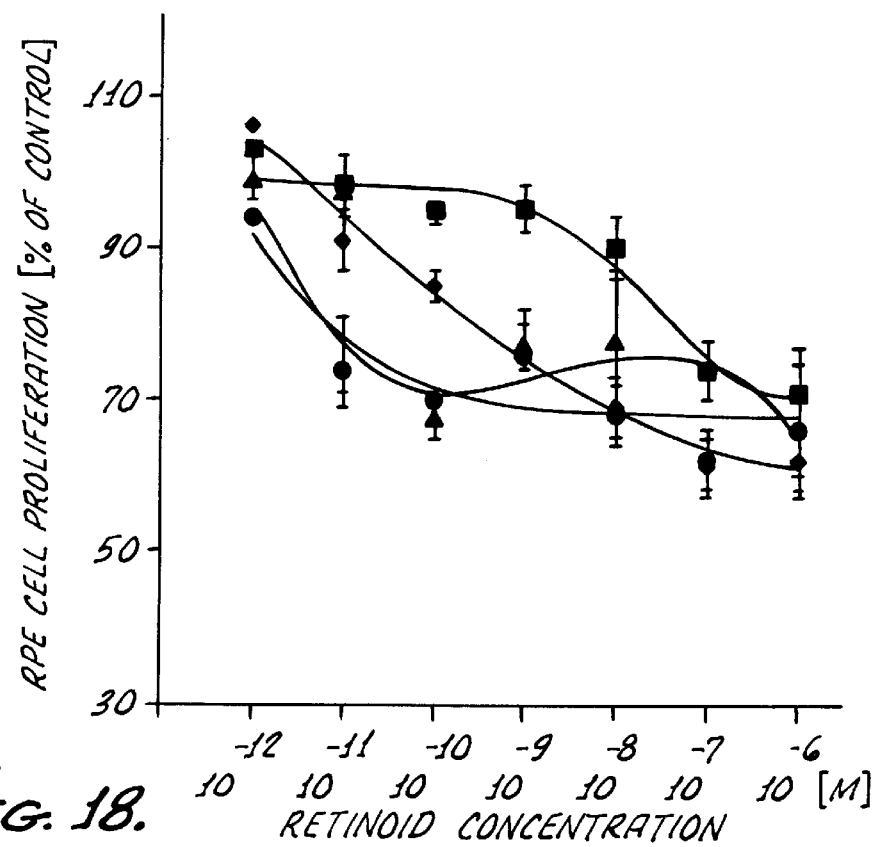
FIG. 18. RETINOID CONCENTRATION

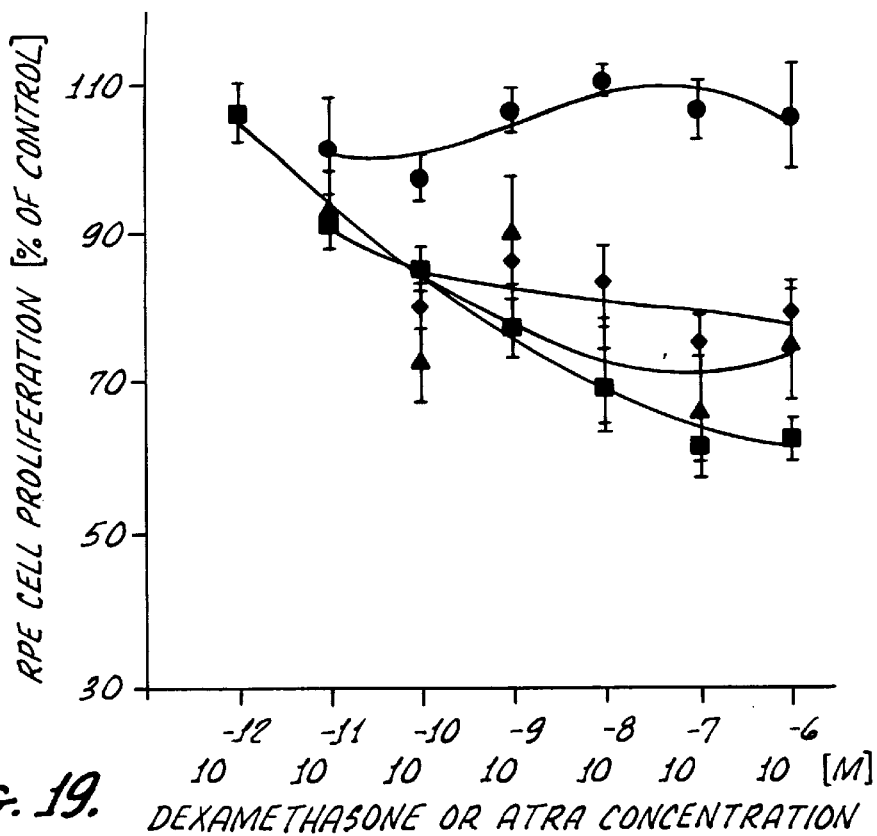
FIG. 19. DEXAMETHASONE OR ATRA CONCENTRATION
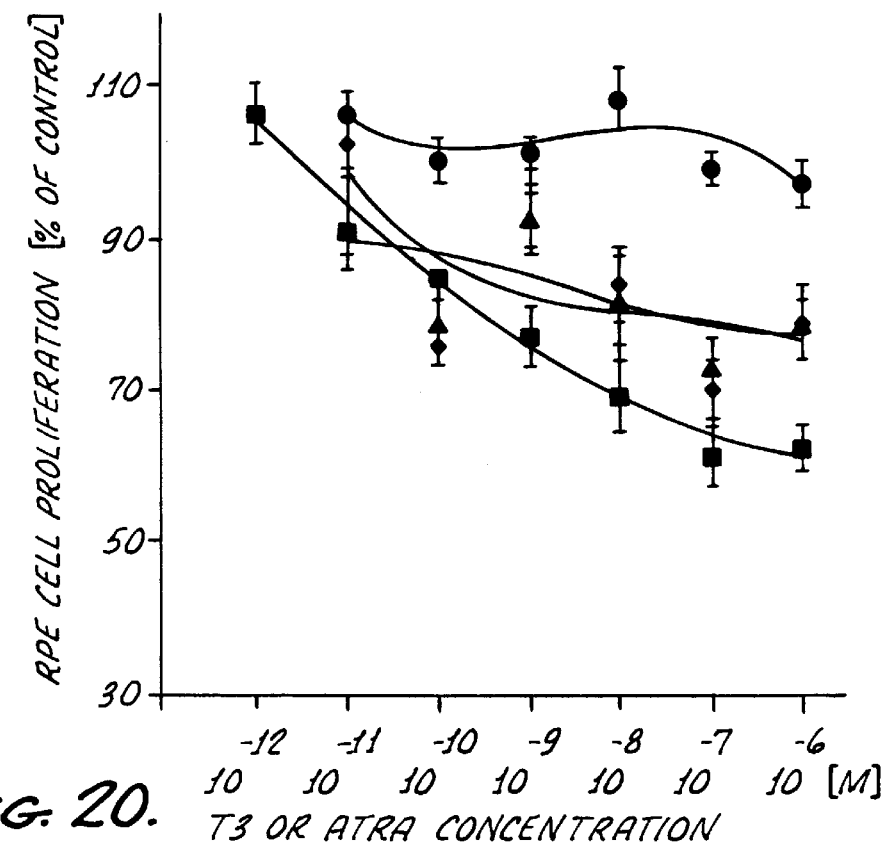
FIG. 20. T3 OR ATRA CONCENTRATION

1

SYNTHESIS AND USE OF RETINOID COMPOUNDS HAVING NEGATIVE HORMONE AND/OR ANTAGONIST ACTIVITIES

RELATED APPLICATIONS

This application is a continuation-in-part of application Ser. No. 08/871,093 filed on Jun. 9, 1997, which is a divisional of application Ser. No. 08/613,863 filed on Mar. 11, 1996 now U.S. Pat. No. 5,776,699 which in turn claims the benefit of priority under 35 U.S.C. § 119(e) of the three following U.S. applications, each of which was filed as a nonprovisional application and converted to a provisional application by separate petitions filed on Jan. 31, 1996: application Ser. No. 08/522,778, filed Sep. 1, 1995; now provisional application Ser. No. 60/019,015; application Ser. No. 08/522,779, filed Sep. 1, 1995, now provisional application Ser. No. 60/064,853; and application Ser. No. 08/542,648, filed Oct. 13, 1995, now provisional application Ser. No. 60/020,501. The complete disclosures of these related applications are hereby incorporated herein by this reference thereto.

FIELD OF THE INVENTION

The present invention relates to novel compounds having retinoid negative hormone and/or retinoid antagonist-like biological activities. More specifically, the invention relates to 4-aryl substituted benzopyran, 4-aryl substituted benzothiopyran, 4-aryl substituted 1,2-dihydroquinoline and 8-aryl substituted 5,6-dihydronaphthalene derivatives which may also be substituted by a substituted 3-oxo-1-propenyl group. These novel compounds have retinoid antagonist like-activity and are useful for treating or preventing retinoid and vitamin A and vitamin A precursor induced toxicity in mammals and as an adjunct to treatment of mammals with retinoids to prevent or ameliorate unwanted or undesired side effects. The invention further relates to the use of retinoid negative hormones for increasing the biological activities of other retinoids and steroid hormones and inhibiting the basal activity of unliganded retinoic acid receptors.

BACKGROUND OF THE INVENTION

Compounds which have retinoid-like activity are well known in the art, and are described in numerous United States and other patents and in scientific publications. It is generally known and accepted in the art that retinoid-like activity is useful for treating mammals, including humans, in order to cure or alleviate the symptoms associated with numerous diseases and conditions.

Retinoids (vitamin A and its derivatives) are known to have broad activities, including effects on cell proliferation and differentiation, in a variety of biological systems. This activity has made retinoids useful in the treatment of a variety of diseases, including dermatological disorders and cancers. The prior art has developed a large number of chemical compounds which have retinoid-like biological activity, and voluminous patent and chemical literature exists describing such compounds. The relevant patent literature includes U.S. Pat. Nos. 4,980,369, 5,006,550, 5,015,658, 5,045,551, 5,089,509, 5,134,159, 5,162,546, 5,234,926, 5,248,777, 5,264,578, 5,272,156, 5,278,318, 5,324,744, 5,346,895, 5,346,915, 5,348,972, 5,348,975, 5,380,877, 5,399,561, 5,407,937, (assigned to the same assignee as the present application) and patents and publications cited therein, which particularly describe or relate to chroman, thiochroman and 1,2,3,4-tetrahydroquinoline derivatives which have retinoid-like biological activity. In addition, several applications are pending which are assigned to the assignee of the present application, and which are directed to further compounds having retinoid-like activity.

U.S. Pat. No. 4,740,519 (Shroot et al.), U.S. Pat. No. 4,826,969 (Maignan et al.), U.S. Pat. No. 4,326,055 (Loeliger et al.), U.S. Pat. No. 5,130,335 (Chandraratna et al.), U.S. Pat. No. 5,037,825 (Klaus et al.), U.S. Pat. No. 5,231,113 (Chandraratna et al.), U.S. Pat. No. 5,324,840 (Chandraratna), U.S. Pat. No. 5,344,959 (Chandraratna), U.S. Pat. No. 5,130,335 (Chandraratna et al.), Reblished European Patent Application Nos. 0 176 034 A (Wuest et al.), 0 350 846 A (Klaus et al.), 0 176 032 A (Frickel et al.), 0 176 033 A (Frickel et al.), 0 253 302 A (Klaus et al.), 0 303 915 A (Bryce et al.), UK Patent Application GB 2190378 A (Klaus et al.), German Patent Application Nos. DE 3715955 A1 (Klaus et al.), DE 3602473 A1 (Wuest et al., and the articles *J. Amer. Acad. Derm.* 15: 756–764 (1986) (Sporn et al.), *Chem. Pharm. Bull.* 33: 404–407 (1985) (Shudo et al.), *J Med Chem.* 31: 2182–2192 (1988) (Kagechika et al.), *Chemistry and Biology of Synthetic Retinoids* CRC Press Inc. 1990 pp. 334–335, 354 (Dawson et al.), describe or relate to compounds which include a tetrahydronaphthyl moiety and have retinoid-like or related biological activity. U.S. Pat. No. 4,391,731 (Boller et al.) describes tetrahydronaphthalene derivatives which are useful in liquid crystal compositions.

An article by Kagechika et al. in *J. Med. Chem* 32:834 (1989) describe certain 6-(3-oxo-1-propenyl)-1,2,3,4-tetramethyl-1,2,3,4-tetrahydronaphthalene derivatives and related flavone compounds having retinoid-like activity. The articles by Shudo et al. in *Chem. Pharm. Bull.* 33:404 (1985) and by Jetten et al. in *Cancer Research* 47:3523 (1987) describe or relate to further 3-oxo-1-propenyl derivatives (chalcone compounds) and their retinoid-like or related biological activity.

Unfortunately, compounds having retinoid-like activity (retinoids) also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types of families of receptors are respectively designated as the RARs and RXRs. Within each type there are subtypes: in the RAR family the subtypes are designated RAR-α, RAR-β and RAR-γ, in RXR the subtypes are: RXR-α, RXB-β and RXR-γ. Both families of receptors are transcription factors that can be distinguished from each other based on their ligand binding specificities. All-trans-RA (ATRA) binds and activates a class of retinoic acid receptors (RARs) that includes RAR-α, RAR-β and RAR-γ. A different ligand, 9-cis-RA (9C-RA), binds and activates both the RARs and members of the retinoid X receptor (RXR) family.

It has also been established in the art that the distribution of the two main retinoid receptor types, and of the several subtypes is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

Relatively recently compounds have been developed in the art which bind to RAR receptors without triggering the response or responses that are triggered by agonists of the same receptors. The compounds or agents which bind to RAR receptors without triggering a "retinoid" response are thus capable of blocking (to lesser or greater extent) the activity of RAR agonists in biological assays and systems. More particularly, regarding the scientific and patent literature in this field, published PCT Application WO 94/14777 describes certain heterocyclic carboxylic acid derivatives which bind to RAR retinoid receptors and are said in the application to be useful for treatment of certain diseases or conditions, such as acne, psoriasis, rheumatoid arthritis and viral infections. A similar disclosure is made in the article by Yoshimura et al. *J Med. Chem.* 38: 3163–3173 (1995). Kaneko et al. *Med Chem Res.* 1:220–225 (1991); Apfel et al. *Proc. Natl. Acad Sci. USA* 89: 7129–7133 Augusty 1992 *Cell Biology*; Eckhardt et al. *Toxicology Letters* 70:299–308 (1994); Keidel et al. *Molecular and Cellular Biology* 14:287–298 (1994); and Eyrolles et al. *J Med. Chem.* 37: 1508–1517 (1994) describe compounds which have antagonist like activity at one or more of the RAR retinoid subtypes.

In addition to undesirable side-effects of therapy with retinoid compounds, there occurs occasionally a serious medical condition caused by vitamin A or vitamin A precursor overdose, resulting either from the excessive intake of vitamin supplements or the ingestion of liver of certain fish and animals that contain high levels of the vitamin. The chronic or acute toxicities observed with hypervitaminosis A syndrome include headache, skin peeling, bone toxicity, dyslipidemias, etc. In recent years, it has become apparent that the toxicities observed with vitamin A analogs, i.e., retinoids, essentially recapitulate those of hypervitaminosis A syndrome, suggesting a common biological cause, i.e., RAR activation. These toxicities are presently treated mainly by supportive measures and by abstaining from further exposure to the causative agent, whether it be liver, vitamin supplements, or retinoids. While some of the toxicities resolve with time, others (e.g., premature epiphyseal plate closure) are permanent.

Generally speaking, specific antidotes are the best treatment for poisoning by pharmacological agents, but only about two dozen chemicals or classes of chemicals out of thousands in existence have specific known antidotes. A specific antidote would clearly be of value in the treatment of hypervitaminosis A and retinoid toxicity. Indeed, as increasingly potent retinoids are used clinically, a specific antidote for retinoid poisoning could be life saving.

SUMMARY OF THE INVENTION

The present invention covers compounds of Formula 1

Formula 1

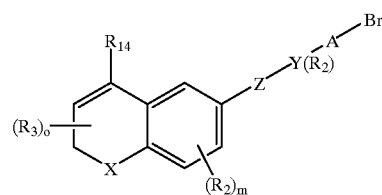

wherein
X is S, O, NR' where R' is H or alkyl of 1 to 6 carbons, or
X is $[C(R_1)_2]_n$ where $R_1$ is independently H or alkyl of 1 to 6 carbons, and n is an integer between 0 and 2;
$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;
$R_3$ is hydrogen, lower alkyl of 1 to 6 carbons or F;
m is an integer having the value of 0–3;
o is an integer having the value of 0–3;
Z is —C≡C—,
  —N=N—,
  —N=$CR_1$—,
  —$CR_1$=N,
  —$(CR_1$=$CR_1)_{n'}$— where n' is an integer having the value 0–5,
  —CO—$NR_1$—,
  —CS—$NR_1$—,
  —$NR_1$—CO,
  —$NR_1$—CS,
  —COO—,
  —OCO—;
  —CSO—;
  —OCS—;
Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or
when Z is —$(CR_1$=$CR_1)_{n'}$— and $_{n'}$ is 3, 4 or 5 then Y represents a direct valence bond between said $(CR_2$=$CR_2)_{n'}$ group and B;
A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;
B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0–5, and $R_{15}$ is independently H, F, Cl, Br, I, $NO_2$, $N(R_8)_2$, $N(R_8)COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons.

The present invention further covers compounds of Formula 101

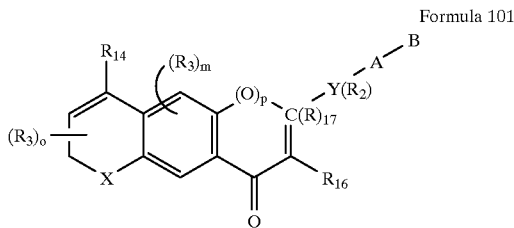

Formula 101 wherein X is S, O, NR' where R' is H or alkyl of 1 to 6 carbons, or

X is $[C(R_1)_2]_n$ where $R_1$ is independently H or alkyl of 1 to 6 carbons, and n is an integer between 0 and 2;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–3;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{14}$ is $(R_{15})_r$-phenyl, $(R_{15})_r$-naphthyl, or $(R_5)_r$-heteroaryl where the heteroaryl group has 1 to 3 heteroatoms selected from the group consisting of O, S and N, r is an integer having the values of 0–5, and $R_{15}$ is independently H, F, Cl, Br, I, $NO_2$, $N(R_8)_2$, $N(R_8)COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons;

$R_{16}$ is H, lower alkyl of 1 to 6 carbons;

$R_{17}$ is H, lower alkyl of 1 to 6 carbons, OH or $OCOR_{11}$, and p is zero or 1, with the proviso that when p is 1 then there is no $R_{17}$ substituent group, and m is an integer between 0 and 2.

The compounds of the present invention are useful for preventing certain undesired side effects of retinoids which are administered for the treatment or prevention of certain diseases or conditions. For this purpose the compounds of the invention may be coadministered with retinoids. The compounds of the present invention are also useful in the treatment of acute or chronic toxicity resulting from overdose or poisoning by retinoid drugs or Vitamin A.

The present invention additionally relates to the use of RAR antagonists for blocking all or some RAR receptor sites in biological systems, including mammals, to prevent or diminish action of RAR agonists on said receptor sites. More particularly, the present invention relates to the use of RAR antagonists for (a) the prevention and (b) the treatment of retinoid (including vitamin A or vitamin A precursor) chronic or acute toxicity and side effects of retinoid therapy.

In one particular aspect of the present invention, there is provided a method of treating a pathological condition in a mammal. The conditions treated are associated with a retinoic acid receptor activity. This method involves administering to the mammal a retinoid antagonist or negative hormone capable of binding to one of the following retinoic acid receptor subtypes: $RAR_\alpha$, $RAR_\beta$ and $RAR_\gamma$. The antagonist or negative hormone is administered in an amount pharmaceutically effective to provide a therapeutic benefit against the pathological condition in the mammal.

As an antidote to acute or chronic retinoid or vitamin A poisoning the RAR antagonist can be administered to a mammal enterally, i.e., intragastric intubation or food/water admixture, or parenterally, e.g., intraperitoneally, intramuscularly, subcutaneously, topically, etc. The only requirement for the route of administration is that it must allow delivery of the antagonist to the target tissue. The RAR antagonist can be formulated by itself or in combination with excipients. The RAR antagonist need not be in solution in the formulation, e.g., in the case of enteral use.

As an adjunct to therapy with retinoids and in order to prevent one or more side effects of the retinoid drug which is administered, the RAR antagonist can similarly be administered enterally or parenterally. The RAR antagonist and RAR agonist need not be administered by the same route of administration. The key is that sufficient quantities of the RAR antagonist be present continuously in the tissue of interest during exposure to the RAR agonist. For the prevention of retinoid toxicity, it is best that the RAR antagonist be administered concurrently or prior to treatment with the RAR agonist. In many situations the RAR antagonist will be administered by a different route than the agonist. For example undesirable skin effects of an enterally administered retinoid may be prevented or ameliorated by an RAR antagonist which is administered topically.

Another aspect of the present invention is a method of identifying retinoid negative hormones. The method includes the following steps: obtaining transfected cells containing a reporter gene transcriptionally responsive to binding of a recombinant retinoid receptor, the recombinant retinoid receptor having at least protein domains located C-terminal to a DNA binding domain of an intact retinoid receptor, measuring a basal level of reporter gene expression in untreated transfected cells, the untreated transfected cells being propagated in the absence of an added retinoid, treating the transfected cells with a retinoid compound to be tested for negative hormone activity, measuring a level of reporter gene expression in treated cells, comparing the levels of reporter gene expression measured in treated cells and untreated cells, and identifying as retinoid negative hormones those retinoid compounds producing a lower level of reporter gene expression in treated cells compared with the basal level of reporter gene expression measured in untreated cells. In certain preferred embodiments of this method the intact receptor is an RAR-α, RAR-β or RAR-γ subtype. In other embodiments, the intact receptor is an RXR-α, RXRβ or RXR-γ subtype. The recombinant receptor can also be either a recombinant RAR or RXR receptor. In some embodiments, the recombinant receptor is a chimeric retinoid receptor having a constitutive transcription activator domain. Such a constitutive transcription activator domain can comprise a plurality of amino acids having a net negative charge or have an amino acid sequence of a viral transcription activator domain, such as the herpes simplex virus VP-16transcription activator domain. In embodiments in which the constitutive transcription activator domain has a net negative charge, the retinoid receptor can be recombinant and have deleted therefrom a DNA binding domain, such as a DNA binding domain specific for a cis-regulatory element other than a retinoic acid responsive element. These elements include an estrogen responsive element. The transfected cell is preferably propagated in a growth medium substantially depleted of endogenous retinoids, such as one that includes activated charcoal extracted serum. In this method, the reporter gene can be the luciferase gene, in which case, the measuring steps can involve luminometry. The reporter gene can also be the β-galactosidase gene, in which case the measuring steps would involve a β-galactosidase assay. The transfected cell can be a transfected mammalian cell, such as a Green monkey cell or a human cell.

Another aspect of the present invention is a method of potentiating a pharmacologic activity of a steroid superfamily receptor agonist administered to a mammal. This method involves coadministering to the mammal with the steroid superfamily receptor agonist a composition comprising a pharmaceutically effective dose of a retinoid negative hormone to potentiate the pharmacologic activity of the steroid superfamily receptor agonist. The pharmacologic activity is measurable in a reporter gene trans-activation assay in vitro, such as by measuring anti-AP-1 activity. The pharmacologic activity to be potentiated can be an antiproliferative activity, such as activity of the type measurable in retinal pigment epithelium. The steroid superfamily receptor agonist can be any of the following: a retinoid receptor agonist, a vitamin D receptor agonist, a glucocorticoid receptor agonist, a thyroid hormone receptor agonist, a peroxisome proliferator-activated receptor agonist or an estrogen receptor agonist. The retinoid receptor agonist can be an RAR agonist, such as all-trans-retinoic acid or 13-cis retinoic acid.

The retinoid receptor agonist can also be an RXR agonist. A preferred vitamin D receptor agonist is 1,25-dihydroxyvitamin $D_3$. A preferred glucocorticoid receptor agonist is dexamethasone. A preferred thyroid hormone receptor agonist is 3,3',5-triiodothyronine. The retinoid negative hormone is an RAR-specific retinoid negative hormone, which preferably has a dissociation constant less than or approximately equal to 30 nM. Example of the RAR-specific retinoid negative hormone include AGN 193109, AGN 193385, AGN 193389 and AGN 193871. The composition comprising a pharmaceutically effective dose of a retinoid negative hormone can be coadministered at the same time as the steroid superfamily agonist and be combined prior to coadministration. These can also be coadministered as separate compositions.

BRIEF DESCRIPTION OF THE DRAWINGS

FIGS. 2A and 2B represent activity at the RAR-α receptor; FIGS. 2C and 2D represent activity at the RAR-β receptor; FIGS. 2E and 2F represent activity at the RAR-γ receptor. In FIGS. 2A, 2C and 2E, open squares represent retinoic acid treatment and filled circles represent AGN 193109 treatment. In FIGS. 2B, 2D and 2F the single lines represent luciferase activity measured after treatment with $10^{-8}$ M ATRA and variable concentrations of AGN 193109.

FIG. 9A shows that negative coactivator proteins and positive coactivator proteins (+) are in a binding equilibrium with the RAR. In the absence of a ligand, basal level transcription of the reporter gene results. As illustrated in FIG. 9B, addition of an RAR agonist promotes the association of positive coactivator proteins with the RAR and results in upregulated reporter gene transcription. As illustrated in FIG. 9C, addition of AGN 193109 promotes the association of negative coactivator proteins with the RAR and prevents reporter gene transcription.

FIG. 17 is a dose response curve showing that AGN 193109 potentiated the antiproliferative activity of ATRA on retinal pigment epithelium (RPE) cells. Samples treated with ATRA alone are represented by filled squares. Samples treated with the combination of ATRA and AGN 193109 ($10^{-7}$M) are represented by filled circles. The ATRA concentration used for treating the various samples is given on the horizontal axis.

FIG. 18 is a dose response curve showing that both 13-cis-RA and ATRA inhibited RPE cell growth, and that AGN 193109 potentiated the antiproliferative activity of 13-cis-RA. The various sample treatments shown in the dose response included 13-cis-RA alone (filled square), 13-cis-RA in combination with AGN 193109 ($10^{-6}$M) (filled circle), 13-cis-RA in combination with AGN 193109 ($10^{-8}$M) (filled triangle), and ATRA (filled diamond). The concentrations of 13-cis-RA and ATRA used in the sample treatments are shown on the horizontal axis.

FIG. 19 is a dose response curve showing that AGN 193109 potentiated the antiproliferative activity of dexamethasone in primary RPE cell cultures. The various sample treatments shown in the dose response included ATRA (filled square), dexamethasone alone (filled circle), dexamethasone in combination with AGN 193109 ($10^{-8}$M) (filled triangle), and dexamethasone in combination with AGN 193109 ($10^{-6}$M) (filled diamond). The concentrations of dexamethasone and ATRA used in the sample treatments are shown on the horizontal axis.

FIG. 20 is a dose response curve showing that AGN 193109 potentiated the antiproliferative activity of thyroid hormone (T3) in primary RPE cell cultures. The various sample treatments shown in the dose response included ATRA (filled square), T3 alone (filled circle), T3 in combination with AGN 193109 ($10^{-8}$M) (filled triangle), T3 in combination with AGN 193109 ($10^{-6}$M) (filled diamond). The concentrations of T3 and ATRA used in the sample treatments are shown on the horizontal axis.

DETAILED DESCRIPTION OF THE INVENTION

Definitions

Figure 1:
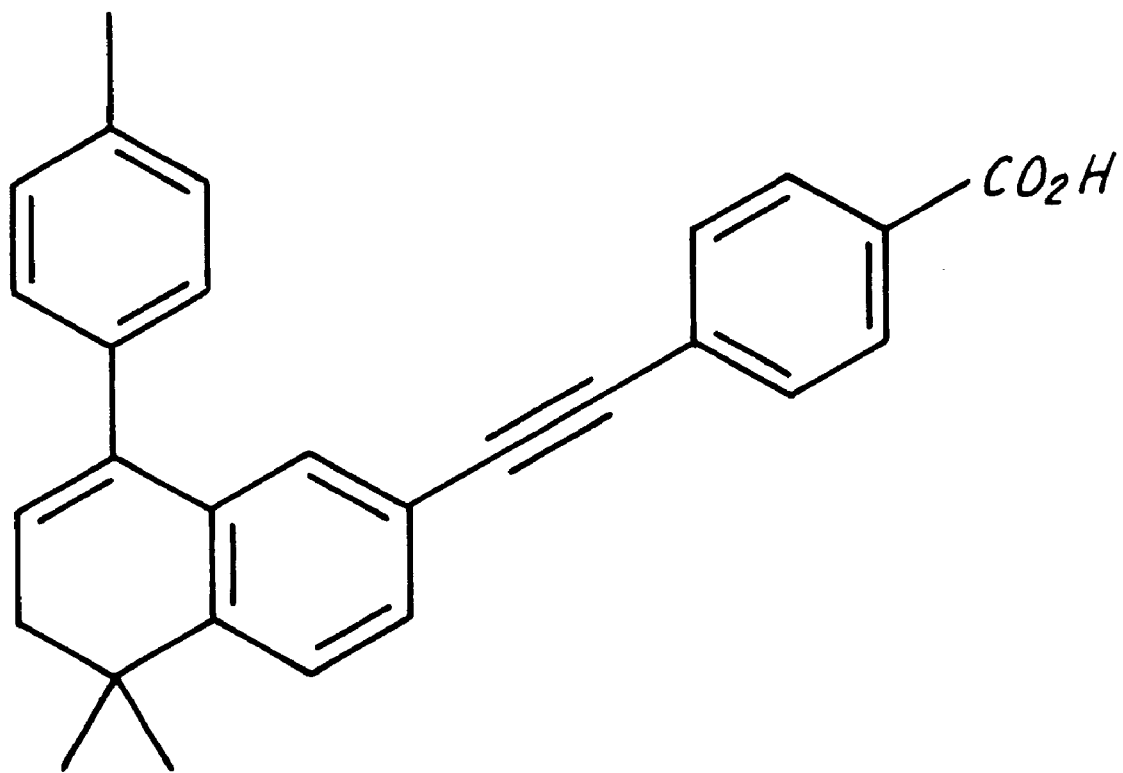
FIG. 1 shows the chemical structure of AGN 193109.

For the purposes of the present invention, an RAR antagonist is defined as a chemical that binds to one or more of the RAR subtypes with a $K_d$ of less than 1 micromolar ($K_d$<1 μM) but which does not cause significant transcriptional activation of that RAR subtypes-regulated genes in a receptor co-transfection assay. Conventionally, antagonists are chemical agents that inhibit the activities of agonists. Thus, the activity of a receptor antagonist is conventionally measured by virtue of its ability to inhibit the activity of an agonist.

An RAR agonist is defined as a chemical that binds to one or more RAR receptor subtype with $K_d$ of less than 1 micromol ($K_d$<1 μM) and causes transcriptional activation of that RAR-subtype-regulated genes in a receptor co-transfection assay. The term "RAR agonist" includes chemicals that may bind and/or activate other receptors in addition to RARs, e.g., RXR receptors.

As used herein, a negative hormone or inverse agonist is a ligand for a receptor which causes the receptor to adopt an inactive state relative to a basal state occurring in the absence of any ligand. Thus, while an antagonist can inhibit the activity of an agonist, a negative hormone is a ligand that can alter the conformation of the receptor in the absence of an agonist. The concept of a negative hormone or inverse agonist has been explored by Bond et al. in *Nature* 374:272 (1995). More specifically, Bond et al. have proposed that unliganded $\beta_2$-adrenoceptor exists in an equilibrium between an inactive conformation and a spontaneously active conformation. Agonists are proposed to stabilize the receptor in an active conformation. Conversely, inverse agonists are believed to stabilize an inactive receptor conformation. Thus, while an antagonist manifests its activity by virtue of inhibiting an agonist, a negative hormone can additionally manifest its activity in the absence of an agonist by inhibiting the spontaneous conversion of an unliganded receptor to an active conformation. Only a subset of antagonists will act as negative hormones. As disclosed herein, AGN 193109 is both an antagonist and a negative hormone. To date, no other retinoids have been shown to have negative hormone activity.

As used herein, coadministration of two pharmacologically active compounds refers to the delivery of two separate chemical entities, whether in vitro or in vivo. Coadministration refers to the simultaneous delivery of separate agents; to the simultaneous delivery of a mixture of agents; as well as to the delivery of one agent followed by delivery of the second agent. In all cases, agents that are coadministered are intended to work in conjunction with each other.

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B (of Formula 1 or Formula 101) is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and disubstituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well. In the present application when no specific mention is made of the configuration (cis, trans or R or S) of a compound (or of an asymmetric carbon) then a mixture of such isomers, or either one of the isomers is intended.

Aryl Substituted Benzopyran. Benzothiopyran. 1,2-Dihydroquinoline and 5,6-Dihydronaphthalene Derivatives Having Retinoid Antagonist Like Biological Activity With reference to the symbol Y in Formula 1, the preferred compounds of the invention are those where Y is phenyl, pyridyl, thienyl or furyl. Even more preferred are compounds where Y is phenyl or pyridyl, and still more preferred where Y is phenyl. As far as substitutions on the Y (phenyl) and Y (pyridyl) groups are concerned, compounds are preferred where the phenyl group is 1,4 (para) substituted by the Z and A-B groups, and where the pyridine ring is 2,5 substituted by the Z and A-B groups. (Substitution in the 2,5 positions in the "pyridine" nomenclature corresponds to substitution in the 6-position in the "nicotinic acid" nomenclature.) In the preferred compounds of the invention either there is no optional $R_2$ substituent on the Y group, or the optional $R_2$ substituent is fluoro (F).

The A-B group of the preferred compounds is $(CH_2)_n$—COOH or $(CH_2)_n$—$COOR_8$, where n and $R_8$ are defined as above. Even more preferably n is zero and $R_8$ is lower alkyl, or n is zero and B is COOH or a pharmaceutically acceptable salt thereof.

In many of the presently preferred examples of compounds of the invention X is $[C(R_1)_2]_n$ where n is 1. Compounds where n is zero (indene derivatives) and where X is S or O (benzothiopyran and benzopyran derivatives) are also preferred. When X is $[C(R_1)_2]_n$ and n is 1, then $R_1$ preferably is alkyl of 1 to 6 carbons, even more preferably methyl.

The $R_2$ group attached to the aromatic portion of the tetrahydronaphthalene, benzopyran, benzothiopyran or dihydroquinoline moiety of the compounds of Formula 1 is preferably H, F, $CF_3$. or alkoxy such as $OCH_3$. $R_3$ is preferably hydrogen or methyl, even more preferably hydrogen.

The $R_2$ group attached to the Y group, when there is such $R_2$ substituent, is preferably, F or $CF_3$.

Referring now to the group Z in the compounds of the invention and shown in Formula 1, in a plurality of preferred examples Z represents an acetylenic linkage (Z=—C≡C—). However, the "linker group." Z is also preferred as a diazo group (Z=—N=N—), as an olefinic or polyolefinic group (Z=—($CR_1$=$CR_1$)$_{n'}$—), as an ester (Z=—COO—), amide (Z=—CO—$NR_2$—) or thioamide (Z=—CS—$NR_2$—) linkage.

Referring now to the $R_{14}$ group, compounds are preferred where $R_{14}$ is phenyl, 2-pyridyl, 3-pyridyl, 2-thienyl, and 2-thiazolyl. The $R_{15}$ group (substituent of the $R_{14}$ group) is preferably H, lower alkyl, trifluoromethyl, chlorine, lower alkoxy or hydroxy.

The presently most preferred compounds of the invention according to Formula 1 are shown in Table 1 with reference to Formula 2, Formula 3, Formula 4, Formula 5, and Formula 5a.

Formula 2

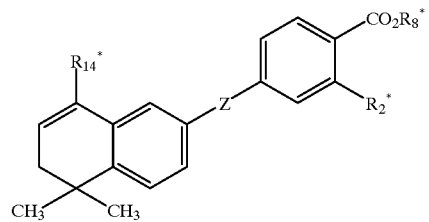

Formula 3

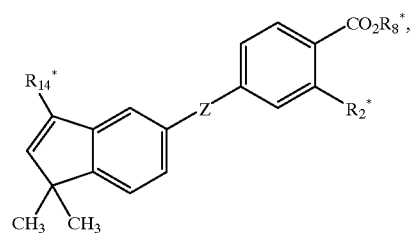

Formula 4

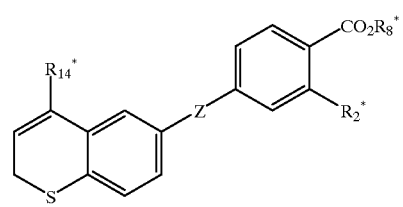

Formula 5

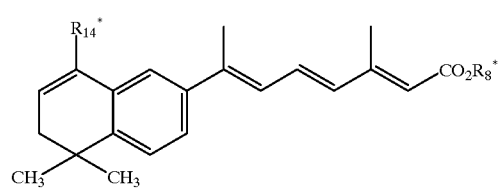

Formula 5a

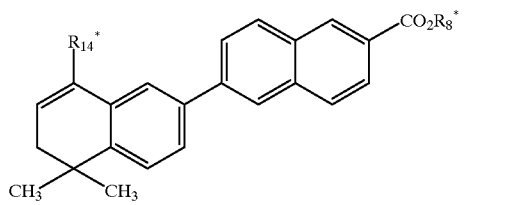

TABLE 1

| Compound # | Formula | $R_{14}$* | Z | $R_2$* | $R_8$* |
| --- | --- | --- | --- | --- | --- |
| 1 | 2 | 4-methylphenyl | —C≡C— | H | Et |
| 1a | 2 | phenyl | —C≡C— | H | Et |

TABLE 1-continued

| Compound # | Formula | $R_{14}$* | Z | $R_2$* | $R_8$* |
|---|---|---|---|---|---|
| 2 | 2 | 3-methylphenyl | —C≡C— | H | Et |
| 3 | 2 | 2-methylphenyl | —C≡C— | H | Et |
| 4 | 2 | 3,5-dimethylphenyl | —C≡C— | H | Et |
| 5 | 2 | 4-ethylphenyl | —C≡C— | H | Et |
| 6 | 2 | 4-t-butylphenyl | —C≡C— | H | Et |
| 7 | 2 | 4-chlorophenyl | —C≡C— | H | Et |
| 8 | 2 | 4-methoxyphenyl | —C≡C— | H | Et |
| 9 | 2 | 4-trifluoromethylphenyl | —C≡C— | H | Et |
| 10 | 2 | 2-pyridyl | —C≡C— | H | Et |
| 11 | 2 | 3-pyridyl | —C≡C— | H | Et |
| 12 | 2 | 2-methyl-5-pyridyl | —C≡C— | H | Et |
| 13 | 2 | 3-hydroxyphenyl | —C≡C— | H | Et |
| 14 | 2 | 4-hydroxy phenyl | —C≡C— | H | Et |
| 15 | 2 | 5-methyl-2-thiazolyl | —C≡C— | H | Et |
| 15a | 2 | 2-thiazolyl | —C≡C— | H | Et |
| 16 | 2 | 4-methyl-2-thiazolyl | —C≡C— | H | Et |
| 17 | 2 | 4,5-dimethyl-2-thiazoly | —C≡C— | H | Et |
| 18 | 2 | 2-methyl-5-pyridyl | —C≡C— | H | H |
| 19 | 2 | 2-pyridyl | —C≡C— | H | H |
| 20 | 2 | 3-methylphenyl | —C≡C— | H | H |
| 21 | 2 | 4-ethylphenyl | —C≡C— | H | H |
| 22 | 2 | 4-methoxyphenyl | —C≡C— | H | H |
| 23 | 2 | 4-trifluoromethylphenyl | —C≡C— | H | H |
| 24 | 2 | 3,5-dimethylphenyl | —C≡C— | H | H |
| 25 | 2 | 4-chlorophenyl | —C≡C— | H | H |
| 26 | 2 | 3-pyridyl | —C≡C— | H | H |
| 27 | 2 | 2-methylphenyl | —C≡C— | H | H |
| 28 | 2 | 3-hydroxyphenyl | —C≡C— | H | H |
| 29 | 2 | 4-hydroxyphenyl | —C≡C— | H | H |
| 30 | 2 | 5-methyl-2-thiazolyl | —C≡C— | H | H |
| 30a | 2 | 2-thiazolyl | —C≡C— | H | H |
| 31 | 2 | 4-methyl-2-thiazolyl | —C≡C— | H | H |
| 32 | 2 | 4,5-dimethyl-2-thiazolyl | —C≡C— | H | H |
| 33 | 2 | 5-methyl-2-thienyl | —C≡C— | H | Et |
| 33a | 2 | 2-thienyl | —C≡C— | H | Et |
| 34 | 2 | 5-methyl-2-thienyl | —C≡C— | H | H |
| 34a | 2 | 2-thienyl | —C≡C— | H | H |
| 35 | 2 | 4-methylphenyl | —CONH— | H | Et |
| 36 | 2 | 4-methylphenyl | —CONH— | H | H |
| 37 | 2 | 4-methylphenyl | —COO— | H | Et |
| 38 | 2 | 4-methylphenyl | —COO— | H | $(CH_2)_2Si(CH_3)$ |
| 39 | 2 | 4-methylphenyl | —COO— | H | H |
| 40 | 2 | 4-methylphenyl | —CONH— | F | Et |
| 41 | 2 | 4-methylphenyl | —CONH— | F | H |
| 42 | 2 | 4-methylphenyl | —CSNH— | H | Et |
| 43 | 2 | 4-methylphenyl | —CSNH— | H | H |
| 44 | 2 | 4-methylphenyl | —CH=CH— | H | Et |
| 45 | 2 | 4-methylphenyl | —CH=CH— | H | H |
| 46a | 2 | 4-methylphenyl | —N=N— | H | Et |
| 46b | 2 | 4-methylphenyl | —N=N— | H | H |
| 47 | 3 | 4-methylphenyl | —C≡C— | H | Et |
| 48 | 3 | 4-methylphenyl | —C≡C— | H | H |
| 49 | 4 | 4-methylphenyl | —C≡C— | H | Et |
| 50 | 4 | 4-methylphenyl | —C≡C— | H | H |
| 51 | 5 | 4-methylphenyl | — | — | Et |
| 52 | 5 | 4-methylphenyl | — | — | H |
| 60 | 2 | 4-methylphenyl | —C≡C— | H | H |
| 60a | 2 | phenyl | —C≡C— | H | H |
| 61 | 2 | 4-t-butylphenyl | —C≡C— | H | H |
| 62 | 2 | 4-methylphenyl | —CSNH | F | Et |
| 63 | 2 | 4-methylphenyl | —CSNH | F | H |
| 64 | 5a | 4-methylphenyl | — | — | Et |
| 65 | 5a | 4-methylphenyl | — | — | H |
| 66 | 2 | 2-furyl | —C≡C— | H | Et |
| 67 | 2 | 2-furyl | —C≡C— | H | H |

Still further most preferred compounds of the invention are in accordance with Formula 5b which are further identified in Table 1a and in the ensuing experimental section.

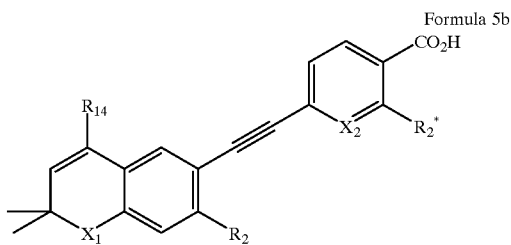

Formula 5b

TABLE 1a

| Compound # Page # | $R_{14}$ | $X_1$ | $X_2$ | $R_2$ | $R_2*$ |
|---|---|---|---|---|---|
| 242 | phenyl | S | CH | H | H |
| 243 | 4-methylphenyl | S | CH | H | H |
| 244 | 4-ethylphenyl | S | CH | H | H |
| 245 | 4-i-propylphenyl | S | CH | H | H |
| 246 | 4-t-butylphenyl | S | CH | H | H |
| 247 | 5-methyl-2-thienyl | S | CH | H | H |
| 248 | 5-ethyl-2-thienyl | S | CH | H | H |
| 249 | 5-t-butyl-2-thienyl | S | CH | H | H |
| 250 | 6-methyl-3-pyridyl | S | CH | H | H |
| 251 | 4-methylphenyl | S | CH | H | F |
| 252 | 4-ethylphenyl | S | CH | H | F |
| 253 | 4-methylphenyl | S | N | H | H |
| 254 | 4-ethylphenyl | S | N | H | H |
| 255 | 4-methylphenyl | S | CH | F | H |
| 256 | 4-methylphenyl | S | CH | $OCH_3$ | H |
| 257 | 5-methyl-2-thienyl | S | CH | F | H |
| 274 | phenyl | O | CH | H | H |
| 275 | 4-methylphenyl | O | CH | H | H |
| 276 | 4-ethylphenyl | O | CH | H | H |
| 277 | 4-isopropylphenyl | O | CH | H | H |
| 278 | 4-t-butylphenyl | O | CH | H | H |
| 279 | 4-methylphenyl | O | CH | H | F |
| 280 | 4-ethylphenyl | O | CH | H | F |

Aryl and (3-Oxo-1-Propenyl)-Substituted Benzopyran. Benzothiopyran, Dihydroquinoline and 5,6-Dihydronaphthalene Derivatives Having Retinoid Antagonist-Like Biological Activity With reference to the symbol Y in Formula 101, the preferred compounds of the invention are those where Y is phenyl, pyridyl, thienyl or furyl. Even more preferred are compounds where Y is phenyl or pyridyl, and still more preferred where Y is phenyl. As far as substitutions on the Y (phenyl) and Y (pyridyl) groups are concerned, compounds are preferred where the phenyl group is 1,4 (para) substituted by the —$CR_{16}$=$CR_{17}$— and A–B groups, and where the pyridine ring is 2,5 substituted by the —$CR_{16}$=$CR_{17}$— and A-B groups. (Substitution in the 2,5 positions in the "pyridine" nomenclature corresponds to substitution in the 6-position in the "nicotinic acid" nomenclature.) In the preferred compounds of the invention there is no optional $R_2$ substituent on the Y group.

The A-B group of the preferred compounds is $(CH_2)_n$—COOH or $(CH_2)_n$—$COOR_8$, where n and $R_8$ are defined as above. Even more preferably n is zero and $R_8$ is lower alkyl, or n is zero and B is COOH or a pharmaceutically acceptable salt thereof.

In the presently preferred examples of compounds of the invention X is $[C(R_1)_2]_n$ where n is 1. Nevertheless, compounds where X is S or O (benzothiopyran and benzopyran derivatives) are also preferred. When X is $[C(R_1)_2]_n$ and n is 1, then $R_1$ preferably is alkyl of 1 to 6 carbons, even more preferably methyl.

The $R_2$ group attached to the aromatic portion of the tetrahydronaphthalene, benzopyran, benzothiopyran or dihydroquinoline moiety of the compounds of Formula 101 is preferably H, F or $CF_3$. $R_3$ is preferably hydrogen or methyl, even more preferably hydrogen.

Referring now to the $R_{14}$ group, compounds are preferred where $R_{14}$ is phenyl, 2-pyridyl, 3-pyridyl, 2-thienyl, and 2-thiazolyl. The $R_{15}$ group (substituent of the $R_{14}$ group) is preferably H, lower alkyl, trifluoromethyl, chlorine, lower alkoxy or hydroxy.

Preferred compounds of the invention according to Formula 101 are shown in Table 2 with reference to Formula 102.

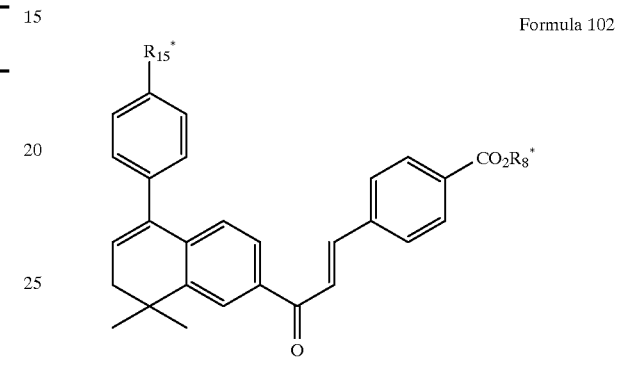

Formula 102

TABLE 2

| Compound | $R_{15}*$ | $R_8*$ |
|---|---|---|
| 101 | $CH_3$ | H |
| 102 | $CH_3$ | Et |
| 103 | H | H |
| 104 | H | Et |

Biological Activity, Modes of Administration

As noted above, the compounds of the present invention are antagonists of one or more RAR receptor subtypes. This means that the compounds of the invention bind to one or more RAR receptor subtypes, but do not trigger the response which is triggered by agonists of the same receptors. Some of the compounds of the present invention are antagonists of all three RAR receptor subtypes (RAR-α, RAR-β and RAR-γ), and these are termed "RAR pan antagonists". Some others are antagonists of only one or two of RAR receptor subtypes. Some compounds within the scope of the present invention are partial agonists of one or two RAR receptor subtypes and antagonists of the remaining subtypes. The compounds of the invention do not bind to RXR receptors, therefore they are neither agonists nor antagonists of RXR.

Depending on the site and nature of undesirable side effects which are desired to be suppressed or ameliorated, compounds used in accordance with the invention may be antagonists of only one or two of RAR receptor subtypes. Some compounds used in accordance with the invention may be partial agonists of one or two RAR receptor subtypes and antagonists of the remaining subtypes. Such compounds are, generally speaking, usable in accordance with the invention if the antagonist effect is on that RAR receptor subtype (or subtypes) which is (are) predominantly responsible for the overdose poisoning or for the undesired side effect or side effects. In this connection it is noted that, generally speaking, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 µM.

Whether a compound is an RAR antagonist and therefore can be utilized in accordance with the present invention, can be tested in the following assays.

A chimeric receptor transactivation assay which tests for agonist-like activity in the RAR-α, RAR-β, RAR-γ, RXR-α receptor subtypes, and which is based on work published by Feigner P. L. and Holm M. *Focus* Vol 11, No. 2 (1989) is described in detail in published PCT Application No. WO94/17796, published on Aug. 18, 1994. The latter publication is the PCT counterpart of U. S. application Ser. No. 08/016, 404, filed on Feb. 11, 1993, which issued as U.S. Pat. No. 5,455,265. PCT publication WO94/17796 and the specification of U.S. Pat. No. 5,455,265 are hereby expressly incorporated by reference. A compound should not cause significant activation of a reporter gene through a given receptor subtype (RAR-α, RAR-β or RAR-γ) in this assay, in order to qualify as an RAR antagonist with utility in the present invention.

A holoreceptor transactivation assay and a ligand binding assay which measure the antagonist/agonist like activity of the compounds of the invention, or their ability to bind to the several retinoid receptor subtypes, respectively, are described in published PCT Application No. WO93/11755 (particularly on pages 30–33 and 37–41) published on Jun. 24, 1993, the specification of which is also incorporated herein by reference. A description of the holoreceptor transactivation assay is also provided below.

Holoreceptor Transactivation Assay

CV1 cells (5,000 cells/well) were transfected with an RAR reporter plasmid MTV-TREp-LUC (50 ng) along with one of the RAR expression vectors (10 ng) in an automated 96-well format by the calcium phosphate procedure of Heyman et al. *Cell* 68: 397–406. For RXR-α and RXR-γ transactivation assays, an RXR-responsive reporter plasmid CRBPII-tk-LUC (50 ng) along with the appropriate RXR expression vectors (10 ng) was used substantially as described by Heyman et al. above, and Allegretto et al. *J. Biol. Chem.* 268: 26625–26633. For RXR-β transactivation assays, an RXR-responsive reporter plasmid CPRE-tk-LUC (50 mg) along with RXR-β expression vector (10 mg) was used as described in above. These reporters contain DRI elements from human CRBPII and certain DRI elements from promotor, respectively (see Mangelsdorf et al. *The Retinoids: Biology, Chemistry and Medicine*, pp. 319–349, Raven Press Ltd., New York and Heyman et al., cited above). A β-galactosidase (50 ng) expression vector was used as an internal control in the transfections to normalize for variations in transfection efficiency. The cells were transfected in triplicate for 6 hours, followed by incubation with retinoids for 36 hours, and the extracts were assayed for luciferase and β-galactosidase activities. The detailed experimental procedure for holoreceptor transactivations has been described in Heyman et al. above, and Allegretto et al. cited above. The results obtained in this assay are expressed in $EC_{50}$ numbers, as they are also in the chimeric receptor transactivation assay. The Heyman et al. *Cell* 68: 397–406, Allegretto et al. *J. Biol Chem.* 268: 26625–26633, and Mangelsdorf et al. *The Retinoids: Biology. Chemistry and Medicine*, pp. 319–349, Raven Press Ltd., New York, are expressly incorporated herein by reference. The results of ligand binding assay are expressed in Kd numbers. (See Cheng et al. *Biochemical Pharmacology* 22: 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

RAR-PGR Holoreceptor Transactivation Assay

CV-1 cells ($4 \times 10^5$ cells/well) were transiently transfected with the luciferase reporter plasmid MTV-4(R5G)-Luc (0.7 ug/well) containing four copies of the R5G retinoid DNA response element along with the RXRα expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RAR,β and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 µl instead of 100 µl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet (1987) Mol. Cell. Biol. 7, 725–737. Luciferase values represent the mean±SEM of triplicate determinations normalized to β-galactosidase activity.

A compound should not cause significant activation of a reporter gene through a given receptor subtype (RAR-α, RAR-β or RAR-γ) in the transactivation assays, in order to qualify as an RAR antagonist with utility in the present invention. Last, but not least, a compound should bind to at least one of the RAR receptor subtypes in the ligand binding assay with a $K_d$ of less than approximately 1 micromolar ($K_d < 1$ µM) in order to be capable of functioning as an antagonist of the bound receptor subtype, provided the same receptor subtype is not significantly activated by the compound.

Table 3 below shows the results of the holoreceptor transactivation assay for certain compounds of Table 1. Table 3a shows the results of the RAR-PGR moloreceptor transactivation assay for the preferred compounds of Table 1a. Tables 4 and 4a disclose the efficacy (in percentage) in these assays of the test compounds relative to all trans retinoic acid, for certain exemplary compounds of the invention. Tables 5 and 5a show the results of the ligand binding assay for certain exemplary compounds of the invention.

TABLE 3

Holoreceptor Transactivation Assay

EC$_{50}$ (nanomolar)

| Compound # | RARα | RARβ | RARγ | RXRα | RXRβ | RXRγ |
|---|---|---|---|---|---|---|
| 18 | 0.00 | 0.00 | 0.00 | 0.00 | 0.00 | 0.00 |
| 19 | 0.00 | 0.00 | 0.00 | 0.00 | 0.00 | 0.00 |
| 20 | 0.00 | 0.00 | 0.00 | 0.00 | 0.00 | 0.00 |
| 21 | 0.00 | 0.00 | 0.00 | 0.00 | 0.00 | 0.00 |
| 22 | 0.00 | 0.00 | 0.00 | 0.00 | 0.00 | 0.00 |
| 23 | 0.00 | 0.00 | 0.00 | 0.00 | 0.00 | 0.00 |
| 24 | 0.00 | 0.00 | 0.00 | 0.00 | 0.00 | 0.00 |
| 25 | 0.00 | 0.00 | 0.00 | 0.00 | 0.00 | 0.00 |
| 26 | 0.00 | 0.00 | 0.00 | 0.00 | 0.00 | 0.00 |
| 27 | 0.00 | 0.00 | 0.00 | 0.00 | 0.00 | 0.00 |
| 28 | 0.00 | 0.00 | 0.00 | 0.00 | 0.00 | 0.00 |
| 29 | 0.00 | 0.00 | 0.00 | 0.00 | 0.00 | 0.00 |
| 30 | 0.00 | 0.00 | 0.00 | 0.00 | 0.00 | 0.00 |
| 31 | 0.00 | 0.00 | 0.00 | 0.00 | 0.00 | 0.00 |
| 32 | 0.00 | 0.00 | 0.00 | 0.00 | 0.00 | 0.00 |
| 34 | 0.00 | 0.00 | 0.00 | 0.00 | 0.00 | 0.00 |
| 36 | 0.00 | 0.00 | 0.00 | 0.00 | 0.00 | 0.00 |
| 39 | 0.00 | 0.00 | 0.00 | 0.00 | 0.00 | 0.00 |
| 41 | 0.00 | 0.00 | 0.00 | 0.00 | 0.00 | 0.00 |
| 45 | 0.00 | 0.00 | 0.00 | 0.00 | 0.00 | 0.00 |
| 46b | 0.00 | 0.00 | 0.00 | 0.00 | 0.00 | 0.00 |
| 52 | 0.00 | 0.00 | 0.00 | 0.00 | 0.00 | 0.00 |
| 60 | 0.00 | 0.00 | 0.00 | 0.00 | 0.00 | 0.00 |
| 61 | 0.00 | 0.00 | 0.00 | 0.00 | 0.00 | 0.00 |
| 63 | 0.00 | 0.00 | 0.00 | 0.00 | 0.00 | 0.00 |
| 101 | 0.00 | 0.00 | 0.00 | 0.00 | 0.00 | 0.00 |
| 103 | 0.00 | 0.00 | 0.00 | 0.00 | 0.00 | 0.00 |

0.0 in Tables 3 and 3a indicates that the compound is less than 20% as active (efficacious) in this assay than all trans retinoic acid.

TABLE 3a

RAR-PGR Holoreceptor Transactivation Assay

EC$_{50}$ (nanomolar)

| Compound No. | RARα | RARβ | RARγ |
|---|---|---|---|
| 242 | 0.00 | 0.00 | 0.00 |
| 243 | 0.00 | 0.00 | 0.00 |
| 244 | 0.00 | 0.00 | 0.00 |
| 245 | 0.00 | 0.00 | 0.00 |
| 246 | 0.00 | 0.00 | 0.00 |
| 247 | 0.00 | 0.00 | 0.00 |
| 248 | 0.00 | 0.00 | 0.00 |
| 249 | 0.00 | 0.00 | 0.00 |
| 250 | 0.00 | 0.00 | 0.00 |
| 251 | 0.00 | 0.00 | 0.00 |
| 252 | 0.00 | 0.00 | 0.00 |
| 253 | 0.00 | 0.00 | 0.00 |
| 254 | 0.00 | 0.00 | 0.00 |
| 255 | 0.00 | 0.00 | 0.00 |
| 256 | 0.00 | 0.00 | 0.00 |
| 257 | 0.00 | 0.00 | 0.00 |
| 274 | 0.00 | 0.00 | 0.00 |
| 275 | 0.00 | 0.00 | 0.00 |
| 276 | 0.00 | 0.00 | 0.00 |
| 277 | 0.00 | 0.00 | 0.00 |
| 278 | 0.00 | 0.00 | 0.00 |
| 279 | 0.00 | 0.00 | 0.00 |
| 280 | 0.00 | 0.00 | 0.00 |

TABLE 4

Transactivation Assay Efficacy (% of RA activity)

| Compound No. | RARα | RARβ | RARγ | RXRα | RXRβ | RXRγ |
|---|---|---|---|---|---|---|
| 18 | 4.00 | 1.00 | 0.00 | 2.00 | 10.00 | 1.0 |
| 19 | 0.00 | 5.0 | 3.0 | 0.0 | 9.0 | 4.0 |
| 20 | 3.0 | 4.0 | 0.00 | 4.00 | 0.00 | 3.0 |
| 21 | 2.00 | 2.00 | 2.00 | 3.00 | 0.00 | 3.00 |
| 22 | 0.00 | 0.00 | 2.00 | 1.00 | 0.00 | 2.00 |
| 23 | 0.00 | 6.00 | 3.00 | 1.00 | 0.00 | 4.00 |
| 24 | 3.00 | 7.00 | 4.00 | 1.00 | 0.00 | 3.00 |
| 25 | 2.00 | 3.00 | 3.00 | 5.00 | 0.00 | 3.00 |
| 26 | 1.00 | 6.00 | 0.00 | 2.00 | 0.00 | 3.00 |
| 27 | 9.00 | 14.00 | 6.00 | 2.00 | 0.00 | 4.00 |
| 28 | 2.00 | 10.00 | 2.00 | 0.00 | 0.00 | 3.00 |
| 29 | 0.00 | 6.00 | 11.00 | 0.00 | 6.00 | 2.00 |
| 30 | 3.00 | 5.00 | 1.00 | 0.00 | 9.00 | 3.00 |
| 31 | 4.00 | 14.00 | 2.00 | 1.00 | 8.00 | 6.00 |
| 32 | 0.00 | 2.00 | 2.00 | 1.00 | 0.00 | 2.00 |
| 34 | 3.00 | 5.00 | 2.00 | 1.00 | 0.00 | 3.00 |
| 36 | 1.00 | 5.00 | 0.00 | 1.00 | 7.00 | 2.00 |
| 39 | 1.00 | 7.00 | 9.00 | 2.00 | 0.00 | 1.00 |
| 41 | 3.00 | 5.00 | 6.00 | 1.00 | 0.00 | 3.00 |
| 45 | 2.00 | 0.00 | 7.00 | 3.00 | 8.00 | 0.00 |
| 46b | 4.00 | 5.00 | 3.00 | 2.00 | 0.00 | 4.00 |
| 52 | 0.00 | 15.00 | 3.00 | 0.00 | 0.00 | 10.00 |
| 60 | 0.00 | 1.00 | 4.00 | 3.00 | 0.00 | 3.00 |
| 61 | 2.00 | 2.00 | 0.00 | 1.00 | 0.00 | 3.00 |
| 63 | 2.00 | 2.00 | 7.00 | 1.00 | 0.00 | 1.00 |
| 101 | 0.00 | 4.00 | 2.00 | 1.00 | 0.00 | 3.0 |
| 103 | 4.00 | 12.0 | 7.0 | 0.00 | 0.0 | 2.0 |

TABLE 4a

Transactivation Assay Efficacy (% of RA Activity)

| Compound No. | RARα | RARβ | RARγ |
|---|---|---|---|
| 242 | 0.00 | 0.00 | 0.00 |
| 243 | 0.00 | 0.00 | 0.00 |
| 244 | 0.00 | 0.00 | 0.00 |
| 245 | 0.00 | 0.00 | 0.00 |
| 246 | 0.00 | 0.00 | 0.00 |
| 247 | 0.00 | 0.00 | 0.00 |
| 248 | 0.00 | 0.00 | 0.00 |
| 249 | 0.00 | 0.00 | 0.00 |
| 250 | 0.00 | 0.00 | 0.00 |
| 251 | 0.00 | 0.00 | 0.00 |
| 252 | 0.00 | 0.00 | 0.00 |
| 253 | 0.00 | 0.00 | 0.00 |
| 254 | 0.00 | 0.00 | 0.00 |
| 255 | 0.00 | 0.00 | 0.00 |
| 256 | 0.00 | 0.00 | 0.00 |
| 257 | 0.00 | 0.00 | 0.00 |
| 274 | 0.00 | 0.00 | 0.00 |
| 275 | 0.00 | 0.00 | 0.00 |
| 276 | 0.00 | 0.00 | 0.00 |
| 277 | 0.00 | 0.00 | 0.00 |
| 278 | 0.00 | 0.00 | 0.00 |
| 279 | 0.00 | 0.00 | 0.00 |
| 280 | 0.00 | 0.00 | 0.00 |

TABLE 5

Ligand Binding Assay

K$_d$ (nanomolar)

| Compound # | RARα | RARβ | RARγ | RXRα | RXRβ | RXRγ |
|---|---|---|---|---|---|---|
| 18 | 24.00 | 11.00 | 24.00 | 0.00 | 0.00 | 0.00 |
| 19 | 565 | 210 | 659 | 0.00 | 0.00 | 0.00 |
| 20 | 130.00 | 22.0 | 34.00 | 0.00 | 0.00 | 0.00 |
| 21 | 16 | 9 | 13 | 0.00 | 0.00 | 0.00 |

TABLE 5-continued

Ligand Binding Assay $K_d$ (nanomolar)

| Compound # | RARα | RARβ | RARγ | RXRα | RXRβ | RXRγ |
|---|---|---|---|---|---|---|
| 22 | 24.0 | 17.0 | 27.0 | 0.00 | 0.00 | 0.00 |
| 23 | 32.00 | 25.00 | 31.00 | 0.00 | 0.00 | 0.00 |
| 24 | 699 | 235 | 286 | 0.00 | 0.00 | 0.00 |
| 25 | 50 | 17 | 20 | 0.00 | 0.00 | 0.00 |
| 26 | 40.00 | 31.00 | 36.00 | 0.00 | 0.00 | 0.00 |
| 27 | 69.00 | 14.00 | 26.00 | 0.00 | 0.00 | 0.00 |
| 28 | 669 | 77 | 236 | 0.00 | 0.00 | 0.00 |
| 29 | 234 | 48 | 80 | 0.00 | 0.00 | 0.00 |
| 30 | 683 | 141 | 219 | 0.00 | 0.00 | 0.00 |
| 31 | 370 | 52.00 | 100.00 | 0.00 | 0.00 | 0.00 |
| 32 | 0.00 | 89.00 | 169.00 | 0.00 | 0.00 | 0.00 |
| 34 | 52.00 | 30.00 | 17.00 | 0.00 | 0.00 | 0.00 |
| 36 | 13.00 | 550.00 | 0.00 | 0.00 | 0.00 | 0.00 |
| 39 | 67.00 | 38.00 | 113.00 | 0.00 | 0.00 | 0.00 |
| 41 | 5.1 | 491 | 725 | 0.00 | 0.00 | 0.00 |
| 45 | 12.0 | 2.80 | 17.0 | 0.00 | 0.00 | 0.00 |
| 46b | 250 | 3.70 | 5.80 | 0.00 | 0.00 | 0.00 |
| 52 | 60.00 | 63.00 | 56.00 | 0.00 | 0.00 | 0.00 |
| 60 | 1.5 | 1.9 | 3.3 | 0.00 | 0.00 | 0.00 |
| 61 | 96 | 15 | 16 | 0.00 | 0.00 | 0.00 |
| 63 | 133 | 3219 | 0.00 | 0.00 | 0.00 | 0.00 |
| 101 | 750 | 143 | 637 | 0.00 | 0.00 | 0.00 |
| 103 | 301 | 273 | 261 | 0.00 | 0.00 | 0.00 |

TABLE 5a

Ligand Binding Assay Kd (nanomolar)

| Compound No. | RARα | RARβ | RARγ |
|---|---|---|---|
| 242 | 8 | 5 | 13 |
| 243 | 4 | 2 | 10 |
| 244 | 3 | 2 | 5 |
| 245 | 7 | 2 | 10 |
| 246 | 13 | 4 | 20 |
| 247 | 12 | 6 | 18 |
| 248 | 6 | 2 | 17 |
| 249 | 19 | 5 | 57 |
| 250 | 4 | 2 | 17 |
| 251 | 2 | 2 | 3 |
| 252 | 4 | 10 | 4 |
| 253 | 45 | 6 | 5 |
| 254 | 70 | 4 | 9 |
| 255 | 3 | 3 | 3 |
| 256 | >$10^3$ | 393 | 203 |
| 257 | 8 | 3 | 7 |
| 274 | 36 | 11 | 49 |
| 275 | 14 | 5 | 14 |
| 276 | 12 | 3 | 24 |
| 277 | 16 | 8 | 39 |
| 278 | 72 | 9 | 108 |
| 279 | 14 | 6 | 28 |
| 280 | 5 | 2 | 16 |

0.0 in Tables 5 and 5a indicates a value greater than 1000 nM.

As it can be seen from the test results summarized in Tables 3, 3a, 4, 4a, 5 and 5a, the therein indicated exemplary compounds of the invention are antagonists of the RAR receptor subtypes, but have no affinity to RXR receptor subtypes. (Other compounds of the invention may be antagonist of some but not all RAR receptor subtypes and agonists of the remaining RAR subtypes.) Due to this property, the compounds of the invention can be used to block the activity of RAR agonists in biological assays. In mammals, including humans, the compounds of the invention can be coadministered with RAR agonists and, by means of pharmacological selectivity or site-specific delivery, preferentially prevent the undesired effects of RAR agonists. The compounds of the invention can also be used to treat Vitamin A overdose, acute or chronic, resulting either from the excessive intake of vitamin A supplements or from the ingestion of liver of certain fish and animals that contain high level of Vitamin A. Still further, the compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the compounds of the present invention block RAR activation, they are suitable for treating the foregoing toxicities.

The compounds of the invention are able to substantially prevent skin irritation induced by RAR agonist retinoids, when the compound of the invention is topically coadministered to the skin. Similarly, compounds of the invention can be administered topically to the skin, to block skin irritation, in patients or animals who are administered RAR agonist compounds systemically. The compounds of the invention can accelerate recovery from pre-existing retinoid toxicity, can block hypertriglyceridemia caused by co-administered retinoids, and can block bone toxicity induced by an RAR agonist (retinoid).

Generally speaking, for therapeutic applications in mammals in accordance with the present invention, the antagonist compounds can be admistered enterally or topically as an antidote to vitamin A, vitamin A precursors, or antidote to retinoid toxicity resulting from overdose or prolonged exposure, after intake of the causative factor (vitamin A precursor or other retinoid) has been discontinued. Alternatively, the antagonist compounds are coadministered with retinoid drugs in accordance with the invention, in situations where the retinoid provides a therapeutic benefit, and where the coadministered antagonist alleviates or eliminates one or more undesired side effects of the retinoid. For this type of application the antagonist may be administered in a site-specific manner, for example as a topically applied cream or lotion while the coadministered retinoid may be given enterally.

For therapeutic applications in accordance with the present invention the antagonist compounds are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For example preparation of topical formulations are well described in *Remington's Pharmaceutical Science*, Edition 17, Mack Publishing Company, Easton, Pa. For topical application, the antagonist compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the antagonist compound will be prepared as a solution or suspension capable of being administered by injection. In certain cases, it may be useful to formulate the antagonist compounds by injection. In certain cases, it may be useful to formulate the antagonist compounds in suppository form or as extended release formulation for deposit under the skin or intramuscular injection.

The antagonist compounds will be administered in a therapeutically effective dose in accordance with the invention. A therapeutic concentration will be that concentration which effects reduction of the particular condition (such as toxicity due to retinoid or vitamin A exposure, or side effect of retinoid drug) or retards its expansion. It should be understood that when coadministering the antagonist compounds to block retinoid-induced toxicity or side effects in accordance with the invention, the antagonist compounds are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of antagonist compound per mililiter of formulation will constitute a therapeutically effective concentration for topical application. If administered systemically, an amount between 0.01 and 5 mg per kg per day of body weight would be expected to effect a therapeutic result.

The basis of the utility of RAR antagonists for the prevention or treatment of RAR agonist-induced toxicity is competitive inhibition of the activation of RAR receptors by RAR agonists. The main distinction between these two applications of RAR antagonists is the presence or absence of preexisting retinoid toxicity. Most of the examples immediately described below relate to the use of retinoids to prevent retinoid toxicity, but the general methods described herein are applicable to the treatment of preexisting retinoid toxicity as well.

DESCRIPTION OF EXPERIMENTS DEMONSTRATING THE USE OF RAR ANTAGONISTS TO PREVENT OR TREAT RETINOID TOXICITY AND/OR SIDE EFFECTS OF RETINOID DRUGS

EXAMPLE 1

Figure 2A:
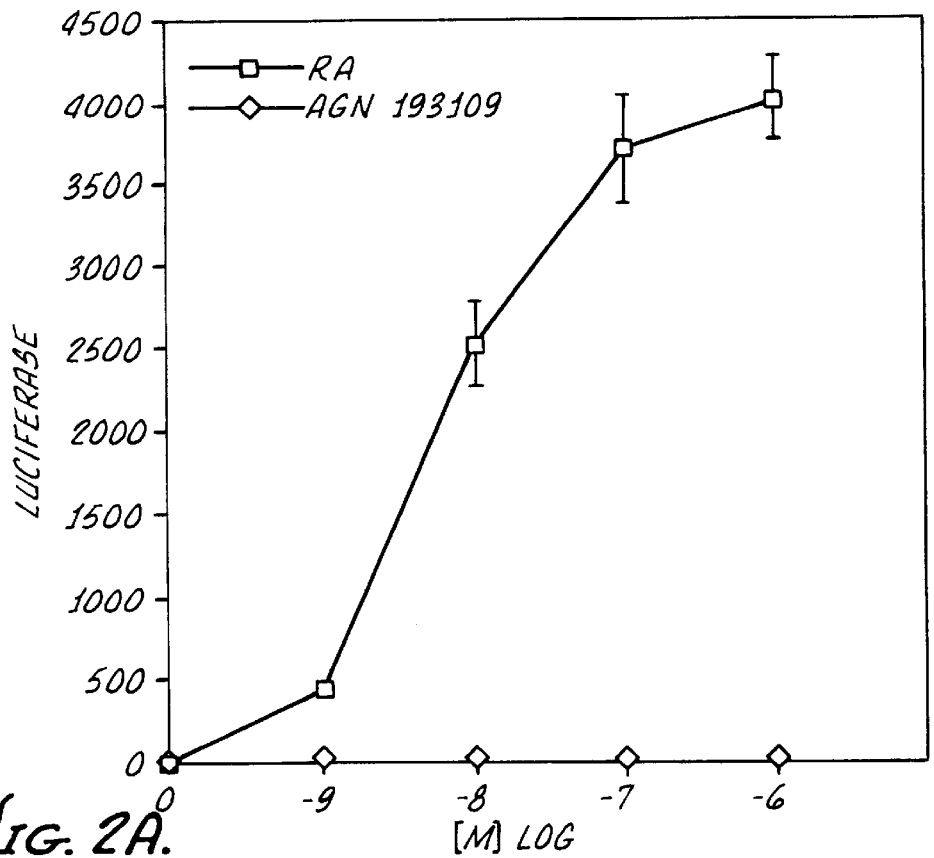
FIGS. 2A–2F are a series of line graphs showing that AGN 193109 inhibited ATRA-dependent transactivation at the RARs.
Figure 2B:
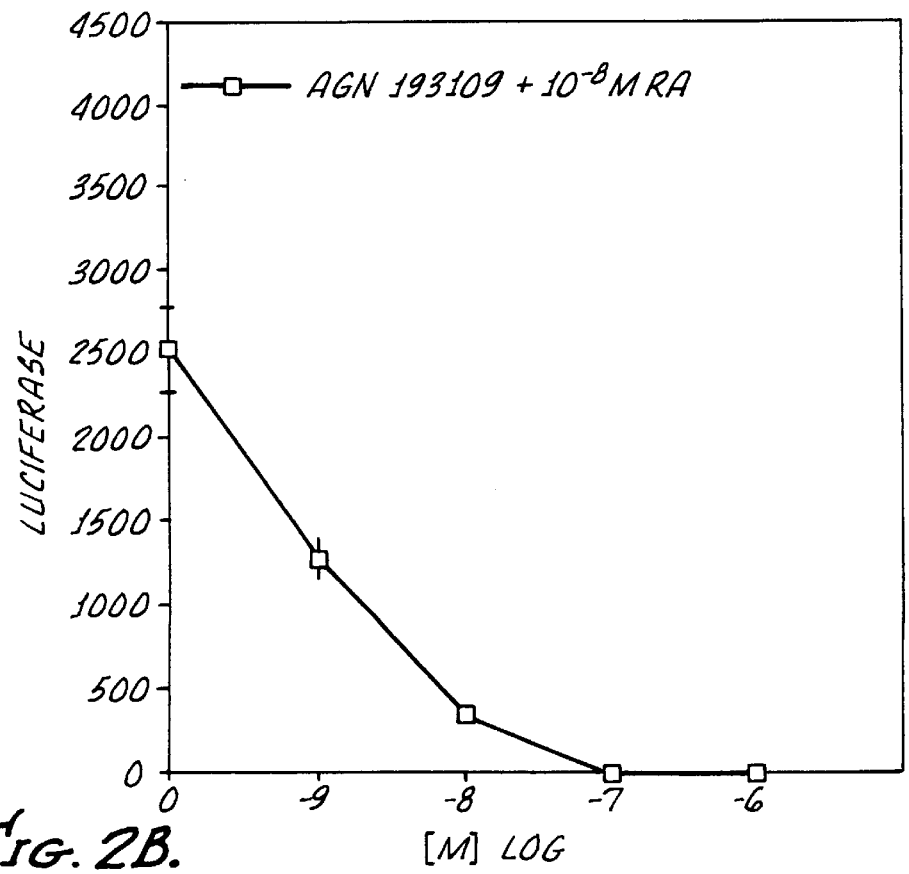
Figure 2C:
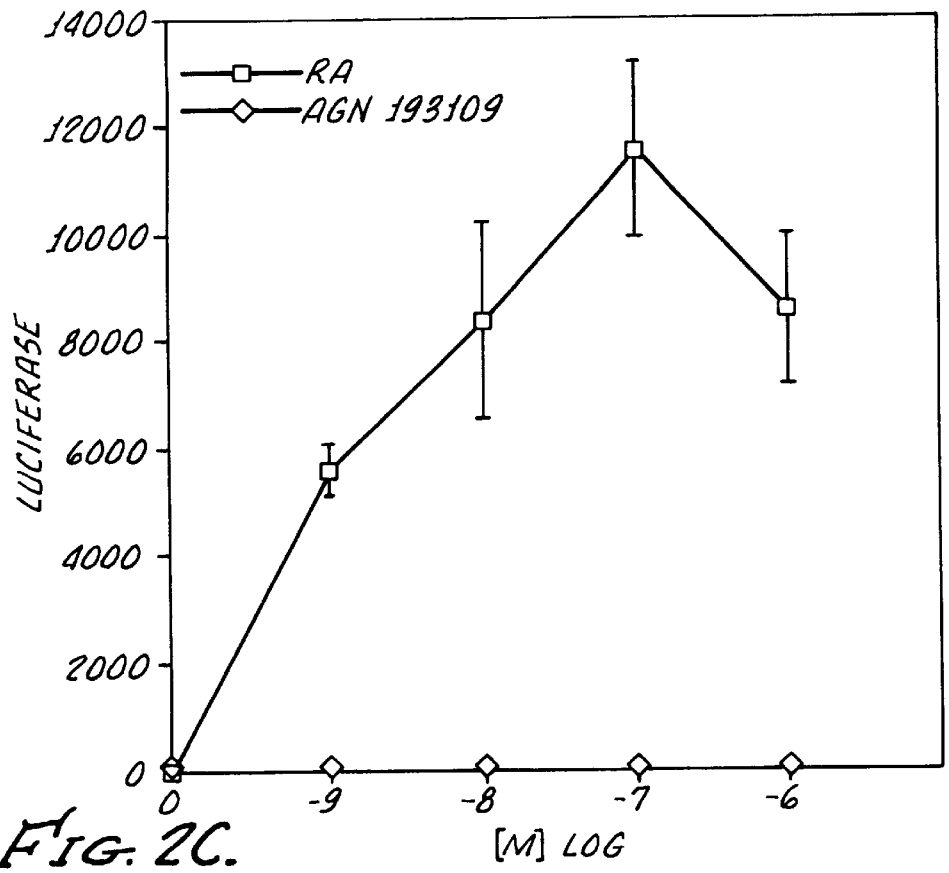
Figure 2D:
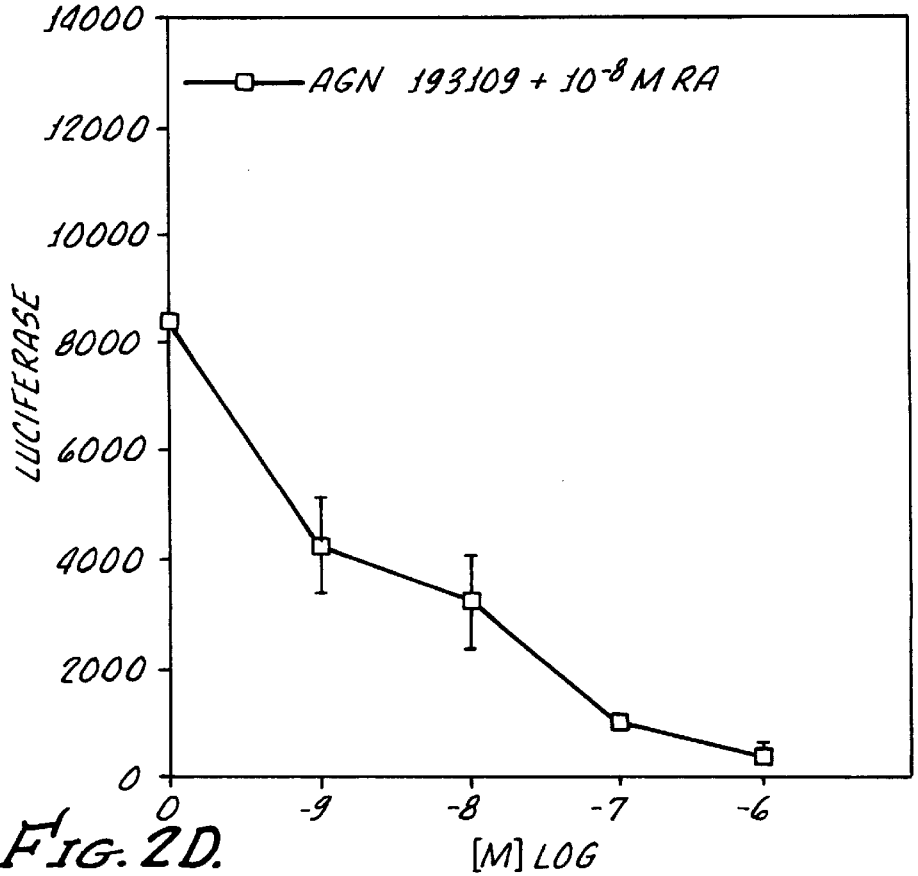
Figure 2E:
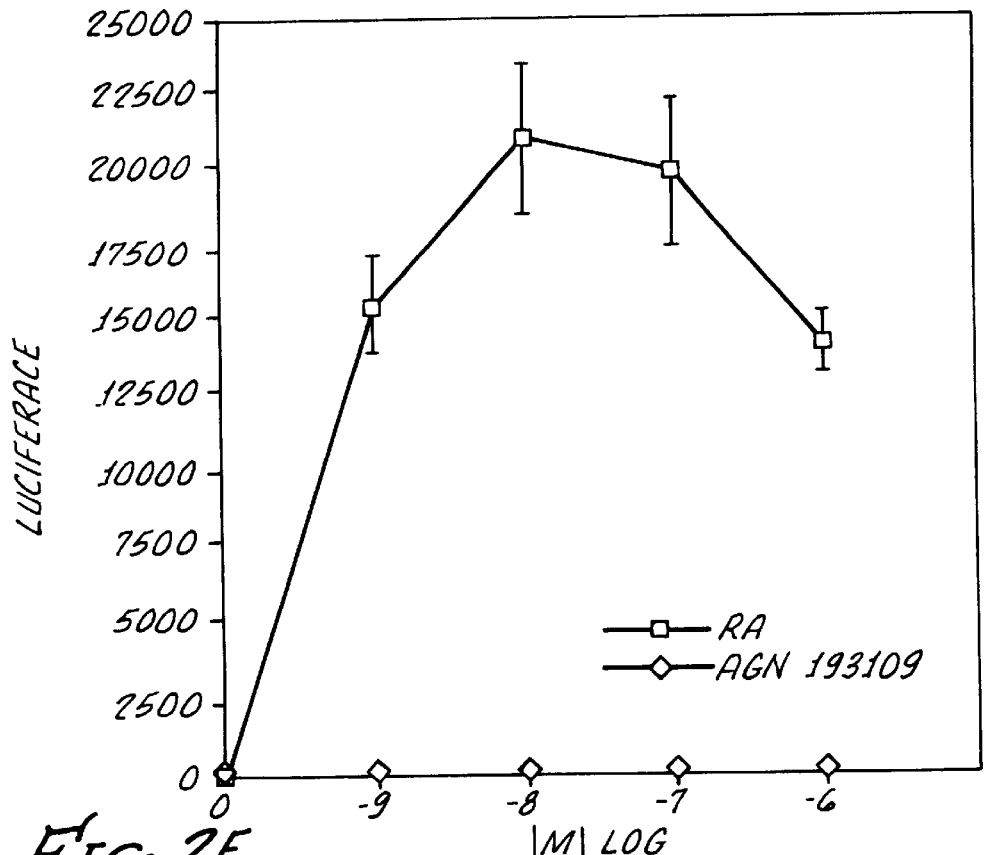
Figure 2F:
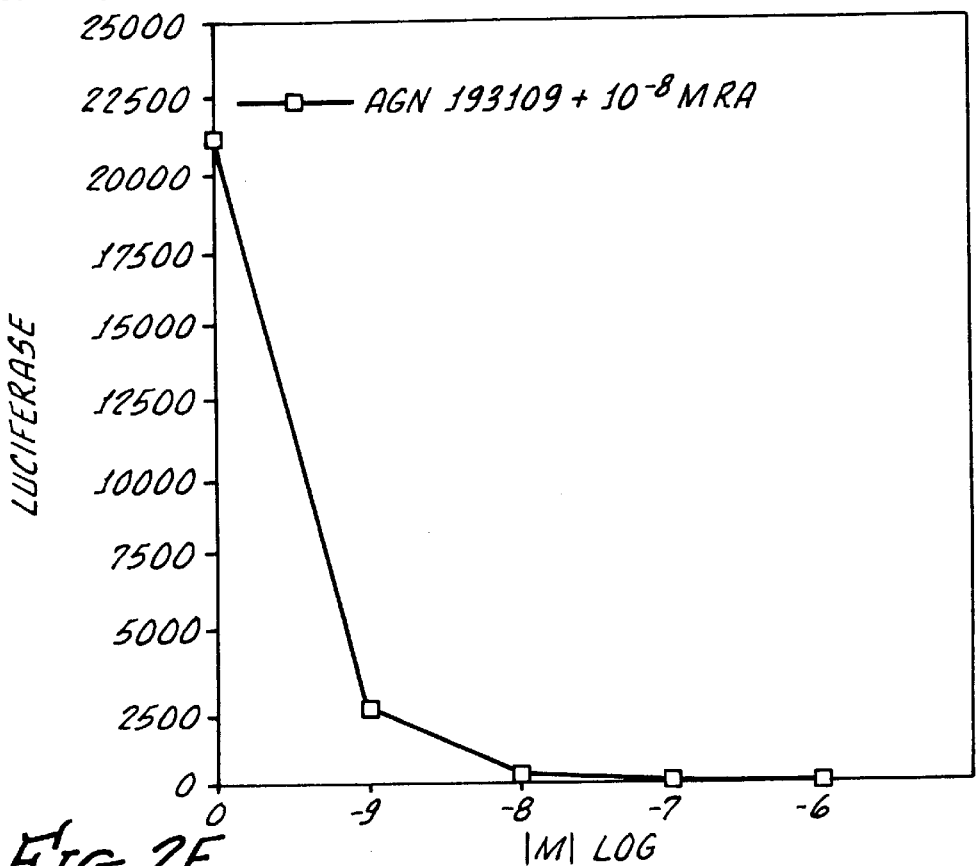

Skin Irritation Induced by Topically Applied Agonist is Treated with Topically Applied Antagonist The compound 4-[(E)-2-(5,6,7,8-tetrahydro-5,5,8,8-tetramethylnaphthalen-2-yl)propen-1-yl]benzoic acid, designated AGN 191183, is known in the prior art as a potent RAR agonist (see for example the descriptive portion and FIG. 2b of U.S. Pat. No. 5,324,840). (The "AGN" number is an arbitrarily designated reference number utilized by the corporate assignee of the present invention for identification of compounds.)

4-[(5,6-dihydro-5,5-dimethyl-8-(phenyl)-2-naphthalenyl) ethynyl]benzoic acid (AGN 192869, also designated Compound 60a) is a compound the preparation of which is described below. This compound is an RAR antagonist.

Skin irritation induced by an RAR agonist, AGN 191183, administered topically, can be blocked by an RAR antagonist, AGN 192869, also administered topically in hairless mice.

More particularly skin irritation was measured on a semi-quantitative scale by the daily subjective evaluation of skin flaking and abrasions. A single number, the topical irritation score, summarizes the skin irritation induced in an animal during the course of an experiment. The topical irritation score is calculated as follows. The topical irritation score is the algebraic sum of a composite flaking score and a composite abrasion score. The composite scores range from 0–9 and 0–8 for flaking and abrasions, respectively, and take into account the maximum severity, the time of onset, and the average severity of the flaking and abrasions observed.

The severity of flaking is scored on a 5-point scale and the severity of abrasions is scored on a 4-point scale, with higher scores reflecting greater severity. The maximum severity component of the composite scores would be the highest daily severity score assigned to a given animal during the course of observation.

For the time of onset component of the composite score, a score ranging from 0 to 4 is assigned as follows:

TABLE 6

| Time to Appearance of Flaking or Abrasions of Severity 2 or Greater | |
|---|---|
| (days) | Time of Onset Score |
| 8 | 0 |
| 6–7 | 1 |
| 5 | 2 |
| 3–4 | 3 |
| 1–2 | 4 |

The average severity component of the composite score is the sum of the daily flaking or abrasion scores divided by the number of observation days. The first day of treatment is not counted, since the drug compound has not had an opportunity to take effect at the time of first treatment.

To calculate the composite flaking and abrasion scores, the average severity and time of onset scores are summed and divided by 2. The result is added to the maximal severity score. The composite flaking and abrasion scores are then summed to give the overall topical irritation score. Each animal receives a topical irritation score, and the values are expressed as the mean ±SD of the individual scores of a group of animals. Values are rounded to the nearest integer.

Female hairless mice [Crl:SKH1-hrBR] (8–12 weeks old, n=6) were treated topically for 5 consecutive days with acetone, AGN 191183, AGN 192869, or some combination of AGN 192869 and 191183. Doses of the respective compounds are given in Table 7. Treatments are applied to the dorsal skin in a total volume of 4 ml/kg (~0.1 ml). Mice were observed daily and scored for flaking and abrasions up to and including 3 days after the last treatment, i.e., day 8.

TABLE 7

Experimental Design and Results, Example 1

| Group | Dose AGN 191183 (mg/kg/d) | Dose AGN 192869 (mg/kg/d) | Molar Ratio (192869: (191183 | Topical Irritation Score) |
|---|---|---|---|---|
| A | 0 | 0 | — | 0 ± 0 |
| B | 0.025 | 0 | — | 8 ± 2 |
| C | 0.025 | 0.06 | 2:1 | 5 ± 2 |
| D | 0.025 | 0.30 | 10:1 | 2 ± 1 |
| E | 0.025 | 1.5 | 50:1 | 1 ± 0 |
| F | 0 | 1.5 | — | 0 ± 0 |

The topical irritation scores for Example 1 are given in Table 7. Neither acetone (vehicle) nor AGN 192869 (antagonist) at a dose of 1.5 mg/kg/d (group F) caused observable topical irritation. AGN 191183, the RAR agonist, caused modest topical irritation at a dose of 0.025 mg/kg/d. However, AGN 191183-induced topical irritation was inhibited in a dose-dependent fashion by AGN 192869, with nearly complete abrogation of irritation in the presence of a 50-fold molar excess of AGN 192869. This demonstrates that a topical RAR antagonist blocks skin irritation caused by a topical RAR agonist. Complete blockade of RAR agonist-induced skin irritation can be achieved with lower molar ratios of antagonist to agonist when the RAR antagonists is more potent, such as the compound 4-[(5,6-dihydro-5,5-dimethyl-8-(4-methylphenyl)-2-naphthalenyl)ethynyl] benzoic acid (AGN 193109, also designated in this application as Compound 60.)

EXAMPLE 2

Skin Irritation Induced by Orally Applied Agonist is Blocked with Topically Applied Antagonist The potent RAR agonist AGN 191183 (4-[(E)-2-(5,6,7,8-tetrahydro-5,5,8,8-tetramethylnaphthalen-2-yl)propen-1-yl]benzoic acid) and the potent RAR antagonist 4-[(5,6-dihydro-5,5-dimethyl-8-(4-methylphenyl)-2-naphthalenyl) ethynyl]benzoic acid (AGN 193109, Compound 60) were used in this example and body weight of the experimental animals (mice) was used as a marker of systemic RAR agonist exposure.

Groups of female hairless mice (8–12 weeks old, n=6) were treated by intragastric intubation with corn oil or AGN 191183 (0.26 mg/kg) suspended in corn oil (5 ml/kg). Mice were simultaneously treated topically on the dorsal skin with vehicle (97.6% acetone/2.4% dimethylsulfoxide) or solutions of AGN 193109 in vehicle (6 ml/kg). Specific doses for the different treatment groups are give in Table 8. Treatments were administered daily for 4 consecutive days. Mice were weighed and graded for topical irritation daily as described in Example 1 up to and including 1 day after the last treatment. Percent body weight change is calculated by subtracting final body weight (day 5) from initial body weight (day 1), dividing by initial body weight, and multiplying by 100%. Topical irritation scores are calculated as described in Example 1.

Topical irritation scores and weight loss for the different groups are given in Table 8. Combined treatment with the topical and oral vehicles, i.e., acetone and corn oil, respectively, caused no topical irritation or weight loss. Similarly, combined treatment with the oral vehicle and the topical antagonist AGN 193109 resulted in no topical irritation or weight loss. Oral AGN 191183 by itself induced substantial weight loss and skin irritation. AGN 191183-induced skin irritation was substantially reduced when combined with the lower dose of AGN 193109 and completely blocked at the higher dose of AGN 193109. AGN 191183-induced weight loss was also blocked in a dose-related fashion by topical AGN 193109, but the blockade was not complete. Thus, topical AGN 193109 preferentially blocked the dermal toxicity of AGN 191183. Presumably, low levels of AGN 193109 were absorbed systemically and thus partially blocked the weight loss induced by AGN 191183. However, such absorption would likely be even less in a species with less permeable skin, such as humans. Alternatively, the weight loss inhibition by AGN 193109 could be due to amelioration of the AGN 191183 induced skin irritation.

TABLE 5

Experimental Design and Results, Example 2

| Group | Dose of Topical AGN 193109 (mg/kg/d) | Dose of Oral AGN 191183 (mg/kg/d) | % Weight Gain or (Loss) | Topical Irritation Score) |
|---|---|---|---|---|
| A | 0 | 0 | 1 ± 2 | 0 ± 0 |
| B | 0 | 0.26 | (21 ± 6) | 8 ± 1 |
| C | 0.12 | 0.26 | (9 ± 5) | 1 ± 1 |
| D | 0.47 | 0.26 | (3 ± 5) | 0 ± 1 |
| E | 0.47 | 0 | 3 ± 3 | 0 ± 0 |

Thus, Example 2 demonstrates that RAR antagonists administered topically can be used to block preferentially the skin irritation induced by an RAR agonist administered orally.

EXAMPLE 3

Topically Applied Antagonist Accelarates Recovery from Prexisting Retinoid Toxicity In this example, weight loss is induced by topical treatment with the RAR agonist AGN 191183 and then the test animals are topically treated with either vehicle or the RAR antagonist AGN 193109.

Female hairless mice (8–12 weeks old, n=5) were treated topically with AGN 191183 (0.13 mg/kg/d) in vehicle (97.6% acetone/2.4% DMSO, 4 ml/kg) daily for 2 days. Groups of these same mice (n=5) were then treated topically either with vehicle or AGN 193109 in vehicle (4 ml/kg) daily for 3 consecutive days beginning on day 3. Mice were weighed on days 1–5 and on day 8. Body weights are expressed as the mean ±SD. Means were compared statistically using an unpaired, two-tailed t-test. Differences were considered significant at $P<0.05$.

TABLE 9

Results, Example 3

| Treatment (days 3–5) | Body Weight (g) | | | | | |
|---|---|---|---|---|---|---|
| | DAY 1 | DAY 2 | DAY 3 | DAY 4 | DAY 5 | DAY 8 |
| vehicle | 24.6 ± 1.5 | 23.9 ± 1.2 | 21.4 ± 1.2 | 20.3 ± 1.7 | 21.0 ± 1.4 | 24.7 ± 1.0 |
| AGN 193109 | 23.9 ± 1.0 | 23.5 ± 1.2 | 21.4 ± 0.6 | 22.2 ± 0.7 | 22.8 ± 0.8 | 25.0 ± 1.1 |

The time course of body weights in Example 3 are given in Table 9. Body weights of both groups of mice were lowered in parallel on days 2 and as a result of AGN 191183 treatment on days 1 and 2. Body weights in the two groups were not significantly different on days 1, 2, or 3. However, AGN 193109 treatment significantly increased body weight relative to vehicle treatment on days 4 and 5. These data indicated that recovery from AGN 191183-induced body weight loss was accelerated by subsequent treatment with AGN 193109. Body weights were not significantly different between the two groups of mice on day 8, indicating that full recovery was achievable in both groups given sufficient time. Thus, RAR antagonists are effective in alleviating RAR agonist-induced toxicity even if RAR agonist-induced toxicity precedes RAR antagonist treatment, i.e., in the RAR agonist poisoning scenario.

EXAMPLE 4

Orally Applied Antagonist Blocks Hypertriglyceridemia Incuded by Orally Coadministered Retinoid Agonist 5-[(E)-2-(5,6,7,8-tetrahydro-3,5,5,8,8-pentamethylnaphthalen-2-yl)propen-1-yl]-2-thiophencarboxylic acid, is a known RAR/RXR panagonist (see U.S. Pat. No. 5,324,840 column 32) and is designated AGN 191659. This compound was used orally to induce acute hypertriglyceridemia in rats, and AGN 193109 Compound 60 was coadministered orally to block the AGN 191659-induced hypertriglyceridemia.

Male Fischer rats (6–7 weeks old, n=5) were treated by intragastric intubation with corn oil (vehicle), AGN 191659, AGN 193109 or a combination of AGN 191659 and AGN 193109. AGN 191659 and AGN 193109 were given as fine suspensions in corn oil. The experimental design, including doses, is given in Table 10.

Blood was withdrawn from the inferior vena cava under carbon dioxide narcosis. Serum was separated from blood by low speed centrifugation. Total serum triglycerides (triglycerides plus glycerol) were measured with a standard spectrophotometric endpoint assay available commercially as a kit and adapted to a 96-well plate format. Serum triglyceride levels are expressed as the mean ±SD. Means were compared statistically by one-way analysis of variance followed by Dunnett's test if significant differences were found. Differences were considered significant at $P<0.05$.

As shown in Table 10, AGN 191659 by itself caused significant elevation of serum triglycerides relative to vehicle treatment. AGN 193109 by itself did not significantly increase serum triglycerides. Importantly, the combination of AGN 193109 and AGN 191659 at molar ratios of 1:1 and 5:1 reduced serum triglycerides to levels that were not significantly different from control.

TABLE 10

Experimental Design and Results, Example 4

| Group | Treatment (dose) | Serum Triglycerides (mg/dl) |
|---|---|---|
| A | vehicle | 55.0 ± 3.1 |
| B | AGN 193109 (19.6 mg/kg) | 52.4 ± 6.3 |
| C | AGN 191659 (3.7 mg/kg) | 122.5 ± 27.6 |
| D | AGN 193109 (3.9 mg/kg) + AGN 191659 (3.7 mg/kg) | 55.7 ± 14.7 |
| E | AGN 193109 (19.6 mg/kg) + AGN 191659 (3.7 mg/kg) | 72.7 ± 8.9 |

Example 4 demonstrates that an RAR antagonist can be used to block hypertriglyceridemia induced by a coadministered retinoid.

EXAMPLE 5

Parenterally Applied Antagonist Blocks Bone Toxicity Incuded by Parenterally Coadministered Retinoid Agonist Example 5 demonstrates that RAR antagonists can block bone toxicity induced by an RAR agonist. In this example, AGN 193109 is used to block premature epiphyseal plate closure caused by a coadministered RAR agonist, AGN 191183, in guinea pigs.

Groups of male Hartley guinea pigs (~3 weeks old, n=4) were implanted intraperitoneally with osmotic pumps containing vehicle (20% dimethylsulfoxide/80% polyethylene glycol-300), AGN 191183 (0.06 mg/ml), or AGN 191183 (0.06 mg/ml) in combination with AGN 193109 (0.34 mg/ml). The osmotic pumps are designed by the manufacturer to deliver ~5 µl of solution per hour continuously for 14 days.

The animals were euthanized by carbon dioxide asphyxiation 14 days after implantation. The left tibia was was removed and placed in 10% buffered formalin. The tibias were decalcified by exposure to a formic acid/formalin solution for 3–4 days, and paraffin sections were prepared. Sections were stained with hematoxylin and eosin by standard methods. The proximal tibial epiphyseal plate was examined and scored as closed or not closed. Epiphyseal plate closure is defined for this purpose as any interruption of the continuity of the epiphyseal growth plate cartilage, i.e., replacement by bone and/or fibroblastic tissue.

None of the four vehicle-treated guinea pigs showed epiphyseal plate closure by the end of the experiment. This was expected, since the proximal epiphyseal plate of guinea pig tibia does not normally close until the animals are at least 10 months old. All four of the AGN 191183-treated guinea pigs showed partial or complete epiphyseal plate closure. However, none of the guinea pigs treated with the combination of AGN 191183 and AGN 193109 demonstrated epiphyseal plate closure. Thus, AGN 193109 at a 5-fold molar excess completely blocked AGN 191183-induced bone toxicity when these compounds were coadministered parenterally.

RAR Antagonist Compounds

The compounds 4-[(5,6-dihydro-5,5-dimethyl-8-(4-methylphenyl)-2-naphthalenyl)ethynyl]benzoic acid (AGN 193109, Compound 60) and 4-[(5,6-dihydro-5,5-dimethyl-8-(phenyl)-2-naphthalenyl)ethynyl]benzoic acid (AGN 192869, Compound 60a) are examples of RAR antagonists which were used in the above-described animal tests for blocking RAR receptors in accordance with the present invention. The compounds of the following formula (Formula 1) serve as further and general examples for additional RAR antagonist compounds for use in accordance with the present invention.

Formula 1

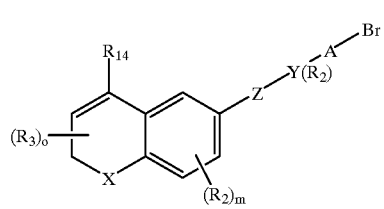

In Formula 1, X is S, O, NR' where R' is H or alkyl of 1 to 6 carbons, or

X is $[C(R_1)_2]_n$ where $R_1$ is H or allyl of 1 to 6 carbons, and n is an integer between 0 or 1;

$R_2$ is hydrogen, lower alkyl of 1 to 6 carbons, F, $CF_3$, fluor substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0–3;

o is an integer having the value of 0–3;

Z is —C≡C—,
—N=N—,
—N=CR$_1$—,
—CR$_1$=N,
—(CR$_1$=CR$_1$)$_{n'}$— where n' is an integer having the value 0–5,
—CO—NR$_1$—,
—CS—NR$_1$—,
—NR$_1$—CO,
—NR$_1$—CS,
—COO—,
—OCO—;
—CSO—;
—OCS—;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups, or
when Z is —(CR$_1$=CR$_1$)$_{n'}$— and n' is 3, 4 or 5 then Y represents a direct valence bond between said (CR$_2$=CR$_2$)$_{n'}$ group and B;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$, —COR$_7$, CR$_7$(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or trimethylsilylalkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons, and R$_{14}$ is (R$_{15}$)$_r$-phenyl, (R$_{15}$)$_r$-naphthyl, or (R$_{15}$)$_r$-heteroaryl where the heteroaryl group has 1 to 3 heteroatoms selected from the group consisting of O, S and N, r is an integer having the values of 0–5, and R$_{15}$ is independently H, F, Cl, Br, I, NO$_2$, N(R$_8$)$_2$, N(R$_8$)COR$_8$, NR$_8$CON(R$_8$)$_2$, OH, OCOR$_8$, OR$_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons.

Synthetic Methods—Aryl Substituted Compounds

The exemplary RAR antagonist compounds of Formula 1 can be made by the synthetic chemical pathways illustrated here. The synthetic chemist will readily appreciate that the conditions set out here are specific embodiments which can be generalized to any and all of the compounds represented by Formula 1.

Reaction Scheme 1

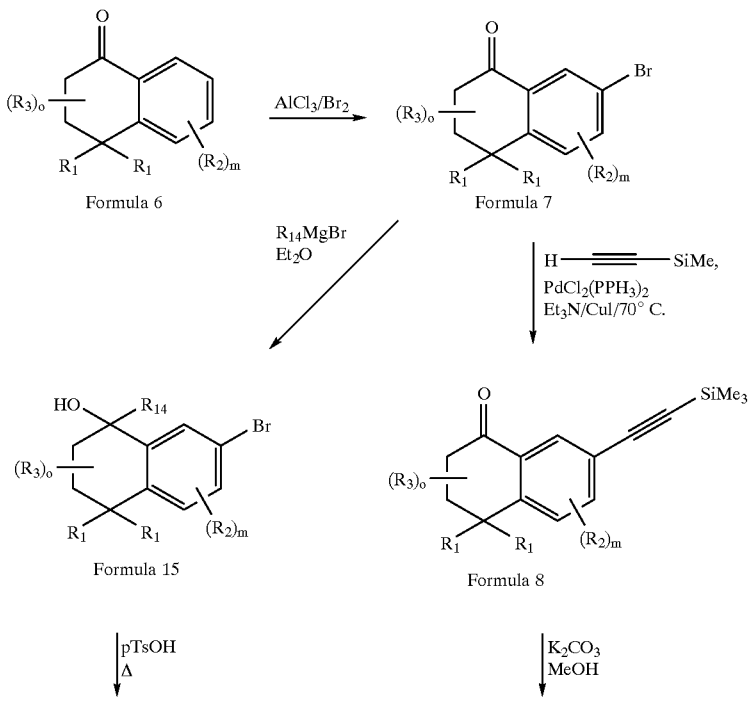

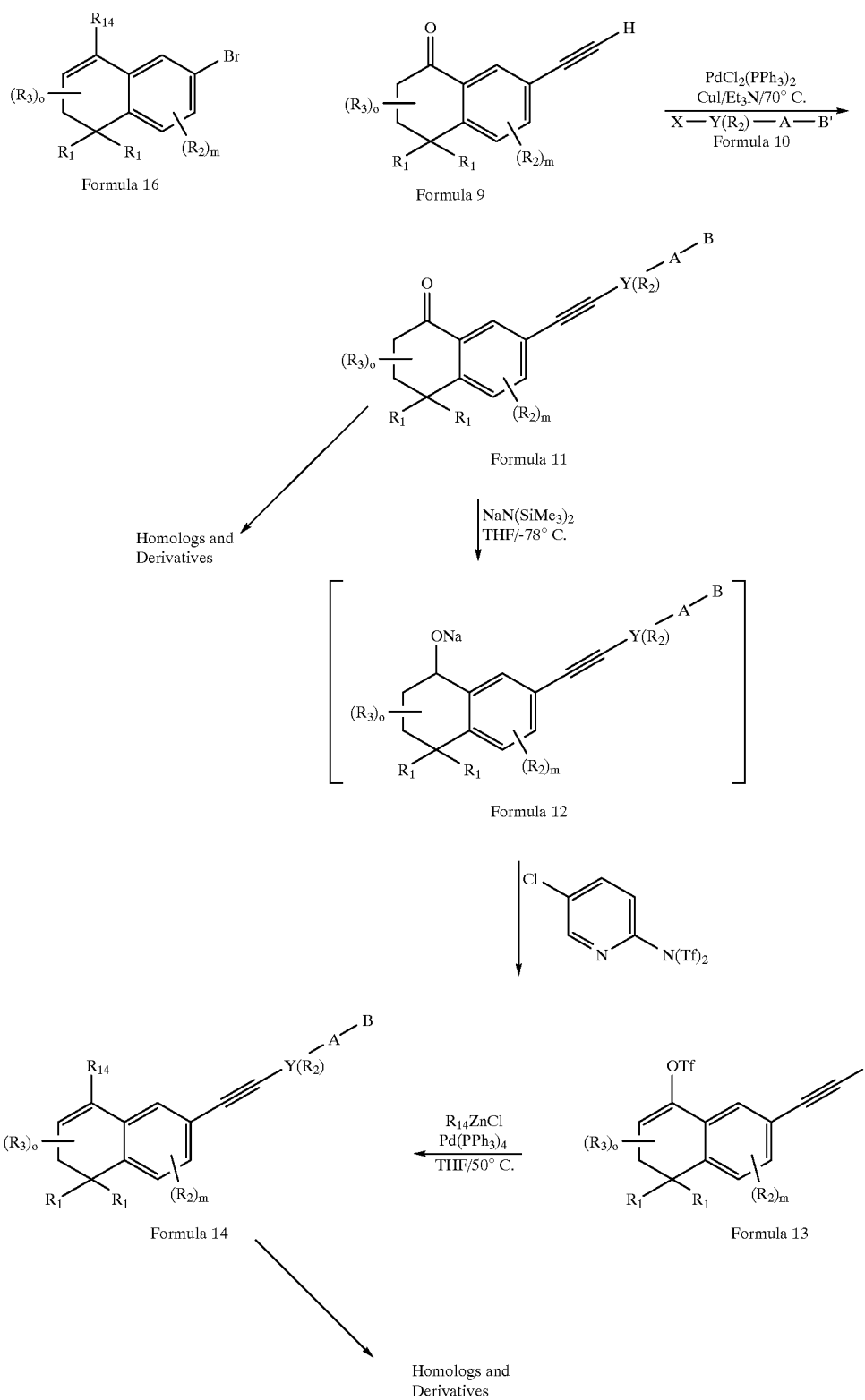

Reaction Scheme 1 illustrates the synthesis of compounds of Formula 1 where the Z group is an ethynyl function (—C≡C—) and X is [C(R$_1$)$_2$]$_n$ where n is 1. In other words, Reaction Scheme 1 illustrates the synthesis of ethynyl substituted dihydronaphthalene derivatives of the present invention. In accordance with this scheme, a tetrahydronaphtalene-1-one compound of Formula 6 is brominated to provide the bromo derivative of Formula 7. The compounds of Formula 6 already carry the desired $R_1$, $R_2$ and $R_3$ substituents, as these are defined above in connection with Formula 1. A preferred example of a compound of Formula 6 is 3,4-dihydro-4,4-dimethyl-1(2H)-naphthalenone, which is described in the chemical literature (Arnold et al. *J. Am. Chem. Soc.* 69: 2322–2325 (1947)). A presently preferred route for the synthesis of this compound from 1-bromo-3-phenylpropane is also described in the experimental section of the present application.

The compounds of Formula 7 are then reacted with (trimethylsilyl)acetylene to provide the (trimethylsilyl) ethynyl-substituted 3,4-dihydro-naphthalen-1(2H)-one compounds of Formula 8. The reaction with (trimethylsilyl) acetylene is typically conducted under heat (approximately 100° C.) in the presence of cuprous iodide, a suitable catalyst, typically having the formula $Pd(PPh_3)_2Cl_2$, an acid acceptor (such as triethylamine) under an inert gas (argon) atmosphere. Typical reaction time is approximately 24 hours. The (trimethylsilyl)ethynyl-substituted 3,4-dihydro-naphthalen-1(2H)one compounds of Formula 8 are then reacted with base (potassium hydroxide or potassium carbonate) in an alcoholic solvent, such as methanol, to provide the ethynyl substituted 3,4-dihydro-1-naphthalen-1 (2H)ones of Formula 9. Compounds of Formula 9 are then coupled with the aromatic or heteroaromatic reagent $X_1$—Y($R_2$)—A—B' (Formula 10) in the presence of cuprous iodide, a suitable catalyst, typically $Pd(PPh_3)_2Cl_2$, an acid acceptor, such as triethylamine, under inert gas (argon) atmosphere. Alternatively, a zinc salt (or other suitable metal salt) of the compounds of Formula 9 can be coupled with the reagents of Formula 10 in the presence of $Pd(PPh_3)_4$ or similar complex. Typically, the coupling reaction with the reagent $X_1$—Y($R_2$)A—B' (Formula 10) is conducted at room or moderately elevated temperature. Generally speaking, coupling between an ethynylaryl derivative or its zinc salt and a halogen substituted aryl or heteroaryl compound, such as the reagent of Formula 10, is described in U.S. Pat. No. 5,264,456, the specification of which is expressly incorporated herein by reference. The compounds of Formula 11 are precursors to exemplary compounds of the present invention, or derivatives thereof protected in the B' group, from which the protecting group can be readily removed by reactions well known in the art. The compounds of Formula 11 can also be converted into further precursors to the exemplary compounds by such reactions and transformations which are well known in the art. Such reactions are indicated in Reaction Scheme 1 by conversion into "homologs and derivatives". One such conversion employed for the synthesis of several exemplary compounds is saponification of an ester group (when B or B' is an ester) to provide the free carboxylic acid or its salt.

The halogen substituted aryl or heteroaryl compounds of Formula 10 can, generally speaking, be obtained by reactions well known in the art. An example of such compound is ethyl 4-iodobenzoate which is obtainable, for example, by esterification of 4-iodobenzoic acid. Another example is ethyl 6-iodonicotinoate which can be obtained by conducting a halogen exchange reaction on 6-chloronicotinic acid, followed by esterification. Even more generally speaking, regarding derivatization of compounds of Formula 11 and/or the synthesis of aryl and heteroaryl compounds of Formula 10 which can thereafter be reacted with compounds of Formula 9, the following well known and published general principles and synthetic methodology can be employed.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, *Advanced Organic Chemistry*, 2nd Edition, McGraw-Hill Book Company, p. 810). Alcohols, aldehydes and ketones all may be protected by forming respectively, ethers and esters, acetals or ketals by known methods such as those described in McOmie, Plenum Publishing Press, 1973 and Protecting Groups, Ed. Greene, John Wiley & Sons, 1981.

To increase the value of n in the compounds of Formula 10 before affecting the coupling reaction of Reaction Scheme 1 (where such compounds corresponding to Formula 10 are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

Compounds of Formula 10, (or other intermediates or exemplary compounds) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of Formula 10 (or other intermediates or exemplary compounds) where the A group has a triple (acetylenic) bond can be made by reaction of a corresponding aromatic methyl ketone with strong base, such as lithium diisopropylamide, reaction with diethyl chlorophosphate and subsequent addition of lithium diisopropylamide.

The acids and salts derived from compounds of Formula 11 (or other intermediates or exemplary compounds) are readily obtainable from the corresponding esters. Basic saponification with an alkali metal base will provide the acid. For example, an ester of Formula 11 (or other intermediates or exemplary compounds) may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine.

Alcohols are made by converting the corresponding acids to the acid chloride with thionyl chloride or other means (J. March, *Advanced Organic Chemistry*, 2nd Edition, McGraw-Hill Book Company), then reducing the acid chloride with sodium borohydride (March, Ibid, p. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, p. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Let.* 399, 1979), or dimethyl sulfoxide/oxalyl chloride in methylene chloride (Omura, K, Swern, D., *Tetrahedron* 34: 1651(1978)).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p. 810.

Compounds of Formula 10 (or other intermediates, or exemplary compounds) where B is H can be prepared from the corresponding halogenated aromatic or hetero aromatic compounds, preferably where the halogen is I.

Referring back again to Reaction Scheme 1, the compounds of Formula 11 are reacted with sodium bis (trimethylsilyl)amide and 2-[N,N-bis(trifluoromethylsulfonyl)amino]-5-chloropyridine in an inert ether type solvent, such as tetrahydrofuran, at low temperatures (−78° C. and 0° C.). This is shown in Reaction Scheme 1 where the usually unisolated sodium salt intermediate is shown in brackets as Formula 12. The reaction results in the trifluoromethylsulfonyloxy derivatives represented in Formula 13. (Tf=SO$_2$CF$_3$). The compounds of Formula 13 are then converted to the exemplary compounds of the invention, shown in Formula 14, by reaction with an organometal derivative derived from the aryl or heteroaryl compound R$_{14}$H, such that the formula of the organometal derivative is R$_{14}$Met (Met stands for monovalent metal), preferably R$_{14}$Li. (R$_{14}$ is defined as in connection with Formula 1.) The reaction with the organometal derivative, preferably lithium derivative of the formula R$_{14}$Li is usually conducted in an inert ether type solvent (such as tetrahydrofuran) in the presence of zinc chloride (ZnCl$_2$) and tetrakis(triphenylphosphine)palladium(0) (Pd(PPh$_3$)$_4$). The organolithium reagent R$_{14}$Li, if not commercially available, can be prepared from the compound R$_{14}$H (or its halogen derivative R$_{14}$—X$_1$ where X$_1$ is halogen) in an ether type solvent in accordance with known practice in the art. The temperature range for the reaction between the reagent R$_{14}$Li and the compounds of Formula 13 is, generally speaking in the range of approximately −78° C. to 50° C. The compounds of Formula 14 can be converted into further homologs and derivatives in accordance with the reactions discussed above.

The intermediate 7-bromo-tetrahydronaphthalene-1-one compounds of Formula 7 shown in Reaction Scheme 1 can also be converted with a Grignard reagent of the formula R$_{14}$MgBr (R$_{14}$ is defined as in connection with Formula 1) to yield the tertiary alcohol of Formula 15. The tertiary alcohol is dehydrated by treatment with acid to provide the 3,4-dihydro-7-bromonaphthalene derivatives of Formula 16, which serve as intermediates for the synthesis of additional compounds of the present invention (see Reaction Schemes 6, 7, and 8).

Reaction Scheme 2

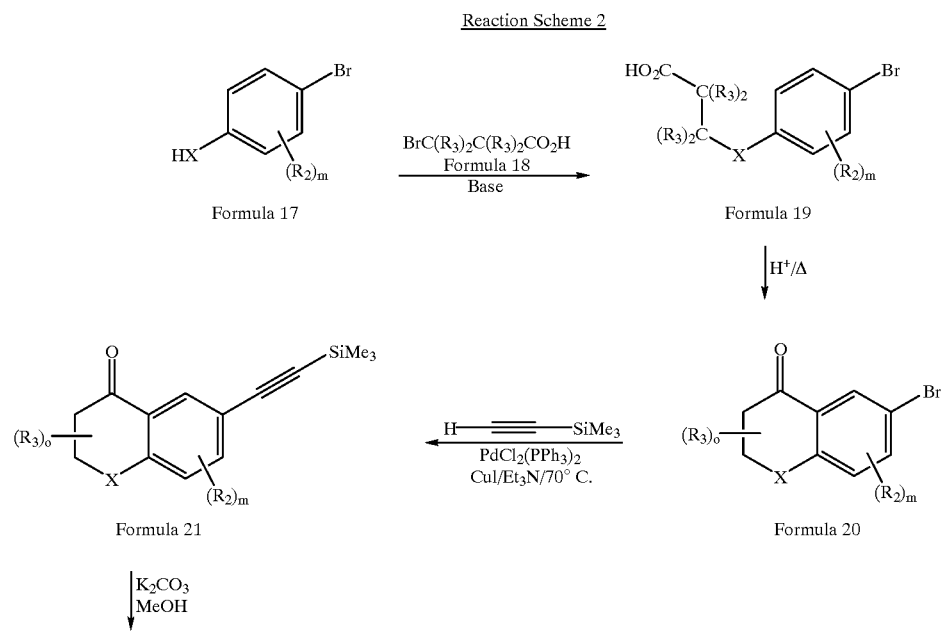

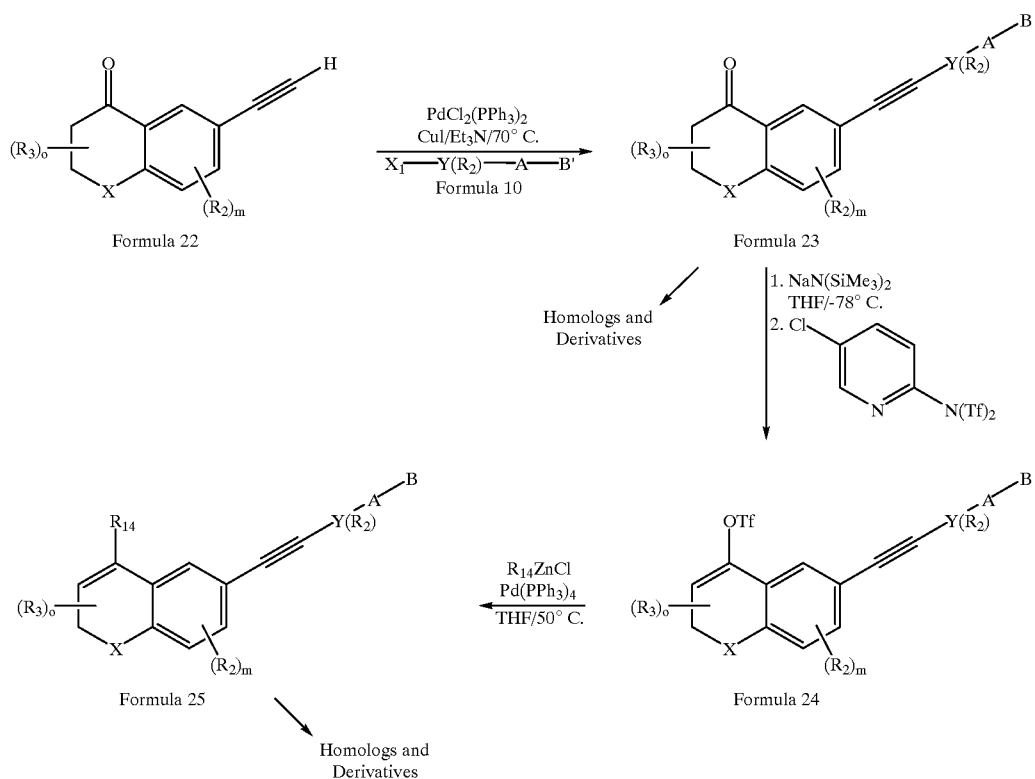

Formula 22

Formula 23

Formula 25

Formula 24

Referring now to Reaction Scheme 2 a synthetic route to those compounds is disclosed where with reference to Formula 1 X is S, O or NR' and the Z group is an ethynyl function (—C≡C—). Starting material for this sequence of the reaction is a bromophenol, bromothiophenol or bromoaniline of the structure shown in Formula 17. For the sake of simplifying the present specification, in the ensuing description X can be considered primarily sulfur as for the preparation of benzothiopyran derivatives. It should be kept in mind, however, that the herein described scheme is also suitable, with such modifications which will be readily apparent to those skilled in the art, for the preparation of benzopyran (X=O) and dihydroquinoline (X=NR') compounds of the present invention. Thus, the compound of Formula 17, preferably para bromothiophenol, para bromophenol or para bromoaniline is reacted under basic condition with a 3-bromo carboxylic acid of the Formula 18. In this reaction scheme the symbols have the meaning described in connection with Formula 1. An example for the reagent of Formula 18 where $R_3$ is hydrogen, is 3-bromopropionic acid. The reaction with the 3-bromocarboxylic acid of Formula 18 results in the compound of Formula 19. The latter is cyclized by treatment with acid to yield the 6-bromothiochroman-4-one derivative (when X is S) or 6-bromochroman derivative (when X is O) of Formula 20. The bromo compounds of Formula 20 are then subjected to substantially the same sequence of reactions under analogous conditions, which are described in Reaction Scheme 1 for the conversion of the bromo compounds of Formula 7 to the compounds of the invention. Thus, briefly summarized here, the bromo compounds of Formula 20 are reacted with (trimethylsilyl)acetylene to provide the 6-(trimethylsilyl)ethynyl substituted thiochroman-4-one or chroman-4-one compounds of Formula 21. The 6-(trimethylsilyl)ethynyl-substituted thiochroman-4-one compounds of Formula 21 are then reacted with base (potassium hydroxide or potassium carbonate) to provide the ethynyl substituted 6-ethynyl substituted thiochroman-4-ones of Formula 22. Compounds of Formula 22 are then coupled with the aromatic or heteroaromatic reagent $X_1$—$Y(R_2)$—A—B' (Formula 10) under conditions analogous to those described for the analogous reactions of Reaction Scheme 1, to yield the compounds of Formula 23.

The compounds of Formula 23 are then reacted still under conditions analogous to the similar reactions described in Reaction Scheme 1 with sodium bis(trimethylsilyl)amide and 2-[N,N-bis(trifluoromethylsulfonyl)amino]-5-chloropyridine to yield the 4-trifluoromethylsulfonyloxy benzothiopyran or benzopyran derivatives represented in Formula 24. The compounds of Formula 24 are then converted to compounds shown in Formula 25, by reaction with an organometal derivative derived from the aryl or heteroaryl compound $R_{14}H$, as described in connection with Reaction Scheme 1.

Similarly to the use of the intermediate 7-bromotetrahydronaphthalene-1-one compounds of Formula 7 of Reaction Scheme 1, the intermediate 6-bromothiochroman-4-one compounds of Formula 20 can also be used for the preparation of further compounds within the scope of the present invention, as described below, in Reaction Schemes 6, 7 and 8. The compounds of Formula 25, can also be converted into further homologs and derivatives, in reactions analogous to those described in connection with Reaction Scheme 1.

Reaction Scheme 3

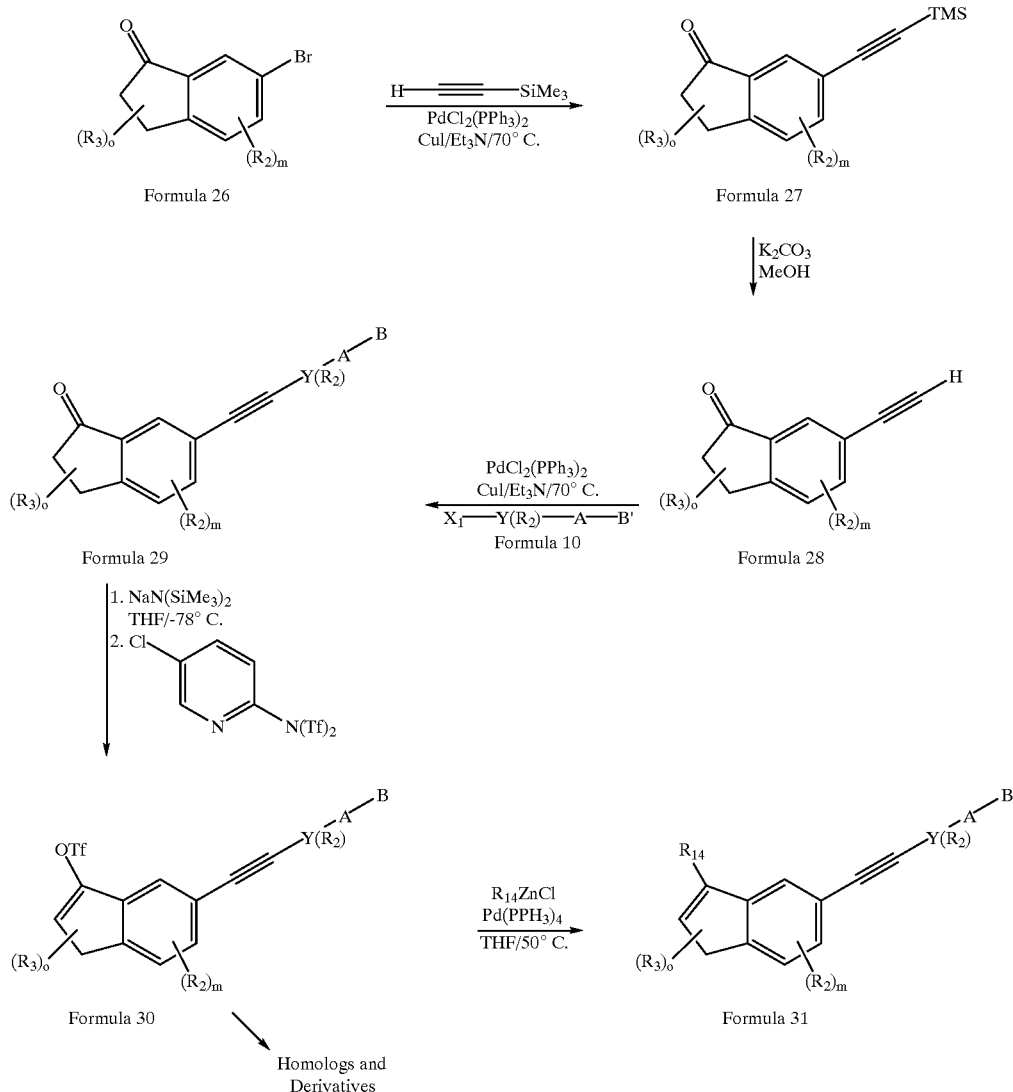

Reaction Scheme 3 discloses a synthetic route to compounds where, with reference to Formula 1, X is $[C(R_1)_2]_n$, n is 0 and the Z group is an ethynyl function (—C≡C—). In accordance with this scheme, a 6-bromo-2,3-dihydro-1H-inden-1-one derivative of Formula 26 is reacted in a sequence of reactions (starting with reaction with trimethylsilylacetylene) which are analogous to the reactions described above in connection with Reaction Schemes 1 and 2, to provide, through intermediates of the formulas 27–30, the indene derivatives of Formula 31. In a preferred embodiment within the scope of Reaction Scheme 3, the starting material is 6-bromo-2,3-dihydro-3,3-dimethyl-1H-inden-1-one that is available in accordance with the chemical literature (See Smith et al. Org. Prep. Proced. Int. 1978 10, 123–131). Compounds of Formula 26, such as 6-bromo-2,3-dihydro-3,3-dimethyl-1H-inden-1-one, can also be used for the synthesis of still further exemplary compounds for use in the present invention, as described below.

Reaction Scheme 4

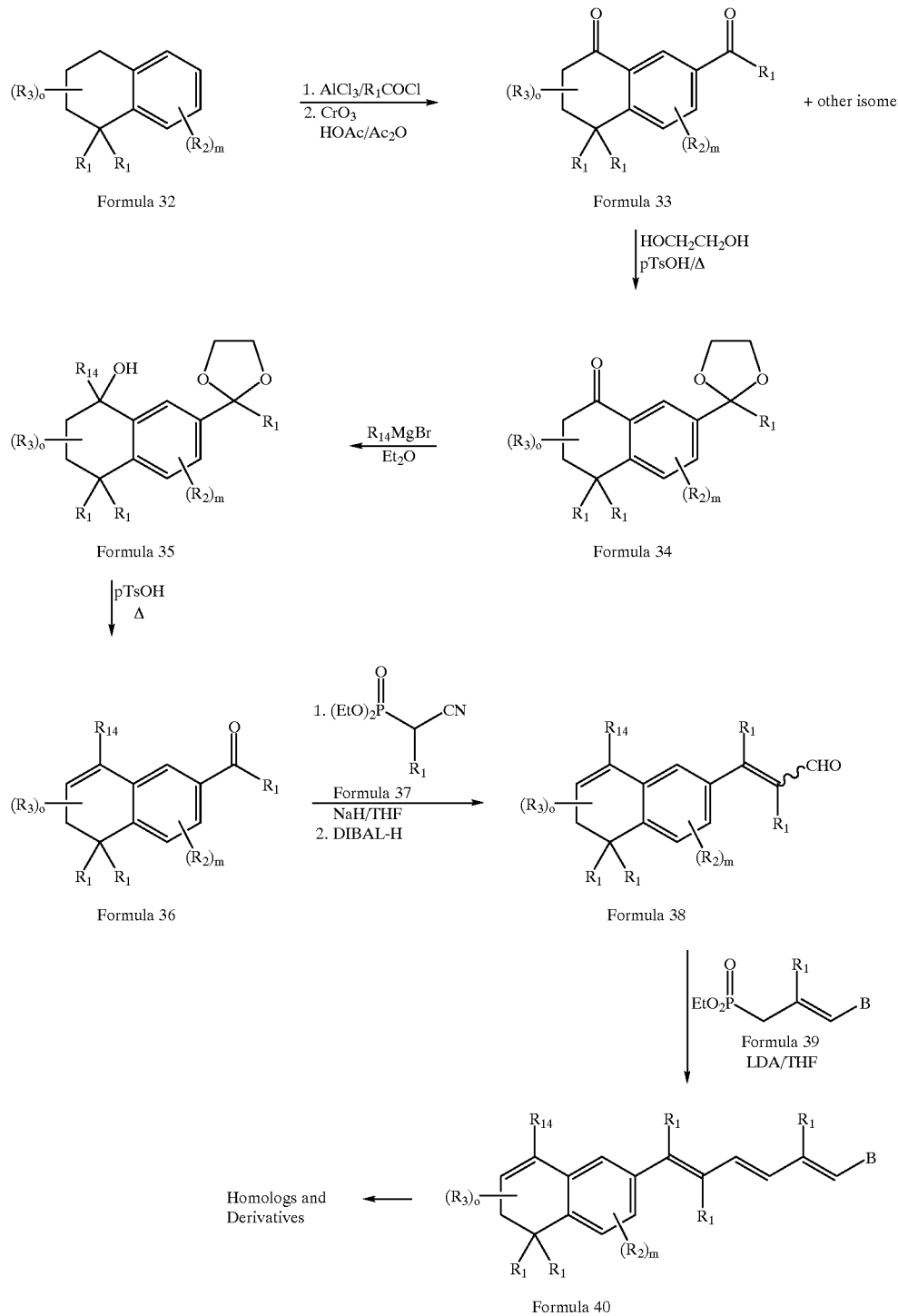

Referring now to Reaction Scheme 4 a synthetic route to exemplary compounds is disclosed where, with reference to Formula 1, Z is —(CR$_1$=CR$_1$)$_{n'}$—, n' is 3, 4 or 5 and Y represents a direct valence bond between the (CR$_1$=CR$_1$)$_{n'}$ group and B. This synthetic route is described for examples where the X group is [C(R$_1$)$_2$]$_n$ and n is 1 (dihydronaphthalene derivatives). Nevertheless, it should be understood that the reactions and synthetic methodology described in Reaction Scheme 4 and further ensuing schemes, is also applicable, with such modifications which will be readily apparent to those skilled in the art, to derivatives where X is is S, O, NR' (benzothiopyran, benzopyran or dihydroquinoline derivatives) or [C(R₁)₂]ₙ and n is 0 (indene derivatives).

In accordance with Reaction Scheme 4, a 1,2,3,4-tetrahydronaphthalene derivative of Formula 32 is reacted with an acid chloride (R₁COCl) under Friedel Crafts conditions, and the resulting acetylated product is oxidized, for example in a Jones oxidation reaction, to yield a mixture of isomeric 6- and 7-acetyl-1(2H)-naphthalenone derivatives of Formula 33. In a specific preferred example of this reaction, the starting compound of Formula 32 is 1,2,3,4-tetrahydro-1,1-dimethylnaphthalene (a known compound) which can be prepared in accordance with a process described in the experimental section of the present application. The 7-acetyl-1(2H)-naphthalenone derivative of Formula 33 is reacted with ethylene glycol in the presence of acid to protect the oxo function of the exocyclic ketone moiety, as a ketal derivative of Formula 34. The ketal of Formula 34 is thereafter reacted with a Grignard reagent of the formula R₁₄MgBr (the symbols are defined as in connection with Formula 1), to yield the tertiary alcohol of Formula 35. Thereafter the dioxolane protective group is removed and the tertiary alcohol is dehydrated by treatment with acid to provide the 3,4-dihydro-7-acetylnaphthalene derivatives of Formula 36. The ketone function of the compounds of Formula 36 is subjeceted to a Horner Emmons (or analogous) reaction under strongly alkaline conditions with a phosphonate reagent of Formula 37, to yield, after reduction, the aldehyde compounds of Formula 38. Still another Horner Emmons (or analogous) reaction under strongly alkaline conditions with a reagent of Formula 39 provides compounds of Formula 40. The latter can be converted into further homologs and derivatives in accordance with the reactions described above. A specific example of the Horner Emmons reagent of Formula 37 which is used for the preparation of a preferred compound is diethylcyanomethylphosphonate; an example of the Horner Emmons reagent of Formula 39 is diethyl-(E)-3-ethoxycarbonyl-2-methylallylphosphonate.

Reaction Scheme 5

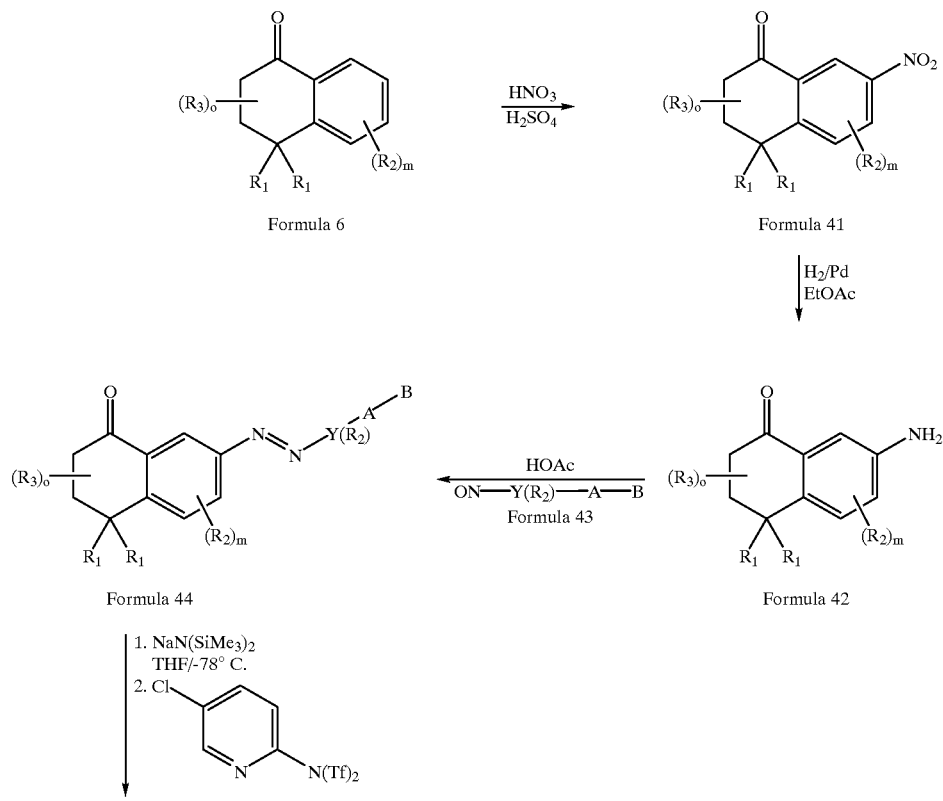

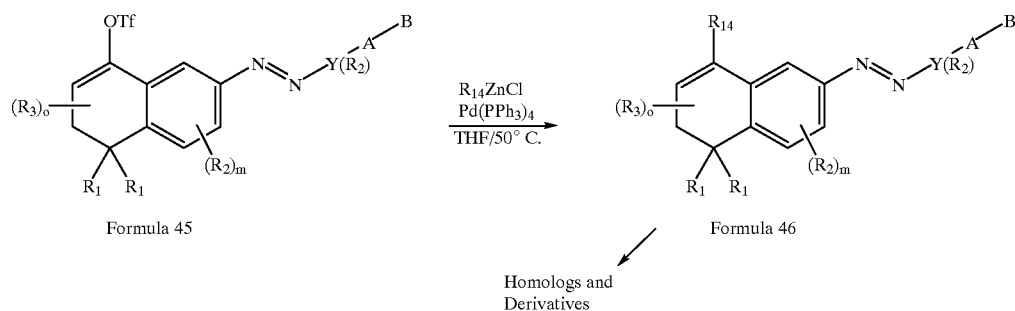

Formula 45 → Formula 46

Homologs and Derivatives

Reaction Scheme 5 discloses a synthetic process for preparing compounds where the Z group is an azo group (—N═N—). As in Reaction Scheme 4 this process is described for examples where the X group is $[C(R_1)_2]_n$ and n is 1 (dihydronaphthalene derivatives). Nevertheless, it should be understood that the synthetic methodology described is also applicable, with such modifications which will be readily apparent to those skilled in the art, to all azo compounds for use in the invention, namely to derivatives where X is is S, O, NR' (benzothiopyran, benzopyran or dihydroquinoline derivatives) or $[C(R_1)_2]_n$ and n is 0 (indene derivatives). Thus, a nitro group is introduced into the starting compound of Formula 6 under substantially standard conditions of nitration, to yield the 3,4-dihydro-7-nitro-1(2H)-naphthalenone derivative of Formula 41. The latter compound is reduced to the 3,4-dihydro-7-amino-1(2H)-naphthalenone derivative of Formula 42 and is thereafter reacted with a nitroso compound of the formula ON—Y(R$_2$)—A—B (Formula 43) under conditions normally employed (glacial acetic acid) for preparing azo compounds.

The nitroso compound of Formula 43 can be obtained in accordance with reactions known in the art. A specific example for such compound, which is used for the synthesis of a preferred compound is ethyl 4-nitrosobenzoate. The azo compound of Formula 44 is thereafter reacted with sodium bis(trimethylsilyl)amide and 2-[N,N-bis(trifluoromethylsulfonyl)amino]-5-chloropyridine to yield the 4-trifluoromethylsulfonyloxy derivatives represented in Formula 45. The compounds of Formula 45 are then converted to the azo compounds shown in Formula 46, by reaction with an organometalic derivative derived from the aryl or heteroaryl compound $R_{14}H$. These latter two reactions, namely the conversion to the 4-trifluoromethylsulfonyloxy derivatives and subsequent reaction with the organometal derivative, have been described above in connection with Reaction Schemes 1, 2 and 3, and are employed in several presently preferred synthetic processes leading to exemplary RAR antagonist compounds.

Reaction Scheme 6

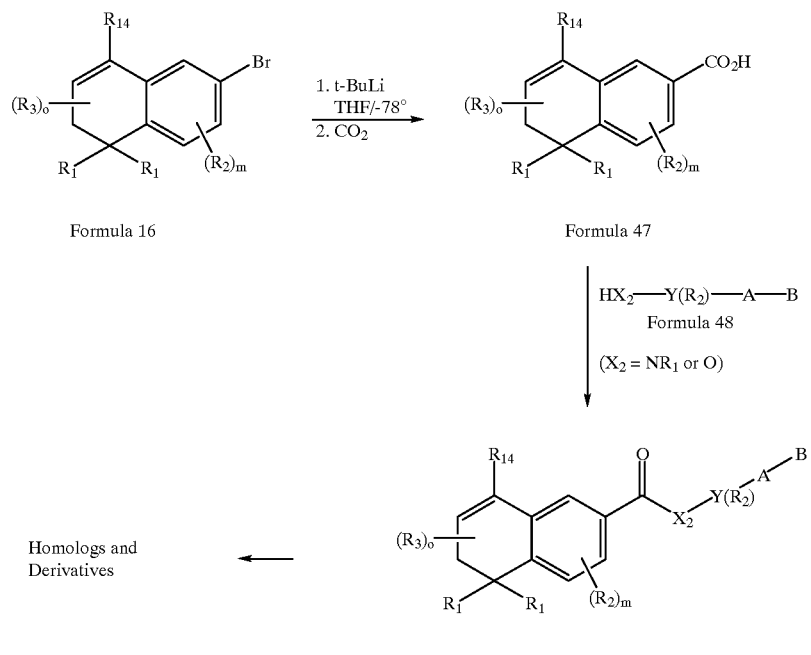

Formula 16 → Formula 47

Formula 48

Homologs and Derivatives ← Formula 49

Reaction Scheme 6 discloses a presently preferred synthetic process for the preparation of compounds where, with reference to Formula 1, the Z group is COO— or CONR$_1$ (R$_1$ is preferably H). These ester and amide derivatives are prepared from the 3,4-dihydro-7-bromonaphthalene derivatives of Formula 16, which can be obtained as described in Reaction Scheme 1. Thus, the compounds of Formula 16 are reacted with strong base, such as t-butyllithium, in an inert ether type solvent, such as tetrahydrofuran, at cold temperature, and carbon dioxide (CO$_2$) is added to provide the 5,6-dihydro-2-naphthalenecarboxylic acid derivatives of Formula 47. Compounds of Formula 47 are then reacted with compounds of the formula X$_2$—Y(R$_2$)—A B (Formula 48) where X$_2$ reperesent an OH or an NR$_1$ group, the R$_1$ preferably being hydrogen. Those skilled in the art will recognize that the compounds of Formula 48 are aryl or heteroaryl hydroxy or amino derivatives which can be obtained in accordance with the state-of-the-art. The reaction between the compounds of Formula 47 and Formula 48 can be conducted under various known ester or amide forming conditions, such as coupling of the two in the presence of 1-(3-dimethylaminopropyl)-3-ethylcarbodiimide hydrochloride and 4-dimethylaminopyridine. Alternatively, the compounds of Formula 47 can be converted into the corresponding acid chloride for coupling with the compounds of Formula 48 in the presence of base. The amide or ester compounds of Formula 49 can be converted into further homologs and derivatives, as described above. Although Reaction Scheme 6 is described and shown for the example where the X group of Formula 1 is [C(R$_1$)$_2$]$_n$ and n is 1 (dihydronaphthalene derivatives), the herein described process can be adapted for the preparation of benzopyran, benzothiopyran, dihydroquinoline and indene derivatives as well.

Compounds of the present invention where with reference to Formula 1, Z is —OCO—, NR$_1$CO, as well as the corresponding thioester and thioamide analogs, can be prepared from the intermediates derived from the compounds of Formula 16 where the bromo function is replaced with an amino or hydroxyl group and in accordance with the teachings of U.S. Pat. Nos. 5,324,744, the specification of which is expressly incorporated herein by reference.

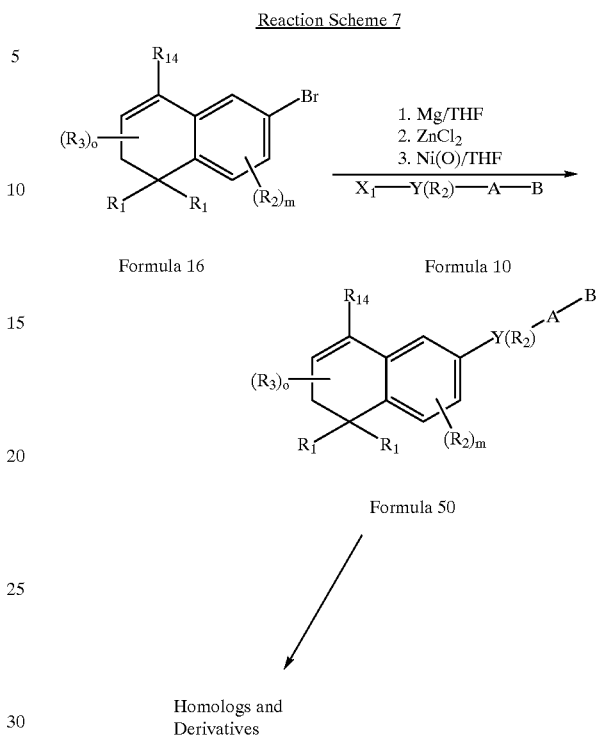

Reaction Scheme 7 discloses a presently preferred synthetic process for the preparation of compounds where with reference to Formula 1, Z is —(CR$_1$=CR$_1$)$_{n'}$— and n' is 0. These compounds of Formula 50 can be obtained in a coupling reaction between compounds of Formula 16 and a Grignard reagent derived from the halo compounds of Formula 10. The coupling reaction is typically conducted in the presence of a zinc salt and a nickel (Ni(0)) catalyst in inert ether type solvent, such as tetrahydrofuran. The compounds of Formula 50 can be converted into further homologs and derivatives, as described above.

Reaction Scheme 8

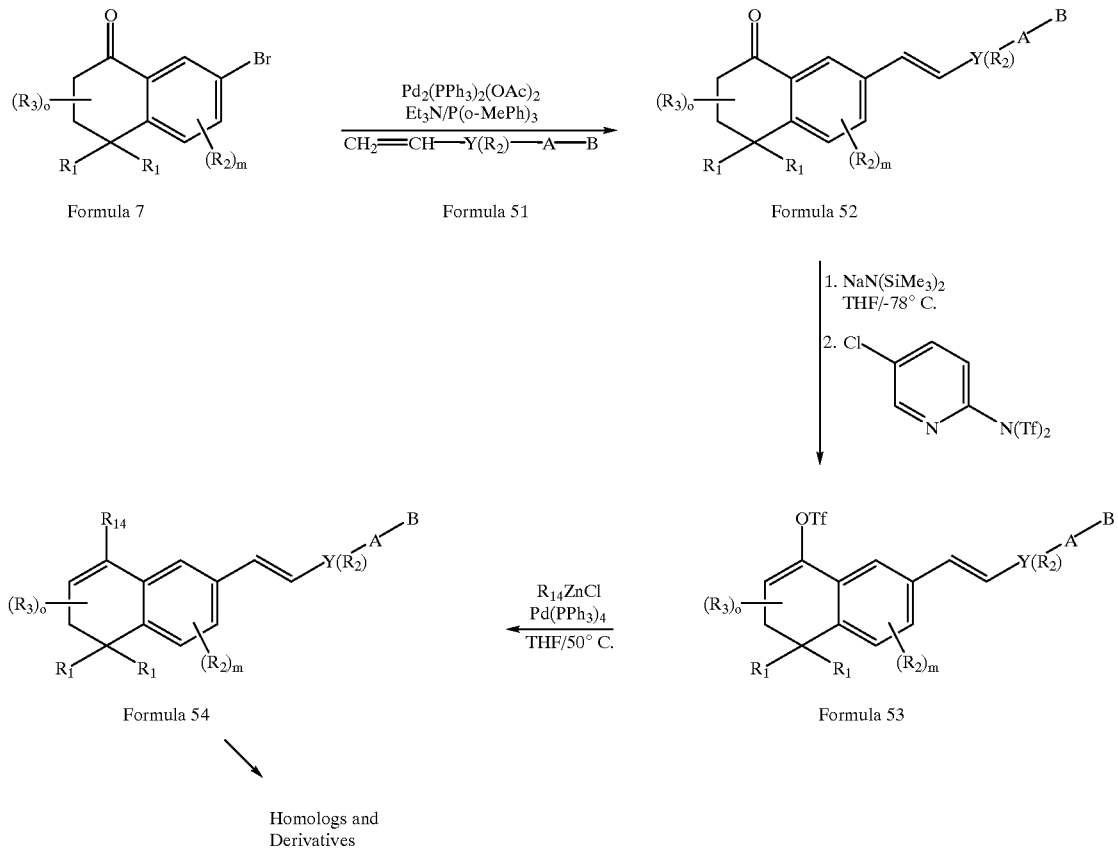

Referring now to Reaction Scheme 8 a presently preferred synthetic process is disclosed for the preparation of compounds where Z is —(CR$_1$═CR$_1$)$_{n'}$— and n' is 1. More particularly, Reaction Scheme 8 discloses the presently preferred process for preparing those compounds which are dihydronaphtalene derivatives and where the Z group represents a vinyl (—CH═CH—) function. However, the generic methodology disclosed herein can be extended, with such modifications which will be apparent to those skilled in the art, to the analogous benzopyran, benzothiopyran, dihydroquinoline compounds, and to compounds where the vinyl group is substituted. Thus, in accordance with Reaction Scheme 8 the 7-bromo-1(2H)-naphthalenone derivative of Formula 7 is reacted with a vinyl derivative of the structure —CH$_2$═CH—Y(R$_2$)—A—B (Formula 51) in the presence of a suitable catalyst, typically having the formula Pd(PPh$_3$), an acid acceptor (such as triethylamine) under an inert gas (argon) atmosphere. The conditions of this reaction are analogous to the coupling of the acetylene derivatives of Formula 9 with the reagent of Formula 10 (see for example Reaction Scheme 1), and this type of reaction is generally known in the art as a Heck reaction. The vinyl derivative of Formula 51 can be obtained in accordance with the state of the art, an example for such a reagent used for the synthesis of a preferred compound to be used in the invention is ethyl 4-vinylbenzoate.

The product of the Heck coupling reaction is an ethenyl derivative of Formula 52, which is thereafter converted into compounds used in the present invention by treatment with sodium bis(trimethylsilyl)amide and 2-[N,N-bis (trifluoromethylsulfonyl)amino]-5-chloropyridine to yield the 4-trifluoromethylsulfonyloxy derivatives of Formula 53, and subsequent reaction with an organometal derivative derived from the aryl or heteroaryl compound R$_{14}$H, as described above. The resulting compounds of Formula 54 can be converted into further homologs and derivatives.

The compounds of Formula 54 can also be obtained through synthetic schemes which employ a Wittig or Horner Emmons reaction. For example, the intermediate of Formula 33 (see Reaction Scheme 4) can be reacted with a triphenyiphosphonium bromide (Wittig) reagent or more preferably with a diethylphosphonate (Horner Emmons) reagent of the structure (EtO)$_2$PO—CH$_2$—Y(R$_2$)—A—B, as described for analogous Horner Emmons reactions in U.S. Pat. No. 5,324,840, the specification of which is incorporated herein by reference. The just mentioned Horner Emmons reaction provides intermediate compounds analogous in structure to Formula 52, and can be converted into compounds of Formula 54 by the sequence of reactions described in Reaction Scheme 8 for the compounds of Formula 52.

Reaction Scheme 9
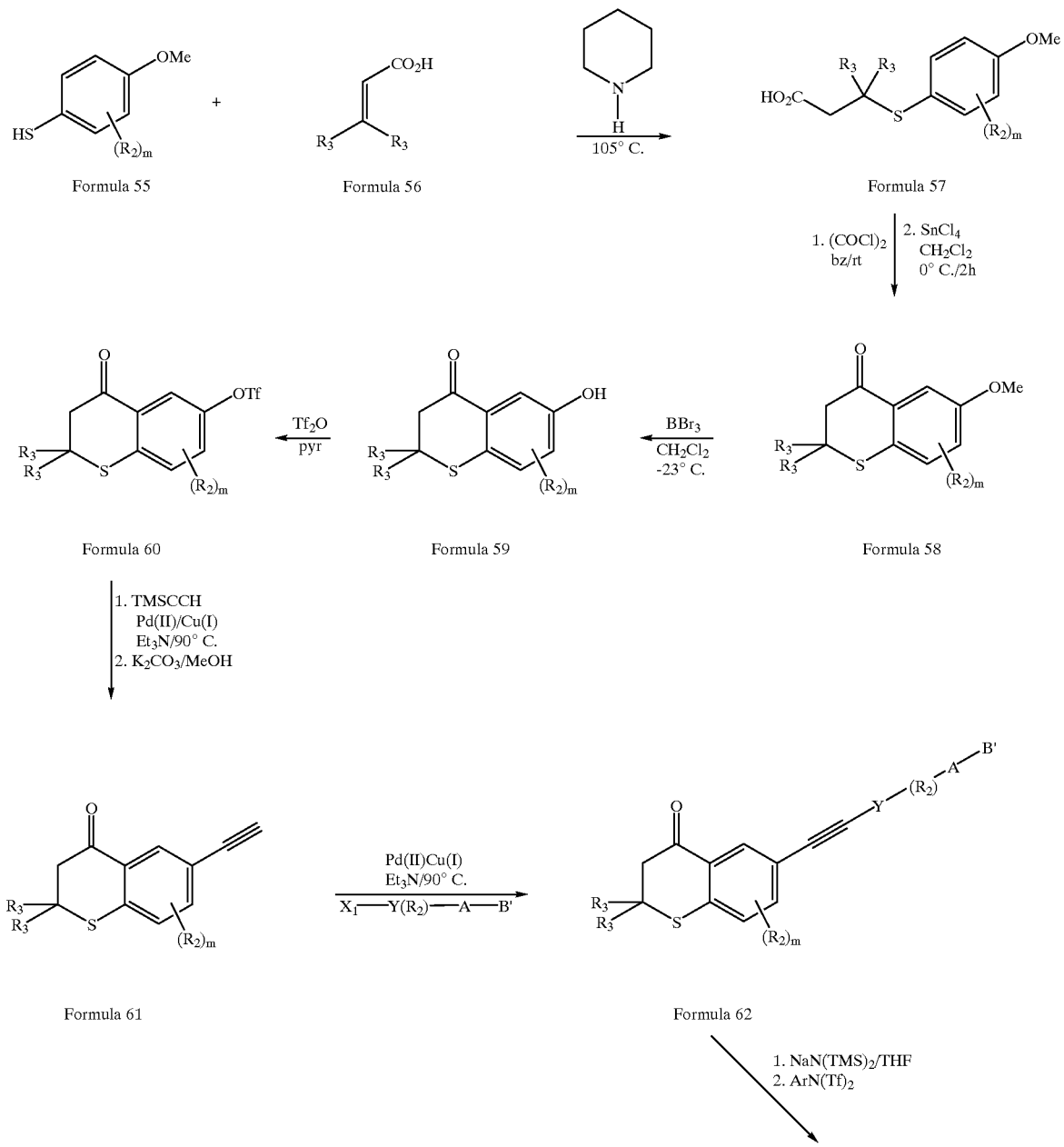

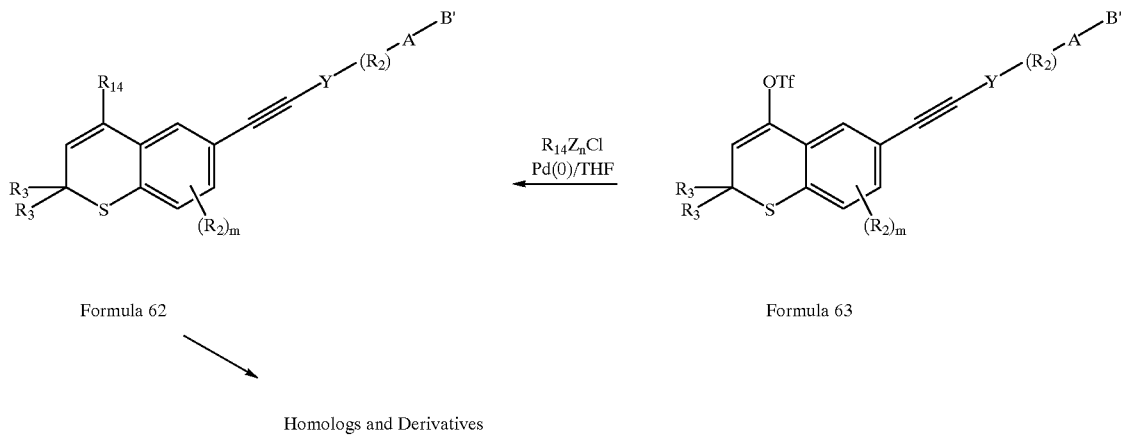

Formula 62          Formula 63

Homologs and Derivatives

A number of particularly preferred compounds of the invention, for example those shown in Formula 5b and Table 1a are prepared in accordance with Reaction Scheme 9. An important feature of the compounds prepared in accordance with Reaction Scheme 9 is that the group X with reference to Formula 1 is S and the 2 position of the benzothiopyrane (thiochromene) ring of the compounds is substituted with alkyl groups.

Referring now to Reaction Scheme 9, a 4-methoxythiophenol of Formula 55 serves as a starting material. The 4-methoxythiophenol of Formula 55 may be substitituted with one or more $R_2$ groups as defined in connection with Formula 1. In the synthesis of the preferred compounds in accordance Reaction Scheme 9 the $R_2$ group of Formula 55 is either H, halogen such as F, or an alkoxy group, preferably methoxy. Examples for compounds of Formula 55 which are used for the synthesis of specific preferred compounds in accordance with the invention are 4-methoxythiophenol and 3-fluoro-4-methoxythiophenol. The thiophenol of Formula 55 is reacted with an alkenoic acid of Formula 56 by heating in piperidine. This reaction results in addition of the thiophenol to the double bond of the alkenoic acid (Michael addition) to give rise to compounds of Formula 57. The alkenoic acid of Formula 56 includes the $R_3$ substituents which for the herein described preferred embodiments are alkyl, most preferably methyl, groups. An example for the alkenoic acid of Formula 56 is 3-methyl-2-butenoic acid. Reaction of thiophenols of Formula 55 with 2-alkenoic acids to synthesize 2,2-dimethyl-thiochroman-4-one derivatives is generally described by Ferreira et al. Synthesis 1987 p 149.

The aromatic acid of Formula 57 is converted to the corresponding acid chloride, for example by reaction with oxalyl chloride, and the resulting acid chloride is thereafter cyclized by heating in an inert solvent such as $CH_2Cl_2$ in the presence of stannic tetrachloride ($SnCl_4$), to give rise to 2,2-disubstituted thiochroman-4-one compounds of Formula 58. The 2,2-disubstituted thiochroman-4-one of Formula 58 is reacted with borontribromide to remove the methyl group from the methoxy function and to yield the 2,2-disubstituted 6-hydroxy-thiochroman-4-one of Formula 59. The hydroxy compound of Formula 59 is thereafter reacted with trifluoromethanesulfonic anhydride in anhydrous pyridine to give rise to the 6-trifluoromethanesulfonyloxy derivative of Formula 60.

The 2,2-disubstituted 6-trifluoromethanesulfonyloxy-thiochroman-4-one of Formula 60, shown in Reaction Scheme 9, is reacted with (trimethylsilyl)acetylene to provide 2,2-disubstituted 6-(trimethylsilyl) ethynylthiochroman-4-one compounds which are subsequently reacted with base ($K_2CO_3$) in an alcoholic solvent, such as methanol, to yield the 2,2-disubstituted 6-ethynyl-thiochroman-4-one compounds of Formula 61. The reaction with (trimethylsilyl)acetylene is typically conducted under heat (approximately 95° C.) in the presence of a suitable catalyst, typically having the formula $Pd(PPh_3)_2Cl_2$, and an acid acceptor (such as triethylamine) under an inert gas (argon) atmosphere. This reaction is analogous to the reactions of the 6-bromo-thiochroman-4-one compounds of Formula 20 with (trimethylsilyl)acetylene, shown in Reaction Scheme 2. Thereafter, the 2,2-disubstituted 6-ethynyl-thiochroman-4-one compound of Formula 61 is coupled with the aromatic or heteroaromatic reagent $X_1$—$Y(R_2)$—A—B' (Formula 10, defined above) under conditions similar to those described for the analogous reactions of Reaction Scheme 1 and Reaction Scheme 2, to yield the compounds of Formula 62. In the synthesis of the herein described specific preferred examples of the compounds of Formula 62 ethyl 4-iodobenzoate, ethyl 2-fluoro-4-iodobenzoate and ethyl 6-iodonicotinate serve as examples for the reagent $X_1$—$Y(R_2)$—A—B' (Formula 10).

The compounds of Formula 62 are then reacted, still under conditions similar to the analogous reactions described in Reaction Scheme 1 and Reaction Scheme 2, with sodium bis(trimethylsilyl)amide and 2-[N,N-bis (trifluoromethylsulfonyl)amino]-5-chloropyridine to yield the 4-trifluoromethylsulfonyloxy benzothiopyran (thiochromene) derivatives represented by Formula 63. The compounds of Formula 63 are then converted to compounds shown in Formula 64, by reaction with an organometal derivative derived from the aryl or heteroaryl compound $R_{14}H$, $R_{14}Br$ or $R_{14}I$ as described in connection with Reaction Scheme 1 and Reaction Scheme 2. Examples of reagents and conditions utilized in accordance with Reaction Scheme 9 to convert the 4-trifluoromethanesulfonyloxy compounds of Formula 63 into preferred compounds of the invention in accordance with Formula 64 are:

4-methylbromobenzene, tetrahydrofuran (THF), t-butyllithium and zinc chloride ($ZnCl_2$) to make the organometal reagent, followed by reaction with the 4-trifluoromethylsulfonyloxy (triflate) derivative in the presence of tetrakis(triphenylphosphine)palladium(0) catalyst;

2-methylthiophene, THF, n-butyllithium and $ZnCl_2$ followed by the reaction with the triflate in the presence of tetrakis(triphenylphosphine)palladium(0);

bromobenzene, THF, t-butyllithium and ZnCl$_2$ followed by the reaction with the triflate in the presence of tetrakis(triphenylphosphine)palladium(0);

4-ethylbromobenzene, THF, t-butyllithium and ZnCl$_2$ followed by the reaction with the triflate in the presence of tetrakis(triphenylphosphine)palladium(0);

4-iso-propylbromobenzene, THF, t-butyllithium and ZnCl$_2$ followed by the reaction with the triflate in the presence of tetrakis(triphenylphosphine)palladium(0);

4-t-butylbromobenzene, THF, t-butyllithium and ZnCl$_2$ followed by the reaction with the triflate in the presence of tetrakis(triphenylphosphine)palladium(0);

2-ethylthiophene, THF, n-butyllithium and ZnCl$_2$ followed by the reaction with the triflate in the presence of tetrakis(triphenylphosphine)palladium(0);

2-t-butylthiophene, THF, n-butyllithium and ZnCl$_2$ followed by the reaction with the triflate in the presence of tetrakis(triphenylphosphine)palladium(0), and 4-bromo-2-methylpyridine, THF, t-butyllithium and ZnCl$_2$ followed by the reaction with the triflate in the presence of tetrakis(triphenylphosphine)palladium(0).

The 4-aryl or 4-heteroaryl benzothiopyran (thiochromene) derivatives represented by Formula 64 are preferred compounds within the scope of the invention. Most preferably the R$_3$ group is methyl in these compounds. The compounds of Formula 64 can be converted to further homologs and derivatives as described above in connection with the preceding reaction schemes. A frequently utilized reaction in this regard, which gives rise to a number of specific examplary compounds of the invention is saponification of an alkyl ester (B or B' represents an esterified carboxylic acid group) to yield a free carboxylic acid or its pharmaceutically acceptable salt.

Reaction Scheme 10

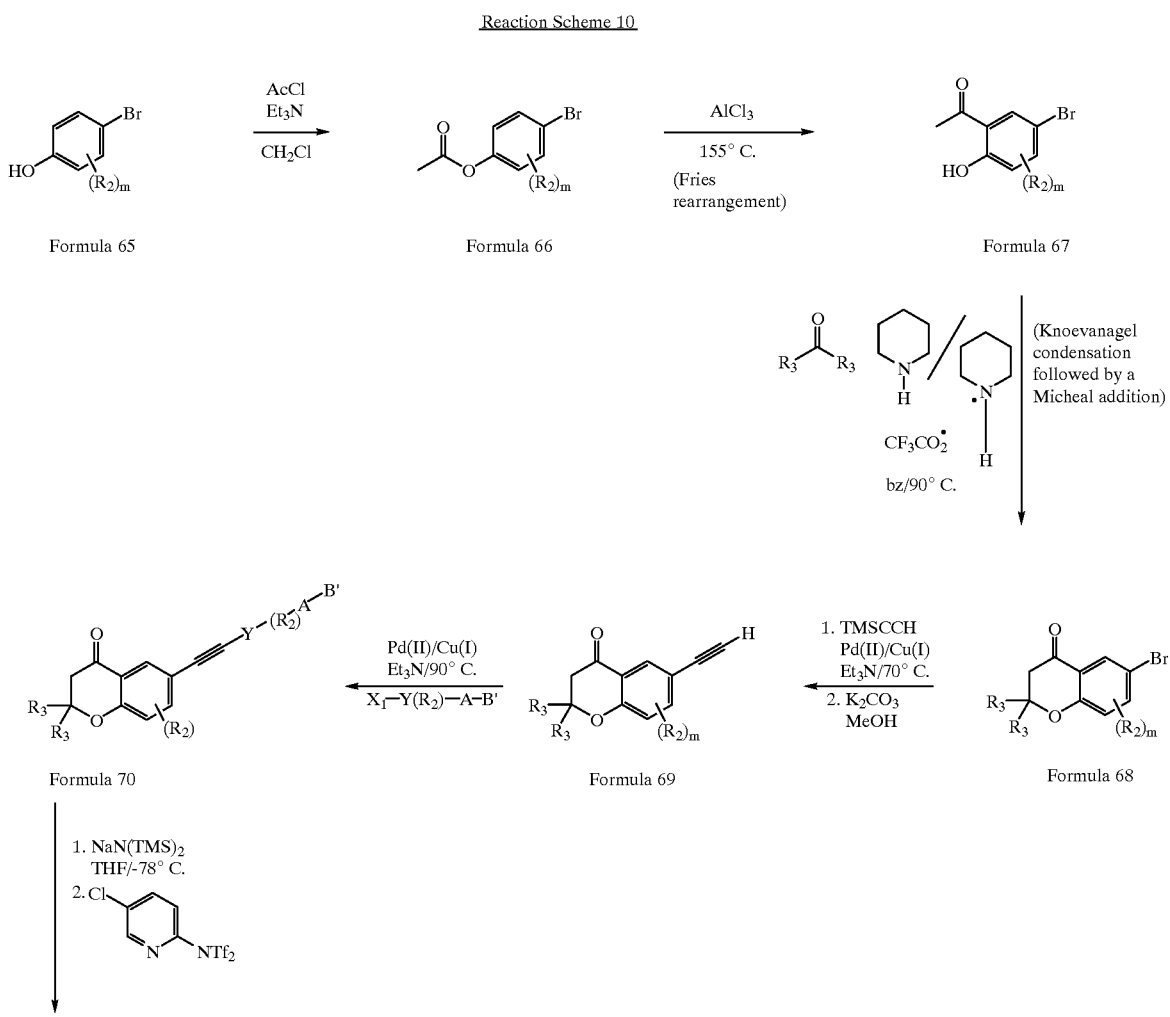

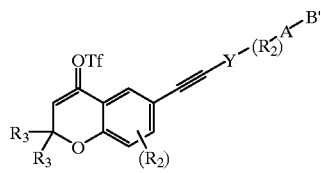

Formula 71

Pd(PPh$_3$)$_4$
THF/50° C.
R$_{14}$ZnCl

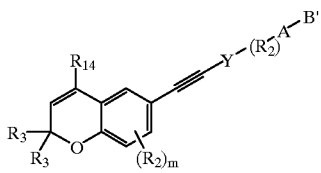

Formula 72

Homologs and Derivatives

A number of particularly preferred compounds of the invention, shown in Formula 5b and Table 1a, where with reference to Formula 1 X is O and the 2-position of the benzopyrane (chromene) ring of the compounds is substituted with alkyl groups, are prepared in accordance with Reaction Scheme 10. A 4-bromophenol compound of Formula 65 serves as a starting material and R$_2$ is defined as in connection with Formula 1, although preferably the 4 bromophenol is unsubstituted, or is alkyl, halogen or alkoxy substituted (the R$_2$ group symbolizes alkyl, halogen or alkoxy). The 4-bromophenol of Formula 65 is acetylated to provide the acetyloxy-4-bromobenzene derivative of Formula 66. The acetyloxy-4-bromobenzene derivative of Formula 66 is then subjected to a rearrangement reaction (Fries rearrangement) by heating with aluminum chloride (AlCl$_3$) to provide the 3-bromo-6-hydroxyacetophenone derivatives of Formula 67. The latter compounds are heated in piperidine in the presence of piperidine trifluoroacetate with a ketone of the formula R$_3$—CO—R$_3$, where the R$_3$ group is lower alkyl, causing the 3-bromo-6-hydroxyacetophenone derivatives of Formula 67 to undergo a Knoevenagel condensation followed by a Michael addition, and thereby ring close and provide the 2,2-dialkyl-6-bromo-chroman-4-one derivatives of Formula 68.

The 2,2-dialkyl-6-bromo-chroman-4-one derivatives of Formula 68 are then reacted with (trimethylsilyl)acetylene under conditions similar to those described for the reaction with (trimethylsilyl)acetylene of the bromo compounds of Formula 15 and 20 in Reaction Schemes 1 and 2, respectively, and for the 6-trifluorosulfonyloxythiochroman-4-one compounds of Formula 60 in Reaction Scheme 9. The resulting 2,2-disubstituted 6-(trimethylsilyl)ethynyl-chroman-4-one compounds (not shown in Reaction Scheme 10) are then treated with base (as in the previously described analogous reactions) to provide 2,2-disubstituted 6-ethynyl-chroman-4-one compounds of Formula 69. The compounds of Formula 69 are then coupled with the aromatic or heteroaromatic reagent X$_1$—Y(R$_2$)—A—B' (Formula 10, defined above) under conditions similar to those described for the analogous reactions of Reaction Scheme 1, Reaction Scheme 2 and Reaction Scheme 9 to yield the compounds of Formula 70. Examples for the reagent X$_1$—Y(R$_2$)—A—B' (Formula 10) used in the synthesis of the herein described specific preferred embodiments of the compounds of Formula 70 are ethyl 4-iodobenzoate and ethyl 2-fluoro-4-iodobenzoate.

Referring still to Reaction Scheme 10, the 6-(aryl) or 6(heteroaryl)ethynyl 2,2-disubstituted chroman-4-one compounds of Formula 70 are converted into the 6-(aryl) or 6-(heteroaryl)ethynyl 2,2-disubstituted 4-trifluoromethylsulfonyloxy benzopyran (chromene) derivatives of Formula 71 by treatment with sodium bis (trimethylsilyl)amide and 2-[N,N-bis (trifluoromethylsulfonyl)amino]-5-chloropyridine. This is in analogy to the conversion of the corresponding thiochroman-4-one compounds (Formula 62) into the corresponding 4-trifluoromethylsulfonyloxy benzothiopyran (thiochromene) derivatives of Formula 63. The 6-(aryl) or 6-(heteroaryl)ethynyl 2,2-disubstituted 4-trifluoromethylsulfonyloxy benzopyran (chromene) derivatives of Formula 71 are then reacted with an organometal derivative derived from the aryl or heteroaryl compound R$_{14}$H, R$_{14}$Br, or R$_{14}$I as described above in connection with Reaction Scheme 1, Reaction Scheme 2 and Reaction Scheme 9, to yield preferred compounds of the invention shown in Formula 72. Examples of reagents and conditions utilized in accordance with Reaction Scheme 10 to to convert the 4-trifluoromethanesulfonyloxy compounds of Formula 71 into preferred compounds of the invention in accordance with Formula 72 are:

bromobenzene, THF, t-butyllithium and ZnCl$_2$ followed by the reaction with the triflate in the presence of tetrakis(triphenylphosphine)palladium(0);

4-methylbromobenzene, THF, t-butyllithium and ZnCl$_2$ followed by the reaction with the triflate in the presence of tetrakis(triphenylphosphine)palladium(0);

4-ethylbromobenzene, THF, t-butyllithium and ZnCl$_2$ followed by the reaction with the triflate in the presence of tetrakis(triphenylphosphine)palladium(0);

4-iso-propylbromobenzene, THF, t-butyllithium and ZnCl$_2$ followed by the reaction with the triflate in the presence of tetrakis(triphenylphosphine)palladium(0), and 4-t-butylbromobenzene, THF, t-butyllithium and ZnCl$_2$ followed by the reaction with the triflate in the presence of tetrakis(triphenylphosphine)palladium(0).

The preferred 2,2-disubstituted benzopyran (chromene) compounds of the invention, represented by Formula 72, can be converted to further homologs and derivatives, as described above. Saponification of the alkyl esters represented by Formula 72 when B' represents an esterified carboxyl group, yields the specially preferred carboxylic acid (or pharmaceutically acceptable salt) compounds of the invention.

Synthetic Methods—Aryl and (3-Oxy-1-Propenyl)-Substituted Compounds

The exemplary RAR antagonist compounds of Formula 101 can be made by the synthetic chemical pathways illustrated here. The synthetic chemist will readily appreciate that the conditions set out here are specific embodiments which can be generalized to any and all of the compounds represented by Formula 101.

Reaction Scheme 101

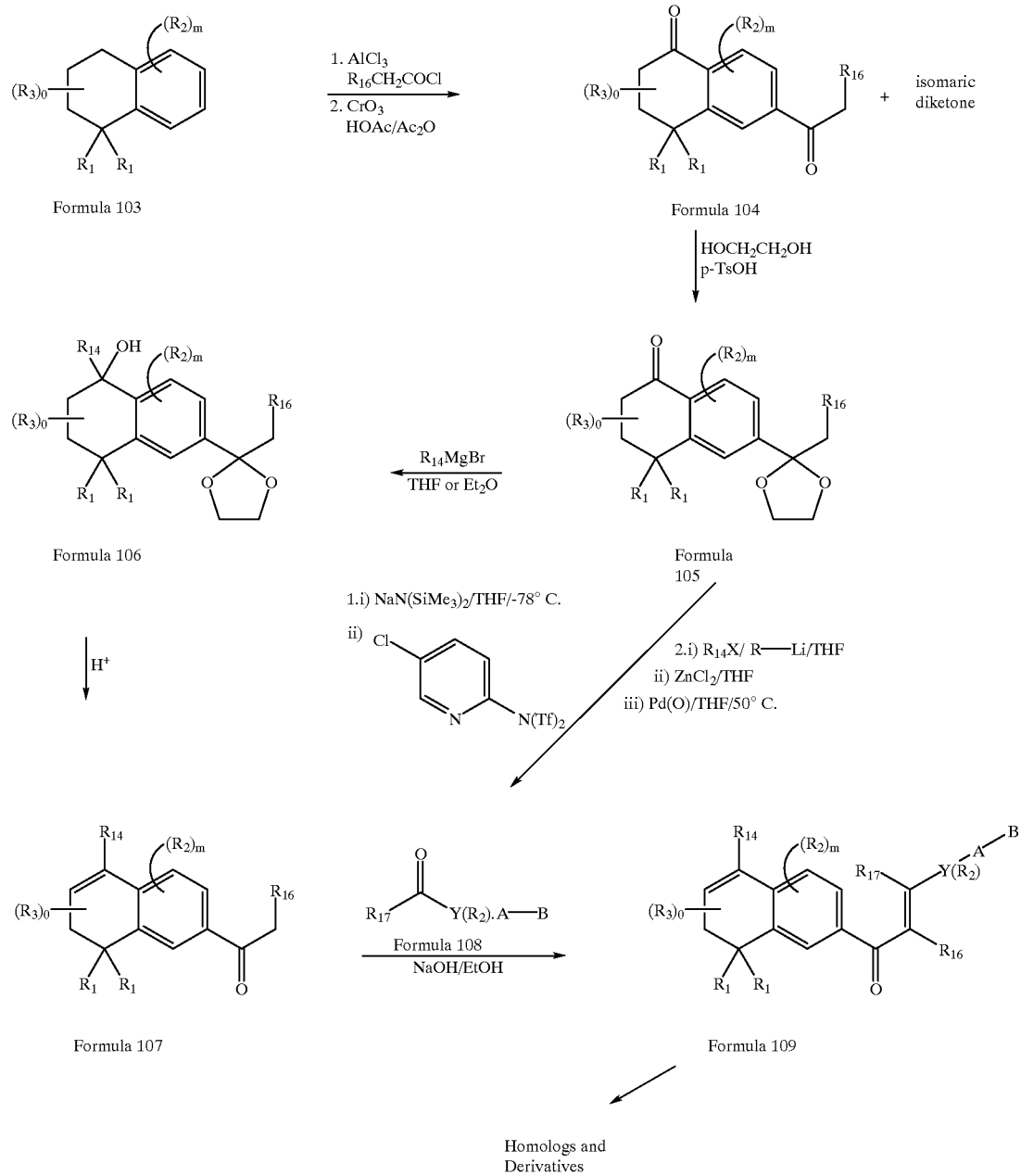

Reaction Scheme 101 illustrates the synthesis of compounds of Formula 101 where X is $[C(R_1)_2]_n$, n is 1, p is zero and $R_{17}$ is H or lower alkyl. In other words, Reaction Scheme 101 illustrates the synthesis of compounds of the invention which are 3,4-dihydronaphthalene derivatives. In accordance with this scheme, a tetrahydronaphthalene compound of Formula 103 which is appropriately substituted with the $R_3$ and $R_2$ groups (as these are defined in connection with Formula 101) serves as the starting material. A preferred example of a compound of Formula 103 is 1,3,3,4-tetrahydro-1,1-dimethyl-naphthalene, which is described in the chemical literature (Mathur et al. *Tetrahedron*, 1985, 41:1509. A presently preferred route for the synthesis of this compound from 1-bromo-3-phenylpropane is also described in the experimental section of the present application.

The compound of Formula 103 is reacted in a Friedel Crafts type reaction with an acid chloride having the structure $R_{16}CH_2COCl$ ($R_{16}$ is defined as in connection with Formula 101) and is thereafter oxidized with chromium trioxide in acetic acid to provide the isomeric 6 and 7 acyl-3,4-dihydro-1(2H)-naphthalenone derivatives. Only the 6-acyl derivative which is of interest from the standpoint of the present invention, is shown by structural formula (Formula 104) in Reaction Scheme 101. In the preparation of the presently preferred compounds of this invention the $R_1$ groups represent methyl, $R_2$, $R_3$ and $R_{16}$ are H, and therefore the preferred intermediate corresponding to Formula 104 is 3,4-dihydro-4,4-dimethyl-6-acetyl-1(2H)-naphthalenone.

The exocyclic ketone function of the compound of Formula 104 is thereafter protected as a ketal, for example by treatment with ethylene glycol in acid, to provide the 1,3-dioxolanyl derivative of Formula 105. The compound of Formula 105 is then reacted with a Grignard reagent of the formula $R_{14}MgBr$ ($R_{14}$ is defined as in connection with Formula 101) to give the 1,2,3,4-tetrahydro-1-hydroxy-naphthalene derivative of Formula 106. The exocyclic ketone function of the compound of Formula 106 is then deprotected by treatment with acid and dehydrated to give the compound of Formula 107.

An alternate method for obtaining the compounds of Formula 107 from the compounds of Formula 105 is by reacting the compounds of Formula 105 with sodium bis(trimethylsilyl)amide and 2-[N,N-bis(trifluoromethylsulfonyl)amino]-5-chloropyridine (Tf=$SO_2CF_3$) in an inert ether type solvent, such as tetrahydrofuran, at low temperatures (−78° C. and 0° C.). This reaction proceeds through a sodium salt intermediate which is usually not isolated and is not shown in Reaction Scheme 101. The overall reaction results in a trifluoromethylsulfonyloxy derivative, which is thereafter reacted with an organometal derivative derived from the aryl or heteroaryl compound $R_{14}H$, such that the formula of the organometal derivative is $R_{14}Met$ (Met stands for monovalent metal), preferably $R_{14}Li$. ($R_{14}$ is defined as in connection with Formula 101.) The reaction with the organometal derivative, preferably lithium derivative of the formula $R_{14}Li$ is usually conducted in an inert ether type solvent (such as tetrahydrofuran) in the presence of zinc chloride ($ZnCl_2$) and tetrakis(triphenylphosphine)palladium(0) ($Pd(PPh_3)_4$). The organolithium reagent $R_{14}Li$, if not commercially available, can be prepared from the compound $R_{14}H$ (or its halogen derivative $R_{14}$—$X_1$ where $X_1$ is halogen) in an ether type solvent in accordance with known practice in the art. The temperature range for the reaction between the reagent $R_{14}Li$ and the trifluoromethylsulfonyloxy derivative is, generally speaking, in the range of approximately −78° C. to 50° C.

The compounds of the invention are formed as a result of a condensation between the ketone compound of Formula 107 and an aldehyde or ketone of Formula 108. In the preparation of the preferred exemplary compounds of the invention the reagent of Formula 108 is 4-carboxybenzaldehyde ($R_{17}$—H). Examples of other reagents within the scope of Formula 108 and suitable for the condensation reaction and for the synthesis of compounds within the scope of the present invention (Formula 101) are: 5-carboxy-pyridine-2-aldehyde, 4-carboxy-pyridine-2-aldehyde, 4-carboxy-thiophene-2-aldehyde, 5-carboxy-thiophene-2-aldehyde, 4-carboxyfuran-2-aldehyde, 5-carboxy-furan-2-aldehyde, 4-carboxyacetophenone, 2-acetyl-pyridine-5-carboxylic acid, 2-acetyl-pyridine-4-carboxylic acid, 2-acetylthiophene-4-carboxylic acid, 2-acetyl-thiophene-5-carboxylic acid, 2-acetylfuran-4-carboxylic acid, and 2-acetyl-furan-5-carboxylic acid. The latter compounds are available in accordance with the chemical literature; see for example Decroix et al., *J. Chem Res.*(S), 4: 134 (1978); Dawson et al., *J. Med. Chem.* 29:1282 (1983); and Queguiner et al., *Bull Soc. Chimique de France* No. 10, pp. 3678–3683 (1969). The condensation reaction between the compounds of Formula 107 and Formula 108 is conducted in the presence of base in an alcoholic solvent. Preferably, the reaction is conducted in ethanol in the presence of sodium hydroxide. Those skilled in the art will recognize this condensation reaction as an aldol condensation, and in case of the herein described preferred examples (condensing a ketone of Formula 107 with an aldehyde of Formula 108) as a Claisen-Schmidt reaction. (See March: *Advanced Organic Chemistry: Reactions, Mechanisms, and Structure*, pp. 694–695 McGraw Hill (1968). The compounds of Formula 109 are within the scope of the present invention, and can also be subjected to further transformations resulting in additional compounds of the invention. Alternatively, the A—B group of Formula 108 may be a group which is within the scope of the invention, as defined in Formula 101, only after one or more synthetic transformations of such a nature which is well known and within the skill of the practicing organic chemist. For example, the reaction performed on the A—B group may be a deprotection step, homologation, esterification, saponification, amide formation or the like.

Generally speaking, regarding derivatization of compounds of Formula 109 and/or the synthesis of aryl and heteroaryl compounds of Formula 108 which can thereafter be reacted with compounds of Formula 107, well known and published general principles and synthetic methodology can be employed which is also described above under the subtitle "Synthetic Methods—Aryl Substituted Compounds".

Reaction Scheme 102

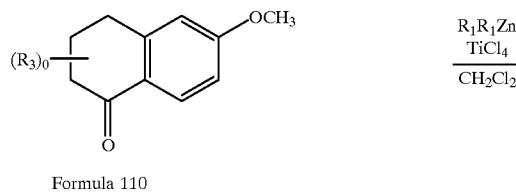

Formula 110

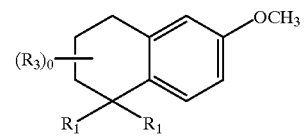

Formula 111

$$\begin{array}{c} CrO_3 \\ HOAc \\ Ac_2O \end{array} \downarrow$$

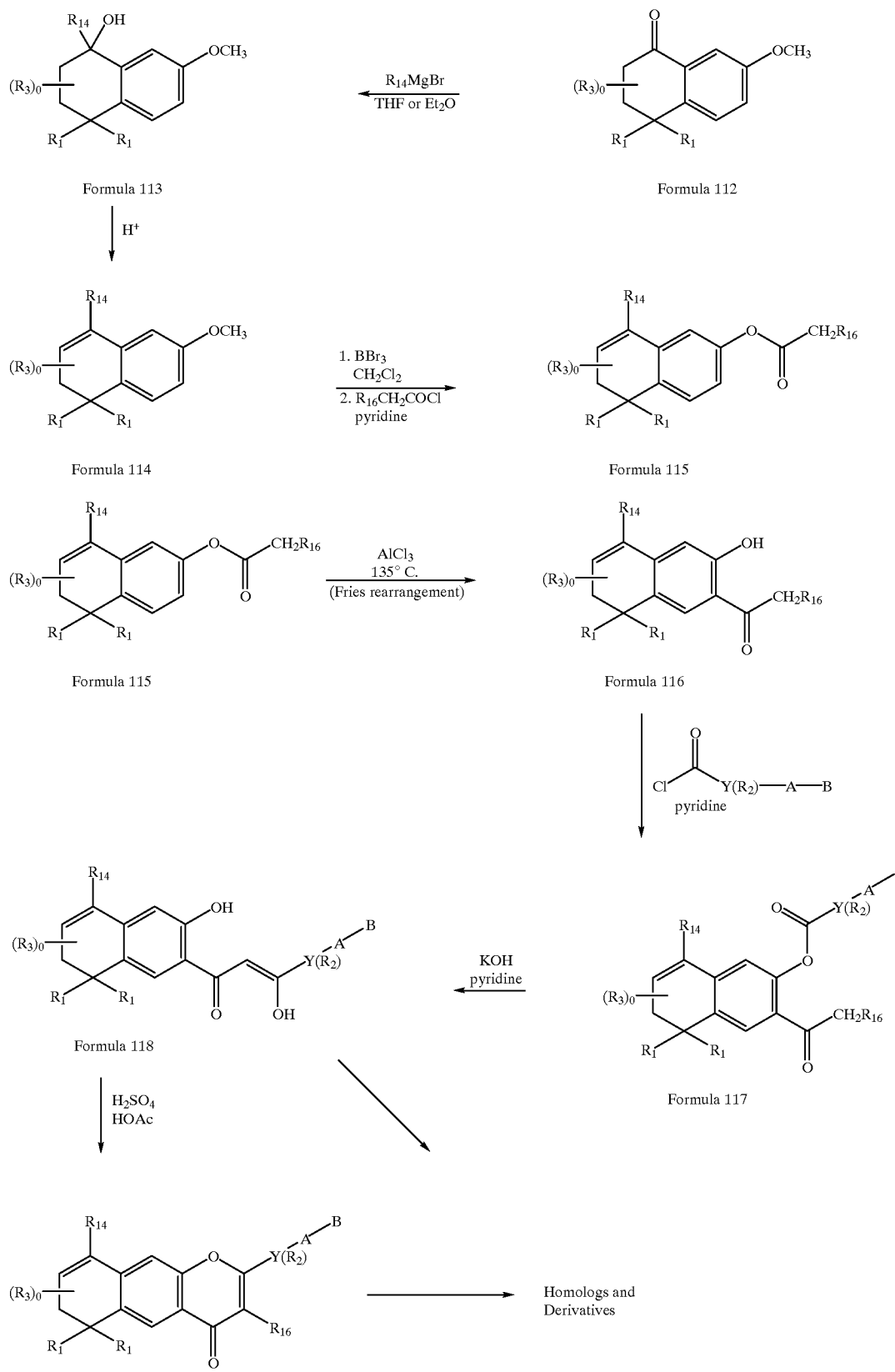

Referring now to Reaction Scheme 102, a synthetic route to those compounds of the invention is described in which, with reference to Formula 101 p is zero, $R_2$ in the aromatic portion of the condensed ring structure is OH and $R_{17}$ is OH. Those skilled in the art will readily recognize that these compounds are β-diketones in the enol form. Reaction Scheme 102 also describes a synthetic route to those compounds of the invention where p is 1. Those skilled in the art will readily recognize that the latter compounds are flavones. Thus, in accordance with this scheme a 1,2,3,4-tetrahydro-6-methoxynaphthalene-1-one derivative of Formula 110 is reacted with dialkyl zinc ($R_1Zn$) in the presence of titanium tetrachloride in a suitable solvent such as $CH_2Cl_2$ to replace the oxo function with the geminal dialkyl group $R_1R_1$, to yield a compound of Formula 111, where $R_1$ is lower alkyl. In preferred embodiments of the compounds of the invention which are made in accordance with Reaction Scheme 102 the $R_3$ group is hydrogen and $R_1$ are methyl. Accordingly, the dialkyl zinc reagent is dimethyl zinc, and the preferred starting material of Formula 110 is 1,2,3,4-tetrahydro-6-methoxynaphthalene-1-one. The latter compound is commercially available, for example from Aldrich Chemical Company. The 1,2,3,4-tetrahydro-1,2-dialkyl-6-methoxy naphthalene derivative of Formula 111 is thereafter oxidized with chromium trioxide in acetic acid and acetic anhydride to give a 1,2,3,4-tetrahydro-3,4-dialkyl-7-methoxy naphthalen-1-one derivative of Formula 112. The ketone compound of Formula 112 is reacted with a Grignard reagent ($R_{14}MgBr$, $R_{14}$ is defined as in connection with Formula 101) to yield a 1-hydroxy-1-aryl-3,4-dihydro-3,4-dialkyl-7-methoxy naphthalene derivative of Formula 113. The hydroxy compound of Formula 113 is subjected to elimination by heating, preferably in acid, to yield the dihydronaphthalene compound of Formula 114. The methyl group is removed from the phenolic methyl ether function of the compound of Formula 114 by treatment with boron tribromide in a suitable solvent, such as $CH_2Cl_2$, and thereafter the phenolic OH is acylated with an acylating agent that introduces the $R_{16}CH_2CO$ group, to give a compound of Formula 115. In the preferred embodiment $R_{16}$ is H, and therefore the acylating agent is acetyl chloride or acetic anhydride. The acetylation reaction is conducted in a basic solvent, such as pyridine. The acylated phenol compound of Formula 115 is reacted with aluminum chloride at elevated temperature, causing it to undergo a Fries rearrangement and yield the 1-aryl-3,4-dialkyl-3,4-dihydro-6-acyl-7-hydroxy-naphthalene compound of Formula 116. The phenolic hydroxyl group of the compound of Formula 116 is acylated with an acylating agent (such as an acid chloride) that introduces the CO—Y($R_2$)—A—B group to yield a compound of Formula 117. In the acid chloride reagent Cl—CO—Y($R_2$)—A—B (or like acylating reagent) the symbols Y, $R_2$ and A—B have the meaning defined in connection with Formula 101. In the preparation of a preferred compound of the invention in accordance with this scheme this reagent is $ClCOC_6H_4COOEt$ (the half ethyl ester half acid chloride of terephthalic acid).

The compound of Formula 117 is reacted with strong base, such as potassium hydroxyde in pyridine, to yield, as a result of an intramolecular Claisen condensation reaction, a compound of Formula 118. The compounds of Formula 118 are within the scope of the invention and of Formula 101, where there is an OH for the $R_2$ substituent in the aromatic portion of the condensed ring moiety and $R_{17}$ is OH. In connection with the foregoing reaction (intramolecular Claisen condensation) and the previously mentioned Fries rearrangement it is noted that these probable reaction mechanisms are mentioned in this description for the purpose of fully explaining the herein described reactions, and for facilitating the work of a person of ordinary skill in the art to perform the herein described reactions and prepare the compounds of the invention. Nevertheless, the present inventors do not wish to be bound by reaction mechanisms and theories, and the herein claimed invention should not be limited thereby.

The compounds of Formula 118 are reacted with strong acid, such as sulfuric acid, in a suitable protonic solvent, such as acetic acid, to yield the flavone compounds of Formula 119. The compounds of Formula 119 are also compounds of the invention, within the scope of Formula 101 where p is 1. Both the compounds of Formula 118 and Formula 119 can be subjected to further reactions and transformations to provide further homologs and derivatives, as described above in connection with Reaction Scheme 101. This is indicated in Reaction Scheme 102 as conversion to homologs and derivatives.

Reaction Scheme 103

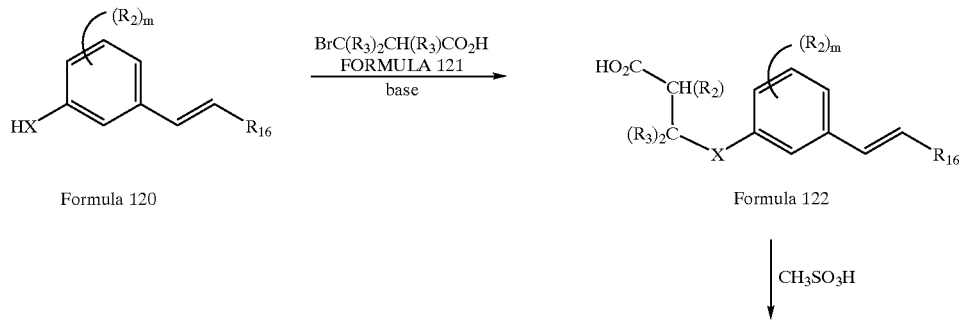

Formula 120

Formula 122

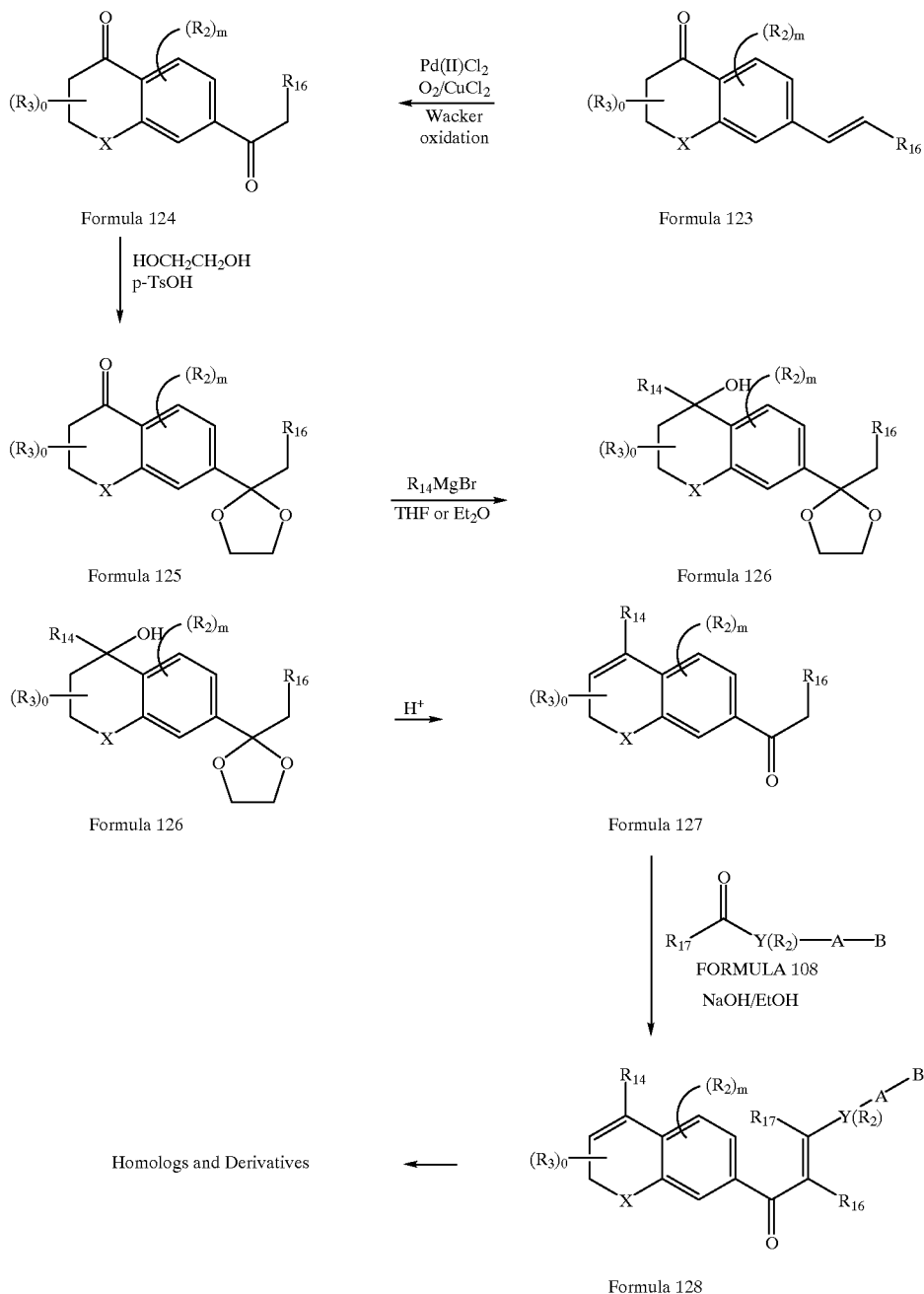

Referring now to Reaction Scheme 103 a synthetic route is shown leading to those compounds of the invention where, with reference to Formula 101 X is S, O or NR', p is zero and $R_{17}$ is H or lower alkyl. However, by applying the generic principles of synthesis shown in Reaction Scheme 102 the presently shown synthetic process can be modified or adapted by those of ordinary skill in the art to also obtain compounds of the invention where X is S, O or NR' and p is 1, or where X is S, O or NR' and p is zero, the $R_2$ group in the aromatic portion of the condensed ring moiety is OH and $R_{17}$ is OH.

The starting compound of Reaction Scheme 103 is a phenol, thiophenol or aniline derivative of Formula 120. In the presently preferred compounds of the invention the $R_2$ and $R_{16}$ groups are both hydrogen, and the preferred starting compounds of Formula 120 are 3-ethenyl-thiophenol or 3-ethenyl-phenol which are known in the chemical literature (Nuyken, et al. *Polym. Bull* (Berlin) 11:165 (1984). For the sake of simplifying the present specification, in the ensuing description X can be considered primarily sulfur as for the preparation of benzothiopyran derivatives of the present invention. It should be kept in mind, however, that the herein described scheme is also suitable, with such modifications which will be readily apparent to those skilled in the art, for the preparation of benzopyran (X=O) and dihydroquinoline (X=NR') compounds within the scope of the present invention. Thus, the compound of Formula 120 is reacted under basic condition with a 3-bromo carboxylic acid of the Formula 121. In this reaction scheme the symbols have the meaning described in connection with Formula 101. An example for the reagent of Formula 121 where $R_3$ is hydrogen, is 3-bromopropionic acid. The reaction with the 3-bromocarboxylic acid of Formula 121 results in the compound of Formula 122. The latter is cyclized by treatment with acid to yield the 7-ethenyl-thiochroman-4-one derivative (when X is S) or 7-ethenyl-chroman derivative (when X is 0) of Formula 123. The 7-ethenyl-thiochroman-4-one or 7-ethenyl-chroman-4-one derivative of Formula 123 is oxidized in the presence of Pd(II)Cl$_2$ and CuCl$_2$ catalysts to provide the corresponding 7-acyl (ketone) compound of Formula 124. Those skilled in the art will recognize the latter reaction as a Wacker oxidation. The exocyclic ketone group of the compound of Formula 124 is protected in the form of a ketal, for example by treatment with ethylene glycol in acid, to provide the 1,3-dioxolanyl derivative of Formula 125. Thereafter the compound of Formula 125 is subjected to a sequence of reactions analogous to those described for the compounds of Formula 105 in Reaction Scheme 101. Thus, the 1,3-dioxolanyl derivative of Formula 125 is reacted with a Grignard reagent of the formula R$_{14}$MgBr to give the tertiary alcohol of Formula 126, which is thereafter dehydrated in acid to provide the benzothiopyran (X is S), benzopyran (X is O) or dihydroquinoline (X is NR') derivative of Formula 127. The ketone compound of Formula 127 is then reacted in the presence of base with the reagent of Formula 108 in an aldol condensation (Claisen-Schmidt) reaction to provide compounds of the invention of Formula 128. The compounds of Formula 128 can be converted into further homologs and derivatives, as described above in connection with Reaction Schemes 101 and 102.

SPECIFIC EXAMPLES 2-hydroxy-2-methyl-5-phenylpentane

To a mixture of magnesium turnings 13.16 g (0.541 mol) in 200 ml of anhydrous Et$_2$O was added 100.0 g (0.492 mol) of 1-bromo-3-phenyl propane as a solution in 100 ml of Et$_2$O. After of 5–10 ml of the solution had been added, the addition was stopped until the formation of the Grignard reagent was in progress. The remaining bromide was then added over 1 hour. The Grignard reagent was stirred for 20 minutes at 35° C. and then 31.64 g (0.541 mol) of acetone was added over a 45 minute period. The reaction was stirred overnight at room temperature before being cooled to 0° C. and acidified by the careful addition of 20% HCl. The aqueous layer was extracted with Et$_2$O (3×200 ml) and the combined organic layers washed with water, and saturated aqueous NaCl before being dried over MgSO$_4$. Removal of the solvent under reduced pressure and distillation of the residue afforded 63.0 g (72%) of the product as a pale-yellow oil, bp 99–102° C./0.5 mm Hg. 1H NMR (CDCl$_3$): δ 7.28–7.18 (5H, m), 2.63 (2H, t, J=7.5 Hz), 1.68 (2H, m), 1.52 (2H, m), 1.20 (6H, s).

1,2,3,4-tetrahydro-1,1-dimethylnaphthalene

A mixture of P$_2$O$_5$ (55.3 g, 0.390 mol) in 400 ml of methanesulfonic acid was heated to 105° C. under argon until all of the solid had dissolved. The resulting solution was cooled to room temperature and 2-hydroxy-2-methyl-5-phenylpentane (63.0 g, 0.354 mol) added slowly with stirring. After 4 hours the reaction was quenched by carefully pouring the solution onto 1 L of ice. The resulting mixture was extracted with Et$_2$O (4×125 ml)and the combined organic layers washed with water, saturated aqueous NaHCO$_3$, water, and saturated aqueous NaCl before being dried over MgSO$_4$. Concentration of the solution under reduced pressure, followed by distillation afforded 51.0 g (90%) of the product as a clear colorless oil, bp. 65–67° C./1.1 mmHg. 1H NMR (CDCl$_3$): δ 7.32 (1H, d, J=7.4 Hz), 7.16–7.05 (3H, m), 2.77 (2H, t, J=6.3 Hz), 1.80 (2H, m), 1.66 (2H, m), 1.28 (6H, s).

3,4-dihydro-4,4-dimethyl-1(2H)-naphthalenone (Compound A)

A solution of 350 ml of glacial acetic acid and 170 ml of acetic anhydride was cooled to 0° C. and CrO$_3$, 25.0 g (0.25 mol) carefully added in small portions. The resulting mixture was stirred for 30 minutes before 120 ml of benzene was added. 1,2,3,4-tetrahydro-1,1-dimethylnaphthalene was added slowly as a solution in 30 ml of benzene. Upon completing the addition the reaction was stirred for 4 hours at 0° C. The solution was diluted with H$_2$O (200 ml) and extracted with Et$_2$O (5×50 ml). The combined organic layers were washed with water, saturated aqueous NaCO$_3$, and saturated aqueous NaCl, before being dried over MgSO$_4$. Removal of the solvents under reduced pressure, and distillation afforded 16.0 g (74%) of the product as a pale-yellow oil, bp 93–96° C./0.3 mm Hg 1H NMR (CDCl$_3$): δ 8.02 (1H, dd, J=1.3, 7.8 Hz), 7.53 (1H, m ), 7.42 (1H, d, J=7.9 Hz), 7.29 (1H, m), 2.74 (2H, t, J=6.8 Hz), 2.02 (2H, t, J=6.8 Hz), 1.40 (6H, s).

3,4-dihydro-4,4-dimethyl-7-bromo-1(2H)-naphthalenone (Compound B)

A 100 ml three-necked flask, fitted with an efficient reflux condenser and drying tube, and addition funnel, was charged with a mixture of AlCl$_3$ 9.5g (71.4 mmol) and 3 ml of CH$_2$Cl$_2$. The 3,4-dihydro-4,4-dimethyl-1(2H) naphthalenone (5.0 g, 28.7 mmol), was added dropwise with stirring (Caution:Exothermic Reaction!) to the mixture at room temperature. Bromine, 5.5 g (34.5 mmol), was then added very slowly, and the resulting mixture stirred for 2 hours at room temperature. (Note: if stirring stops, the mixture can be warmed to 70° C. until stirring resumes.) The reaction was then quenched by the slow addition of ice-cold 6M HCl. The mixture was extracted with Et$_2$O and the combined organic layers washed with water, saturated aqueous NaHCO$_3$, and saturated NaCl, before being dried over MgSO$_4$. Removal of the solvent under reduced pressure, and distillation of the residue afforded 5.8 g (80%) of the product as a pale-yellow oil which solidified on standing, bp: 140° C./0.4 mm Hg. 1H NMR (CDCl$_3$): δ 8.11 (1H, d, J=3.0 Hz), 7.61 (1H, dd, J=3.0, 9.0 Hz), 7.31 (1H, d, J=9.0 Hz), 2.72 (2H, t, J=6.0 Hz), 2.01 (2H, t, J=6.0 Hz), 1.28 (6H, s).

1,2,3,4-tetrahydro-1-hydroxy-1-(4-methylphenyl)-4,4-dimethyl-7-bromonaphthalene (Compound C)

To a mixture of magnesium turnings (648.0 mg, 27.0 mmol) in 25 ml of THF was added a solution of 4-bromotoluene (5.40 g, 31.8 mmol) in 10 ml of THF in two portions. The reaction was initiated by the addition of 2 ml of the solution, followed by the slow addition of the remaining solution via an addition funnel. The mixture was stirred at room temperature for 1 hour, and then the solution was transferred to a second flask using a canula. To the resulting Grignard reagent was added 4.0 g (15.9 mmol) of 3,4-dihydro-4,4-dimethyl-7-bromo-1-(2H)-naphthalenone (Compound B) as a solution in 15 ml of THF. The resulting solution was heated to reflux overnight, cooled to room temperature, and the reaction quenched by the careful addition of ice-cold 10% HCl. Extraction with Et$_2$O was followed by washing of the combined organic layers with H$_2$O and saturated aqueous NaCl, then drying over MgSO$_4$. Removal of the solvent under reduced pressure provided an oil which afforded the product as a colorless solid after column chromatography (hexanes/EtOAc, 96:4). 1H NMR (CDCl$_3$): δ 7.36 (1H, dd, J=2.1, 7.6 Hz), 7.26 (3H, m), 7.12 (3H, s), 2.34 (3H, s), 2.24–2.04 (2H, m), 1.81 (1H, m), 1.55 (1H, m), 1.35 (3H, s), 1.30 (3H, s).

3,4-dihydro-1-(4-methylphenyl)-4,4-dimethyl-7-bromonaphthalene (Compound D)

A flask equipped with a Dean-Stark trap was charged with 3.4 g of (9.85 mmol) of 1,2,3,4-tetrahydro-1-hydroxy-1-(4-methylphenyl)-4,4-dimethyl-7-bromonaphthalene (Compound C) and 40 ml of benzene. A catalytic amount of p-toluenesulfonic acid monohydrate was added and the resulting solution heated to reflux for 2 hours. Upon cooling to room temperature, $Et_2O$ was added and the solution washed with $H_2O$, saturated aqueous $NaHCO_3$, and saturated aqueous NaCl then dried over $MgSO_4$. Removal of the solvents under reduced pressure, and column chromatography (100% hexane/silica gel) afforded the title compound as a colorless solid. 1H NMR ($CDCl_3$): δ 7.32 (1H, dd, J=2.1, 8.2 Hz), 7.21 (5H, m), 7.15 (1H, d, J=2.1 Hz), 5.98 (1H, t, J=4.7 Hz), 2.40 (3H, s), 2.32 (2H, d, J=4.7 Hz), 1.30 (6H, s).

7-Ethynvl-3,4-dihydro-4,4-dimethylnaphthalen-1(2H)-one (Compound E)

To a solution (flushed for 15 minutes with a stream of argon) of 7 g. (27.6 mmol) of 3,4-dihydro-4,4-dimethyl-7-bromo-1-(2H)-naphthalenone (Compound B) in 150 ml of triethylamine was added 0.97 g (1.3 mmol) of bis(triphenylphosphine)palladium(II) chloride and 0.26 g (1.3 mmol) of cuprous iodide. The solution mixture was flushed with argon for 5 minutes and then 39 ml (36.6 mmol) of (trimethylsilyl)acetylene was added. The reaction mixture was sealed in a pressure tube and placed in a preheated oil bath (100° C.) for 24 hours. The reaction mixture was then filtered through Celite, washed with $Et_2O$ and the filtrate concentrated in vacuo to give crude 7-(trimethylsilyl)ethynyl-3,4-dihydro-4,4-dimethylnaphthalen-1-(2H)-one. To a solution of this crude TMS-acetylenic compound in 50 ml of methanol was added 0.6 g (4.3 mmol) of $K_2CO_3$. The mixture was stirred for 8 hours at ambient temperature and then filtered. The filtrate was concentrated in vacuo, diluted with $Et_2O$, washed with water, 10% HCl and brine, dried over $MgSO_4$ and concentrated in vacuo. Purification by column chromatography (silica, 10% EtOAc-hexane) yielded the title compound as a white solid. PMR ($CDCl_3$): δ 1.39 (6H, s), 2.02 (2H, t, J=7.0 Hz), 2.73 (2H, t, J=7.0 Hz), 3.08 (1H, s), 7.39 (1H, d, J=8.2 Hz), 7.61 (1H, dd, J=1.8, 8.2 Hz), 8.14 (1H, d, J=91.8 Hz).

Ethyl-4-iodobenzoate

To a suspension of 10 g (40.32 mmol) of 4-iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated $NaHCO_3$ and saturated NaCl solutions and dried ($MgSO_4$). Solvent was then removed in vacuo and the residue Kugelrohr distilled (100° C.; 0.55 mm) to give the title compound as a colorless oil, PMR ($CDCl_3$): δ 1.42 (3H, t, J~7 Hz), 4,4 (2H, q, J~7 Hz), 7.8 (4H).

6-iodonicotinic acid

Sodium iodide (20.59 g, 137.40 mmol) was cooled to −78° C. under argon and then hydriodic acid (97.13 g, 759.34 mmol) was added. The cooling bath was removed and the suspension was stirred for 5 minutes. To this mixture was added 6-chloronicotinic acid (22.09 g, 140.20 mmol) and the resulting mixture was slowly warmed to ambient temperature with stirring. The mixture was heated to reflux at 125° C. for 24 hours, cooled to ambient temperature and poured into acetone (500 ml) at 0° C. The yellow solid was collected by filtration and washed with 200 ml of 1N aqueous $NaHSO_3$ solution. Recrystallization from methanol (crystals were washed with ethyl ether) afforded the title compound as white crystals: mp 177–179° C. [lit. mp 187–192, Newkome et al. "Reductive Dehalogenation of Electron-Poor Heterocycles: Nicotinic Acid Derivatives" *J. Org. Chem.* 51: 953–954 (1986). 1H NMR (DMSO-d6): δ 8.81 (1H, dd, J=0.8, 2.4 Hz), 8.01 (1H, dd, J=0.8, 8.2 Hz), 7.91 (1H, dd, J=2.4, 8.2 Hz).

Ethyl 6-iodonicotinoate

To a suspension of 6-iodonicotinic acid (23.38 g, 94.20 mmol) in dichloromethane (100 ml) was added a solution of 1-(3-dimethylaminopropyl)-3-ethylcarbodiimide hydrochloride (19.86 g, 103.6 mmol) in dichloromethane (250 ml). To this mixture was added ethanol (12.40 g, 269.27 mmol) followed by dimethylaminopyridine (1.15 g, 9.41 mmol). The mixture was heated at 50° C. for 24.5 hours, concentrated in vacuo, and diluted with water (200 ml) then extracted with ethyl ether (550 ml). The combined organic phases were washed with saturated aqueous NaCl, dried ($MgSO_4$) and concentrated to a yellow solid. Purification by flash chromatography (silica, 10% EtOAc-hexane) afforded the title compound as white needles: mp 48–49° C.; 1H NMR ($CDCl_3$): δ 8.94 (1H, d, J=2.1 Hz), 7.91 (1H, dd, J=2.1, 8.2 Hz), 7.85 (1H, d, J=8.2 Hz), 4.41 (2H, q, J=7.1 Hz), 1.41 (3H, t, J=7.1 Hz).

Ethyl 4-[(5,6,7,8-tetrahydro-5,5-dimethyl-8-oxo-2-naphthalenyl)ethynvl]benzoate (Compound F)

To a solution of 4 g (21.7 mmol) of 7-ethynyl-3,4-dihydro-4,4-dimethylnaphthalen-1-(2H)-one (Compound E) flushed for 15 minutes with a stream of argon, and 6 g (21.7 mmol) of ethyl 4-iodobenzoate in 100 ml of triethylamine was added 5 g (7.2 mmol) of bis(triphenylphosphine) palladium(II) chloride and 1.4 g (7.2 mmol) of cuprous iodide. The mixture was flushed with argon for 5 minutes and then stirred at ambient temperature for 18 hours. The reaction mixture was filtered through Celite and the filtrate was concentrated in vacuo. Purification by flash chromatography (silica, 10% EtOAc-hexane) yielded the title compound as a white solid. PMR ($CDCl_3$): δ 1.41 (3H, t, J=7.2 Hz), 1.41 (6H, s), 2.04 (2H, t, J=6.5 Hz), 2.76 (2H, t, J=6.5 Hz), 4.40 (2H, q, J=7.2 Hz), 7.44 (1H, d, J=8.2 Hz), 7.59 (2H, d, J=8.4 Hz), 7.68 (1H, dd, J=1.8, 8.2 Hz), 8.04 (2H, d, J=8.4 Hz), 8.15 (1H, d, J=1.8 Hz).

Ethyl 4-[(5,6-dihydro-5,5-dimethyl-8-(trifluoromethylsulfonvl)oxy-2-naphthalenyl)ethynyl)]benzoate (Compound G)

To a cold solution (−78° C.) of 291.6 mg (1.59 mmol) of sodium bis(trimethylsily)amide in 5.6 ml of THF was added a solution of 500.0 mg (1.44 mmol) of ethyl 4-[(5,6,7,8-tetrahydro-5,5-dimethyl-8-oxo-2-naphthalenyl)ethynyl]benzoate (Compound F) in 4.0 ml of THF. The reaction mixture was stirred at −78° C. for 35 minutes and then a solution of 601.2 mg (1.59 mmol) of 5-chloro(2-bis-triflouromethylsulfonyl)imide in 4.0 ml of THF was added. After stirring at −78° C. for 1 hour, the solution was warmed to 0° C. and stirred for 2 hours. The reaction was quenched by the addition of saturated aqueous $NH_4Cl$. The mixture was extracted with EtOAc (50 ml) and the combined organic layers were washed with 5% aqueous NaOH, water, and brine. The organic phase was dried over $Na_2SO_4$ and then concentrated in vacuo to a yellow oil. Purification by column chromatography (silica, 7% EtOAc-hexanes) yielded the title compound as a colorless solid. 1H NMR ($CDCl_3$): δ 8.04 (2H, dd, J=1.8, 8.4 Hz), 7.60 (2H, dd, J=1.8, 8.4 Hz), 7.51 (2H, m), 7.32 (1H, d, J=8.0 Hz), 4.40 (2H, q, J=7.1 Hz), 6.02 (1H, t, J=5.0 Hz), 2.44 (2H, d, J=5.0 Hz), 1.43 (3H, t, J=7.1 Hz), 1.33 (6H, s).

Ethyl 4-[(5,6-dihydro-5,5-dimethyl-8-(4-methylphenvl)-2-naphthalenyl)ethynyl]benzoate (Compound 1)

A solution of 4-lithiotoluene was prepared by the addition of 189.9 mg (1.74 ml, 2.96 mmol) of t-butyl lithium (1.7M solution in hexanes) to a cold solution (−78° C.) of 253.6 mg (1.482 mmol) of 4-bromotoluene in 2.0 ml of THF. After stirring for 30 minutes a solution of 269.4 mg (1.977 mmol) of zinc chloride in 3.0 ml of THF was added. The resulting solution was warmed to room temperature, stirred for 30 minutes, and added via cannula to a solution of 472.9 mg (0.988 mmol) of ethyl 4-[(5,6-dihydro-5,5-dimethyl-8-(trifluoromethylsulfonyl) oxy-2-naphthalenyl)ethynyl]benzoate (Compound G) and 50 mg (0.04 mmol) of tetrakis(triphenylphosphine)palladium(0) in 4.0 ml of THF. The resulting solution was heated at 50° C. for 45 minutes, cooled to room temperature and diluted with sat. aqueous $NH_4Cl$. The mixture was extracted with EtOAc (40 ml) and the combined organic layers were washed with water and brine. The organic phase was dried over $NHa_2SO_4$ and concentrated in vacuo to a yellow oil. Purification by column chromatography (silica, 5% EtOAc-hexanes) yielded the title compound as a colorless solid. 1H NMR (d6-acetone): δ 1.35 (6H, s), 1.40 (3H, t, J=7.1 Hz), 2.36 (2H, d, J=4.7 Hz), 2.42 (3H,s), 4.38 (2H, q, J=7.1 Hz), 5.99 (1H, t, J=4.7 Hz), 7.25 (5H, m), 7.35 (2H, m), 7.52 (2H, d, J=8.5 Hz), 7.98 (2H, d, J=8.5 Hz).

Ethyl 4-[(5,6-dihydro-5,5-dimethyl-8-phenyl-2-naphthalenyl)ethynyl]benzoate (Compound 1a)

Employing the same general procedure as for the preparation of ethyl 4-[(5,6-dihydro-5,5-dimethyl-8-(4-methylphenyl)-2-naphthalenyl)ethynyl]benzoate (Compound 1), 203.8 mg (0.43 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 58.2 mg (0.36 ml, 0.69 mmol) of phenyllithium (1.8M solution in cyclohexane/$Et_2O$), 116.1 mg (0.85 mmol) of zinc chloride and 13.8 mg (0.01 mmol) of tetrakis(triphenylphosphine)palladium(0). PMR ($CDCl_3$): δ 1.36 (6H, s), 1.40 (3H, t, J=7.1 Hz), 2.37 (2H, d, J=4.7 Hz), 4.38 (2H, q, J=7.1 Hz), 6.02 (1H, t, J=4.7 Hz), 7.20 (1H, d, J=1.5 Hz), 7.27 (1H, m), 7.39 (6H, m), 7.52 (2H, d, J=8.2 Hz), 7.98 (2H, d, J=8.2 Hz).

Ethyl 4-[(5,6-dihydro-5,5-dimethyl-8-(3-methylphenyl)-2-naphthalenyl)ethynyl]benzoate (Compound 2)

Employing the same general procedure as for the preparation of ethyl 4-[(5,6-dihydro-5,5-dimethyl-8-(4-methylphenyl)-2-naphthalenyl)ethynyl]benzoate (Compound 1), 250.0 mg (0.522 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 284.8 mg (2.090 mmol) of zinc chloride, 24 mg (0.02 mmol) of tetrakis(triphenylphosphine)palladium(0) in 2.0 ml of THF, and 3-methylphenyl lithium (prepared by adding 201.2 mg (1.86 ml, 3.14 mmol) of tert-butyllithium (1.7M solution in pentane) to a cold solution (−78° C.) of 274.0 mg (1.568 mmol) of 3-methylbromobenzene in 2.0 ml of THF). 1H NMR ($CDCl_3$): δ 7.99 (2H, d, J=8.4 Hz), 7.51 (2H, d, J=8.4 Hz), 7.39–7.14 (7H, m), 5.99 (1H, t, J=4.7 Hz), 4.37 (2H, q, J=7.1 Hz), 2.60 (3H, s), 2.35 (2H, d, J=4.7 Hz), 1.39 (3H, t, J=7.1 Hz), 1.34 (6H, s).

Ethyl 4-[(5,6-dihydro-5,5-dimethyl-8-(2-methylphenyl)-2-naphthalenyl)ethynyl]benzoate (Compound 3)

Employing the same general procedure as for the preparation of ethyl 4-[(5,6-dihydro-5,5-dimethyl-8-(4-methylphenyl)-2-naphthalenyl)ethynyl]benzoate (Compound 1), 200.0 mg (0.418 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 199.4 mg (1.463 mmol) of zinc chloride, 24 mg (0.02 mmol) of tetrakis(triphenylphosphine)palladium(0) in 4.0 ml of THF, and 2-methylphenyl lithium (prepared by adding 133.9 mg (1.23 ml, 2.09 mmol) of tert-butyllithium (1.7M solution in pentane) to a cold solution (−78° C.) of 178.7 mg (1.045 mmol) of 2-methylbromobenzene in 2.0 ml of THF). 1H NMR ($CDCl_3$): δ 7.97 (2H, d, J=8.4 Hz), 7.50 (2H, d, J=8.4 Hz), 7.49–7.19 (6H, m), 6.81 (1H, d, J=1.6 Hz), 5.89 (1H, t, J=4.5 Hz), 4.36 (2H, q, J=7.1 Hz), 2.43–2.14 (2H, dq, J=3.7, 5.4 Hz), 2.15 (3H, s), 1.39–1.34 (9H, m).

Ethyl 4-[(5,6-dihydro-5,5-dimethyl-8-(3,5-dimethylphenyl)-2-naphthalenyl)ethynyl]benzoate (Compound 4)

Employing the same general procedure as for the preparation of ethyl 4-[(5,6-dihydro-5,5-dimethyl-8-(4-methylphenyl)-2-naphthalenyl)ethynyl]benzoate (Compound 1), 250.0 mg (0.522 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 249.0 mg (1.827 mmol) of zinc chloride, 24 mg (0.02 mmol) of tetrakis(triphenylphosphine)palladium(0) in 2.0 ml of THF, and 3,5-dimethylphenyl lithium (prepared by adding 167.7 mg (1.54 ml, 2.62 mmol) of tert-butyllithium (1.7M solution in pentane) to a cold solution (−78° C.) of 249.0 mg (1.305 mmol) of 3,5-dimethylbromobenzene in 2.0 ml of THF). 1H NMR ($CDCl_3$): δ 7.98 (2H, d, J=8.4 Hz), 7.52 (2H, d, J=8.4 Hz), 7.40–7.33 (2H, m), 7.20 (1H, d, J=1.6 Hz), 7.00 (1H, s), 6.97 (2H, s), 5.97 (1H, t, J=4.8 Hz), 4.37 (2H, q, J=7.1 Hz), 2.36 (6H, s), 2.34 (2H, d, J=4.8 Hz), 1.39 (3H, t, J=7.1 Hz), 1.37 (6H, s).

Ethyl 4-[(5,6-dihydro-5,5-dimethyl-8-(4-ethylphenyl)-2-naphthalenyl)ethynyl]benzoate (Compound 5)

Employing the same general procedure as for the preparation of ethyl 4-[(5,6-dihydro-5,5-dimethyl-8-(4-methylphenyl)-2naphthalenyl)ethynyl]benzoate (Compound 1), 250.0 mg (0.522 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 249.0 mg (1.827 mmol) of zinc chloride, 24 mg (0.02 mmol) of tetrakis(triphenylphosphine)palladium(0) in 2.0 ml of THF, and 4-ethylphenyl lithium (prepared by adding 167.7 mg (1.54 ml, 2.62 mmol) of tert-butyllithium (1.7M solution in pentane) to a cold solution (−78° C.) of 244.0 mg (1.305 mmol) of 4-ethylbromobenzene in 2.0 ml of THF).

1H NMR ($CDCl_3$): δ 7.99 (2H, d, J=8.4 Hz), 7.51 (2H, d, J=8.4 Hz), 7.42–7.24 (7H, m), 5.99 (1H, t, J=4.7 Hz), 4.37 (2H, q, J=7.1 Hz), 2.71 (2H, q, J=7.6 Hz), 2.35 (2H, d, J=4.7 Hz), 1.39 (3H, t, J=7.1 Hz), 1.34 (6H, s).

Ethyl 4-[(5,6-dihydro-5,5-dimethyl-8-(4-(1,1-dimethylethyl)phenyl)-2-naphthalenyl)ethynyl]benzoate (Compound 6)

Employing the same general procedure as for the preparation of ethyl 4-[(5,6-dihydro-5,5-dimethyl-8-(2-thiazolyl)-2-naphthalenyl)ethynyl]benzoate (Compound 1), 250.0 mg (0.52 mmol) of ethyl 4-[(5,6-dihydro-5,5-dimethyl-8-(trifluoromethylsulfonyl) oxy-2-naphthalenyl)ethynyl]benzoate (Compound G) was converted into the title compound (colorless solid) using 142.4 mg (1.045 mmol) of zinc chloride and 4-tert-butylphenyl lithium (prepared by adding 100.6 mg (0.97 ml, 1.57 mmol) of tert-butyllithium (1.5M solution in pentane) to a cold solution (−78° C.) of 167.0 mg (0.78 mmol) of 4-tert-butylbromobenzene in 1.0 ml of THF). 1H NMR ($CDCl_3$): δ 7.99 (2H, d, J=8.4 Hz), 7.55 (2H, d, J=8.4 Hz), 7.28–7.45 (7H, m), 6.02 (1H, t, J=4.9 Hz), 4.38 (2H, q, J=7.2 Hz), 2.36 (2H, d, J=4.9 Hz), 1.59 (3H, s), 1.40 (3H, t, J=7.2 Hz), 1.39 (9H, s), 1.35 (6H, s).

Ethyl 4-[(5,6-dihydro-5,5-dimethyl-8-(4-chlorophenyl)-2-naphthalenyi)ethynyl]benzoate (Compound 7)

Employing the same general procedure as for the preparation of ethyl 4-[(5,6-dihydro-5,5-dimethyl-8-(4-methylphenyl)-2-naphthalenyl)ethynyl]benzoate (Compound 1), 250.0 mg (0.522 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 249.0 mg (1.827 mmol) of zinc chloride, 24 mg (0.02 mmol) of tetrakis(triphenylphosphine)palladium(0) in 2.0 ml of THF, and 4-chlorophenyl lithium (prepared by adding 167.7 mg (1.54 ml, 2.62 mmol) of tert-butyllithium (1.7M solution in pentane) to a cold solution (−78° C.) of 252.4 mg (1.305 mmol) of 4-chloro-1-bromobenzene in 2.0 ml of THF). 1H NMR (CDCl$_3$): δ 7.98 (2H, d, J=8.4 Hz), 7.53 (2H, d, J=8.4 Hz), 7.40–7.27 (6H, m), 7.12 (1H, d, J=1.6 Hz), 6.00 (1H, t, J=4.8 Hz), 4.37 (2H, q, J=7.1 Hz), 2.35 (2H, d, J=4.8 Hz), 1.40 (2H, t, J=7.1 Hz), 1.34 (6H, s).

Ethyl 4-[(5,6-dihydro-5,5-dimethyl-8-(4-methoxphenvl-2naphthalenyl)ethynyl]benzoate (Compound 8)

Employing the same general procedure as for the preparation of ethyl 4-[(5,6-dihydro-5,5-dimethyl-8-(4-methylphenyl)-2-naphthalenyl)ethynyl]benzoate (Compound 1), 250.0 mg (0.522 mmol) of ethyl 4-[(5,6-dihydro-5,5-dimethyl-8-(trffluoromethylsulfonyl)oxy-2-naphthalenyl)ethynyl]benzoate (Compound G) was converted into the title compound (colorless solid) using 249.0 mg (1.827 mmol) of zinc chloride, 24 mg (0.02 mmol) of tetrakis(triphenylphosphine)palladium(0) in 2.0 ml of THF, and 4-methoxyphenyl lithium (prepared by adding 167.7 mg (1.54 ml, 2.62 mmol) of tert-butyllithium (1.7M solution in pentane) to a cold solution (−78° C.) of 244.1 mg (1.305 mmol) of 4-methoxy-1-bromobenzene in 2.0 ml of THF). 1H NMR (CDCl$_3$): δ 7.98 (2H, d, J=8.5 Hz), 7.52 (2H, d, J=8.6 Hz), 7.40–7.21 (5H, m), 6.95 (2H, d, J=8.7 Hz), 5.97 (1H, t, J=4.7 Hz), 4.37 (2H, q, J=7.1 Hz), 4.34 (3H, s), 2.34 (2H, d, J=4.7 Hz), 1.39 (3H, t, J=7.1 Hz), 1.34 (6H, s).

Ethyl 4-[(5,6-dihydro-5,5-dimethyl-8-(4-trifluoromethylphenyl)-2-naphthalenyi)ethynyl]benzoate (Compound 9)

Employing the same general procedure as for the preparation of ethyl 4-[(5,6-dihydro-5,5-dimethyl-8-(4-methylphenyl)-2-naphthalenyl)ethynyl]benzoate (Compound 1), 250.0 mg (0.522 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 249.0 mg (1.827 mmol) of zinc chloride, 24 mg (0.02 mmol) of tetrakis(triphenylphosphine)palladium(0) in 2.0 ml of THF, and 4-trifluoromethylphenyl lithium (prepared by adding 167.7 mg (1.54 ml, 2.62 mmol) of tert-butyllithium (1.7M solution in pentane) to a cold solution (−78° C.) of 296.6 mg (1.305 mmol) of 4-trifluoromethylbromobenzene in 2.0 ml of THF). 1H NMR (CDCl$_3$): δ 7.98 (2H, d, J=8.5 Hz), 7.67 (2H, d, J=8.3 Hz), 7.54–7.36 (6H, m), 7.10 (1H, d, J=1.6 Hz), 6.06 (1H, t, J=4.8 Hz), 4.37 (2H, q, J=7.1 Hz), 2.38 (2H, d, J=4.8 Hz), 1.39 (3H, t, J=7.1 Hz), 1.35 (6H, s).

Ethyl 4-[(5,6-dihydro-5,5-dimethl-8-(2-pyridyl)-2-naphthalenyl)ethynyl]benzoate (Compound 10)

Employing the same general procedure as for the preparation of ethyl 4-[(5,6-dihydro-5,5-dimethyl-8-(4-methylphenyl)-2-naphthalenyl)ethynyl]benzoate (Compound 1), 250.0 mg (0.52 mmol) of ethyl 4-[(5,6-dihydro-5,5-dimethyl-8-(trifluoromethylsulfonyl)oxy-2naphthalenyl)ethynyl]benzoate (Compound G) was converted into the title compound (colorless solid) using 142.4 mg (1.045 mmol) of zinc chloride and 2-lithiopyridine (prepared by the addition of 100.6 mg (0.97 ml, 1.57 mmol) of tert-butyllithium (1.5M solution in pentane) to a cold solution (−78° C.) of 123.8 mg (0.784 mmol) of 2-bromopyridine in 1.0 ml of THF). 1H NMR (d6-acetone): δ 8.64 (1H, m), 7.99 (2H, d, J=8.5 Hz), 7.85 (1H, ddd, J=1.8, 7.7, 9.5 Hz), 7.58 (2H, d, J=8.4 Hz), 7.50 (1H, d, J=7.7 Hz), 7.47 (2H, d, J=1.1 Hz), 7.35 (2H, m), 6.32 (1H, t, J=4.8 Hz), 4.34 (2H, q, J=7.2 Hz), 2.42 (2H, d, J=7.4 Hz), 1.35 (3H, t, J=7.0 hz), 1.35 (6H, s).

Ethyl 4-[(5,6-dihydro-5,5-dimethyl-8-(3-pyridyl)-2-naphthalenyl)ethynyl]benzoate (Compound 11)

Employing the same general procedure as for the preparation of ethyl 4-[(5,6-dihydro-5,5-dimethyl-8-(4-methylphenyl)-2-naphthalenyl)ethynyl]benzoate (Compound 1), 170.0 mg (0.35 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 142.4 mg (1.045 mmol) of zinc chloride and 3-lithiopyridine (prepared by the addition of 100.2 mg (0.92 ml, 1.56 mmol) of tert-butyllithium (1.5M solution in pentane) to a cold solution (−78° C.) of 123.8 mg (0.784 mmol) of 3-bromopyridine in 1.0 ml of THF). 1H NMR (CDCl$_3$): δ 8.63–8.61 (2H, dd, J=1.7 Hz), 7.99 2H, d, J=8.4 Hz), 7.67 (1H, dt, J=7.9 Hz), 7.52 (2H, d, J=8.4 Hz), 7.43–7.34 (3H, m), 7.10 (1H, d, J=1.6 Hz), 6.07 (1H, t, J=4.7 Hz), 4.37 (2H, q, J=7.1 Hz), 2.40 (2H, d, J=4.7 Hz), 1.390 (3H, t, J=7.1 Hz), 1.36 (6H, s).

Ethyl 4-[(5,6-dihydro-5,5-dimethyl-8-(2-methyl-5-pyridyl)-2-naphthalenyl)ethynyl]benzoate (Compound 12)

Employing the same general procedure as for the preparation of ethyl 4-[(5,6-dihydro-5,5-dimethyl-8-(4-methylphenlyl)-2-naphthalenyl)ethynyl]benzoate (Compound 1), 250.0 mg (0.522 mmol) of ethyl 4-[(5,6-dihydro-5,5-dimethyl-8-(trifiluoromethylsulfonyl)oxy-2-naphthalenyl)ethynyl]benzoate (Compound G) was converted into the title compound (colorless solid) using 142.4 mg (1.045 mmol) of zinc chloride and 2-methyl-5-lithiopyridine (prepared by the addition of 100.5 mg (0.92 ml, 1.57 mmol) of tert-butyllithium (1.7M solution in pentane) to a cold solution (−78° C.) of 134.8 mg (0.784 mmol) of 2-methyl-5-bromopyridine in 1.0 ml of THF). 1H NMR (CDCl$_3$): δ 8.50 (1H, d, J=2.2 Hz), 7.99 (2H, d, J=8.3 Hz), 7.56 (1H, dd, J=2.3, 8.0 Hz), 7.53 (2H, d, J=8.4 Hz), 7.43 (1H, dd, J=2.3, 8.0 Hz), 7.37 (2H, d, J=8.0 Hz), 7.21 (1H, d, J=8.1 Hz), 7.11 (1H, d, J=1.5 Hz), 6.04 (1H, t, J=4.7 Hz), 4.38 (2H, q, J=7.2 Hz), 2.63 (3H, s), 2.38 (2H, d, J=4.6 Hz), 1.40 (3H, t, J=7.1 Hz), 1.35 (6H, s).

Ethyl 4-[(5,6-dihydro-5,5-dimethyi-8-(3-((2,2-dimethylethyl)dimethylsiloxy)phenyl)-2-naphthalenyl)ethynyl]benzoate (Compound H)

Employing the same general procedure as for the preparation of ethyl 4-[(5,6-dihydro-5,5-dimethyl-8-(4-methylphenyl)-2-naphthalenyl)ethynyl]benzoate (Compound G), 150.0 mg (0.314 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 150.0 mg (1.10 mmol) of zinc chloride, 24 mg (0.02 mmol) of tetrakis(triphenylphosphine)palladium(0) in 2.0 ml of THF, and 3-((2,2-dimethylethyl)dimethylsiloxy)phenyl lithium (prepared by adding 100.2 mg (0.92 ml, 1.564 mmol) of tert-butyllithium (1.7M solution in pentane) to a cold solution (−78° C.) of 226.0 mg (0.787 mmol) of 3-((2, 2-dimethylethyl)dinethylsiloxy)bromobenzene in 2.0 ml of THF). 1H NMR (CDCl$_3$): δ 7.98 (2H, d, J=8.4 Hz), 7.51

(2H, d, J=8.4 Hz), 7.40–7.22 (4H, m), 6.95 (1H, d, J=7.6 Hz), 6.84–6.82 (2H, m), 6.00 (1H, t, J=4.7 Hz), 4.37 (2H, q, J=7.1 Hz), 2.35 (2H, d, J=4.7 Hz), 1.39 (3H, t, J=7.1 Hz), 1.34 (3H, s), 0.99 (9H, s), 0.23 (6H, s).

Ethyl 4-[(5,6-dihydro-5,5-dimethyl-8-(4-((2,2-dhmethylethyl)dimethylsiloxy)phenyl)-2-naphthalenyl)ethynyl]benzoate (Compound I)

Employing the same general procedure as for the preparation of ethyl 4-[(5,6-dihydro-5,5-dimethyl-8-(4-methylphenyl)-2-naphthalenyl)ethynyl]benzoate (Compound 1), 210.0 mg (0.439 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 209.0 mg (1.53 mmol) of zinc chloride, 24 mg (0.02 mmol) of tetrakis(triphenylphosphine)palladium(0) in 2.0 ml of THF, and 4-((2,2-dimethylethyl)dimethylsiloxy)phenyl lithium (prepared by adding 140.3 mg (1.30 ml, 2.19 mmol) of tert-butyllithium (1.7M solution in pentane) to a cold solution (−78° C.) of 315.0 mg (1.09 mmol) of 4-((2,2-dimethylethyl)dimethylsiloxy)bromobenzene in 2.0 ml of THF). 1H NMR (CDCl$_3$): δ 7.98 (2H, d, J=8.4 Hz), 7.51 (2H, d, J=8.4 Hz), 7.39–7.25 (3H, m), 7.21 (2H, d, J=8.5 Hz), 5.87 (2H, d, J=8.5 Hz), 5.96 (1H, t, J=4.7 Hz), 4.37 (2H, q, J=7.1 Hz), 2.33 (2H, d, J=4.7 Hz), 1.39 (3H, t, J=7.1 Hz), 1.33 (6H, s), 1.01 (9H, s), 0.25 (6H, s).

Ethyl 4-[(5,6-dihydro-5,5-dimethyl-8-(3-hydroxyphenyl)-2-naphthalenyl)ethynyl]benzoate (Compound 13)

To a solution of ethyl 4-[(5,6-dihydro-5,5-dimethyl-8-(3-((2,2-dimethylethyl)-dimethylsiloxy)-phenyl)-2-naphthalenyl)ethynyl]benzoate (Compound H) 60.0 mg (0.114 mmol) in 1.0 ml of THF at room temperature was added 91.5 mg (0.35 ml, 0.35 mmol) of tetrabutylamonium flouride (1M solution in THF). After stirring overnight, the solution was diluted with EtOAc and washed with H$_2$O and saturated aqueous NaCl, before being dried over MgSO$_4$. Removal of the solvents under reduced pressure, followed by column chromatography (4:1, Hexanes:EtOAc) afforded the title compound as a colorless solid. 1H NMR (CDCl$_3$): δ 7.98 (2H, d, J=7.8 Hz), 7.52 (2H, d, J=8.3 Hz), 7.39–7.21 (4H, m), 6.93 (1H, d, J=7.5 Hz), 6.84 (1H, d, 7.1 Hz), 6.83 (1H, s), 6.01 1H, t, J=4.7 Hz), 4.91 (1H, s), 4.39 (2H, q, J=7.1 Hz), 2.35 (2H, d, J=4.7 Hz), 1.39 (3H, t, J=7.1 Hz), 1.34 (6H, s).

Ethyl 4-[(5,6-dihydro-5,5-dimethyl-8-(4-hydroxphenl)-2-naphthalenyl)ethynyl]benzoate (Compound 14)

To a solution of ethyl 4-[(5,6-dihydro-5,5-dimethyl-8-(4-((2,2dimethylethyl)-dimethylsiloxy)phenyl)-2-naphthalenyl)ethynyl]benzoate (Compound I) 50.0 mg (0.095 mmol) in 1.0 ml of THF at room temperature was added 73.2 mg (0.29 ml, 0.29 mmol) of tetrabutylamonium fluoride (1M solution in THF). After stirring overnight, the solution was diluted with EtOAc and washed with H$_2$O and saturated aqueous NaCl, before being dried over MgSO$_4$. Removal of the solvents under reduced pressure, followed by column chromatography (4:1, Hexanes:EtOAc) afforded the title compound as a colorless solid. 1H NMR (CDCl$_3$): δ 7.98 (2H, d, J=8.2 Hz), 7.52 (2H, d, J=8.3 Hz), 7.41–7.20 (5H, m), 6.88 (2H, d, J=8.4 Hz), 5.96 (1H, t, J=4.5 Hz), 4.37 (2H, q, J=7.1 Hz), 2.34 (2H, d, J=4.5 Hz), 1.39 (3H, t, J=7.1 Hz), 1.34 (6H, s).

Ethyl 4-[(5,6-dihydro-5,5-dimethyl-8-(5-methylthiazol-2-yl)-2- naphthalenyl)ethynyl]benzoate (Compound 15)

Employing the same general procedure as for the preparation of ethyl 4-[(5,6-dihydro-5,5-dimethyl-8-(4-methylphenyl)-2-naphthalenyl)ethynyl]benzoate (Compound 1), 264.0 mg (0.552 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 150.0 mg (1.10 mmol) of zinc chloride, 14 mg (0.012 mmol) of tetrakis(triphenylphosphine)palladium(0) in 4.0 ml of THF, and 5-methylthiazol-2-yl lithium (prepared by adding 53.2 mg (0.53 ml, 0.83 mmol) of n-butyllithium (1.55M solution in hexanes) to a cold solution (−78° C.) of 82.0 mg (0.83 mmol) of 5-methylthiazole in 5.0 ml of THF). 1H NMR (CDCl$_3$): δ 7.99 (2H, d, J=7.8 Hz), 7.88 (1H, d, J=1.5 Hz), 7.55 (2H, d, J=7.8 Hz), 7.54 (1H, s), 7.45 (1H, dd, J=1.5, 8.0 Hz), 7.35 (1H, d, J=7.9 Hz), 6.48 (1H, t, J=4.8 Hz), 4.38 (2H, q, J=7.1 Hz), 2.51 (3H, s), 2.38 (2H, d, J=4.8 Hz), 1.40 (3H, s), 1.32 (6H, s).

Ethyl 4-[(5,6-dihydro-5,5-dimethyl-8-(2-thiazolyl)-2-naphthalenyl)ethynyl]benzoate (Compound 15a)

A solution of 2-lithiothiazole was prepared by the addition of 41.2 mg (0.42 ml, 0.63 mmol) of n-butyl-lithium (1.5M solution in hexanes) to a cold solution (−78° C.) of 53.4 mg (0.63 mmol) of thiazole in 1.0 ml of THF. The solution was stirred at for 30 minutes and then a solution of 113.9 mg (0.84 mmol) of zinc chloride in 1.5 ml of THF was added. The resulting solution was warmed to room temperature, stirred for 30 minutes and then the organozinc was added via cannula to a solution of 200.0 mg (0.42 mmol) of ethyl 4-[(5,6-dihydro-5,5-dimethyl-8-(trifluoromethylsulfonyl)oxy-2-naphthalenyl)ethynyl]benzoate (Compound G) and 12.4 mg (0.01 mmol) of tetrakis(triphenylphosphine) palladium(0) in 1.5 ml of THF. The resulting solution was heated at 50° C. for 45 minutes, cooled to room temperature and diluted with sat. aqueous NH$_4$Cl. The mixture was extracted with EtOAc (40 ml) and the combined organic layers were washed with water and brine. The organic phase was dried over Na$_2$SO$_4$ and concentrated in vacuo to a yellow oil. Purification by column chromatography (silica, 20% EtOAc-hexanes) yielded the title compound as a colorless oil. PMR (CDCl$_3$): δ 1.35 (6H, s), 1.40 (3H, t, J=7.1 Hz), 2.42 (2H, d, J=4.8 Hz), 4.38 (2H, q, J=7.1 Hz), 6.57 (1H, t, J=4.8 Hz), 7.33 (1H, d, J=3.3 Hz), 7.36 (1H, d, J=8.0 Hz), 7.46 (1H, dd, J=1.7, 8.1 Hz), 7.55 (2H, d, J=8.4 Hz), 7.87 (1H, d, J=1.7 Hz), 7.92 (1H, d, J=3.3 Hz), 8.00 (2H, d, J=8.4 Hz).

Ethyl 4-[(5,6-dihydro-5,5-dirmethyI-8-(4-methylthiazol-2-1)-2-naphthalenyl)ethynyl]benzoate (Compound 16)

Employing the same general procedure as for the preparation of ethyl 4-[(5,6-dihydro-5,5-dimethyl-8-(4-methylphenyl)-2-naphthalenyl)ethynyl]benzoate (Compound 1), 295.0 mg (0.617 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 168.0 mg (1.23 mmol) of zinc chloride, 16 mg (0.014 mmol) of tetrakis(triphenylphosphine)palladium(0) in 6.0 ml of THF, and 4-methylthiazol-2-yl lithium (prepared by adding 59.6 mg (0.60 ml, 0.93 mmol) of n-butyllithium (1.55M solution in hexanes) to a cold solution (−78° C.) of 92.0 mg (0.93 mmol) of 4-methylthiazole in 6.0 ml of THF). 1H NMR (CDCl$_3$): δ 8.00 (2H, d, J=8.4 Hz), 7.80 (1H, d, J=1.7 Hz), 7.55 (2H, d, J=8.4 Hz), 7.45 (1H, dd, J=1.7, 8.0 Hz), 7.35 (1H, d, J=8.0 Hz), 6.87 (1H, s), 6.52 (1H, t, J=4.7 Hz), 4.37 (2H, q, J=7.2 Hz), 2.54 (3H, s), 2.39 (2H, d, J=4.7 Hz), 1.40 (3H, t, J=7.2 Hz), 1.33 (3H, s).

Ethyl 4-[(5,6-dihydro-5,5-dimethyl-8-(4,5-dimethylthiazol-2-yl)-2-naphthalenyl) ethynyl]benzoate (Compound 17)

Employing the same general procedure as for the preparation of ethyl 4-[(5,6-dihydro-5,5-dimethyl-8-(4-methylphenyl)-2-naphthalenyl)ethynyl]benzoate (Compound 1), 200.0 mg (0.418 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 110.0 mg (0.84 mmol) of zinc chloride, 12 mg (0.011 mmol) of tetrakis(triphenylphosphine)palladium(0) in 2.0 ml of THF, and 4,5-dimethylthiazol-2-yl lithium (prepared by adding 40.2 mg (0.39 ml, 0.63 mmol) of n-butyllithium (1.55M solution in hexanes) to a cold solution (−78° C.) of 71.0 mg (0.63 mmol) of 4,5-dimethylthiazole in 2.0 ml of THF). 1H NMR (CDCl$_3$): δ 8.00 (2H, d, J=8.4 Hz), 7.82 (1H, d, J=1.7 Hz), 7.54 (2H, d, J=8.4 Hz), 7.43 (1H, dd, J=1.7, 8.0 Hz), 7.33 91H, d, J=8.0 Hz), 6.45 (1H, t, J=4.9 Hz), 4.38 (2H, q, J=7.1 Hz), 2.41 (3H, s), 2.40 (3H, s), 2.37 (2H, d, J=4.9 Hz), 1.40 (3H, t, J=7.1 Hz), 1.32 (6H, s).

4-[(5,6-Dihydro-5,5-dimethyl-8-(2-methyl-5-pyridyl)-2-naphthalenyl)ethmyl]benzoic acid (Compound 18)

A solution of 81.7 mg (0.194 mmol) of ethyl 4-[(5,6-dihydro-5,5-dimethyl-8-(2-methyl-5-pyridyl)-2-naphthalenyl)ethynyl]benzoate (Compound 12) and 40.7 mg (0.969 mmol) of LiOH-H$_2$O in 3 ml of THF/water (3:1, v/v), was stirred overnight at room temperature. The reaction was quenched by the addition of saturated aqueous NH$_4$Cl and extracted with EtOAc. The combined organic layers were washed with water and brine, dried over Na$_2$SO$_4$ and concentrated in vacuo to give the title compound as a colorless solid. 1H NMR (d6-DMSO): δ 8.41 (1H, d, J=1.9 Hz), 7.90 (2H, d, J=8.3 Hz), 7.63 (1H, dd, J=2.3, 7.9 Hz), 7.59 (2H, d, J=8.3 Hz), 7.49 (2H, m), 7.33 (1H, d, J=7.8 Hz), 6.95 (1H, s), 6.11 (1H, t, J=4.5 Hz), 2.52 (3H, s), 2.37 (2H, d, J=4.6 Hz), 1.31 (6H, s).

4-[(5,6-Dihydro-5,5-dimethyl-8-(2-pyidyl)-2-naphthalenyl)ethynl]benzoic acid (Compound 19)

A solution of 80.0 mg (0.196 mmol) of ethyl 4-[(5,6-dihydro-5,5-dimethyl-8-(2-pyridyl)-2-naphthalenyl)ethynyl]benzoate (Compound 10) and 20.6 mg (0.491 mmol) of LiOH-H$_2$O in 3 ml of THF/water (3:1, v/v), was stirred overnight at room temperature. The reaction was quenched by the addition of saturated aqueous NH$_4$Cl and extracted with EtOAc. The combined organic layers were washed with water and brine, dried over Na$_2$SO$_4$ and concentrated in vacuo to give the title compound as a colorless solid. 1H NMR (d6-DMSO): δ 8.64 (1H, m), 7.94 (2H, d, J=8.3 Hz), 7.87 (1H, dt, J=1.7, 7.8 Hz), 7.58 (2H, d, J=8.3 Hz), 7.50 (1H, d, J=8.2 Hz), 7.47 (2H, s), 7.37 (1H, m), 7.25 (1H, s), 6.30 (1H, t, J=4.6 Hz), 2.39 (2H, d, J=4.6 Hz), 1.31 (6H, s).

4-[(5,6-Dihydro-5,5-dimethyl-8-(3-methylphenyl)-2-naphthalenyl)ethynyl]benzoic acid (Compound 20)

To a solution of ethyl 4-[(5,6-dihydro-5,5-dimethyl-8-(3-methylphenyl)-2-naphthalenyl)ethynyl]benzoate (Compound 2) 30.0 mg (0.071 mmol) in 3 ml of EtOH and 2 ml of THF was added 28.0 mg (0.70 mmol, 0.7 ml) of NaOH (1.0M aqueous solution). The solution was heated to 50° C. for 2 hours, cooled to room temperature, and acidified with 10% HCl. Extraction with EtOAc, followed by drying over Na$_2$SO$_4$, and removal of the solvents under reduced pressure afforded the title compound as a colorless solid. 1H NMR (DMSO): δ 7.90 (2H, d, J=8.5 Hz), 7.59 (2H, d, J=8.5 Hz), 7.46 (2H, s), 7.32–7.13 (4H, m), 7.10 (1H, s), 6.98 (1H, t, J=4.5 Hz), 2.34 (3H, s), 2.31 (2H, d, J=4.5 Hz), 1.30 (6H, s).

4-[(5,6-Dihydro-5,5-dimethyl-8-(4-ethylphenyl)-2-naphthalenl)ethynyl]benzoic acid (Compound 21)

To a solution of ethyl 4-[(5,6-dihydro-5,5-dimethyl-8-(4-ethylphenyl)-2-naphthalenyl)ethynyl]benzoate (Compound 5) 47.0mg (0.108 mmol) in 3 ml of EtOH and 2 ml of THF was added 28.0 mg (0.70 mmol, 0.7 ml) of NaOH (1.0M aqueous solution). The solution was heated to 50° C. for 2 hours, cooled to room temperature, and acidified with 10% HCl. Extraction with EtOAc, followed by drying over Na$_2$SO$_4$, and removal of the solvents under reduced pressure afforded the title compound as a colorless solid. 1H NMR (DMSO): δ 7.90 (2H, d, J=8.3 Hz), 7.59 (2H, d, J=8.3 Hz), 7.46 (2H, s), 7.29–7.21 (4H, m), 7.02 (1H, s), 6.01 (1H, t, J=4.5 Hz), 2.64 (2H, q, J=7.5 Hz), 2.33 (2H, d, J=4.5 Hz), 1.29 (6H, s), 1.22 (3H, t, J=7.5 Hz).

4-[(5,6-Dihydro-5,5-dimethyl-8-(4-methoxyphenyl)-2-naphthalenyl)ethynyl]benzoic acid (Compound 22)

To a solution of ethyl 4-[(5,6-dihydro-5,5-dimethyl-8-(4-methoxyphenyl)-2-naphthalenyl)ethynyl]benzoate (Compound 8) 80.0 mg (0.183 mmol) in 3 ml of EtOH and 2 ml of THF was added 40.0 mg (1.00 mmol, 1.0 ml) of NaOH (1.0M aqueous solution). The solution was heated to 50° C. for 2 hours, cooled to room temperature, and acidified with 10% HCl. Extraction with EtOAc, followed by drying over Na$_2$SO$_4$, and removal of the solvents under reduced pressure afforded the title compound as a colorless solid. 1H NMR (DMSO): δ 7.90 (2H, d, J=8.3 Hz), 7.60 (2H, d, J=8.3 Hz), 7.45 (2H, s), 7.24 (2H, d, J=8.6 Hz), 7.02-6.89 (3H, m), 5.98 (1H, t, J=4.4 Hz), 3.79 (3H, s), 2.31 (2H, d, J=4.7 Hz), 1.29 (6H, s).

4-[(5,6-Dihydro-5,5-dimethyl-8-(4-trifluoromethylphenyl)-2-naphthalenyl)ethynyl]benzoic acid (Compound 23)

To a solution of ethyl 4-[(5,6-dihydro-5,5-dimethyl-8-(4-trifluoromethylphenyl)-2-naphthalenyl)ethynyl]benzoate (Compound 9) 70.0 mg (0.148 mmol) in 3 ml of EtOH and 2 ml of THF was added 60.0 mg (1.50 mmol, 1.50 ml) of NaOH (1.0M aqueous solution). The solution was heated to 50° C. for 2 hours, cooled to room temperature, and acidified with 10% HCl. Extraction with EtOAc, followed by drying over Na$_2$SO$_4$, and removal of the solvents under reduced pressure afforded the title compound as a colorless solid. 1H NMR (DMSO): δ 7.90 (2H, d, J=8.3 Hz), 7.80 (2H, d, J=8.1 Hz), 7.61–7.47 (6H, m), 6.97 (2H, s), 6.16 (1H, t, J=4.5 Hz), 2.37 (2H, d, J=4.6 Hz), 1.30 (6H, s).

4-[(5,6-Dihydro-5,5-dimethyl-8-(3,5-dimethylphenyl)-2-naphthalenyl)ethynyl]benzoic acid (Compound 24)

To a solution of ethyl 4-[(5,6-dihydro-5,5-dimethyl-8-(3,5-ethylphenyl)-2-naphthalenyl)ethynyl]-benzoate (Compound 4) 90.0 mg (0.207 mmol) in 3 ml of EtOH and 2 ml of THF was added 48.0 mg (1.20 mmol, 1.20 ml) of NaOH (1.0M aqueous solution). The solution was heated to 50° C. for 2 hours, cooled to room temperature, and acidified with 10% HCl. Extraction with EtOAc, followed by diying over Na$_2$SO$_4$, and removal of the solvents under reduced pressure afforded the title compound as a colorless solid. 1H NMR (DMSO): δ 7.90 (2H, d, J=8.2 Hz), 7.59 (2H, d, J=8.2 Hz), 7.45 (2H, s), 7.00 (1H, s), 6.97 (1H, s), 5.97 (1H, t, J=4.5 Hz), 2.31 (2H, d, J=4.5 Hz), 2.30 (6H, s), 1.29 (6H, s).

4-[(5,6-Dihydro-5,5-dimethyl-8-(4-chlorophenyl)-2-naphthalenyl)ethynyl]benzoic acid (Compound 25)

To a solution of ethyl 4-[(5,6-dihydro-5,5-dimethyl-8-(4-chlorophenyl)-2-naphthalenyl)ethynyl]benzoate (Compound 7) 80.0 mg (0.181 mmol) in 3 ml of EtOH and 2 ml of THF was added 48.0 mg (1.20 mmol, 1.20 ml) of NaOH (1.0M aqueous solution). The solution was heated to 50° C. for 2 hours, cooled to room temperature, and acidified with 10% HCl. Extraction with EtOAc, followed by drying over Na$_2$SO$_4$, and removal of the solvents under reduced pressure afforded the title compound as a colorless solid. 1H NMR (DMSO): δ 7.90 (2H, d, J=8.3 Hz), 7.60 (2H, d, J=8.3 Hz), 7.51–7.48 (4H, m), 7.34 (2H, d, J=8.4 Hz), 6.97 (1H, s), 6.07 (1H, t, J=4.5 Hz), 2.34 (2H, d, J=4.6 Hz), 1.29 (6H, s).

4-[(5,6-Dihydro-5,5-dimethyl-8-(3-pyridyl)-2-naphthalenyl)ethynyl]benzoic acid (Compound 26)

To a solution of ethyl 4-[(5,6-dihydro-5,5-dimethyl-8-(3-pyridyl)-2-naphthalenyl)ethynyl]benzoate (Compound 11) 45.0 mg (0.110 mmol) in 3 ml of EtOH and 2 ml of THF was added 48.0 mg (1.20 mmol, 1.20 ml) of NaOH (1.0M aqueous solution). The solution was heated to 50° C. for 2 hours, cooled to room temperature, and acidified with 10% HCl. Extraction with EtOAc, followed by drying over $Na_2SO_4$, and removal of the solvents under reduced pressure afforded the title compound as a colorless solid. 1H NMR (DMSO): δ 8.60 (1H, d, J=4.6 Hz), 8.55 (1H, s), 7.90 (2H, d, J=8.3 Hz), 7.76 (1H, d, J=7.5 Hz), 7.60 (2H, d, J=8.3 Hz), 7.51–7.46 (3H, m), 6.94 (1H, s), 6.14 (1H, t, J=4.5 Hz), 2.37 (2H, d, J=4.5 Hz), 1.31 (6H, s).

4-[(5,6-Dihydro-5,5-dimethyl-8-(2-methylphenyl)-2-naphthalenyl)ethynyl]benzoic acid (Compound 27)

To a solution of ethyl 4-[(5,6-dihydro-5,5-dimethyl-8-(2-methylphenyl)-2-naphthalenyl)ethynyl]-benzoate (Compound 3) 80.0 mg (0.190 mmol) in 3 ml of EtOH and 2 ml of THF was added 60.0 mg (1.50 mmol, 1.50 ml) of NaOH (1.0M aqueous solution). The solution was heated to 50° C. for 2 hours, cooled to room temperature, and acidified with 10% HCl. Extraction with EtOAc, followed by drying over $Na_2SO_4$, and removal of the solvents under reduced pressure afforded the title compound as a colorless solid. 1H NMR (DMSO): δ 7.89(2H, d, J=8.4 Hz), 7.57 (2H, d, J=8.4 Hz), 7.46 (2H, s), 7.29–7.14 (4H, m), 6.59 (1H, s), 5.90 (1H, t, J=4.7 Hz), 2.39 (2H, m), 2.60 (3H, s), 1.39 (3H, s), 1.29 (3H, s).

4-[(5,6-Dihydro-5,5-dimethyl-8-(3-hydroxhenyl)-2-naphthalenyl)ethynyl]benzoic acid (Compound 28)

To a solution of ethyl 4-[(5,6-dihydro-5,5-dimethyl-8-(3-((2,2-dimethylethyl)-dimethylsiloxy)phenyl)-2-naphthalenyl)ethynyl]benzoate (Compound H) 40.0 mg (0.076 mmol) in 3 ml of EtOH and 2 ml of THF was added 40.0 mg (1.00 mmol, 1.00 ml) of NaOH (1.0M aqueous solution). The solution was heated to 50° C. for 2 hours, cooled to room temperature, and acidified with 10% HCl. Extraction with EtOAc, followed by drying over $Na_2SO_4$, and removal of the solvents under reduced pressure afforded the title compound as a colorless solid. 1H NMR (d6-acetone): δ 7.90 (2H, d, J=8.3 Hz), 7.49 (2H, d, J=8.4 Hz), 7.35 (2H, s), 7.15–7.07 (2H, m), 6.77–6.69 (3H, m), 5.92 (1H, t, J=4.7 Hz), 2.25 (2H, d, J=4.7 Hz), 1.23 (6H, s).

4-[(5,6-Dihydro-5,5-dimethyl-8-(4-hydrogphenyl)-2-naphthalenyl)ethynyl]benzoic acid (Compound 29)

To a solution of ethyl 4-[(5,6-dihydro-5,5-dimethyl-8-(4-((2,2-dimethylethyl)-dimethylsiloxy)phenyl)-2-naphthalenyl)ethynyl]benzoate (Compound I) 75.0 mg (0.143 mmol) in 3 ml of EtOH and 2 ml of THF was added 60.0 mg (1.50 mmol, 1.50 ml) of NaOH (1.0M aqueous solution). The solution was heated to 50° C. for 2 hours, cooled to room temperature, and acidified with 10% HCl. Extraction with EtOAc, followed by drying over $Na_2SO_4$, and removal of the solvents under reduced pressure afforded the title compound as a colorless solid. 1H NMR (d6-acetone): δ 8.01 (2H, d, J=8.3 Hz), 7.59 (2H, d, J=8.4 Hz), 7.45 (2H, s), 7.20–7.17 (3H, m), 6.92–6.89 (2H, m), 5.97 (1H, t, J=4.7 Hz), 2.35 (2H, d, J=4.7 Hz), 1.34 (6H, s).

4-[(5,6-Dihydro-5,5-dimethyl-8-(5-methylthiazol-2-yl)-2-naphthalenyl)ethyl]benzoic acid (Compound 30)

To a solution of ethyl 4-[5,6-dihydro-5,5-dimethyl-8-(5-methylthiazol-2-yl)-2-naphthalenyl)ethynylbenzoate (Compound 15) (100 mg, 0.23 mmol) and 4 ml of EtOH at room temperature was added aqueous NaOH (1 ml, 1M, 1 mmol). The resulting solution was warmed to 50° C. for 1 hour and concentrated in vacuo. The residue was suspended in a solution of $CH_2Cl_2$ and ether (5:1) and acidified to pH 5 with 1M aqueous HCl. The layers were separated and the organic layer was washed with brine, dried ($Na_2SO_4$), filtered and the solvents removed under reduced pressure to give the title compound as a white solid. 1H NMR (d6-DMSO): δ 7.96 (1H, d, J=1.7 Hz), 7.95 (2H, d, J=8.0 Hz), 7.65 (2H, d, J=8.0 Hz), 7.64 (1H, s), 7.53 (1H, dd, J=1.7, 8.0 Hz), 7.46 (1H, d, J=8.0 Hz), 6.59 (1H, t, J=4.5 Hz), 2.50 (3H, s), 2.39 (2H, d, J=4.5 Hz), 1.27 (6H, s).

4-[(5,6-dihydro-5,5-dimethyl-8-(2-thiazolyl)-2-naphthalenyl)ethynyl]benzoic acid (Compound 30a)

A solution of 33.9 mg (0.08 mmol) of ethyl 4-[(5,6-dihydro-5,5-dimethyl-8-(2-thiazolyl)-2-naphthalenyl)ethynyl]benzoate (Compound 15a) and 8.5 mg (0.20 mmol) of LiOH-$H_2O$ in 3 ml of THF/water (3:1, v/v), was stirred overnight at room temperature. The reaction was quenched by the addition of sat. aqueous $NH_4Cl$ and extracted with EtOAc. The combined organic layers were washed with water and brine, dried over $Na_2SO_4$ and concentrated in vacuo to give the title compound as a colorless solid. PMR ($d_6$-DMSO): δ 1.29 (6H, s), 2.42 (2H, d, J=4.6 Hz), 6.68 (1H, t, J=4.6 Hz), 7.51 (2H, m), 7.62 (2H, d, J=8.2 Hz), 7.77 (1H, d, J=3.3 Hz), 7.93 (2H, d, J=8.2 Hz), 7.98 (1H, d, J=3.3 Hz).

4-[(5,6-Dihydro-5,5-dimethyl-8-(4-methylthiazol-2-yl)-2-naphthalepml)ethyl]benzoic acid (Compound 31)

To a solution of ethyl 4-[5,6-dihydro-5,5-dimethyl-8-(4-methylthiazol-2-yl)-2-naphthalenyl)ethyny]benzoate (Compound 16) (145.0 mg, 0.34 mmol) and 4 ml of EtOH at room temperature was added aqueous NaOH (1 ml, 1M, 1 mmol). The resulting solution was warmed to 50° C. for 1 hour and concentrated in vacuo. The residue was suspended in a solution of $CH_2Cl_2$ and ether (5:1) and acidified to pH 5 with 1M aqueous HCl. The layers were separated and the organic layer was washed with brine, dried ($Na_2SO_4$), filtered and the solvents removed under reduced pressure to give the title compound as a white solid. 1H NMR (d6-DMSO): δ 7.94 (2H, d, J=8.1 Hz), 7.87 (1H, d, J=1.6 Hz), 7.63 (2H, d, J=8.3 Hz), 7.50 (1H, dd, J=1.6, 8.1 Hz), 7.45 (1H, d, J=8.1 Hz), 7.27 (1H, s), 6.58 (1H, t, J=4.8 Hz), 2.43 (3H, s), 2.37 (2H, d, J=4.8 Hz), 1.26 (6H, s).

4-[(5,6-Dihydro-5,5-dimethyl-8-(4,5-dimethylthiazol-2-yl)-2-naphthalenyl)ethynyl]benzoic acid (Compound 32)

To a solution of ethyl 4-[5,6-dihydro-5,5-dimethyl-8-(4,5-dimethylthiazol-2-yl)-2-naphthalenyl]ethynylbenzoate (Compound 17) (58.0 mg, 0.13 mmol) and 4 ml of EtOH at room temperature was added aqueous NaOH (1 ml, 1M, 1 mmol). The resulting solution was warmed to 50° C. for 1 hour and concentrated in vacuo. The residue was suspended in a solution of $CH_2Cl_2$ and ether (5:1) and acidified to pH 5 with 1M aqueous HCl. The layers were separated and the organic layer was washed with brine, dried ($Na_2SO_4$), filtered and the solvents removed under reduced pressure to give the title compound as a white solid. 1H NMR (d6-DMSO): δ 7.94 (2H, d, J=8.4 Hz), 7.86 (1H, d, J=1.6 Hz), 7.61 (2H, d, J=8.3 Hz), 7.50 (1H, dd, J=1.6, 8.0 Hz), 7.45 (1H, d, J=8.0 Hz), 6.51 (1H, t, J=4.9 Hz), 2.37 (3H, s), 2.36 (2H, d, J=4.6 Hz), 2.32 (3H, s), 1.26 (6H, s).

Ethyl 4-[(5,6-dihydro-5,5-dimethyl-8-(5-methyl-2-thienyl)-2-naphthalenyl ethynyl]benzoate (Compound 33)

Employing the same general procedure as for the preparation of ethyl 4-[(5,6-dihydro-5,5-dimethyl-8-(4-methylphenyl)-2-naphthalenyl)ethynyl]benzoate (Compound 1), 170.0 mg (0.366 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 202.0 mg (1.48 mmol) of zinc chloride, 24 mg (0.022 mmol) of tetrakis(triphenylphosphine)palladium(0) in 2.0 ml of THF, and 5-methyl-2-lithiothiophene (prepared by adding 58.6 mg (0.36 ml, 0.915 mmol) of n-butyllithium (2.5M solution in hexanes) to a cold solution (−78° C.) of 89.8 mg (0.915 mmol) of 2-methylthiophene in 2.0 ml of THF).

1H NMR (CDCl$_3$): δ 8.00 (2H, d, J=8.3 Hz), 7.59 (1H, d, J=1.7 Hz), 7.55 (2H, d, J=8.2 Hz), 7.43 (1H, dd, J=1.7, 8.0 Hz), 7.35 (1H, d, J=8.0 Hz), 6.87 (1H, d, J=3.5 Hz), 6.74 (1H, d, J=2.8 Hz), 6.15 (1H, t, J=4.8 Hz), 4.38 (2H, q, J=7.1 Hz), 2.52 (3H, s), 2.32 (2H, d, J=4.8 Hz). 1.40 (3H, t, 7.1 Hz), 1.32 (6H, s).

Ethyl 4-[(5,6-dihydro-5,5-dimethyl-8-(2-thienyl)-2-naphthalenyl)ethynyl]benzoate (Compound 33a)

Employing the same general procedure as for the preparation of ethyl 4-[(5,6-dihydro-5,5-dimethyl-8-(4-methylphenyl)-2-naphthalenyl)ethynyl]benzoate (Compound 1), 250.0 mg (0.52 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 186.8 mg (1.37 mmol) of zinc chloride 37.1 mg (0.03 mmol) of tetrakis(triphenylphosphine)palladium(0) and 2-lithiothiophene (prepared by the addition of 65.9 mg (0.69 ml, 1.03 mmol) of n-butyllithium (1.5M solution in hexane) to a cold solution (−78° C.) of 86.5 mg (1.03 mmol) of thiophene in 1.0 ml of THF). PMR (CDCl$_3$): δ 1.33 (6H, s), 1.36 (3H, t, J=7.1 Hz), 2.38 (2H, d, J=4.7 Hz), 4.34 (2H, q, J=7.2 Hz), 6.25 (1H, t, J=4.7 Hz), 7.13 (2H, m), 7.47 (4H, m), 7.62 (2H, d, J=8.5 Hz), 8.00 (2H, d, J=8.5 Hz).

4-[(5,6-Dihydro-5,5-dimeth -8-(5-methyl-2-thienyl)-2-nahthalenl ethyl]benzoic acid (Compound 34)

To a solution of ethyl 4-[5,6-dihydro-5,5-dimethyl-8-(5-methyl-2-thienyl)-2-naphthalenyl]ethynyl]benzoate (Compound 33) (35.0 mg, 0.082 mmol) in 2 ml of EtOH and 1 ml THF at room temperature was added aqueous NaOH (1 ml, 1M, 1 mmol). The resulting solution was stirred at room temperature overnight and then acidified with 10% HCl. Extraction with EtOAc, followed by drying over Na$_2$SO$_4$, and removal of the solvents under reduced pressure afforded the title compound as a colorless solid. 1H NMR (d6-acetone): δ 8.03 (2H, d, J=8.6 Hz), 7.63 (2H, d, J=8.6 Hz), 7.54–7.48 (3H, m), 6.89 (1H, m), 6.18 (1H, t, J=4.7 Hz), 2.49 (3H, s), 2.35 (2H, d, J=4.7 Hz), 1.32 (6H, s).

4-[(5,6-dihydro-5,5-dimethyl-8-(2-thienyl)-2-naphthaleyl)ethynyl]benzoic acid (Compound 34a)

Employing the same general procedure as for the preparation of 4-[(5,6-dihydro-5,5-dimethyl-8-(2-thiazolyl)-2-naphthalenyl)ethynyl]benzoic acid (Compound 30a), 70.0 mg (0.17 mmol) of ethyl 4-[(5,6-dihydro-5,5-dimethyl-8-(2-thienyl)-2-naphthalenyl)ethynyl]benzoate (Compound 33a) was converted into the title compound (colorless solid) using 17.8 mg (0.42 mmol) of LiOH in H$_2$O. PMR (d$_6$-DMSO): δ 1.27 (6H, s), 2.33 (2H, d, J=4.9 Hz), 6.23 (1H, t, J=4.9 Hz), 7.14 (2H, m), 7.38–7.56 (4H, m), 7.61 (2H, d, J=8.3 Hz), 7.92 (2H, d, J=8.3 Hz).

5,6-Dihydro-5,5-dimethyl-8-(4-methylphenyl)-2-naphthalenecarboxylic acid (Compound K)

A solution of 3,4-dihydro-1-(4-methylphenyl)-4,4-dimethyl-7-bromonaphthalene (Compound D) (250.0 mg, 0.764 mmol) in 2.0 ml of THF was cooled to −78° C. and 1.0 ml of t-butyllithium (1.68 mmol, 1.7M solution in pentane) was added slowly. After stirring for 1 hour at −78° C. gaseous CO$_2$ (generated by evaporation of Dry-Ice, and passed though a drying tube) was bubbled through the reaction for 1 hour. The solution was then allowed to warm to room temperature and the reaction was quenched by the addition of 10% HCl. Extraction with EtOAc was followed by washing the combined organic layers with H$_2$O and saturated aqueous NaCl, and drying over MgSO$_4$. Removal of the solvents under reduced pressure and washing of the solid with hexanes afforded the title compound as a colorless solid. 1H NMR (CDCl$_3$): δ 7.94 (1H, dd, J=1.8, 8.1 Hz), 7.76 (1H, d, J=1.8 Hz), 7.45 (1H, d, J=8.1 Hz), 7.24 (4H, m), 6.01 (1H, t, J=4.7 Hz), 2.40 (3H, s), 2.36 (2H, d, J=4.7 Hz), 1.35 (6H, s).

Ethyl 4-[[(5,6-dihydro-5,5-dimethyl-8-(4-methylphenyl)-2-naphthalenyl)carbonyl]amino]-benzoate (Compound 35)

A solution of 170.0 mg (0.58 mmol) 5,6-dihydro-5,5-dimethyl-8-(4-methylphenyl)-2-naphthalenecarboxylic acid (Compound K) 115.0 mg (0.70 mmol) of ethyl 4-aminobenzoate, 145.0 mg (0.76 mmol) of 1-(3-dimethylaminopropyl)-3-ethylcarbodiimide hydrochloride, and 92.4 mg (0.76 mmol) of 4-dimethylaminopyridine in 6.0 ml of DMF was stirred overnight at room temperature. Ethyl acetate was added and the resulting solution washed with H$_2$O, saturated aqueous NaHCO$_3$, and saturated aqueous NaCl, then dried over MgSO$_4$. After removal of the solvent under reduced pressure, the product was isolated as a colorless solid by column chromatography (10 to 15% EtOAc/hexanes). 1H NMR (CDCl$_3$): δ 8.02 (2H, d, J=8.7 Hz), 7.72 (2H, m), 7.65 (2H, d, J=8.7 Hz), 7.52 (1H, d, J=1.8 Hz), 7.48 (1H, d, J=8.0 Hz), 7.25 (4H, m), 6.15 (1H, t, J=4.9 Hz), 4.36 (2H, q, J=7.1 Hz), 2.40 (3H, s), 2.38 (2H, d, J=4.9 Hz), 1.39 (3H, t, J=7.1 Hz), 1.37 (6H, s).

4-[[(5,6-Dihydro-5,5-dimethyl-8-(4-methylphenyl)-2-naphthalenyl)carbonyl]amino]-benzoic acid (Compound 36)

To a solution of 26.5 mg (0.06 mmol) ethyl 4[[(5,6-dihydro-5,5-dimethyl-8-(4-methylphenyl)-2-naphthalenyl)carbonyl]amino]-benzoate (Compound 35) in 3.0 ml EtOH and 4.0 ml of THF was added 240.1 mg NaOH (6.00 mmol, 3.0 ml of a 2M aqueous solution). After stirring at room temperature for 72 hours, the reaction was quenched by the addition of 10% HCl. Extraction with EtOAc, and drying of the organic layers over MgSO$_4$, provided a solid after removal of the solvent under reduced pressure. Crystallization from CH$_3$CN afforded the title compound as a colorless solid. 1H NMR (d6-DMSO): δ 10.4 (1H, s), 7.91–7.81 (5H, m), 7.54 (1H, d, J=8.1 Hz), 7.45 (1H, d, J=1.7 Hz), 7.23 (4H, s), 6.04 (1H, t, J=4.7 Hz), 2.35 (5H, s), 1.33 (6H, s).

Ethyl 4-[[(5,6-dihydro-5,5-dimethyl-8-(4-methyl-phenyl)-2-naphthalenyl)carbonyl]oxy]-benzoate (Compound 37)

A solution of 25.0 mg (0.086 mmol) 5,6-dihydro-5,5-dimethyl-8-(4-methylphenyl)-2-naphthalenecarboxylic acid (Compound K) 17.5 mg (0.103 mmol) of ethyl 4-hydroxybenzoate, 21.4 mg (0.112 mmol) of 1-(3-dimethylaminopropyl)-3-ethylcarbodiimide hydrochloride, and 12.6 mg (0.103 mmol) of 4-dimethylaminopyridine in 2.0 ml of DMF was stirred overnight at room temperature. Ethyl acetate was added and the resulting solution washed with H$_2$O, saturated aqueous NaHCO$_3$, and saturated aqueous NaCl, before being dried over MgSO$_4$. After removal of the solvent under reduced pressure, the product was isolated by column chromatography as a pale-yellow solid (10% EtOAc/hexanes). 1H NMR (CDCl$_3$): δ 8.08 (2H, d, J=8.1 Hz), 8.05 (1H, dd, J=1.8, 8.1 Hz), 7.89 (1H, d, J=1.8 Hz), 7.50 (2H, d, J=8.1 Hz), 7.22 (5H, m), 6.05 (1H, t, J=4.7 Hz), 4.37 (2H, q, J=7.1 Hz), 2.39 (2H, d, J=4.7 Hz), 2.38 (3H, s), 1.39 (3H, t, J=7.1 Hz), 1.37 (6H, s).

2-Trimethylsilvlethyl 4-[[(5,6-dihydro-5,6-dimethyl-8-(4-methylphenyl)-2-naphthalenyl)carbonyl]oxy]-benzoate (Compound 38)

A solution of 93.5 mg (0.320 mmol) 5,6-dihydro-5,5-dimethyl-8-(4-methylphenyl)-2-naphthalenecarboxylic acid (Compound K) 76.0 mg (0.319 mmol) of 2-trimethylsilylethyl-4-hydroxybenzoate, 80.0 mg (0.417 mmol) of 1(3-dimethylaminopropyl)-3-ethylcarbodiimide hydrochloride, and 51.0 mg (0.417 mmol) of 4-dimethylaminopyridine in 4.0 ml of DMF was stirred overnight at room temperature. Ethyl acetate was added and the resulting solution washed with $H_2O$, saturated aqueous $NaHCO_3$, and saturated aqueous NaCl, before being dried over $MgSO_4$. After removal of the solvent under reduced pressure, the product was isolated as a colorless solid by column chromatography (5% EtOAc/hexanes). 1H NMR ($CDCl_3$): δ 8.08 (2H, d, J=8.8 Hz), 8.05 (1H, dd, J=1.8, 8.1 Hz), 7.50 (1H, d, J=8.1 Hz), 7.26–7.18 (6H, m), 6.05 (1H, t, J=4,7 Hz), 4.42 (2H, t, J=8.4 Hz), 2.40 (2H, d, J=4.7 Hz), 2.39 (3H, s), 1.38 (6H, s), 0.09 (9H, s).

4-[[(5,6-Dihydro-5,5-dimethyl-8-(4-methylphenyl)-2-naphthalenyl)carbonyl]oxy]-benzoic acid (Compound 39)

A solution of 110.0 mg (0.213 mmol) 2-trimethylsilylethyl 4[[(5,6-dihydro-5,5-dimethyl-8-(4-methylphenyl)-2-naphthalenyl)carbonyl]oxy]benzoate (Compound 38) and 167.3 mg of tetrabutylammonium flouride (0.640 mmol, 0.64 ml of a 1M solution in THF) in 2.0 ml THF was stirred at room temperature for 22 hours. Ethyl acetate was added and the resulting solution washed with $H_2O$ and saturated aqueous NaCl then dried over $MgSO_4$. Removal of the solvents under reduced pressure and washing of the residual solid with EtOAc and $CH_3CN$ afforded the title compound as a colorless solid. 1H NMR (d6-acetone): δ 8.10 (2H, d, J=8.8 Hz), 8.06 (1H, dd, J=2.0, 8.1 Hz), 7.82 (1H, d, J=1.9 Hz), 7.64 (1H, d, J=8.1 Hz), 7.35 (2H, d, J=8.6 Hz), 7.25 (4H, m), 6.08 (1H, t, J=4.7 Hz), 2.42 (2H, d, J=4.7 Hz), 2.35 (3H, s), 1.39 (6H, s).

Ethyl 2-fluoro-4-[[(5,6-dihydro-5,5-dimethyl-8-(4-methylphenyl)-2-naphthalenyl)carbonyl]amino]-benzoate (Compound 40)

A solution of 115.0 mg (0.41 mmol) 5,6-dihydro-5,5-dimethyl-8-(4-methylphenyl)-2-naphthalenecarboxylic acid (Compound K) 89.0 mg (0.49 mmol) of ethyl 2-fluoro-4-aminobenzoate, 102.0 mg (0.53 mmol) of 1-(3dimethylaminopropyl)-3-ethylcarbodiimide hydrochloride, and 65.0 mg (0.53 mmol) of 4-dimethylaminopyridine in 5.0 ml of DMF was stirred at 50° C. for 1 hour and then overnight at room temperature. Ethyl acetate was added and the resulting solution washed with $H_2O$, saturated aqueous $NaHCO_3$, and saturated aqueous NaCl, before being dried over $MgSO_4$. After removal of the solvent under reduced pressure, the product was isolated as a colorless solid by column chromatography (20% EtOAc/hexanes). 1H NMR ($CDCl_3$): δ 7.96 (1H, s), 7.89 (1H, t, J=8.4 Hz), 7.70 (2H, m), 7.52 (1H, d, J=1.9 Hz), 7.45 (1H, d, J=8.1 Hz), 7.23 (5H, m), 6.04 (1H, t, J=4.8 Hz), 4.36 (2H, q, J=7.1 Hz), 2.38 (3H, s), 2.35 (2H, d, J=4.8 Hz), 1.39 (3H, t, J=7.1 Hz), 1.36 (6H, s).

2-Fluoro-4-[[(5,6-dihydro-5,5-dimethyl-8-(4-methylphenyl)-2-naphthalengl)carbonyl]amino]-benzoic acid (Compound 41)

To a solution of 41.6 mg (0.091 mmol) ethyl 2-fluoro-4-[[(5,6-dihydro-5,5-dimethyl-8-(4-methylphenyl)-2-naphthalenyl)carbonyl]amino]-benzoate (Compound 40) in 2.0 ml EtOH and 2.0 ml of THF was added 40.0 mg NaOH (1.00 mmol, 1.0 ml of a 1M aqueous solution). After stirring at room temperature for overnight, the reaction was quenched by the addition of 10% HCl. Extraction with EtOAc, and drying of the organic layers over $MgSO_4$, provided a solid after removal of the solvent under reduced pressure. Crystallization from $CH_3CN$ afforded the title compound as a pale-yellow solid. 1H NMR (d6-acetone): δ 9.84 (1H, s), 7.94–7.83 (3H, m), 7.64 (1H, dd, J=2.0 Hz), 7.53 (2H, d, J=8.1 Hz), 7.23 (4H, s), 6.04 (1H, t, J=4.7 Hz), 2.38 (2H, d, J=4.7 Hz), 2.36 (3H, s), 1.35 (6H, s)

Ethyl 4[[(5,6-dihydro-5,5-dimethyl-8-(4-methylphenyl)-2-naphthalenyl)thiocarbonyl]amino]-benzoate (Compound 42)

A solution of 110.0 mg (0.25 mmol) ethyl 4-[[(5,6-dihydro-5,5, dimethyl-8-(4-methylphenyl)-2-naphthalenyl) carbonyl]amino]-benzoate (Compound 35) and 121.0 mg (0.30 mmol) of [2,4-bis(4-methoxyphenyl)-1,3-dithia-2,4-diphosphetane-2,4-disulfide] (Lawesson's Reagent) in 12.0 ml of benzene was refluxed overnight. Upon cooling to room temperature, the mixture was filtered and the filtrate concentrated under reduced pressure. The title compound was isolated by column chromatography (10 to 25% EtOAc/hexanes) as a yellow solid. 1H NMR ($CDCl_3$): δ 8.92 (1H, s), 8.06 (2H, t, J=8.5 Hz), 7.88–7.70 (3H, m), 7.42 (2H, d, J=8.1 Hz), 7.18 (4H, m), 6.03 (1H, t, J=4.7 Hz), 4.37 (2H, q, J=7.1 Hz), 2.38 (3H, s), 2,36 (2H, d, J=4.7 Hz), 1.56 (3H, t, J=7.1 Hz), 1.35 (6H, s).

4-[[(5,6-Dihydro-5,5-dimethyl-8-(4-methylphenyl)-2-naphthalenyl)thiocarbonal]amino]-benzoic acid (Compound 43)

To a solution of 84.0 mg (0.184 mmol) ethyl 4[[(5,6-dihydro-5,5-dimethyl-8-(4-methylphenyl)-2-naphthalenyl) thiocarbonyl]amino]-benzoate (Compound 42) in 2.0 ml EtOH and 2.0 ml of THF was added 60.0 mg NaOH (1.50 mmol, 1.5 ml of a 1M aqueous solution). After stirring at room temperature overnight, the reaction was quenched by the addition of 10% HCl. Extraction with EtOAc, and drying of the organic layers over $MgSO_4$, provided a solid after removal of the solvent under reduced pressure. Crystallization from $CH_3CN$ afforded the title compound as a yellow solid. 1H NMR (d6-acetone): δ 10.96 (1H, s), 8.05 (4H, m), 7.72 (1H, dd, J=2.0, 8.0 Hz), 7.54 (1H, s), 7.46 (1H, d, J=8.1 Hz), 7.20 (4H, m), 6.04 (1H, t, J=4.7 Hz), 2.38 (2H, d, J=4.7 Hz), 2.33 (3H, s), 1.35 (6H, s).

2-acetyl-6-bromonaphthalene (Compound L)

To a cold (10° C.) mixture of 44.0 g (0.212 mol) of 2-bromonaphthalene and 34.0 g (0.255 mol) of aluminum chloride in 400 ml of nitrobenzene was added 21.0 g (267 mmol) of acetyl chloride. The mechanically stirred reaction mixture was warmed to room temperature, and heated to 40° C. for 18 hours. After cooling to 0° C. in an ice bath, the reaction was quenched by the addition of 12M HCl (70 ml). The layers were separated and the organic phase was washed with water and dilute aqueous $Na_2CO_3$. Kugelrohr distillation, followed by recrystallization from 10% EtOAc-hexane yielded 23 g of the title compound as a tan solid. 1H NMR ($CDCl_3$): δ 8.44 (1H, br s), 8.04–8.10 (2H, m), 7.85 (1H, d, J=8.5 Hz), 7.82 (1H, d, J=8.8 Hz), 7.64 (1H, d, J=8.8 Hz), 2.73 (3H, s).

6-bromo-2-naphthalenecarboxylic acid (Compound M)

To a solution of sodium hypochlorite (62 ml, 5.25% in water (w/w), 3.6 g, 48.18 mmol) and sodium hydroxide (6.4 g, 160.6 mmol) in 50 ml of water was added a solution of 2-acetyl-6-bromonaphthalene (Compound L) 4 g, (16.06 mmol) in 50 ml of 1,4-dioxane. The yellow solution was heated to 70° C. in an oil bath for 2 hours, cooled to ambient temperature, and extracted with ethyl ether (2×50 ml). The aqueous layers were diluted with $NaHSO_3$ solution (until KI indicator solution remained colorless) and then acidified (pH<2) with IN sulfuric acid to give a white precipitate. The mixture was extracted with ethyl ether, and the combined organic phase washed with saturated aqueous NaCl, dried ($MgSO_4$) and concentrated to give 3.54 g (88%) of the title compound as a solid. 1H NMR (DMSO-d6): δ 8.63 (1H, br s), 8.32 (1H, d, J=2.0 Hz), 8.10 (1H, d, J=8.8 Hz), 8.00–8.05 (2H, m), 7.74 (1H, dd, J=2.0, 8.8 Hz).

Ethyl 6-bromo-2-naphthalenecarboxylate (Compound N)

To a solution of 6-bromo-2-naphthalenecarboxylic acid (Compound M) 3.1 g, (12.43 mmol) in ethanol (30 ml, 23.55 g, 511.0 mmol) was added 18M sulfuric acid (2 ml). The solution was refluxed for 30 minutes, cooled to room temperature, and the reaction mixture partitioned between pentane (100 ml) and water (100 ml). The aqueous phase was extracted with pentane (100 ml) and the combined organic layers washed with saturated aqueous NaCl (100 ml), dried ($MgSO_4$), and concentrated to yield an off-white solid. Purification by flash chromatography (silica, 10% EtOAc-hexane) afforded the title compound as a white solid. 1H NMR ($CDCl_3$): δ 8.58 (1H, br s), 8.10 (1H, dd, J=1.7, 9 Hz), 8.06 (1H, d, J=2 Hz), 7.83 (1H, d, J=9 Hz), 7.80 (1H, d, J=9 Hz), 7.62 (1H, dd, J=2, 9 Hz).

Ethyl (E)-4-[2-(5,6,7,8-tetrahydro-5,5-dimethyl-8-oxo-2-naphthalenyl)ethenyl]-benzoate (Compound O)

To a solution of 520.0 mg (2.00 mmol) of 3,4-dihydro-4,4-dimethyl-7-bromo-1-(2H)-naphthalenone (Compound B) and 510.0 mg (2.90 mmol) of ethyl 4-vinylbenzoate in 4.0 ml of triethylamine (degassed by sparging with argon for 25 minutes), was added 124.0 mg (0.40 mmol) of tris(2-methylphenyl) phosphine, followed by 44.0 mg (0.20 mmol) of palladium(II)acetate. The resulting solution was heated to 95° C. for 2.5 hours, cooled to room temperature, and concentrated under reduced pressure. Purification by column chromatography (10% EtOAc/hexanes) afforded the title compound as a colorless solid. 1H NMR ($CDCl_3$): δ 8.19 (1H, d, J=2.0 Hz), 8.03 (2H, d, J=8.4 Hz), 7.69 (1H, dd, J=2.0, 8.2 Hz), 7.57 (2H, d, J=8.4 Hz), 7.45 (1H, d, J=8.2 Hz), 7.20 (2H, s), 4.39 (2H, q, J=7.1 Hz), 2.76 (2H, t, J=6.5 Hz), 2.04 (2H, t, J=6.5 Hz), 1.41 (3H, t, J=7.1 Hz, and 6H, s).

Ethyl (E)-4-[2-(5,6-dihydro-5,5-dimethyl-8-(trifluoromethylsulfonyl)oxy-2-naphthalenyl)ethenyl]-benzoate (Compound P)

To a cold (−78° C.) solution of 440.0 mg (2.40 mmol) of sodium bis(trimethylsilyl)amide in 10.0 ml of THF was added 700.0 mg (2.00 mmol) of ethyl (E)-4-[2-(5,6,7,8-tetrahydro-5,5-dimethyl-8-oxo-2-naphthalenyl)ethenyl]-benzoate (Compound O) as a solution in 25.0 ml of THF. After stirring at −78° C. for 1.5 hours, 960.0 mg (2.40 mmol) of 2[N,N-bis(trifluoromethylsulfonyl)amino]-5-chloropyridine was added in one portion. After 30 minutes the solution was warmed to 0° C. and stirred for 3 hours. The reaction was quenched by the addition of saturated aqueous $NH_4Cl$, and extracted with EtOAc. The combined extracts were washed with 5% aqueous NaOH, dried ($Na_2SO_4$), and the solvents removed under reduced pressure. The title compound was isolated as a colorless solid by column chromatography (7% EtOAc/hexanes). 1H NMR ($CDCl_3$): δ 8.04 (1H, d, J=8.4 Hz), 7.57 (2H, d, J=8.4 Hz), 7.52 (1H, s), 7.49 (1H, d, J=8.0 Hz), 7.33 (1H, d, J=8.0 Hz), 7.20 (1H, d, J=16.4 Hz), 7.10 (1H, d, J=16.4 Hz), 6.00 (1H, t, J=4.9 Hz), 4.39 (2H, q, J=7.1 Hz), 2.43 (2H, d, J=4.9 Hz), 1.41 (3H, t, J=7.1 Hz), 1.32 (6H, s).

Ethyl (E)-4-[2-(5,6-dihydro-5,5-dimethyl-8-(4-methylphenyl)-2-naphthalenyl)ethenyl]-benzoate (Compound 44)

A solution of 4-lithiotoluene was prepared at −78° C. by the addition of 130.7 mg of t-butyllithium (2.04 mmol; 1.20 ml of a 1.7M solution in pentane) to a solution of 374.5 mg (2.20 mmol) of 4-bromotoluene in 2.5 ml of THF. After 30 minutes a solution of 313.4 mg (2.30 mmol) of $ZnCl_2$ in 2.0 ml of THF was added. The resulting solution was warmed to room temperature, stirred for 1.25 hour and then added via canula to a solution of 285.0 mg (0.590 mmol) of ethyl (E)-4-[2-(5,6-dihydro-5,5-dimethyl-8-(trifluoromethylsulfonyl)oxy-2-naphthalenyl)ethenyl]-benzoate (Compound P) and 29.0 mg (0.025 mmol) of tetrakis(triphenylphosphine)palladium(0) in 2.0 ml of THF. The resulting solution was stirred at room temperature for 1 hour and then at 55° C. for 2 hours. Upon cooling to room temperature the reaction was quenched by the addition of saturated aqueous $NH_4Cl$. The mixture was extracted with EtOAc, and the combined extracts were washed with 5% aqueous NaOH, saturated aqueous NaCl, and dried over $Na_2SO_4$ before being concentrated under reduced pressure. The title compound was isolated by column chromatography (10% EtOAC/hexanes) as a colorless solid. 1H NMR ($CDCl_3$): δ 7.96 (2H, d, J=8.1 Hz), 7.47 (2H, d, J=8.1 Hz), 7.43–7.16 (7H, m), 7.07 (1H, d, J=16.3 Hz), 6.93 (1H, d, J=16.3 Hz), 5.97 (1H, t, J=4.7 Hz), 4.39 (2H, q, J=7.0 Hz), 2.41 (3H, s), 2.33 (1H, d, J=4.7 Hz), 1.38 (3H, t, J=7.0 Hz), 1.33 (6H, s).

(E)-4-[2-(5,6-Dihydro-5,5-dimethyl-8-(4-methylphenyl)-2-naphthalenyl)ethenyl]-benzoic acid Compound 45

To a solution of 65.0 mg (0.190 mmol) of ethyl (E)-4-[2-(5,6dihydro-5,5-dimethyl-8-(4-methylphenyl)-2-naphthalenyl)ethenyl]-benzoate (Compound 44) in 4.0 ml of THF was added 30.0 mg of LiOH (0.909 mmol, 1.0 ml of a 1.1M solution) and 1.0 ml of MeOH. The solution was heated to 55° C. for 3 hours, cooled to room temperature, and concentrated under reduced pressure. The residue was dissolved in $H_2O$ and extracted with hexanes. The aqueous layer was acidified to pH 1 with 10% HCl, and extracted with $Et_2O$. The combined organic layers were washed with saturated aqueous NaCl, diluted with EtOAc to give a clear solution, and dried over $Na_2SO_4$. The solvents were removed under reduced pressure to give the title compound as a colorless solid. 1H NMR (d6-DMSO): δ 7.86 (2H, d, J=8.4 Hz), 7.66 (2H, d, J=8.4 Hz), 7.58 (1H, dd, J=1.7, 8.1 Hz), 7.41 (1H, d, J=8.1 Hz), 7.28 (1H, d, J=16.5 Hz), 7.23 (4H, s), 7.08 (1H, d, J=1.7 Hz), 7.07 (1H, d, J=16.5 Hz), 5.97 (1H, t, J=4.6 Hz), 2.35 (3H, s), 2.31 (1H, d, J=4.6 Hz), 1.29 (6H, s).

Ethyl 4-[2-(1.1-dimethyl-3-(4-methylphenyl)-5-indenyl)ethynyl]benzoate (Compound 47)

A solution of 32.0 mg (0.187 mmol) of 4-bromotoluene in 1.0 ml THF was cooled to −78° C. and 24.0 mg of t-butyllithium (0.375 mmol, 0.22 ml of a 1.7M solution in pentane) was slowly added. The yellow solution was stirred for 30 minutes at which time 29.8 mg (0.219 mmol) of $ZnCl_2$ was added as a solution in 1.0 ml THF. The resulting solution was warmed to room temperature and after 30 minutes added to a second flask containing 29.0 mg (0.062 mmol) of ethyl 4-[2-(1,1-dimethyl-3-(trifluoromethylsulfonyl)oxy-5-indenyl) ethynyl]benzoate (Compound FF) and 2.9 mg (0.003 mmol) of tetrakis (triphenylphosphine)palladium (0) in 1.0 ml THF. The resulting solution was warmed to 50° C. for 1 hour and then stirred at room temperature for 4 hours. The reaction was quenched by the addition of saturated aqueous $NH_4Cl$, and then extracted with $Et_2O$. The combined organic layers were washed with water, saturated aqueous NaCl, and dried over $MgSO_4$ before being concentrated under reduced pressure. The title compound was isolated as a colorless oil by column chromatography (10% $Et_2O$/hexanes). 1H NMR (300 MHz, $CDCl_3$): δ 8.03 (2H, d, J=8.5 Hz), 7.66 (1H, s), 7.58 (2H, d, J=8.5 Hz), 7.50 (2H, d, J=8.0 Hz), 7.46 (1H, d, J=7.9 Hz), 7.38 (1H, d, J=7.7 Hz), 7.28 (2H, d, J=9 Hz), 6.43 (1H, s), 4.40 (2H, q, J=7.2 Hz), 2.43 (3H, s), 1.41 (3H, t; +6H, s).

4-[2-(1,1-dimethyl-3-(4-methylphenyl)-5-indenyl)ethynyl] benzoic acid (Compound 48)

To a solution of 10.0 mg (0.025 mmol) of ethyl 4-[2-(1, 1-dimethyl-3-(4-methylphenyl)-5-indenyl)ethynyl]benzoate (Compound 47) in 0.5 ml THF/$H_2O$ (3:1 v/v) was added 5.2 mg (0.12 mmol) LiOH $H_2O$. After stirring at room temperature for 48 hours the solution was extracted with hexanes and the aqueous layer was acidified with saturated aqueous $NH_4Cl$. Solid NaCl was added and the resulting mixture extracted with EtOAc. The combined organic layers were dried ($Na_2SO_4$) and concentrated under reduced pressure to give the title compound as a colorless solid. 1H NMR (300 MHz, $d_6$-DMSO): δ 7.95 (2H, d, J=8.3 Hz), 7.65 (2H, d, J=8.3 Hz), 7.57 (2H, m), 7.49 (3H, m), 7.30 (2H, d, J=7.9 Hz), 6.61 (1H, s), 2.36 (3H, s), 1.36 (6H, s).

3-(4-bromothiophenoxy)propionic acid

To a solution of 1.44 g (35.7 mmol) of NaOH in 20.0 ml degassed $H_2O$ (sparged with argon) was added 6.79 g (35.7 mmol) of 4-bromothiophenol. The resulting mixture was stirred at room temperature for 30 minutes. A second flask was charged with 2.26 g (16.3 mmol) of $K_2CO_3$ and 15 ml of degassed $H_2O$. To this solution was added (in portions) 5.00 g (32.7 mmol) of 3-bromopropionic acid. The resulting potassium carboxylate solution was added to the sodium thiolate solution, and the resulting mixture stirred at room temperature for 48 hours. The mixture was filtered and the filtrate extracted with benzene, and the combined organic layers were dicarded. The aqueous layer was acidified with 10% HCl and extracted with EtOAc. The combined organic layers were washed with saturated aqueous NaCl, dried over $MgSO_4$, and concentrated under reduced pressure. The resulting solid was recrystallized from $Et_2O$ -hexanes to give the title compound as off-white crystals. 1H NMR ($CDCl_3$): δ 7.43 (2H, d, J=8.4 Hz), 7.25 (2H, d, J=8.4 Hz), 3.15 (2H, t, J=7.3 Hz), 2.68 (2H, t, J=7.3 Hz).

2,3-dihydro-6-bromo-(4H)-1-benzothiopyran-4-one

A solution of 3.63 g (13.9 mmol) of 3-(4-bromothiophenoxy)propionic acid in 60 ml methanesulfonic acid was heated to 75° C. for 1.5 hours. After cooling to room temperature the solution was diluted with $H_2O$ and extracted with EtOAc. The combined organic layers were washed with 2N aqueous NaOH, $H_2O$, and saturated aqueous NaCl and then dried over $MgSO_4$. Removal of the solvent under reduced pressure afforded a yellow solid from which the product was isolated by column chromatography (3% hexanes) as a pale-yellow solid. 1H NMR ($CDCl_3$): δ 8.22 (1H, d, J=2.1 Hz), 7.48 1H, dd, J=2.1, 8.3 Hz), 7.17 (1H, d, J=8.5 Hz), 3.24 (2H, t, J=6.4 Hz), 2.98 (2H, t, J=6.7 Hz).

2,3-dihydro-6-(2-trimethylsilylethynyl)-(4H)-1-benzothiopyran-4-one

A solution of 1.00 g (4.11 mmol) 2,3-dihydro-6-bromo-(4H)-1-benzothiopyran-4-one and 78.3 mg (0.41 mmol) CuI in 15.0 ml THF and 6.0 ml $Et_2NH$ was sparged with argon for 5 minutes. To this solution was added 2.0 ml (1.39 g, 14.2 mmol) of (trimethylsilyl)acetylene followed by 288.5 mg (0.41 mmol) of bis(triphenylphosphine)palladium(II) chloride. The resulting dark solution was stirred at room temperature for 3 days and then filtered through a pad of Celite, which was washed with EtOAc. The filtrate was washed with $H_2O$ and saturated aqueous NaCl before being dried over $MgSO_4$. The title compound was isolated as an orange oil by column chromatography (4% EtOAc-hexanes). 1H NMR ($CDCl_3$): δ 8.13 (1H, d, J=1.9 Hz), 7.36 (1H, dd, J=2.1, 8.2 Hz), 7.14 (1H, d, J=8.2 Hz), 3.19 (2H, d, J=6.3 Hz), 2.91 (2H, d, J=6.3 Hz), 0.21 (9H, s).

2,3-dihydro-6-ethynyl-(4H)-1-benzothiopyran-4-one

A solution containing 600.0 mg (2.25 mmol) of 2,3-dihydro-6-(2-trimethylsilylethynyl)-(4H)-1-benzothiopyran-4-one and 100.0 mg (0.72 mmol) $K_2CO_3$ in 15 ml MeOH was stirred at room temperature for 20 hours. The solution was diluted with $H_2O$ and extracted with $Et_2O$. The combined organic layers were washed with $H_2O$ and saturated aqueous NaCl before being dried over $MgSO_4$. Removal of the solvents under reduced preesure afforded the title compound as an orange solid. 1H NMR ($CDCl_3$): δ 8.17 (1H, d, J=1.8 Hz), 7.40 (1H, dd, J=1.8, 8.2 Hz), 7.19 (1H, d, J=8.2 Hz), 3.22 (2H, t, J=6.3 Hz), 3.08 (1H, s) 2.94 (2H, t, J=6.3 Hz).

Ethyl 4-[2-(6-(2,3-dihydro-(4H)-1-benzothiopyran-4-onyl)) ethynyl]benzoate

A solution of 405.0 mg (2.15 mmol) 2,3-dihydro-6-ethynyl-(4H)-1-benzothiopyran-4-one and 594.0 mg (2.15 mmol) of ethyl 4-iodobenzoate in 15 ml $Et_3N$ and 3 ml THF was sparged with argon for 15 minutes. To this solution was added 503.0 mg (0.72 mmol) of bis(triphenylphosphine) palladium(II) chloride and 137.0 mg (0.72 mmol) CuI. This solution was stirred for 20 hours at room temperature and then filtered through a pad of Celite, which was washed with EtOAc. Removal of the solvents under reduced pressure afforded a brown solid. Column chromatography (3% EtOAc-hexanes) afforded the title compound as an orange solid. 1H NMR ($d_6$-acetone): δ 8.15 (1H, d, J=2.0 Hz), 8.02 (2H, d, J=8.5 Hz), 7.69 (2H, d, J=8.5 Hz), 7.61 (1H, dd, J=2.1, 8.3 Hz), 7.40 (1H, d, J=8.2 Hz), 4.35 (2H, q, J=7.1 Hz), 3.40 (2H, t, J=6.3 Hz), 2.96 (2H, t, J=6.3 Hz), 1.37 (3H, t, J=7.1 Hz).

Ethyl 4-[2-(6-(4-(trifluoromethylsulfonyl)oxy-(2H)-1-benzothiopyrsnyl) ethynyl]benzoate To a solution of 221.9 mg (1.21 mmol) of sodium bis (trimethylsilyl)amide in 3.0 ml THF cooled to −78° C. was added 370.0 mg (1.10 mmol) of ethyl 4-[2-(6-(2,3-dihydro-(4H)-1-benzothiopyran-4-onyl))ethynyl]benzoate in 4.0 ml THF. After 30 minutes, a solution of 2[N,N-bis-trifluoromethysulfonyl)amino]-5-chloropyridine in 4.0 ml THF was slowly added. The reaction was slowly warmed to room temperature and after 5 hours quenched by the addition of saturated aqueous $NH_4Cl$. The mixture was extracted with EtOAc, and the combined organic layers were washed with 5% aqueous NaOH, $H_2O$, and saturated aqueous NaCl before being dried over $MgSO_4$. Removal of the solvents under reduced pressure, followed by column chromatography (4% EtOAc-hexanes) afforded the title compound as a pale-yellow solid. 1H NMR ($d_6$-acetone): δ 8.12 (2H, d, J=8.5 Hz), 7.66 (2H, d, J=8.5 Hz), 7.56 (1H, d, J=1.7 Hz), 7.49 (1H. dd, J=1.7, 8,1 Hz), 7.40 (1H, d, J=8.1 Hz), 6.33 (1H, t, J=5.7 Hz), 4.35 (2H, q, J=7.1 Hz), 3.82 (2H, d, J=5.7 Hz), 1.37 (3H, t, J=7.1 Hz).

Ethyl 4-[2-(6-(4-(4-methylphenyl)-(2H)-1-benzothiopyranyl))ethynyl]benzoate (Compound 49)

To a solution of 120.8 mg (0.70 mmol) of 4-bromotoluene in 2.0 ml THF at −78° C. was added 88.4 mg (1.38 mmol, 0.81 ml of a 1.7M solution in pentane) of t-butyllithium. After 30 minutes a solution of 131.6 mg (0.97 mmol) $ZnCl_2$ in 2.0 ml THF was added and the reulting pale-yellow solution warmed to room temperature. Stirring for 40 minutes was followed by addition of this solution to a second flask containing 129.2 mg (0.28 mmol) of ethyl 4-[2-(6-(4-(trifluoromethylsulfonyl)oxy-(2H)-1-benzothiopyranyl)) ethynyl]benzoate, 14.0 mg (0.012 mmol) tetrakis (triphenylphosphine)palladium (0), and 2.0 ml THF. The resulting solution was heated to 50° C. for 5 hours, cooled to room temperature, and quenched by the addition of saturated aqueous $NH_4Cl$. The mixture was extracted with EtOAc, and the combined organic layers were washed with H₂O and saturated aqueous NaCl, then dried (MgSO₄) and concentrated to an orange oil. The title compound was isolated as a colorless solid by column chromatography (3 to 5% EtOAc-hexanes). 1H NMR (d₆-acetone): δ 7.98 (2H, d, J=8.3 Hz), 7.58 (2H, d, J=8.2 Hz), 7.44–7.38 (2H, m), 7.26–7.15 (5H, m), 6.14 (1H, t, J=5.8 Hz), 4.34 (2H, q,-J=7.1 Hz), 3.53 (2H, d, J=5.8 Hz), 2.37 (2H, s), 1.35 (3H, t, J=7.1 Hz).

4-[2-(6-(4-(4-methylphen1)-(2H)-1-benzothiopylapvl)) ethynyl]-benzoic acid (Compound 50)

To a solution of 29.0 mg (0.07 mmol) ethyl 4-[2-(6-(4-(4-methylphenyl)-(2H)-1-benzothiopyranyl))ethynyl]benzoate (Compound 49) in 2.0 ml THF and 2.0 ml EtOH was added 160.0 mg (4.00 mmol, 2.0 ml of a 2M aqueous solution). The resulting solution was stirred at 35° C. for 2 hours, and then cooled to room temperature and stirred an additional 2 hours. The reaction was quenched by the addition of 10% aqueous HCl and extracted with EtOAc. The combined organic layers were washed with H₂O and saturated aqueous NaCl, and dried over Na₂SO₄ Removal of the solvents under reduced pressure afforded a solid which was washed with CH₃CN and dried under high vacuum to give the title compound as a pale-yellow solid. 1H NMR (d₆-DMSO): δ 7.90 (2H, d, J=8.4 Hz), 7.59 (2H, d, J=8.4 Hz), 7.40 (4H, m), 7.25–7.13 (4H, m), 7.02 (1H, d, J=1.7 Hz), 6.11 (1H, t, J=5.7 Hz), 3.54 (2H, d, J=5.7 Hz), 2.34 (3H, s).

3,4-Dihydro-4,4-dimethyl-7-acetyl-1(2H)-naphthalenone (Compound R): and 3,4-dihydro-4,4-dimethyl-6-acetvl-1 (2H)-naphthalenone (Compound S)

To a cold (0° C.) mixture of aluminum chloride (26.3 g, 199.0 mmols) in dichloromethane (55 ml) was added acetylchloride (15 g, 192 mmols) and 1,2,3,4-tetrahydro-1,1-dimethylnaphthalene (24.4 g, 152 mmols) in dichloromethane (20 ml) over 20 minutes. The reaction mixture was warmed to ambient temparature and stirred for 4 hours. Ice (200 g) was added to the reaction flask and the mixture diluted with ether (400 ml). The layers were separated and the organic phase washed with 10% HCl (50 ml), water (50 ml), 10% aqueous sodium bicarbonate, and saturated aqueous NaCl (50 ml) before being dried over MgSO₄. Ths solvent was removed by distillation to afford a yellow oil which was dissolved in benzene (50 ml).

To a cold(0° C.) solution of acetic acid (240 ml) and acetic anhydride (120 ml) was added chromiumtrioxide (50 g, 503 mmols) in small portions over 20 minutes under argon. The mixture was stirred for 30 mins at 0° C. and diluted with benzene (120 ml). The benzene solution prepared above was added with stirring via an addition funnel over 20 minutes. After 8 hours, the reaction was quenched by careful addition of isopropanol (50 ml) at 0° C., followed by water (100 ml). After 15 minutes, the reaction mixture was diluted with ether (1100 ml) and water (200 ml), and then neutralized with solid sodium bicarbonate (200 g). The ether layer was washed with water (100 ml), and saturated aqueous NaCl (2×100 ml), and dried over MgSO₄. Removal of the solvent under reduced pressure afforded a mixture of the isomeric diketones which were separated by chromatography ( 5% EtOAc/hexanes). (Compound R): 1H NMR (CDCl₃): δ 8.55 (1H, d, J=2.0 Hz), 8.13 (1H, dd, J=2.0, 8.3 Hz), 7.53 (1H, d, J=8.3 Hz), 2.77 (2H, t, J=6.6 Hz), 2.62 (3H, s), 2.05 (2H, t, J=6.6 Hz), 1.41 (6H, s). (Compound S): 1H NMR (CDCl₃): δ 8.10 (1H, d, J=8.1 Hz), 8.02 (1H, d, J=1.6 Hz), 7.82 (1H, dd, J=1.6, 8.1 Hz), 2.77 (2H, t, J=7.1 Hz), 2.64 (3H, s), 2.05 (2H, t, J=7.1 Hz), 1.44 (6H, s).

3,4-Dihydro-4,4-dimethyl-7-(2-(2-methyl-1,3-dioxolanyl))-1-(2H)-naphthalenone (Compound T)

A mixture of 3,4-dihydro-4,4-dimethyl-7-acetyl-1(2H)-naphthalenone (Compound R) (140.0 mg, 0.60 mmol), ethylene glycol (55.0 mg, 0.90 mmol), p-toluenesulfonic acid monohydrate (4 mg) and benzene (25 ml) was refluxed using a Dean-Stark apparatus for 12 hours. The reaction was quenched by the addition of 10% aqueous sodium bicarbonate, and extracted with ether (2×75 ml). The combined organic layers were washed with water (5 ml), and saturated aqueous NaCl (5 ml), and dried over MgSO₄. Removal of the solvent under reduced pressure afforded the title compound as an oil. 1H NMR (CDCl₃): δ 8.13 (1H, d, J=2.0 Hz), 7.64 (1H, dd, J=2.0, 8.2 Hz), 7.40 (1H, d, J=8.2 Hz), 3.97–4.10 (2H, m), 3.70–3.83 (2H, m), 2.73 (2H, t, J=6.5 Hz), 2.01 (2H, t, J=6.5 Hz), 1.64 (3H, s), 1.39 (6H, s).

1,2,3,4-Tetrahydro-1-hydroxy-1-(4-methylphenyl)-4,4-dimethyl-7-(2-(2-methyl-1,3-dioxolanyl))naphthalene (Compound U)

To a solution of 195.4 mg (1.00 mmol) p-tolulylmagnesiumbromide (1.0 ml; 1M solution in ether) in 2 ml THF was added a solution of 3,4-dihydro-4,4-dimethyl-7-(2-(2-methyl-1,3-dioxolanyl))-1-(2H)-naphthalenone (Compound T) 135.0 mg, 0.52 mmol) in 5 ml THF. The solution was refluxed for 16 hours, cooled to room temperature, and diluted with ether (50 ml). The solution was washed with water (5 ml), saturated aqueous NH₄Cl (5 ml), and dried over MgSO₄. Removal of the solvents under reduced pressure and column chromatography (5% EtOAc/hexanes) afforded the title compound as a solid. 1H NMR (CDCl₃): δ 7.37 (2H, d), 7.21 (1H, s), 7.13 (2H, d, J=8.5 Hz), 7.08 (2H, d, J=8.5 Hz), 3.88–3.99 (2H, m), 3.58-3.75 (2H, m), 2.34 (3H, s), 2.12–2.30 (2H, m), 1.79–1.90 (1H, m), 1.57 (3H, s), 1.48–1.58 (1H, m), 1.38 (3H, s), 1.31 (3H, s).

3,4-Dihydro-1-(4-methylphenyl)-4,4-dimethyl-7-acetylnaphthalene (Compound V)

A mixture of 1,2,3,4-tetrahydro-1-hydroxy-1-(4-methylphenyl)-4,4-dimethyl-7-(2-(2-methyl-1,3-dioxolanyl))naphthalene (Compound U) 130.0 mg (0.38 mmol), p-toluenesulfonic acid monohydrate (4 mg) and benzene (5 ml) was refluxed for 16 hours. Upon cooling to room temperature, the reaction mixture was diluted with ether (100 ml) and washed with 10% aqueous sodium bicarbonate, water, and saturated aqueous NaCl. The organic layer was dried over MgSO₄ and the solvents were removed under reduced pressure to give the title compound as a solid. 1H NMR (CDCl₃): δ 7.83 (1H, dd, J=1.8,8.0 Hz), 7.66 (1H, d, J=1.8 Hz), 7.45 (1H, d, J=8.0 Hz), 7.25 (2H, d, J=8.5 Hz), 7.22 (2H, d, J=8.5 Hz), 6.03 (1H, t, J=6.3Hz), 2.47 (3H, s), 2.41 (3H, s), 2.37 (2H, d, J=6.3Hz), 1.36 (6H, s).

(E)-3-(5,6-dihydro-5,5-dimethyl-8-(4-methylphenyl)-2-naphthaleyl)-2-butenenitrile (Compound W)

To a slurry of NaH (48.0 mg, 2.00 mmol) in THF (6 ml), was added diethylcyanomethylphosphonate (450.0 mg, 2.50 mmol). After 40 mins, a solution of 3,4-dihydro-1-(4-methylphenyl)-4,4-dimethyl-7-acetylnaphthalene (Compound V) 95.0 mg, (0.33 mmol) in THF (4 ml) was added. The mixture was stirred for 16 hours, diluted with ether (100 ml), and washed with water, and saturated aqueous NaCl before being dried over MgSO₄. Removal of the solvents under reduced pressure, and column chromatography (3% EtOAc/hexanes) afforded the title compound as a solid. 1H NMR (CDCl₃):δ 7.39 (1H, d, J=1H), 7.32 (1H, dd, J=2.0, 8.1Hz), 7.20–7.25 (4H, brs), 7.15 (1H, d, J=2.0 Hz), 6.03 (1H, t, J=6.0 Hz), 5.44 (1H, s), 2.42 (3H, s), 2.36 (2H, d, J=6.0 Hz), 2.35 (3H, s), 1.35 (6H, s).

(E)-3-(5,6-dihydro-5,5-dimethy1-8-(4-methylphenyl)-2-naphtalenyl)-2-butenal (Compound X)

To a cold solution (−78° C.) of (E)-3-(5,6-dihydro-5,5-dimethyl-8-(4-methylphenyl)-2-naphthalenyl)-2- butenenitrile (Compound W) 84.0 mg, 0.29 mmol) in dichloromethane (4 ml) was added 0.50 ml (0.50 mmol) of diisobutylaluminumhydride (1M solution in dichloromethane). After stirring for 1 hour, the reaction was quenched at −78° C. by adding 2-propanol (1 ml) diluted with ether (100 ml). Upon warming to room temperature, the solution was washed with water, 10% HCl, and saturated aqueous NaCl. The organic layer was dried over $MgSO_4$ and the solvent removed under reduced pressure to give the title compound as an oil. 1H NMR ($CDCl_3$): δ 10.12 (1H, d, J=7.9 Hz), 7.43 (2H, s), 7.19–7.28 (5H, m), 6.27 (1H, d, J=7.9 Hz), 6.03 (1H, t, J=4.8 Hz), 2.47 (3H, s), 2.42 (3H, s), 2.37 (2H, d, J=4.8 Hz), 1.37 (6H, s).

Ethyl (E,E,E)-3-methyl-7-(5,6-dihydro-5,5-dimethyl-8-(4-methylphenyl)-2-naphthalenyl)-2,4,6-octatrienoate (Compound 51)

To a cold (−78° C.) solution of diethyl-(E)-3-ethoxycarbonyl-2methylallylphosphonate [prepared in accordance with *J. Or. Chem.* 39: 821 (1974)] 264.0 mg, (1.00 mmol) in THF (2 ml) was added 26.0 mg (0.41 mmol, 0.65 ml) of n-butyllithium in hexanes (1.6M solution) followed immediately by the addition of (E)-3-(5,6-dihydro-5,5-dimethyl-8-(4-methylphenyl)-2-naphthalen-yl)-2-butenal (Compound X) 82.0 mg, 0.26 mmol) in THF (3 ml). After 1 hour, the reaction mixture was diluted with ether (60 ml), washed with water (5 ml), saturated aqueous NaCl (5 ml) and dried over $MgSO_4$. After removal of the solvents under reduced pressure, the title compound was isolated as an oil by column chromatography (5% EtOAc/hexanes, followed by HPLC using 1% EtOAc/hexanes). 1H NMR (acetoned6): δ 7.36–7.43 (2H, m), 7.18–7.27 (4H, m), 7.17 (1H, d, J=1.7 Hz), 7.08 (1H, dd, J=11.2, 15.2 Hz), 6.46 (1H, d, J=11.2 Hz), 6.38 (1H, d, J=15.2 Hz), 5.98 (1H, t, J=4.7 Hz), 5.78 (1H, s), 4.10 (2H, q, J=7.1 Hz), 2.35 (3H, s), 2.33 (3H, s), 2.32 (2H, d, J=4.7 Hz), 2.12 (3H, s), 1.31 (6H, s), 1.22 (3H, t, J=7.1 Hz).

(E,E,E)-3-methyl-7-(5,6-dihydro-5,5-dimethyl-8-(4-methylphenyl)-2-naphthalenyl)-2,4,6-octatrienoic acid (Compound 52)

To a solution of ethyl (E,E,E)-3-methyl-7-(5,6-dihydro-5,5-dimethyl- 8-(4-methylphenyl)-2-naphthalenyl)-2,4,6-octatrienoate (Compound 51) 85.0 mg, 0.20 mmol) in THF (1 ml) and methanol (1 ml) was added 12.0 mg (0.50 mmol) of LiOH (0.5 ml, 1M solution). The mixture was stirred for 6 hours, diluted with ether (60 ml), acidified with 10% HCl (1 ml). The solution was washed with water, and saturated aqueous NaCl, before being dried over $MgSO_4$. Removal of the solvents under reduced pressure afforded the title compound as a solid, which was purified by recrystallization from acetone. 1H NMR (acetone-d6): δ 7.35–7.45 (2H, m), 7.19–7.28 (4H, m), 7.17 (1H, d, J=1.8Hz), 7.09 (1H, dd, J=11.5, 15.1 Hz), 6.48 (1H, d, J=11.5 Hz), 6.42 (1H, d, J=15.1Hz), 5.99 (1H, t, J=4.7 Hz), 5.82 (1H, s), 2.36 (3H, s), 2.33 (2H, d, J=4.7Hz), 2.32 (3H, s), 2.13 (3H, s), 1.32 (6H, s).

3,4-dihydro-4,4-dimethyl-7-nitro-1-(2H)-naphthalenone (Compound Y)

To 1.7 ml (3.0 g, 30.6 mmol, 18M) $H_2SO_4$ at −5° C. (ice-NaCl bath) was slowly added 783.0 mg (4.49 mmol) of 3,4-dihydro-4,4-dimethyl-1-(2H)-naphthalenone. A solution of 426.7 mg (6.88 mmol, 0.43 ml, 16M) $HNO_3$, and 1.31 g (0.013 mol, 0.74 ml, 18M) $H_2SO_4$ was slowly added. After 20 minutes, ice was added and the resulting mixture extracted with EtOAc. The combined extracts were concentrated under reduced pressure to give a residue from which the title compound, a pale yellow solid, was isolated by column chromatography (10% EtOAC/hexanes). 1H NMR ($CDCl_3$): δ (1H, d, J=2.6 Hz), 8.31 (1H, dd, J=2.8, 8.9 Hz), 7.62 (1H, d, J=8.7 Hz), 2.81 (2H, t, J=6.5 Hz), 2.08 (2H, t, J=6.5 Hz), 1.45 (6H, s).

3,4-dihydro-4,4-dimethyl-7-amino-1(2H)-naphthalenone (Compound Z)

A solution of 230.0 mg (1.05 mmol) 3,4-dihydro-4,4-dimethyl-7-nitro-1-(2H)-naphthalenone (Compound Y) in 5.0 ml of EtOAc was stirred at room temperature with a catalytic amount of 10% Pd-C under 1 atm of $H_2$ for 24 hours. The catalyst was removed by filtration through a pad of Celite, and the filtrate concentrated under reduced pressure to give the title compound as a dark green oil. 1H NMR ($CDCl_3$): δ 7.30 (1H, d, J=2.7 Hz), 7.22 (1H, d, J=8.4 Hz), 6.88 (1H, dd, J=2.7, 8.5 Hz), 2.70 (2H, t, J=6.6 Hz), 1.97 (2H, t, J=6.6 HZ), 1.34 (6H, s).

Ethyl 4-[(5,6,7,8-tetrahydro-5,5-dimethyl-8-oxo-2-naphthalenyl)azo]-benzoate (Compound AA)

To a solution of 198.7 mg (1.05 mmol) 3,4-dihydro-4,4-dimethyl-7-amino-1-(2H)-naphthalenone (Compound Z) in 5.0 ml glacial acetic acid was added 180.0 mg (1.00 mmol) of ethyl 4-nitrosobenzoate. The resulting solution was stirred overnight at room temperature, and then concentrated under reduced pressure. The product was isolated from the residual oil as a red solid, by column chromatography (15% EtOAc—hexanes). 1H NMR ($CDCl_3$): δ 8.57 (1H, d, J=2.0 Hz), 8.19 (2H, d, J=8.4 Hz), 8.07 (1H, d, J=8.0 Hz), 7.94 (2H, d, J=8.4 Hz), 7.58 (1H, d, J=8.6 Hz), 4.41 (2H, q, J=7.1 Hz), 2.79 (2H, t, J=6.6 Hz), 2.07 (2H, t, J=7.02 Hz), 1.44 (6H, s), 1.42 (3H, t, J=7.1 Hz).

Ethyl 4-[(5,6-dihydro-5,5-dimethyl-8-(trffluoromethylsulfonyl)oxy-2-naphthalenyl)azo]-benzoate (Compound BB)

To a solution of 90.4 mg sodium bis(trimethylsilyl)amide (0.48 mmol, 0.48 ml of a 1.0M THF solution) in 2.0 ml THF at −78° C., was added 153.0 mg (0.437 mmol) of ethyl 4-[(5,6,7,8-tetrahydro-5,5-dimethyl-8-oxo-2-naphthalenyl)azo]-benzoate (Compound AA) in 2.0 ml THF. The dark red solution was stirred at −78° C. for 30 minutes and then 204.0 mg (0.520 mmol) of 2-[N,N-bis(trifluoromethylsulfonyl)amino]-5-chloropyridine was added as a solution in 2.0 ml THF. The reaction mixture was allowed to warm to room temperature and after 3 hours it was quenched by the addition of $H_2O$. The organic layer was concentrated to a red oil under reduced pressure. The product was isolated by column chromatography (25% EtOAc/hexanes) as a red oil. 1H NMR ($CDCl_3$): δ 8.21 (2H, d, J=8.6 Hz), 7.96 (2H, d, J=8.6 Hz), 7.94 (2H, m), 7.49 (1H, d, J=8.2 Hz), 6.08 (1H, t, J=2.5 Hz), 4.42 (2H, q, J=7.1 Hz), 2.49 (2H, d, J=4.8 Hz), 1.44 (3H, t, J=7.1 Hz), 1.38 (6H, s).

Ethyl 4-[(5,6-dihydro-5,5-dimethyl-8-(4-methylphenyl)-2-naphthalenyl)azo]-benzoate (Compound 46a)

A solution of 4-lithiotoluene was prepared by the addition of 62.9 mg (0.58 ml, 0.98 mmol) of t-butyl lithium (1.7M solution in pentane) to a cold solution (−78° C.) of 84.0 mg (0.491 mmol) of 4-bromotoluene in 1.0 ml of HF. After stirring for 30 minutes a solution of 107.0 mg (0.785 mmol) of zinc chloride in 2.0 ml of THF was added. The resulting solution was warmed to room temperature, stirred for 30 minutes, and added via cannula to a solution of 94.7 mg (0.196 mmol) of ethyl 4-[(5,6-dihydro-5,5-dimethyl-8-(trifluoromethylsulfonyl)oxy-2-naphthalenyl)azo]-benzoate (Compound BB) and 25 mg (0.02 mmol) of tetrakis(triphenylphosphine)palladium(0) in 2.0 ml of THF. The resulting solution was heated at 50° C. for 1.5 hours, cooled to room temperature and diluted with sat. aqueous $NH_4Cl$. The mixture was extracted with EtOAc (40 ml) and the combined organic layers were washed with water and brine.

The organic phase was dried over $Na_2SO_4$, concentrated in vacuo, and the title compound isolated as a red solid by column chromatography (25% EtOAc—hexanes) 1H NMR ($CDCl_3$): δ 8.21 (2H, d, J=8.6 Hz), 7.96 (2H, d, J=8.6 Hz), 7.94 (2H, m), 7.49 (1H, d, J=8.2 Hz), 6.08 (1H, t, J 2.5 Hz), 4.42 (2H, q, J=7.1 Hz), 2.49 (2H, d, J=4.8 Hz), 1.44 (3H, t, J=7.1 Hz), 1.38 (6H, s).

4-[(5,6-dihydro-5,5-diinetbyl-8-(4-methylphenyl)-2-naphthalenyl)azo]-benzoic acid (Compound 46b)

To a solution of ethyl 4-[(5,6-dihydro-5,5-dimethyl-8-(4-methylphenyl)-2-naphthalenyl)azo]-benzoate (Compound 46a) 16.5 mg, 0.042 mmol) in THF (2 ml) and ethanol (1 ml) was added 80.0 mg (2.00 mmol) of NaOH (2.0 ml, 1M aqueous solution). The mixture was stirred for 12 hours at room temperature, acidified with 10% HCl, and extracted with EtOAc. The combined organic layers were washed with water, and saturated aqueous NaCl, then dried over $MgSO_4$. Removal of the solvents under reduced pressure, and recrystallization of the residue from EtOAC/hexane, afforded the title compound as a red solid. 1H NMR (acetone-d6): δ 8.19 (2H, d, J=8.4 Hz), 7.92 (2H, d, J=8.5 hz), 7.88 (2H, dd, J=2.1, 6.1 Hz), 7.66 (1H, s), 7.64 (2H, d, J=2.3 Hz), 7.28 (4H, d, J=3.0 Hz), 6.09 (1H, t, J=2.5 Hz), 2.42 (2H, d, J=4.8 Hz), 2.39 (3H, s), 1.40 (6H, s).

6-(2-Trimethylsilyl)ethynyl-2,3-dihydro-3,3-dimethyl-1H-inden-1-one (Compound CC)

To a solution of 815.0 mg (3.41 mmol) 6-bromo-2,3-dihydro-3,3dimethyl-1H-inden-1-one (See Smith et al. Org. Prep. Proced. Int. 1978 10 123–131) in 100 ml of degassed $Et_3N$ (sparged with argon for 20 min) was added 259.6 mg (1.363 mmol) of copper(I) iodide, 956.9 mg (1.363 mmol) of bis(triphenylphosphine)palladium(II)chloride, and 3.14 g (34.08 mmol) of (trimethylsilyl)acetylene. This mixture was heated at 70° C. for 42 hours, cooled to room temperature, and filtered through a pad of silica gel and washed with ether. The filtrate was washed with water, 1M HCl, water, and finaly with saturated aqueous NaCl before being dried over $MgSO_4$. Concentration of the solution under reduced pressure, followed by column chromatography (silica gel; 10% $Et_2O$—hexanes) afforded the title compound as a brown oil. 1H NMR (300 MHz, $CDCl_3$): δ 7.79(1H, d, J=1.4 Hz), 7.69 (1H, dd, J=1.6, 8.3 Hz), 7.42 (1H, d, J=8.5 Hz), 2.60 (2H, s), 1.41 (6H, s), 0.26 (9H, s).

6-Ethynyl-2,3-dihydro-3,3-dimethyl-1H-inden-1-one (Compound DD)

To a solution of 875.0 mg (3.41 mmol) 6-(2-trimethylsilyl)ethynyl-2,3-dihydro-3,3-dimethyl-1H-inden-1-one (Compound CC) in 28 ml of MeOH, was added 197.3 mg (1.43 mmol) of $K_2CO_3$ in one portion. After stirring for 6 hours at room temperature the mixture was filtered though a pad of Celite and the filtrate concentrated under reduced pressure. The residual oil was placed on a silica gel column and eluted with 5% EtOAc—hexanes to give the title product as a colorless oil. 1H NMR (300 MHz, $CDCl_3$): δ 7.82 (1H, s), 7.72 (1H, dd, J=1.6, 7.8 Hz), 7.47 (1H, d, J=8.4 Hz), 3.11 (1H, s), 2.61 (2H, s), 1.43 (6H, s).

Ethyl 4-[2-(5,6-dihydro-5,5-dimethyl-7-oxo-2-indenyl) ethynyl]benzoate (Compound EE)

A solution of 280.0 mg (1.520 mmol) 6-ethynyl-2,3-dihydro-3,3-dimethyl-1H-inden-1-one (Compound DD) and 419.6 mg (1.520 mmol) ethyl 4-iodobenzoate in 5 ml $Et_3N$ was sparged with argon for 40 minutes. To this solution was added 271.0 mg (1.033 mmol) of triphenylphosphine, 53.5 mg (0.281 mmol) of copper(I) iodide, and 53.5 mg (0.076 mmol) of bis(triphenylphosphine)palladium(II) chloride. The resulting mixture was heated to reflux for 2.5 hours, cooled to room temperature, and diluted with $Et_2O$. After filtration through a pad of Celite, the filtrate was washed with $H_2O$, 1M HCl, $H_2O$, and saturated aqueous NaCl, then dried over $MgSO_4$, and concentrated under reduced pressure. The title compound was isolated as a pale-yellow solid by column chromatography (15% EtOAc—hexanes). 1H NMR (300 MHz, d6-acetone): δ 8.05 (2H, d, J=8.6 Hz), 7.87 (1H, dd, J=1.4, 8.1 Hz), 7.75 (2H, m), 7.70 (2H, d, J=8.5 Hz), 4.36 (2H, q, J=7.1 Hz), 2.60 (2H, s), 1.45 (6H, s), 1.37 (3H, t, J=7.1 Hz).

Ethyl 4-[2-(1,1-dimethyl-3-(trifluoromethyl-sulfonyl)oxy-5-indenyl)ethynyl]benzoate (Compound FF)

A solution of 88.0 mg (0.48 mmol) of sodium bis (trimethylsilyl)amide in 0.5 ml THF was cooled to −78° C. and 145.0 mg (0.436 mmol) of ethyl 4-[2-(5,6-dihydro-5,5-dimethyl-7-oxo-2-indenyl)ethynyl]benzoate (Compound EE) was added as a solution in 1.0 ml THF. After 30 minutes 181.7 mg (0.480 mmol) of 2-(N,N-bis (trifluoromethansulfonyl)amino)-5-chloro-pyridine was added as a solution in 1.0 ml THF. The reaction was allowed to slowly warm to room temperature and quenched after 5 hours by the addition of saturated aqueous $NH_4Cl$. The mixture was extracted with EtOAc, and the combined organic layers washed with 5% aqueous NaOH, $H_2O$, and saturated aqueous NaCl, then dried ($MgSO_4$) and concentrated under reduced pressure. The product was isolated as a colorless solid by column chromatography (10% $Et_2O$-hexanes). 1H NMR (300 MHz, d6-acetone): δ 8.05 (2H, d, J=8.3 Hz), 7.69 (2H, d, J=8.4 Hz), 7.63 (2H, s), 7.55 (1H, s), 4.36 (2H, q, J=7.1 Hz), 1.44 (6H, s), 1.37 (3H, t, J=7.1 Hz).

4-[(5,6-dihydro-5,5-dimethyl-8-(4-methylphenyl)-2-naphthalenyl)ethynyl]benzoic acid (Compound 60)

A solution of 142.6 mg (0.339 mmol) of ethyl 4-[(5,6-dihydro-5,5-dimethyl-8-(4-methylphenyl)-2-naphthalenyl) ethynyl]benzoate (Compound 1) and 35.6 mg (0.848 mmol) of $LiOH-H_2O$ in 12 ml of TBh/water (4:1, v/v), was stirred overnight at room temperature. The reaction mixture was extracted with hexanes, and the hexane fraction extracted with 5% aqueous NaOH. The aqueous layers were combined and acidified with 1M HCl, and then extracted with EtOAc and $Et_2O$. The combined organic layers were dried over $Na_2SO_4$ and concentrated in vacuo to give the title compound as a colorless solid. 1H NMR ($d_6$-DMSO): δ 7.91 (2H, d, J=8.4 Hz); 7.60 (2H, d, J=8.4 Hz), 7.47 (2H, s), 7.23 (4H, q, J=8.1 Hz), 7.01 (1H, s), 6.01 (1H, t, J=4.6 Hz), 2.35 (3H, s), 2.33 (2H, d, J=4.8 Hz), 1.30 (6H, s).

4-[(5,6-dihydro-5,5-dimethyl-8-phenyl-2-naphthalenyl) ethynyl ]benzoic acid (Compound 60a)

Employing the same general procedure as for the preparation of 4-[(5,6-dihydro-5,5-dimethyl-8-(2-thiazolyl)-2-naphthalenyl)ethynyl]benzoic acid (Compound 30a), 27.0 mg (0.07 mmol) of ethyl 4-[(5,6-dihydro-5,5-dimethyl-8-phenyl-2-naphthalenyl)ethynyl]benzoate (Compound 1a) was converted into the title compound (colorless solid) using 5.9 mg (0.14 mmol) of LiOH in $H_2O$. PMR ($d_6$-DMSO): δ 1.31 (6H, s), 2.35 (2H, d, J=4.5 Hz), 6.05 (1H, t, J=J=4.5 Hz), 7.00 (1H, s), 7.33 (2H, d, J=6.2 Hz), 7.44 (4H, m), 7.59 (2H, d, J=8.1 Hz), 7.90 (2H, d, J=8.1 Hz).

4-[(5,6-Dihydro-5,5-dimethyl-8-(4-(1,1-dimethylethyl) phenyl)-2-naphthalenyl)ethynyl]benzoic acid (Compound 61)

A solution of 80.0 mg (0.173 mmol) of ethyl 4-[(5,6-dihydro-5,5-dimethyl-8-(4-(1,1-dimethylethyl)phenyl)-2-naphthalenyl)ethynyl]benzoate (Compound 6) and 18.1 mg (0.432 mmol) of $LiOH-H_2O$ in 6 ml of reaction mixture was extracted with hexanes, and the remaining aqueous layer acidified with 1M HCl, and then extracted with EtOAc. The combined organic layers were dried over $Na_2SO_4$ and concentrated in vacuo to give the title compound as a colorless solid. 1H NMR (d$_6$-DMSO): δ 7.82 (2H, d, J=8.2 Hz), 7.44 (6H, m), 7.25 (2H, d, J=8.3 Hz), 7.02 (1H, s), 6.01 (1H, t, J=4.6 Hz), 2.32 (2H, d, J=4.7 Hz), 1.32 (9H, s), 1.29 (6H, s).

Ethyl 2-fluoro-4-[[(5,6-dihydro-5,5-dimethyl-8-(4-methylphenyl)-2-naphthalenyl)thiocarbonyl]amino]-benzoate (Compound 62)

A solution of 54.4 mg (0.119 mmol) ethyl 2-fluoro-4-[[(5,6-dihydro-5,5-dimethyl-8-(4-methylphenyl)-2-naphthalenyl)carbonyl]amino]-benzoa (Compound 40) and 57.7 mg (0.143 mmol) of [2,4-bis(4-methoxyphenyl)-1,3-dithia-2,4-diphosphetane-2,4-disulfide] (Lawesson's Reagent) in 12.0 ml of benzene was refluxed overnight. Upon cooling to room temperature, the mixture was filtered and the filtrate concentrated under reduced pressure. The title compound was isolated by column chromatography (10 to 25% EtOAc/hexanes) as a yellow solid. 1H NMR (CDCl$_3$): δ 9.08 (1H, s), 7.92 (1H, br s), 7.90 (1H, t, J=8.2 Hz), 7.66 (1H, dd, J=2.0, 6.0 Hz), 7.38 (3H, m), 7.18 (4H, m), 6.01 (1H, t, J=4.7 Hz), 4.35 (2H, q, J=7.1 Hz), 2.36 (3H, s), 2.33 (2H, d, J=4.7 Hz), 1.38 (3H, t, J=7.1 Hz), 1.33 (6H, s).

2-fluoro-4-[[(5,6-dihydro-5,5-dimethyl-8-(4-methylphenyl)-2-naphthalenyl)thiocarbonyl]amino]-benzoic acid (Compound 63)

To a solution of 46.5 mg (0.098 mmol) ethyl 2-fluoro-4-[[(5,6-dihydro-5,5-dimethyl-8-(4-methylphenyl)-2-naphthalenyl)thiocarbonyl]amino]-benzoate (Compound 62) in 1.0 ml EtOH and 1.0 ml of THF was added 55 mg NaOH (1.4 mmol) and 1.0 ml of H$_2$O. After stirring at room temperature for overnight EtOAc was added, and the reaction quenched by the addition of 10% HCl. Extraction with EtOAc was followed by washing of the combined organic layers with H$_2$O, saturated aqueous NaCl, and drying over MgSO$_4$. Removal of the solvent under reduced pressure provided a solid which after crystallization from CH$_3$CN afforded the title compound as a pale-yellow solid. 1H NMR (d$_6$-acetone): δ 11.05 (1H, s), 8.02 (1H, m), 7.99 (1H, t, J=8.3 Hz), 7.75 (1H, m), 7.69 (1H, dd, J=2.0, 6.1 Hz), 7.52 (1H, s), 7.46 (1H, d, J=8.1 Hz), 7.21 (4H, m), 6.04 (1H, t, J=4.8 Hz), 2.37 (2H, d, J=4.8 Hz), 2.33 (3H, s), 1.36 (6H, s).

Ethyl 5', 6'-dihydro-5', 5'-dimethy-8'-(4-methylphenyl)-[2,2'-binaphthalene]-6-carboxylate (Compound 64)

A solution of 3,4-dihydro-1-(4-methylphenyl)-4,4-dimethyl-7-bromonaphthalene Compound D) 0.45 g, 1.40 mmol) and THF (2.1 ml) was added to magnesium turnings (0.044 g, 1.82 mmol) at room temperature under argon. Two drops of ethylene dibromide were added, and the solution, which slowly became cloudy and yellow, was heated to reflux for 1.5 hours. In a second flask was added zinc chloride (0.210 g, 1.54 mmol), which was melted under high vacuum, cooled to room temperature and dissolved in THF (3 ml). The Grignard reagent was added to the second flask and, after 30 minutes at room temperature, a solution of ethyl 6-bromo-2-naphthalinecarboxylate (Compound N) 0.293 g, (1.05 mmol) and THF (2 ml) were added. In a third flask was prepared a solution of Ni(PPh$_3$)$_4$ and THF as follows: To a solution of NiCl$_2$(PPh$_3$)$_2$ (0.82 g, 1.25 mmol) and PPh$_3$ (0.66 g, 2.5 mmol) in THF (3.5 ml) was added a 1M solution of diisobutylaluminum hydride and hexanes (2.5 ml, 2.5 mmol), and the resulting solution diluted with THF to a total volume of 15 ml and stirred at room temperature for 15 minutes. Three 0.60 ml aliquots of the Ni(PPh$_3$)$_4$ solution were added at 15 minutes intervals to the second flask. The resulting suspension was stirred at room temperature for 2 hours. The reaction was quenched by the addition of 5 ml 1N aqueous HCl and stirred for 1 hour before extracting the products with ethyl acetate. The organic layers were combined, washed with brine, dried (MgSO$_4$), filtered and the solvent removed in-vacuo. The residue was crystalized from hexanes to give 130 mg of pure material. The mother liquor was concentrated under reduced pressure and the residue purified by silica gel chromatography (95:5hexanes:ethyl acetate) to give an additional 170 mg of the title compound (overall yield=300 mg, 64%) as a colorless solid. 1H NMR (CDCl$_3$)δ 8.57 (s, 1H), 8.05 (dd, 1H, J=1.7, 8.0 Hz), 7.84–7.95 (overlapping d's, 3H), 7.66 (dd, 1H, J=1.7, 8.5 Hz), 7.58 (dd, 1H, J=2.0, 8.0 Hz), 7.48 (d, 1H, J=8.0 Hz), 7.43 (d, 1H, J=2.0 Hz), 7.32 (d, 2H, J=8.0 Hz), 7.21 (d, 2H, J=8.0 Hz), 6.04 (t, 1H, J=4.8 Hz), 4.44 (q, 2H, J=7.1 Hz), 2.40 (s, 3H), 2.39 (d, 2H, J=4.8 Hz), 1.45 (t, 3H, J=7.1 Hz), 1.39 (s, 6H).

5',6'-Dihydro-5',5'-dimethyl-8'-(4-methylhenyl)-[2,2'-binaphthalene]-6-carboxylic acid (Compound 65)

A solution of ethyl 5',6'-dihydro-5',5'-dimethyl-8'-(4-methylphenyl)-[2,2'-binaphthalene]-6-carboxylate (Compound 64) 0.19 g, 0.43 mmol), EtOH (8 ml) and 1N aqueous NaOH (2 ml) was heated to 60° C. for 3 hours. The solution was cooled to 0° C. and acidified with 1N aqueous HCl. The product was extracted into ethyl acetate, and the organic layers combined, washed with water, brine, dried (MgSO$_4$), filtered and the solvent removed in-vacuo. The residue was recrystalized from THF/ethyl acetate at 0° C. to give 35 mg of pure material. The mother liquor was concentrated under reduced pressure and the residue purified by silica gel chromatography (100% ethyl acetate) to give an additional 125 mg of the title compound (overall yield=160 mg, 90%) as a colorless solid. 1H NMR (DMSO-d$_6$) δ 8.57 (s, 1H), 8.11 (d, 1H, J=8.7 Hz), 7.96–7.82 (overlapping d's, 3H),7.65 (d, 2H, J=7.6 Hz), 7.50 (d, 1H, J=7.9 Hz), 7.28 (s, 1H), 7.26 (d, 2H, J=8.3 Hz), 7.21 (d, 2H, J=8.3 Hz), 6.01 (t, 1H, J=4.5 Hz), 3.34 (br s, 1H), 2.31 (s, 3H), 2.31 (d, 2H, J=4.5 Hz), 1.31 (s, 6H).

Ethyl 4-[(5,6-dihydro-5,5-dimethyl-8-(2-furyl)-2-naphthalenyl)ethynyl]benzoate (Compound 66)

Employing the same general procedure as for the preparation of ethyl 4-[(5,6-dihydro-5,5-dimethyl-8-(4-methylphenyl)-2-naphthalenyl)ethynyl]benzoate (Compound 1), 250.0 mg (0.52 mmol) of ethyl 4-[(5,6-dihydro-5,5-dimethyl-8-(trifluoromethylsulfonyl)oxy-2-naphthalenyl)ethynyl]benzoate (Compound G) was converted into the title compound (colorless solid) using 142.4 mg (1.045 mmol) of zinc chloride, 24.1 mg (0.02 mmol) of tetrakis(triphenylphosphine)palladium(0) and 24 lithiofuran (prepared by the addition of 53.4 mg (0.52 ml, 0.78 mmol) of n-butyllithium (1.5M solution in hexane) to a cold solution (−78° C.) of 53.4 mg (0.784 mmol) of furan in 1.0 ml of THF). PMR (CDCl$_3$): δ 1.32 (6H, s), 1.41 (3H, t, J=7.1 Hz), 2.35 (2H, d, J=5.0 Hz), 4.39 (2H, q, J=7.1 Hz), 6.41 (1H, t, J=5.0 Hz), 6.50 (2H, s), 7.36 (1H, d, J=8.0 Hz), 7.45 (1H, dd, J=1.7, 8.0 Hz), 7.49 (1H, s), 7.57 (2H, d, J=8.2 Hz), 7.63 (1H, d, J=1.7 Hz), 8.02 (2H, d, J=8.2 Hz).

4-[(5,6-dihydro-5,5-dimethyl-8-(2-furyl)-2-naphthalenyl)ethynyl]benzoic acid (Compound 67)

Employing the same general procedure as for the preparation of 4[(5,6-dihydro-5,5-dimethyl-8-(2-thiazolyl)-2-naphthalenyl)ethynyl]benzoic acid (Compound 30a), ethyl 4-[(5,6-dihydro-5,5-dimethyl-8-(2-furyl)-2-naphthalenyl) ethynyl]benzoate (Compound 66) was converted into the title compound (colorless solid) using 16.0 mg (0.38 mmol) of LiOH in H$_2$O. PMR (d$_6$-DMSO): δ 1.26 (6H, s), 2.33 (2H, d, J=4.9 Hz), 6.41 (1H, t, J=4.9 Hz), 6.60 (2H, m), 7.45–7.53 (3H, m), 7.64 (2H, d, J=8.3 Hz), 7.75 (1H, d, J=1.6 Hz), 7.93 (2H, d, J=8.3 Hz).

3,4-dihydro-4,4-dimethyl-7-acetyl-1-(2H)-naphthalenone (Compound 100C) and 3,4-dihydro-4,4-dimethyl-6-acetyl-1-(2H)-naphthalenone (Compound 100D)

To a cold(0° C.) mixture of aluminum chloride (26.3 g, 199.0 mmols) in dichloromethane (55 ml) was added acetylchloride (15 g, 192 mmols) and 1,2,3,4-tetrahydro-1,1-dimethylnaphthalene (24.4 g, 152 mmols) in dichloromethane (20 ml) over 20 minutes. The reaction mixture was warmed to ambient temparature and stirred for 4 hours. Ice (200 g) was added to the reaction flask and the mixture diluted with ether (400 ml). The aqueous and organic layers were separated and the organic phase was washed with 10% HCl (50 ml), water (50 ml), 10% aqueous sodium bicarbonate, and saturated aqueous NaCl (50 ml) and then dried over $MgSO_4$. The solvent was removed by distillation to afford a yellow oil which was dissolved in benzene (50 ml).

To a cold(0° C.) solution of acetic acid (240 ml) and acetic anhydride (120 ml) was added chromium trioxide (50 g, 503 mmols) in small portions over 20 minutes under argon. The mixture was stirred for 30 minutes at 0° C. and diluted with benzene (120 ml). The benzene solution prepared above was added with stirring via an addition funnel over 20 minutes. After 8 hours, the reaction was quenched by the careful addition of isopropanol (50 ml) at 0° C., followed by water (100 ml). After 15 minutes, the reaction mixture was diluted with ether (1100 ml) and water (200 ml), and then neutralized with solid sodium bicarbonate (200 g). The ether layer was washed with water (100 ml),and saturated aqueous NaCl (2×100 ml), and dried over $MgSO_4$. Removal of the solvent under reduced pressure afforded a mixture of the isomeric diketones which were separated by chromatography ( 5% EtOAc/hexanes). (Compound 100C): 1H NMR ($CDCl_3$): δ 8.55 (1H, d, J=2.0 Hz), 8.13 (1H, dd, J=2.0, 8.3 Hz), 7.53 (1H, d, J=8.3 Hz), 2.77 (2H, t, J=6.6 Hz), 2.62 (3H, s), 2.05 (2H, t, J=6.6 Hz), 1.41 (6H, s). (Compound 100D): 1H NMR ($CDCl_3$): δ 8.10 (1H, d, J=8.1 Hz), 8.02 (1H, d, J=1.6 Hz), 7.82 (1H, dd, J=1.6, 8.1 Hz), 2.77 (2H, t, J=7.1 Hz), 2.64 (3H, s), 2.05 (2H, t, J=7.1 Hz), 1.44 (6H, s).

3,4-dihydro-4,4-dimethyl-6-(2-(2-methyl-1,3-dioxolanyl))-1-(2H)-naphthalenone (Compound 100E)

A solution of 1.80 g (8.34 mmol) of a 1:5 mixture of 3,4-dihydro-4,4-dimethyl-7-acetyl-1-(2H)-naphthalenone (Compound 100C); and 3,4-dihydro-4,4-dimethyl-6-acetyl-1-(2H)-naphthalenone (Compound 100D) in 50 ml benzene was combined with 517.7 mg (8.34 mmol) of ethylene glycol and 20.0 mg (0.11 mmol) of p-toluenesulfonic acid monohydrate. The resulting solution was heated to reflux for 18 hours, cooled to room temperature, and concentrated under reduced pressure. The title compound was isolated by column chromatography (10% EtOAc—hexanes) as a colorless oil. 1H NMR ($CDCl_3$): δ 8.01 (1H, d, J=8.2 Hz), 7.51 (1H, s), 7.43 (1H, dd, J=1.7, 6.4 Hz), 4.07 (2H, m), 3.79 (2H, m), 2.74 (2H, t, J=6.5 Hz), 2.04 (2H, t, J=7.1 Hz), 1.67 (3H, s), 1.46 (6H, s).

1,2,3,4-tetrahydro-1-hydroxy-1-(4-methylphenyl)-4,4-dimethyl-6-(2-(2methyl-1,3-dioxolanyl))naphthalene (Compound 100F)

To a solution of 496.2 mg (2.54 mmol) p-tolylmagnesiumbromide in 20 ml THF (2.54 ml; 1M solution in ether) was added a solution of 3,4-dihydro-4,4-dimethyl-6-(2-(2-methyl-1,3-dioxolan-yl))-1-(2H)-naphthalenone (Compound 100E, 200.0 mg, 0.769 mmol) in THF (5 ml). The solution was refluxed for 16 hours, cooled to room temperature, and washed with water, saturated aqueous $NH_4Cl$, and dried over $MgSO_4$. Removal of the solvents under reduced pressure and column chromatography (10% EtOAc/hexanes) afforded the title compound as a colorless solid. 1H NMR ($CDCl_3$): δ 7.49 (1H, d, J=1.7 Hz), 7.19 (2H, m), 7.10 (2H, d, J=7.9 Hz), 7.04 (1H, d, J=8.2 Hz), 4.05 (2H, m), 3.80 (2H, m), 2.34 (3H, s), 2.21 (1H, m), 2.10 (1H, m), 1.88 (1H, m), 1.65 (3H, s), 1.54 (1H, m), 1.39 (3H, s), 1.33 (3H, s).

3,4-dihydro-1-(4-methylphenyl)-4,4-dimethyl-6-acetylnaphthalene (Compound 100G)

A solution of 1,2,3,4-tetrahydro-1-hydroxy-1-(4-methylphenyl)-4,4-dimethyl-6-(2-(2-methyl-1,3-dioxolanyl))naphthalene (Compound 100F 160.0 mg, 0.52 mmol), p-toluenesulfonic acid monohydrate (4 mg) and 30 ml benzene was refluxed for 12 hours. After cooling to room temperature, the reaction mixture was diluted with ether (100 ml) and washed with 10% aqueous sodium bicarbonate, water, and saturated aqueous NaCl. The organic layer was dried over $MgSO_4$ and the solvents were removed under reduced pressure to give the title compound, which was isolated by column chromatography (10% EtOAc-hexanes) as a yellow oil. 1H NMR ($CDCl_3$): δ 7.97 (1H, d, J=1.8 Hz), 7.67 (1H, dd, J=1.7, 6.4 Hz), 7.22 (4H, s), 7.13 (1H, d, J=8.1 Hz), 6.10 (1H, t, J=4.5 Hz), 2.59 ( 3H, s), 2.40 (3H, s), 2.38 (2H, d, J=4.7 Hz), 1.38 (6H, s).

4-[3-oxo-3-(7,8-dihydro-5-(4-metlpheal)-8,8-dimethyl-2-naphthaleny-1-propenyl]-benzoic acid (Compound 101)

To a solution of 78.7 mg (0.272 mmol) 3,4-dihydro-1-(4-methylphenyl)-4,4-dimethyl-6-acetylnaphthalene (Compound 100G) in 4.0 ml of MeOH was added 53.1 mg (0.354 mmol) of 4-carboxy benzaldehyde, and 80 mg (2.00 mmol; 2.0 ml of 1M aqueous NaOH). The resulting solution was stirred at room temperature for 12 hours, concentrated under reduced pressure, and the residual oil dissolved in EtOAc. The solution was treated with 10% HCl, and the organic layer was washed with $H_2O$, and saturated aqueous NaCl, then dried over $Na_2SO_4$. Removal of the solvents under reduced pressure gave the title compound as a colorless solid which was purified by recrystallization from $CH_3CN$. 1H NMR (acetone-d6): δ 8.00 (7H, m), 7.83 (1H, d, J=15.6 Hz), 7.24 (4H, s), 7.13 (1H, d, J=8.1 Hz), 6.12 (1H, t, J=4.5 Hz), 2.42 (2H, d, J=4.8 Hz), 2.38 (3H, s), 1.41 (6H, s).

3,4-dihydro-1-phenyl-4,4-dimethyl-6-acetylnaphthalene (Compound 100H)

To a solution of 508.0 mg (1.95 mmol) of 3,4-dihydro-4,4-dimethyl-6(2-(2-methyl-1,3-dioxolanyl))-1(2H)-naphthalenone (Compound 100E) in 10 ml of THF was added 496.2 mg (2.54 mmol; 2.54 ml of a 1M solution in $Et_2O$) of phenylmagnesium bromide. The resulting solution was heated to reflux for 8 hours, $H_2O$ was added and heating continued for 30 minutes. The THF was removed under reduced pressure and the aqueous residue was extracted with EtOAc. The combined organic layers were dried ($MgSO_4$), concentrated under reduced pressure, and the title compound isolated from the residue by column chromatography (10% EtOAc—hexanes) as a colorless oil. 1H NMR ($CDCl_3$): δ 7.97 (1H, d, J=1.8 Hz), 7.67 (1H, dd, J=2.1, 8.0 Hz), 7.34 (5H, m), 7.10 (1H, d, J=8.1 Hz), 6.12 (1H, d, J=4.6 Hz), 2.59 (3H, s), 2.39 (2H, d, J=4.8 Hz), 1.38 (6H, s).

4-[3-oxo-3-(7,8-dibydro-5-phenyl-8,8-dimethyl-2-naphthalenyl)-1-propenyl]benzoic acid (Compound 103)

To a solution of 115.0 mg (0.42 mmol) of 3,4-dihydro-1-phenyl-4,4-dimethyl-6-acetylnaphthalene (Compound 100H) and 65.0 mg (0.43 mmol) of 4-formyl-benzoic acid in 5.0 ml EtOH and 1.0 ml THF, was added 120.0 mg (3.00 mmol; 3.0 ml of a 1M aqueous solution) of NaOH. The resulting yellow solution was stirred at room temperature for 12 hours. The solution was acidified with 6% aqueous HCl and extracted with EtOAc. The combined organic layers were dried (MgSO$_4$), concentrated under reduced pressure, and the title compounds was isolated by column chromatography (50% EtOAc—hexanes) as a pale yellow solid. 1H NMR (CDCl$_3$): δ 8.13 (2H, d, J=7.7 Hz), 8.04 (1H, s), 7.81 (1H, d, J=15.5 Hz), 7.75 (3H, m), 7.60 (1H, d, J=15.5 Hz), 7.35 (5H, m), 7.14 (1H, d, J=8.1 Hz), 6.15 (1H, t, J=4.2 Hz), 2.41 (2H, d, J=4.2 Hz), 1.41 (6H, s).

3-Fluoro-4-methoxothiophenol (Compound 200)

A flask containing Mg-turnings (651.9 mg, 26.8 g-atoms) was carefully flame dried under argon. Upon cooling to room temperature the flask was charged with 14.0 mL of THF, the mixture was heated to reflux temperature and 3-fluoro-4-methoxy-1-bromobenzene (5.00 g, 24.4 mmol) was slowly added while the mixture was at reflux. After 6 hours the formation of the Grignard reagent appeared complete. The resulting opaque orange solution was cooled to 0° C. and sulfur (781.8 mg, 24.4 g-atoms) was added in three portions over five minutes. After stirring overnight at room temperature the brown mixture was carefully poured into an ice 10% aqueous HCl mixture. Extraction with EtOAc was followed by washing the combined organic layers with H$_2$O and saturated aqueous NaCl and drying over MgSO$_4$. Removal of the solvents under reduced pressure and distillation (bulb-to-bulb) of the residue afforded 2.14 g (55%) of the title compound as a colorless oil, (bp 90–100° C./5 mm). $^1$H NMR (300 MHz, CDCl$_3$)δ: 7.06 (2H, m), 6.85 (1H, t, J=8.6 Hz), 3.87 (3H, s), 3.43 (1H, s).

3-(3-fluoro-4-methoxy-phenylsulfanyl)-3-methyl-butyric acid (Compound 201)

A heavy-walled screw cap tube was charged with 3-methyl-2-butenoic acid (1.23 g, 12.33 mmol), 3-fluoro-4-methoxy thiophenol (Compound 200, 1.95 g, 12.33 mmol), and piperidine (314.8 mg, 3.70 mmol). This mixture was heated to 105° C. for 23 hours, cooled to room temperature and dissolved in EtOAc (100mL). The resulting solution was washed with 1M aqueous HCl, H$_2$O, and saturated aqueous NaCl before being dried over Na$_2$SO$_4$. Concentration of the dry solution under reduced pressure afforded 3.22 g of a clear yellow oil which was used in the next reaction without further purification. $^1$H NMR (300 MHz, CDCl$_3$) δ: 7.32 (2H, m), 6.94 (1H, t, J=8.4 Hz), 3.92 (3H, s), 2.54 (2H, s), 1.41 (6H, s).

3-(3-fluoro-4-methoxy-phenysulfanyl)-3-methyl-butyroyl chloride (Compound 202)

To a solution of 3-(3-fluoro-4-methoxy-phenylsulfanyl)-3-methyl-butyric acid (Compound 201, 3.00 g, 11.6 mmol) in 40 mL of benzene at room temperature was added a solution of oxalyl chloride (2.21 g, 17.4 mmol) in 5 mL of benzene over 30 minutes. After 3 hours, the solution was washed with ice cold 5% aqueous NaOH (CAUTION: a large volume of gas is released during this procedure), followed by ice cold H$_2$O, and finally saturated aqueous NaCl. The solution was dried (Na$_2$SO$_4$) and concentrated under reduced pressure to give 2.83 g of a clear yellow oil. This material was used without further purification in the next step. $^1$H NMR (300 MHz, CDCl$_3$)δ: 7.27 (2H, m), 6.96 (1H, t, J=8.4 Hz), 3.93 (3H, s), 3.13 (2H, s), 1.42 (6H, s).

6-Methoxy-7-fluoro-2,2-dimethyl-thiochroman-4-one (Compound 203)

To a solution of the acyl chloride (Compound 202, 2.80 g, 10.1 mmol) in 35 mL of CH$_2$Cl$_2$ at 0° C. was added dropwise a solution of SnCl$_4$ (2.64 g, 10.1 mmol) in 5 mL of CH$_2$Cl$_2$. After 2.5 hours the reaction was quenched by the slow addition of 20 mL H$_2$O. The organic layer was washed with 1M aqueous HCl, 5% aqueous NaOH, H$_2$O, and finally saturated aqueous NaCl before being dried over MgSO$_4$. Concentration under reduced pressure afforded 1.90 g (78%) the title compound as a tan solid. $^1$H NMR (300 MHz, CDCl$_3$)δ: 7.72 (1H, d, J=8.9 Hz), 6.95 (1H, d, J=11.0 Hz), 3.91 (3H, s), 2.85 (2H, s), 1.47 (6H,s).

6-Hydroxy-7-fluoro-2,2-dimethylthiochroman-4-one (Compound 204)

To a solution of 6-methoxy-7-fluoro-2,2-dimethyl-thiochroman-4-one (Compound 203, 1.75 g, 7.29 mmol) in 25 mL CH$_2$Cl$_2$ cooled to −23° C. was added BBr$_3$ (5.46 g, 21.8 mmol; 21.8 mL of a 1M solution in CH$_2$Cl$_2$) over a 10 minute period. After stirring for 23 hours at −230° C. the solution was warmed to 0° C. for 3 hours, and then cooled to −78° C. and quenched by the slow addition of 25 mL of H$_2$O. Upon warming to room temperature the aqueous layer was extracted with CH$_2$Cl$_2$ and the combined organic layers were washed with saturated aqueous NaHCO$_3$, H$_2$O, and saturated aqueous NaCl before being dried over MgSO$_4$. Removal of the solvents under reduced pressure, followed by column chromatography (10 to 20% EtOAc/hexanes) afforded 1.12 g (68%) of the title compound as a colorless solid. $^1$H NMR (300 MHz, CDCl$_3$)δ: 7.82 (1H, d J=9.3 Hz), 6.97 (1H, d, J=10.4 Hz), 5.54 (1H, s), 2.86 (2H,s), 1.46 (6H, s).

2,2-Dimethyl-4-oxo-7-fluoro-thiochroman-6-yl trifluoromethanesulfonate (Compound 205)

To a solution of 6-hydroxy-7-fluoro-2,2-dimethylthiochroman-4-one (Compound 204, 1.12 g, 4.94 mmol) in 25.0 mL of anhydrous pyridine at 0° C. was added trifluoromethanesulfonic anhydride (1.61 g, 5.68 mmol). After 18 hours at 0° C. the solution was concentrated and the residual oil dissolved in Et$_2$O, washed with H$_2$O followed by saturated aqueous NaCl, and dried over MgSO$_4$. Removal of the solvents under reduced pressure and column chromatography (5 to 8% EtOAc/hexanes) afforded 1.28 g (72%) of the title compound as a colorless solid. $^1$H NMR (300 MHz, CDCl$_3$) δ: 8.07 (1H, d, J=7.8 Hz), 7.13 (1H, d, J=9.7 Hz), 2.89 (2H, s), 1.50 (6H, s).

2,2-Dimethyl-6-trimethylsilanylethynyl-7-fluoro-thiochroman-4-one (Compound 206)

A solution of 2,2-dimethyl-4-oxo-7-fluoro-thiochroman-6-yl trifluoromethanesulfonate (Compound 205, 1.28 g, 3.57 mmol) in 6.0 mL Et$_3$N and 15.0 mL DMF was sparged with argon for 15 minutes. To this solution was added trimethylsilylacetylene (2.0 g, 20.4 mmol) and bis (triphenylphosphine)-palladium(II) chloride (100.0 mg, 0.14 mmol). The solution was heated to 95° C. for 6 hours, cooled to room temperature and stirred overnight. The solution was diluted with H$_2$O and extracted with EtOAc. The combined organic layers were washed with H$_2$O, saturated aqueous NaCl and dried over MgSO$_4$. Concentration of the dry solution under reduced pressure and isolation of the product by column chromatography (3 to 5% EtOAc/hexanes) afforded 850.0 mg (78%) of the title compound as an orange solid. $^1$H NMR (300 MHz, CDCl$_3$)δ: 8.22 (1H, d, J=7.5 Hz), 6.92 (1H, d, J=9.3 Hz), 2.85 (2H, s), 1.46 (6H, s), 0.25 (9H, S).

6-Ethynyl-7-fluoro-2,2-dimethylthiochroman-4-one (A) (Compound 207), and 6-Ethynyl-7-methoxy-2,2-dimethylthiochroman-4-one (B) (Compound 208)

A solution of 2,2-dimethyl-6-trimethylsilanylethynyl-7-fluror-thiochroman-4-one (Compound 206, 850.0 mg, 2.78mmol) and K$_2$CO$_3$ (180.0 mg, 1.30 mmol) in 20.0mL MeOH was stirred overnight at room temperature. The solution was concentrated to one-third of the original volume, diluted with EtOAc, washed with H$_2$O and saturated aqueous NaCl, and dried over MgSO$_4$. Removal of the solvent under reduced pressure followed by column chromatography (5 to 10% EtOAc/hexanes) of the residual solid afforded 330.0 mg (51%) of Compound 207 as a yellow solid, and 217.0 mg (32%) of Compound 208 as a yellow solid. (Compound 207): $^1$H NMR (300 MHz, CDCl$_3$)δ: 8.18 (1H, d, J=7.5 Hz), 6.90 (1H, d, J=8.3 Hz), 3.28 (1H, s), 2.81 (2H, s), 1.42 (6H, s). (Compound 208); $^1$H NMR (300 MHz, CDCl$_3$)δ: 8.19 (1H, s), 6.64 (1H, s), 3.90 (3H, s), 3.26 (1H, s), 2.80 (2H, s), 1.44 (6H, s).

Ethyl 4-[(2,2-dimethyl-4-oxo-7-fluoro-thiochroman-6-yl) ethyl]-benzoate (Compound 209)

A solution of 6-ethynyl-7-fluoro-2,2-dimethylthiochroman-4-one (Compound 207, 330.0 mg, 1.41 mmol) and ethyl 4-iodobenzoate (392 mg, 1.41 mmol) in 10.0 mL Et$_3$N was purged with argon for 15 minutes. To this solution was added bis(triphenylphosphine)-palladium (II) chloride (247 mg, 0.35 mmol) and copper(I) iodide (67.0 mg, 0.35 mmol). After sparging for an additional 10 minutes with argon, the solution was stirred overnight at room temperature. The reaction mixture was diluted with EtOAc and filtered through a pad of Celite using an EtOAc wash. Concentration of the filtrate under reduced pressure, followed by column chromatography (3 to 5% EtOAc/hexanes) of the residual solid afforded 490.0 mg (91%) of the title compound as a yellow solid. $^1$H NMR (300 MHz, CDCl$_3$)δ: 8.31 (1H, d, J=7.6 Hz), 8.04 (2H, d, J=8.3 Hz), 7.60 (2H, d, J=8.3 Hz), 7.00 (1H, d, J=9.3 Hz), 4.40 (2H, q, J=7.1 Hz), 2.89 (2H, s), 1.50 (6H, s), 1.41 (3H, t, J=7.1 Hz).

Ethyl 4-[(2,2-dimethyl-4-oxo-7-methoxy-thiochroman-6-yl) ethynyl]-benzoate (Compound 210)

A solution of 6-ethynyl-7-methoxy-2,2-dimethylthiochroman-4-one (Compound 208, 217.0 mg, 0.88 mmol) and ethyl 4-iodobenzoate (245.0 mg, 0.89 mmol) in 10.0 mL Et$_3$N and 2 mL THF was purged with argon for 15 minutes. To this solution was added bis (triphenylphosphine)-palladium(II) chloride (154.0 mg, 0.22 mmol) and copper(I) iodide (42.0 mg, 0.22 mmol). After sparging for an additional 10 minutes with argon, the solution was stirred overnight at room temperature. The reaction mixture was diluted with EtOAc and filtered through a pad of Celite using an EtOAc wash. Concentration of the filtrate under reduced pressure, followed by column chromatography (5 to 10% EtOAc/hexanes) of the residual solid afforded 320.0 mg (92%) of the title compound as an orange solid. $^1$H NMR (300 MHz, CDCQ$_3$)δ: 8.29 (1H, s), 8.03 (2H, d, J=8.4 Hz), 7.60 (2H, d, J=8.4 Hz), 6.70 (1H, s), 4.40 (2H, q, J=7.1 Hz), 3.96 (3H, s), 2.86 (2H, s), 1.50 (6H, s), 1.41 (3H, t, J=7.1 Hz).

Ethyl 4-(2,2-dimethyl-4-trifluoromethanesulfonyloxy-7-fluoro-(2H)-thiochroman-6-ylethynyl)-benzoate (Compound 211)

A solution of sodium bis(trimethylsilyl)amide (256.7 mg, 1.44 mmol) in 3.4 mL of THF was cooled to −78° C. and a solution of ethyl 4-(2,2-dimethyl-4-oxo-7-fluoro-thiochroman-6-ylethynyl)-benzoate (Compound 209, 460.0 mg, 1.20 mmol) in 3.0 mL was added slowly. After 30 minutes a solution of 2-[N,N-bis(trifluoromethanesulfonyl)amino]-5-pyridine (518.0 mg, 1.32 mmol) in 2.0 mL of THF was added. After 5 minutes the solution was warmed to room temperature and stirred for 6 hours. The reaction was quenched by the addition of saturated aqueous NH$_4$Cl and extracted with EtOAc. The combined organic layers were washed with 5% aqueous NaOH and H$_2$O before being dried (MgSO$_4$) and concentrated under reduced pressure. The title compound, 549.0 mg (89%), was isolated by column chromatography (3–5% EtOAc/hexanes) as a pale-yellow solid. $^1$H NMR (300 MHz, CDCl$_3$) δ: 8.04 (2H, d, J=8.4 Hz), 7.61 (2H, d, J=8.4 Hz), 7.60 (1H, d, J=6.7 Hz), 7.08 (1H, d, J=9.0 Hz), 5.88 (1H, s), 4.40 (2H, q, J=7.1 Hz), 1.53 (6H, s), 1.41 (3H, t, J=7.1 Hz).

Ethyl 4-(2,2-dimethyl-4-trifluoromethanesulfonyloxy-7-methoxy-(2H)-thiochroman-6-ylethynyl)-benzoate (Compound 212)

A solution of sodium bis(trimethylsilyl)amide (155.9 mg, 0.85 mmol) in 2.9 mL of THF was cooled to −78° C. and a solution of ethyl 4-(2,2-dimethyl-4-oxo-7-methoxy-thiochroman-6-ylethynyl)-benzoate (Compound 210, 280.0 mg, 0.71 mmol) in 3.0 mL was added slowly. After 30 minutes a solution of 2-[N,N-bis(trifluoromethanesulfonyl)amino]-5-pyridine (355.0 mg, 0.85 mmol) in 2.0 mL of THF was added. After 5 minutes the solution was warmed to room temperature and stirred fo 6 hours. The reaction was quenched by the addition of saturated aqueous NH$_4$Cl and extracted with EtOAc. The combined organic layers were washed with 5% aqueous NaOH and H$_2$O before being dried (MgSO$_4$) and concentrated under reduced pressure. The title compound, 300.0 mg (80%), was isolated by column chromatography (15% EtOAc/hexanes) as an orange solid. $^1$H NMR (300 MHz, CDCl$_3$) δ: 8.02 (2H, d, J=8.3 Hz), 7.61 (2H, d, J=8.3 Hz), 7.57 (1H, s), 6.82 (1H, s), 5.76 (1H, s), 4.38 (2H, q, J=7.1 Hz), 3.92 (3H, s), 1.51 (6H, s), 1.40 (3H, t, J=7.1 Hz).

Ethyl 4-[[4-(4-methylphenyl)-2,2-dimethyl-7-fluoro-(2H)-thiochroman-6-yl]-ethynyl]-benzoate (Compound 213)

A solution of 4-methylbromobenzene (290.0 mg, 1.69 mmol) in 2.0 mL of THF was cooled to −78° C. and tert-butyllithium (217.2 mg, 3.39 mmol, 2.0 mL of a 1.7M solution in pentane) was added to give a yellow solution. After 30 minutes a solution of ZnCl$_2$ (409.0 mg, 3.00 mmol) in 4.0 mL THF was slowly added via cannula. The resulting solution was warmed to room temperature and transferred via cannula to a solution of ethyl 4-(2,2-dimethyl-4-trifluoromethanesulfonyloxy-7-fluoro-(2H)-thiochroman-6-ylethynyl)-benzoate (Compound 211, 158.0 mg, 0.31 mmol) and tetrakis(triphenylphosphine)palladium(0) (24.0 mg, 0.02 mmol) in 2.0 mL THF. This solution was heated to 50° C. for 2 hours, cooled to room temperature, and the reaction quenched by the addition of saturated aqueous NH$_4$Cl. This solution was extracted with EtOAc and the combined organic layers washed with H$_2$O and saturated aqueous NaCl before being dried (MgSO$_4$) and concentrated under reduced pressure. The title compound, 120.0 mg (86%), was isolated by column chromatography (3% EtOAc/hexanes). $^1$H NMR (300 MHz, CDCl$_3$) δ: 8.00 (2H, d, J=8.3 Hz), 7.54 (2H, d, J=8.3 Hz), 7.27–7.13 (6H, m), 5.79 (1H, s), 4.38 (2H, q, J=7.1 Hz), 2.42 (3H, s), 1.48 (6H, s), 1.40 (3H, t, J=7.1 Hz).

Ethyl 4-[[4-(5-methyl-thiophen-2yl)-2,2-dimethly-7-fluoro-(2H)-thiochromen-6-yl]-ethynyl]-benzoate (Compound 214)

A solution of 2-methylthiophene (130.0 mg, 1.30 mmol) in 2.0 mL of THF was cooled to −78° C. and n-butyllithium (83.3 mg, 1.30 mmol, 0.84 ml of a 1.6M solution in hexanes) was added and the solution warmed to 0° C. during 1.5 hours. A solution of ZnCl$_2$ (341.0 mg, 2.50 mmol) in 3.0 mL THF was slowly added via cannula. The resulting solution was warmed to room temperature, stirred for 40 minutes, and transferred via cannula to a solution of ethyl 4-[(2,2-dimethyl-4-trifluoromethanesulfonyloxy-7-fluoro-(2H)-thiochromen-6-yl)ethynyl]-benzoate (Compound 211, 158.0 mg, 0.31 mmol) and tetrakis(triphenylphosphine) palladium (0) (24.0 mg, 0.02 mmol) in 2.0 mL THF. This solution was heated to 50° C. for 2 hours, cooled to room temperature, and the reaction quenched by the addition of saturated aqueous NH$_4$Cl. Thei solution was extracted with EtOAc and the combined organic layers washed with H$_2$O and saturated aqueous NaCl before being dried (MgSO$_4$) and concentrated under reduced pressure. The title compound, 70.0 mg (50%), was isolated by column chromatography (3% EtOAc/hexanes) as a waxy solid. $^1$H NMR (300 MHz, CDCl$_3$) δ:8.01 (2H, d, J=8.3 Hz), 7.61 (1H, d, J=7.5 Hz), 7.58 (2H, d, J=8.3 Hz), 7.13 (1H, d, J=7.2 Hz), 6.82 (1H, d, J=4.4 Hz), 6.73 1H, d, J=4.4 Hz), 5.96 (1H, s), 4.39 (2H, q, J=7.1 Hz), 2.52 (3H, s), 1.46 (6H, s), 1.41 (3H, t, J=7.1 Hz).

Ethyl 4-[[4-(4-methylphenyl)-2,2-dimethyl-7-methoxy-(2H)-thiochromen-6-yl]-ethynyl]-benzoate (Compound 215)

A solution of 4-methylbromobenzene (499.0 mg, 2.92 mmol) in 2.0 mL of THF was cooled to −78° C. and tert-butyllithium (374.2 mg, 5.84 mmol, 3.4 ml of a 1.7M solution in pentane) was added to give a yellow solution. After 30 minutes a solution of ZnCl$_2$ (613.0 mg, 4.50 mmol) in 4.0 mL THF was slowly added via cannula. The resulting solution was warmed to room temperature and transferred via cannula to a solution of ethyl 4-(2,2-dimethyl-4-trifluoromethanesulfonyloxy-7-methoxy-(2H)-thiochromen-6-ylethynyl)-benzoate (Compound 212, 285.0 mg, 0.54 mmol) and tetrakis(triphenylphosphine)palladium (0) (24.0 mg, 0.02 mmol) in 2.0 mL THF. This solution was heated to 50° C. for 2 hours, cooled to room temperature, and the reaction quenched by the addition of saturated aqueous NH$_4$Cl. The solution was extracted with EtOAc and the combined organic layers were washed with H$_2$O and saturated aqueous NaCl before being dried (MgSO$_4$) and concentrated under reduced pressure. The title compound, 200.0 mg (79%), was isolated by column chromatography (2–5% EtOAc/hexanes) as a colorless solid. $^1$H NMR (300 MHz, CDCl$_3$) δ: 7.98 (2H, d, J=8.3 Hz), 7.54 (2H, d, J=8.3 Hz), 7.23–7.21 (5H, m), 5.71 (1H, s), 4.38 (2H, q, J=7.1 Hz), 3.95 (3H, s), 2.41 (3H, s), 1.49 (6H, s), 1.40 (3H, t, J=7.1 Hz).

3-(4-methoxy-phenylsulfanyl)-3-methyl-butgric acid (Compound 216)

A heavy-walled screw cap tube was charged with 3-methyl-2-butenoic acid (13.86 g, 138.4 mmol), 4-methoxy thiophenol (20.0 g, 138.4 mmol), and piperidine (3.45 g, 41.6 mmol). This mixture was heated to 105° C. for 32 hours, cooled to room temperature and dissolved in EtOAc (700 mL). The resulting solution was washed with 1M aqueous HCl, H$_2$O, and saturated aqueous NaCl before being dried over Na$_2$SO$_4$. Concentration of the dry solution under reduced pressure afforded an oil which upon standing in the freezer provided a crystalline solid. The title compound was isolated as paleyellow crystals by washing the crystalline solid with pentane. (27.33 g, 82%). $^1$H NMR (300 MHz, CDCl$_3$) δ: 7.48 (2H, d, J=9.0 Hz), 6.89 (2H, d, J=8.9 Hz), 3.83 (3H, s), 2.54 (2H, s), 1.40 (6H, s).

3-(4-methoxy-phenylsulfanyl)-3-methyl-butyroyl chloride (Compound 217)

To a solution of 3-(4-methoxy-phenylsulfanyl)-3-methyl-butyric acid (Compound 216, 20.0 g, 83.2 mmol) in 250 mL of benzene at room temperature was added a solution of oxalyl chloride (15.84 g, 124.8 mmol) in 10 mL of benzene over 30 minutes. After 4 hours the solution was washed with ice cold 5% aqueous NaOH (CAUTION: a large volume of gas is released during this procedure), followed by ice cold H$_2$O, and finally saturated aqueous NaCl. The solution was dried (Na$_2$SO$_4$) and concentrated under reduced pressure to give a clear yellow oil. This material was used without further purification in the next step. $^1$H NMR (300 MHz, CDCl$_3$) δ: 7.45 (2H, d, J=8.8 Hz), 6.90 (2H, d, J=8.8 Hz), 3.84 (3H, s), 3.12 (2H, s), 1.41 (6H, s).

6-Methoxy-2,2-dimethyl-thiochroman-4-one (Compound 218)

To a solution of the acyl chloride (Compound 217, 21.5 g, 83.2 mmol) in 250 mL of CH$_2$Cl$_2$ at 0° C. was added dropwise a solution of SnCl$_4$ (21.7 g, 83.2 mmol) in 30 mL of CH$_2$Cl$_2$. After 2 hours the reaction was quenched by slow addition of 150 mL H$_2$O. The organic layer was washed with 1M aqueous HCl, 5% aqueous NaOH, H$_2$O, and finally saturated aqueous NaCl before being dried over MgSO$_4$. Concentration under reduced pressure and vacuum distillation of the residual oil (Bulb-to-bulb, 125–135° C., 5 mm/Hg) afforded 14.48 g (78%) of the title compound as a pale-yellow oil. $^1$H NMR (300 MHz, CDCl$_3$) δ: 7.62 (1H, d, J=2.9 Hz), 7.14 (1H, d, J=8.6 Hz), 7.03 (1H, dd, J=2.8, 8.3 Hz), 3.83 (3H, s), 2.87 (2H, s), 1.46 (6H, s).

6-Hydroxy-2,2-dimethylthiochroman-4-one (Compound 219)

To a solution of 6-methoxy-2,2-dimethyl-thiochroman-4-one (Compound 218, 6.0 g, 27 mmol) in 50 mL CH$_2$Cl$_2$ cooled to −23° C. was added BBr$_3$ (20.0 g, 80.0 mmol; 80.0 mL of a 1M solution in CH$_2$Cl$_2$) over a 20 minute period. After stirring for 5 hours at −23° C. the solution was cooled to −78° C. and quenched by the slow addition of 50 mL of H$_2$O. Upon warming to room temperature the aqueous layer was extracted with CH$_2$Cl$_2$ and the combined organic layers were washed with saturated aqueous NaHCO$_3$, H$_2$O, and saturated aqueous NaCl before being dried over MgSO$_4$. Removal of the solvents under reduced pressure gave a green-brown solid which upon recrystalization (Et$_2$O/hexanes) afforded 2.25 g (40%) of the title compound as a light brown solid. $^1$H NMR (300 MHz, CDCl$_3$) δ:7.63 (1H, d, J=2.8 Hz), 7.15 (1H, d, J=8.5 Hz), 7.01 (1H, dd, J=2.8, 8.5 Hz), 2.87 (2H, s), 1.46 (6H, s).

2,2-Dimethyl-4-oxo-thiochroman-6-yl trifluoromethanesulfonate (Compound 220)

To a solution of 6-hydroxy-2,2-dimethylthiochroman-4-one (Compound 219, 165.0 mg, 0.79 mmol) in 5.0 mL of anhydrous pyridine at 0° C. was added trifluoromethanesulfonic anhydride (245.0 mg, 0.87 mmol). After 4 hours at 0° C. the solution was concentrated and the residual oil dissolved in Et$_2$O, washed with H$_2$O followed by saturated aqueous NaCl, and dried over MgSO$_4$. Removal of the solvents under reduced pressure and column chromatography (5% EtOAc/hexanes) afforded 126.0 mg (47%) of the title compound as a colorless solid. $^1$H NMR (300 MHz, CDCl$_3$) δ: 7.97 (1H, s), 7.32 (2H, s), 2.90 (2H, s), 1.49 (6H, s).

2,2-Dimethyl-6-trimethylsilanylethynyl-thiochroman-4-one (Compound 221)

A solution of 2,2-dimethyl-4-oxo-thiochroman-6-yl trifluoromethanesulfonate (Compound 220, 2.88 g, 8.50 mmol) in 10 mL Et$_3$N and 20.0 mL DMF was sparged with argon for 10 minutes. To this solution was added trimethylsilylacetylene (4.15 g, 42.0 mmol) and bis(triphenylphosphine)-palladium(II) chloride (298.0 mg, 0.425 mmol). The solution was heated to 95° C. for 5 hours, cooled to room temperature, and diluted with H$_2$O. Extraction with EtOAc was followed by washing the combined organic layers with H$_2$O and saturated aqueous NaCl and drying over MgSO$_4$. Concentration of the dry solution under reduced pressure and isolation of the product by column chromatography (3% EtOAc/hexanes) afforded 2.23 g (91%) of the title compound as an orange oil. $^1$H NMR (300 MHz, CDCl$_3$) δ: 8.18 (1H, d, J=1.9 Hz), 7.34 (1H, dd, J=1.9, 8.1 Hz), 7.15 (1H, d, J=8.1 Hz), 2.85 (2H, s), 1.45 (6H, s), 0.23 (9H, s).

6-Ethynyl-2,2-dimethylthiochroman-4-one (Compound 222)

A solution of 2,2-dimethyl-6-trimethylsilanylethynyl-thiochroman-4-one (Compound 221, 110.0 mg, 0.38 mmol) and $K_2CO_3$ (40.0 mg, 0.29 mmol) in 10.0 mL MeOH was stirred overnight at room temperature. The solution was diluted with $H_2O$ and extracted with $Et_2O$. The combined organic layers were washed with $H_2O$ and saturated aqueous NaCl and dried over $MgSO_4$. Removal of the solvent under reduced pressure afforded 81 mg (99%) of the title compound as an orange oil. $^1H$ NMR (300 MHz, $CDCl_3$) δ:8.20 (1H, d, J=1.9 Hz), 7.46 (1H, dd, J=1.9, 8.1 Hz), 7.18 (1H, d, J=8.1 Hz), 3.08 (1H, s), 2.86 (2H, s), 1.46 (6H, s).

Ethyl 4-[(2,2-dimethyl-4-oxo-thiochroman-6-yl)ethynyl]-benzoate (Compound 223)

A solution of 6-ethynyl-2,2-dimethylthiochroman-4-one (Compound 222, 82.0 mg, 0.38 mmol) and ethyl 4-iodobenzoate (104.9 mg, 0.38 mmol) in 5.0 mL $Et_3N$ was purged with argon for 10 minutes. To this solution were added bis(triphenylphosphine)-palladium(II) chloride (88.0 mg, 0.12 mmol) and copper(I) iodide (22.9 mg, 0.12 mmol). After sparging for an additional 5 minutes with argon, the solution was stirred overnight at room temperature. The reaction mixture was filtered through a pad of Celite using an $Et_2O$ wash. Concentration of the filtrate under reduced pressure, followed by column chromatography of the residual solid, afforded 100 mg (72%) of the title compound as a yellow solid. $^1H$ NMR (300 MHz, $CDCl_3$) δ: 8.25 (1H, d, J=1.8 Hz), 8.00 (2H, d, J=8.4 Hz), 7.55 (2H, d, J=8.4 Hz), 7.53 (1H, dd, J=1.8, 8.2 Hz), 7.21 (1H, d, J=8.2 Hz), 4.37 (2H, q, J=7.1 Hz), 2.88 (2H, s), 1.47 (6H, s), 1.39 (3H, t, J=7.1 Hz).

Ethyl 4-((2,2-dimethyl-4-trifluoromethanesulfonyloxy-(2H)-thiochromen-6-yl)ethynyl)-benzoate (Compound 224)

A solution of sodium bis(trimethylsilyl)amide (1.12 g, 6.13 mmol) in 16.2 mL of THF was cooled to −78° C. and a solution of ethyl 4-(2,2-dimethyl-4-oxo-thiochroman-6-ylethynyl)-benzoate (Compound 223, 1.86 g, 5.10 mmol) in 15.0 mL was added slowly. After 30 minutes a solution of 2-[N,N-bis(trifluoromethanesulfonyl)amino]-5-pyridine (2.40 g, 6.13 mmol) in 10 mL of THF was added. After 5 minutes the solution was warmed to room temperature and stirred overnight. The reaction was quenched by the addition of saturated aqueous $NH_4Cl$ and extracted with EtOAc. The combined organic layers were washed with 5% aqueous NaOH and $H_2O$ before being dried ($MgSO_4$) and concentrated under reduced pressure. The title compound, 1.53 g (61%), was isolated by column chromatography (2% EtOAc/hexanes) as a yellow solid. $^1H$ NMR (300 MHz, $CDCl_3$)δ: 8.03 (2H, d, J=8.4 Hz), 7.61 (1H, d, J=1.8 Hz), 7.59 (2H, d, J=8.4 Hz), 7.41 (1H, dd, J=1.8, 8.1 Hz), 7.29 (1H, d, J=8.1 Hz), 5.91 (1H, s), 4.39 (2H, q, J=7.1 Hz), 1.53 (6H, s), 1.41 (3H, t, J=7.1 Hz).

Ethyl 4-[[4-phenyl-2,2-dimethyl-(2H)-thiochromen-6-yl]-ethynyl]-benzoate (Compound 225)

A solution of bromobenzene (190.0 mg, 1.18 mmol) in 2.0 mL of THF was cooled to −78° C. and tert-butyllithium (151.2 mg, 2.36 mmol, 1.4 mL of a 1.7M solution in pentane) was added to give a yellow solution. After 30 minutes a solution of $ZnCl_2$ (225.0 mg, 1.4 mmol) in 4.0 mL THF was slowly added via cannula. The resulting solution was warmed to room temperature and transferred via cannula to a solution of ethyl 4-(2,2-dimethyl-4-trifluoromethanesulfonyloxy-(2H)-thiochromen-6-ylethynyl)-benzoate (Compound 224, 200.0 mg, 0.40 mmol) and tetrakis(triphenylphosphine)palladium(0) (24.0 mg, 0.02 mmol) in 2.0 mL THF. This solution was heated to 50° C. for 2 hours, cooled to room temperature, and the reaction quenched by the addition of saturated aqueous $NH_4Cl$. The solution was extracted with EtOAc and the combined organic layers were washed with H20 and saturated aqueous NaCl before being dried ($MgSO_4$) and concentrated under reduced pressure. The title compound, 155.0 mg (91%), was isolated by column chromatography (5% EtOAc/hexanes) as a colorless solid. $^1H$ NMR (300 MHz, $CDCl_3$) δ: 7.99 (2H, d, J=8.4 Hz), 7.52 (2H, d, J=8.4 Hz), 7.42–7.24 (8H, m), 5.78 (1H, s), 4.38 (2H, q, J=7.1 Hz), 1.50 (6H, s), 1.40 (3H, t, J=7.1 Hz).

Ethyl 4-[[4-(4-methylphenyl)-2,2-dimethyl-(2H-thiochromen-6-yl ]-ethynyl]-benzoate (Compound 226)

A solution of 4-methylbromobenzene (203.0 mg, 1.15 mmol) in 2.0 mL of THF was cooled to −78° C. and tert-butyllithium (147.4 mg, 2.30 mmol, 1.4 ml of a 1.7M solution in pentane) was added to give a yellow solution. After 30 minutes a solution of $ZnCl_2$ (219.4 mg, 1.4 mmol) in 4.0 mL THF was slowly added via cannula. The resulting solution was warmed to room temperature and transferred via cannula to a solution of ethyl 4-(2,2-dimethyl-4-trifluoromethanesulfonyloxy-(2H)-thiochromen-6-ylethynyl)-benzoate (Compound 224, 230.0 mg, 0.46 mmol) and tetrakis(triphenylphosphine)palladium(0) (24.0 mg, 0.02 mmol) in 2.0 mL THF. This solution was heated to 50° C. for 2 hours, cooled to room temperature, and the reaction quenched by the addition of saturated aqueous $NH_4Cl$. The solution was extracted with EtOAc and the combined organic layers were washed with $H_2O$ and saturated aqueous NaCl before being dried ($MgSO_4$) and concentrated under reduced pressure. The title compound, 165.0 mg (82%), was isolated by column chromatography (5% EtOAc/hexanes) as a colorless solid. $^1H$ NMR (300 MHz, $CDCl_3$) δ: 7.98 (2H, d, J=8.4 Hz), 7.51 (2H, d, J=8.4 Hz), 7.35–7.21 (7H, m), 5.84 (1H, s), 4.38 (2H, q, J=7.1 Hz), 2.42 (3H, s), 1.48 (6H, s), 1.40 (3H, s).

Ethyl 4-[[4-(4-ethylphenyl)-2,2-dimethyl-(2H)-thiochromen-6-yl]-ethynyl]-benzoate (Compound 227)

A solution of 4-ethylbromobenzene (670.9 mg, 3.63 mmol) in 4.0 mL of THF was cooled to −78° C. and tert-butyllithium (464.5 mg, 7.25 mmol, 4.26 mL of a 1.7M solution in pentane) was added to give a yellow solution. After 30 minutes a solution of $ZnCl_2$ (658.7 mg, 4.83 mmol) in 8.0 mL THF was slowly added via cannula. The resulting solution was warmed to room temperature and transferred via cannula to a solution of ethyl 4-(2,2-dimethyl-4-trifluoromethanesulfonyloxy-(2H)-thiochromen-6-ylethynyl)-benzoate (Compound 224, 1.20 g, 2.42 mmol) and tetrakis(triphenylphosphine)palladium(0) (111.7 mg, 0.097 mmol) in 8.0 mL THF. This solution was heated to 50° C. for 1 hour, cooled to room temperature, and the reaction quenched by the addition of saturated aqueous $NH_4Cl$. The solution was extracted with EtOAc and the combined organic layers were washed with $H_2O$ and saturated aqueous NaCl before being dried ($MgSO_4$) and concentrated under reduced pressure. The title compounds was isolated by column chromatography (5% EtOAc/hexanes) as a colorless oil. $^1H$ NMR (300 MHz, $CDCl_3$) δ: 7.99 (2H, d, J=8.2 Hz), 7.52 (2H, d, J=8.4 Hz), 7.40 (5H, m), 7.35 (2H, m), 5.85 (1H, s), 4.38 (2H, q, J=7.1 Hz), 2.72 (2H, q, J=7.6 Hz), 1.48 (6H, s), 1.40 (3H, t, J=7.1 Hz), 1.30 (3H, t, J=7.6 Hz).

Ethyl 4-[[4-(4-isopropylphenyl)-2,2-dimethyl-(2H-thiochromen-6-yl-]-ethynyl]-benzoate (Compound 228)

A solution of 4-isopropylbromobenzene (161.0 mg, 0.81 mmol) in 2.0 mL of THF was cooled to −78° C. and tert-butyllithium (103.8 mg, 1.62 mmol, 0.95 ml of a 1.7M solution in pentane) was added to give a yellow solution. After 30 minutes a solution of $ZnCl_2$ (175.5 mg, 1.3 mmol) in 4.0 mL THF was slowly added via cannula. The resulting solution was warmed to room temperature and transferred via cannula to a solution of ethyl 4-(2,2-dimethyl-4-trifluoromethanesulfonyloxy-(2H)-thiochromen-6-ylethynyl)-benzoate (Compound 224, 160.0 mg, 0.32 mmol) and tetrakis(triphenylphosphine) palladium(0) (24.0 mg, 0.02 mmol) in 2.0 mL THF. This solution was heated to 50° C. for 2 hours, cooled to room temperature, and the reaction quenched by the addition of saturated aqueous $NH_4Cl$. This solution was extracted with EtOAc and the combined organic layers were washed with $H_2O$ and saturated aqueous NaCl before being dried ($MgSO_4$) and concentrated under reduced pressure. The title compound, 128.0 mg (85%), was isolated by column chromatography (5% EtOAc/hexanes) as a colorless oil. $^1H$ NMR (300 MHz, $CDCl_3$) δ: 7.99 (2H, d, J=8.4 Hz), 7.53 (2H, d, J=8.1 Hz), 7.38–7.22 (7H, m), 5.86 (1H, s), 4.38 (2H, q, J=7.1 Hz), 2.98 (1H, hept, 7.0 Hz), 1.49 (6H, s), 1.43 (3H, t, J=7.1 Hz), 1.32 (6H, d, J=7.0 Hz).

Ethyl 4-[[4-(4-tert-butylphenyl)-2,2-dimethyl-(2H)-thiochromen-6-yl]-ethynyl]-benzoate (Compound 229)

A solution of 4-tert-butylbromobenzene (149.0 mg, 0.70 mmol) in 2.0 mL of THF was cooled to −78° C. and tert-butyllithium (92.6 mg, 1.44 mmol, 0.85 ml of a 1.7M solution in pentane) was added to give a yellow solution. After 30 minutes a solution of $ZnCl_2$ (133.0 mg, 0.98 mmol) in 4.0 mL THF was slowly added via cannula. The resulting solution was warmed to room temperature and transferred via cannula to a solution of ethyl 4-(2,2-dimethyl-4-trifluoromethanesulfonyloxy-(2H)-thiochromen-6-ylethynyl) benzoate (Compound 224, 140.0 mg, 0.28 mmol) and tetrakis(triphenylphosphine) palladium(0) (24.0 mg, 0.02 mmol) in 2.0 mL THF. This solution was heated to 50° C. for 2 hours, cooled to room temperature, and the reaction quenched by the addition of saturated aqueous $NH_4Cl$. The solution was extracted with EtOAc and the combined organic layers were washed with $H_2O$ and saturated aqueous NaCl before being dried ($MgSO_4$) and concentrated under reduced pressure. The title compound, 94.0 mg (70%), was isolated by column chromatography (5% EtOAc/hexanes) as a colorless solid. $^1H$ NMR (300 MHz, $CDCl_3$) δ: 7.98 (2H, d, J=8.3 Hz), 7.52 (2H, d, J=8.3 Hz), 7.43–7.22 (7H, m), 5.86 (1H, s), 4.38 (2H, q, J=7.1 Hz), 1.47 (6H, s), 1.40 (3H, t, J=7.1 Hz), 1.38 (9H, s).

Ethyl 4-[[4-(5-methyl-thiophen-2-yl)-2,2-dimethyl-(2H)-thiochromen-6-yl]ethynyl]-benzoate (Compound 230)

A solution of 2-methylthiophene (100.0 mg, 1.00 mmol) in 2.0 mL of THF was cooled to −78° C. and n-butyllithium (64.0 mg, 1.00 mmol, 0.63 ml of a 1.6M solution in hexanes) was added and the solution warmed to 0° C. during 1.5 hours. A solution of $ZnCl_2$ (218.0 mg, 1.60 mmol) in 3.0 mL THF was slowly added via cannula. The resulting solution was warmed to room temperature, stirred for 40 minutes, and transferred via cannula to a solution of ethyl 4-[(2,2-dimethyl-4-trifluoromethanesulfonyloxy-(2H)-thiochromen-6-yl)ethynyl]-benzoate (Compound 224, 200.0 mg, 0.40 mmol) and tetrakis(triphenylphosphine) palladium (0) (24.0 mg, 0.02 mmol) in 2.0 mL THF. This solution was heated to 50° C. for 2 hours, cooled to room temperature, and the reaction quenched by the addition of saturated aqueous $NH_4Cl$. The solution was extracted with EtOAc and the combined organic layers were washed with $H_2O$ and saturated aqueous NaCl before being dried ($MgSO_4$) and concentrated under reduced pressure. The title compound, 170.0 mg (96%), was isolated by column chromatography (5% EtOAc/hexanes) as a pale-yellow solid. $^1H$ NMR (300 MHz, $CDCl_3$) δ: 8.01 (2H, d, J=8.3 Hz), 7.63 (1H, s), 7.55 (2H, d, J=8.3 Hz), 7.35 (2H, s), 6.82 (1H, d, J=3.5 Hz), 6.72 (1H, m), 6.00 (1H, s), 4.38 (2H, q, J=7.1 Hz), 2.52 (3H, s), 1.46 (6H, s), 1.40 (2H, t, J=7.1 Hz).

Ethyl 4-[[4-(2-ethyl-thiophen-2-yl)-2,2-dimethyl-(2H)-thiochromen-6-yl]-ethynyl]-benzoate (Compound 231)

A solution of 2-ethylthiophene (112.0 mg, 1.00 mmol) in 2.0 mL of THF was cooled to −78° C. and n-butyllithium (64.0 mg, 1.00 mmol, 0.63 ml of a 1.6M solution in hexanes) was added and the solution warmed to 0° C. during 1.5 hours. A solution of $ZnCl_2$ (218.0 mg, 1.60 mmol) in 3.0 mL THF was slowly added via cannula. The resulting solution was warmed to room temperature, stirred for 40 minutes, and transferred via cannula to a solution of ethyl 4-[(2,2-dimethyl-4-trifluoromethanesulfonyloxy-(2H)-thiochromen-6-yl)ethynyl]-benzoate (Compound 224, 200.0 mg, 0.40 mmol) and tetrakis(triphenylphosphine) palladium (0) (24.0 mg, 0.02 mmol) in 2.0 mL THF. This solution was heated to 50° C. for 2 hours, cooled to room temperature, and the reaction quenched by the addition of saturated aqueous $NH_4Cl$. The solution was extracted with EtOAc and the combined organic layers were washed with $H_2O$ and saturated aqueous NaCl before being dried ($MgSO_4$) and concentrated under reduced pressure. The title compound, 29.0 mg (16%), was isolated by HPLC (1.25% EtOAc/hexanes) as a pale-yellow solid. $^1H$ NMR (300 MHz, $CDCl_3$) δ: 8.01 (2H, d, J=8.4 Hz), 7.65 (1H, s), 7.55 (2H, d, J=8.4 Hz), 7.35 (2H, s), 6.84 (1H, d, J=3.5 Hz), 6.77 (1H, m), 6.02 (1H, s), 4.39 (2H, q, J=7.1 Hz), 2.88 (2H, q, J=7.6 Hz), 1.46 (6H, s), 1.41 (2H, t, J=7.1 Hz), 1.35 (2H, t, J=7.6 Hz), Ethyl 4-[[4-(5-tert-butyl-thiophen-2-yl)-2,2-dimethyl-(2H)-thiochromen-6-yl]-ethynyl]-benzoate (Compound 232)

A solution of 2-tert-butylthiophene (105.0 mg, 0.75 mmol) in 2.0 mL of THF was cooled to −78° C. and n-butyllithium (48.1 mg, 0.75 mmol, 0.47 ml of a 1.6M solution in hexanes) was added and the solution warmed to 0° C. during 1.5 hours. A solution of $ZnCl_2$ (163.2 mg, 1.20 mmol) in 3.0 mL THF was slowly added via cannula. The resulting solution was warmed to room temperature, stirred for 40 minutes, and transferred via cannula to a solution of ethyl 4-[(2,2-dimethyl-4-trifluoromethanesulfonyloxy-(2H)-thiochromen-6-yl)ethynyl]-benzoate (Compound 224, 200.0 mg, 0.40 mmol) and tetrakis(triphenylphosphine) palladium(0) (20.0 mg, 0.02 mmol) in 2.0 mL THF. This solution was heated to 50° C. for 2 hours, cooled to room temperature, and the reaction quenched by the addition of saturated aqueous $NH_4Cl$. The solution was extracted with EtOAc and the combined organic layers were washed with $H_2O$ and saturated aqueous NaCl before being dried ($MgSO_4$) and concentrated under reduced pressure. The title compound, 110.0 mg (76%), was isolated by column chromatography (5% EtOAc/hexanes) as a colorless solid. $^1H$ NMR (300 MHz, $CDCl_3$) δ: 8.01 (2H, d, J=8.3 Hz), 7.68 (1H, s), 7.56 (2H, d, J 8.3 Hz), 7.36 (2H, m), 6.82 (2H, m), 6.04 (1H, s), 4.39 (2H, q, J=7.1 Hz), 1.46 (6H, s), 1.43 (9H, s), 1.41 (2H, t, J=7.1 Hz).

Ethyl 4-[[4-(6-methyl-pyridin-3-yl)-2,2-dimethyl-(2H)-thiochromen-6-yl]-ethynyl]-benzoate (Compound 233)

A solution of 4-bromo-2-methylpyridine (220.0 mg, 1.28 mmol) in 2.0 mL of THF was cooled to −78° C. and tert-butyllithium (164.0 mg, 2.56 mmol, 1.5 ml of a 1.7M solution in pentane) was added to give a red-orange solution. After 30 minutes a solution of $ZnCl_2$ (348.0 mg, 2.56 mmol) in 4.0 mL THF was slowly added via cannula. The resulting solution was warmed to room temperature, stirred for 40 minutes, and transferred via cannula to a solution of ethyl 4-(2,2-dimethyl-4-trifluoromethanesulfonyloxy-(2H) thiochromen-6-yl-ethynyl)-benzoate (Compound 224, 172.0 mg, 0.35 mmol) and tetrakis(triphenylphosphine) palladium (0) (24.0 mg, 0.02 mmol) in 2.0 mL THF. This solution was heated to 50° C. for 2 hours, cooled to room temperature, and the reaction quenched by the addition of saturated aqueous NH$_4$Cl. The solution was extracted with EtOAc and the combined organic layers were washed with H$_2$O and saturated aqueous NaCl before being dried (MgSO$_4$) and concentrated under reduced pressure. The title compound, 109.0 mg (72%) was isolated by column chromatography (5% EtOAc/hexanes) as a pale-yellow solid. $^1$H NMR (300 MHz, CDCl$_3$) δ: 8.45 (1H, d, J=2.0 Hz), 8.00 (2H, d, J=8.5 Hz), 7.52 (2H, d, J=8.5 Hz), 7.49 (1H, dd, J=2.3, 8.1 Hz), 7.36 (2H, m), 7.20 (1H, d, J=8.1 Hz), 7.16 (1H, d, J=1.5 Hz), 5.86 (1H, s), 4.38 (2H, q, J=7.1 Hz), 2.63 (3H, s), 1.50 (6H, s), 1.40 (3H, t, J=7.1 Hz).

Ethyl 4-[(2,2-dimethyl-4-oxo-thiochroman-6-yl)ethyvnl]-2-fluorobenzoate (Compound 234)

A solution of 6-ethynyl-2,2-dimethylthiochroman-4-one (Compound 222, 1.37 g, 6.34 mmol) and ethyl 2-fluro-4-iodobenzoate (1.86 g, 6.34 mmol) in 40.0 mL Et$_3$N was purged with argon for 20 minutes. To this solution was added bis(triphenylphosphine)-palladium(II) chloride (1.05 g, 1.5 mmol) and copper(I) iodide (286.0 mg, 1.5 mmol). After sparging for an additional 10 minutes with argon, the solution was stirred overnight at room temperature. The reaction mixture was filtered through a pad of Celite using an Et$_2$O wash. Concentration of the filtrate under reduced pressure, followed by column chromatography (5% EtOAc/hexanes) of the residual solid afforded 1.88 g (78%) the title compound as a yellow solid. $^1$H NMR (300 MHz, CDCl$_3$) δ: 8.27 (1H, d, J=1.9 Hz), 7.92 (1H, d, J=7.8 Hz), 7.52 (1H, dd, J=1.9, 8.2 Hz), 7.36–7.24 (3H, m), 4.41 (2H, q, J=7.1 Hz), 2.90 (2H, s), 1.50 (6H, s), 1.41 (3H, t, J=7.1 Hz).

Ethyl 4-(2,2-dimethyl-4-trifluoromethanesulfonyloxy-(2H)-thiochromen-6-ylethynyl)-2-fluorobenzoate (Compound 235)

A solution of sodium bis(trimethylsilyl)amide (0.82 g, 5.90 mmol) in 16.2 mL of THF was cooled to −78° C. and a solution of ethyl 4-[(2,2-dimethyl-4-oxo-thiochroman-6-yl)ethynyl]-2-flourobenzoate (Compound 234, 1.88 g, 4.91 mmol) in 15.0 mL was added slowly. After 30 minutes a solution of 2-[N,N-bis(trifluoromethanesulfonyl)amino]-5-pyridine (2.32 g, 5.90 mmol) in 10 mL of THF was added. After 5 minutes the solution was warmed to room temperature and stirred overnight. The reaction was quenched by the addition of saturated aqueous NH$_4$Cl and extracted with EtOAc. The combined organic layers were washed with 5% aqueous NaOH and H$_2$O before being dried (MgSO$_4$) and concentrated under reduced pressure. The title compound, 1.80 g (71%), was isolated by column chromatography (5% EtOAc/hexanes) as a yellow solid. $^1$H NMR (300 MHz, CDCl$_3$) δ: 7.93 (1H, d, J=7.8 Hz), 7.61 (1H, d, J=1.6 Hz), 7.43–7.27 (4H, m), 5.92 (1H, s), 4.41 (2H, q, J=7.1 Hz), 1.53 (6H, s), 1.42 (3H, t, J=7.1 Hz).

Ethyl 4-[[4-(4-methylphenly)-2,2-dimethyl-(2H)-thiochromen-6-yl]-ethynyl]-2-fluorobenzoate (Compound 236)

A solution of 4-methylbromobenzene (280.0 mg, 1.64 mmol) in 2.0 mL of THF was cooled to −78° C. and tert-butyllithium (209.5 mg, 3.27 mmol, 1.9 mL of a 1.7M solution in pentane) was added to give a yellow solution. After 30 minutes a solution of ZnCl$_2$ (680.0 mg, 5.0 mmol) in 4.0 mL THF was slowly added via cannula. The resulting solution was warmed to room temperature and transferred via cannula to a solution of ethyl 4-(2,2-dimethyl-4-trifluoromethanesulfonyloxy-(2H)-thiochromen-6-ylethynyl)-2-fluorobenzoate (Compound 234, 200.0 mg, 0.39 mmol) and tetrakis(triphenylphosphine)palladium(0) (24.0 mg, 0.02 mmol) in 2.0 mL THF. This solution was heated to 50° C. for 1 hour, cooled to room temperature, and the reaction quenched by the addition of saturated aqueous NH$_4$Cl. The solution was extracted with EtOAc and the combined organic layers were washed with H$_2$O and saturated aqueous NaCl before being dried (MgSO$_4$) and concentrated under reduced pressure. The title compound, 177.0 mg (79%), was isolated by column chromatography (5% EtOAc/hexanes) as a pale-yellow solid. $^1$H NMR (300 MHz, CDCl$_3$) δ: 7.88 (1H, d, J=7.8 Hz), 7.28–7.18 (9H, m), 5.84 (1H, s), 4.39 (2H, q, J=7.1 Hz), 2.42 (3H, s), 1.48 (6H, s), 1.40 (3H, t, J=7.1 Hz).

Ethyl 4-[[4-(4-ethylphenyl)-2,2-dimethyl-(2H)-thiochromen-6-yl]-ethynyl]-2-fluorobenzoate (Compound 237)

A solution of 4-ethylbromobenzene (185.0 mg, 1.00 mmol) in 2.0 mL of THF was cooled to −78° C. and tert-butyllithium (128.5 mg, 2.0 mmol, 1.2 mL of a 1.7M solution in pentane) was added to give a yellow solution. After 30 minutes a solution of ZnCl$_2$ (204.5 mg, 1.5 mmol) in 4.0 mL THF was slowly added via cannula. The resulting solution was warmed to room temperature and transferred via cannula to a solution of ethyl 4-(2,2-dimethyl-4-trifluoromethylsulfonyloxy-(2H)-thiochromen-6-ylethynyl)-2-fluorobenzoate (Compound 234, 200.0 mg, 0.39 mmol) and tetrakis(triphenylphosphine)palladium(0) (24.0 mg, 0.02 mmol) in 2.0 mL THF. This solution was heated to 50° C. for 1 hour, cooled to room temperature, and the reaction quenched by the addition of saturated aqueous NH$_4$Cl. The solution was extracted with EtOAc and the combined organic layers were washed with H$_2$O and saturated aqueous NaCl before being dried (MgSO$_4$) and concentrated under reduced pressure. The title compound, 158.0 mg (86%), was isolated by column chromatography (5% EtOAc/hexanes) as a pale-yellow solid. $^1$H NMR (300 MHz, CDCl$_3$) δ: 7.88 (1H, d, J=7.8 Hz), 7.39–7.20 (9H,m), 5.86 (1H, s), 4.40 (2H, q, J=7.1 Hz), 2.72 (2H, q, J=7.6 Hz), 1.49 (6H, s), 1.40 (3H, t, J=7.1 Hz), 1.30 (3H, t, J=7.6 Hz).

Ethyl 6-[(2,2-dimethyl-4-oxo-thiochroman-6-yl)ethynyl]-nicotinate (Compound 238)

A solution of 6-ethynyl-2,2-dimethylthiochroman-4-one (Compound 222, 510.0 mg, 2.36 mmol) and ethyl 6-iodonicotinate (654.0 mg, 2.36 mmol) in 20.0 mL Et$_3$N was purged with argon for 20 minutes. To this solution was added bis(triphenylphosphine)-palladium(II) chloride (425.0 mg, 0.60 mmol) and copper(I) iodide (115.0 mg, 0.60 mmol). After sparging for an additional 10 minutes with argon, the solution was stirred overnight at room temperature. The reaction mixture was diluted with EtOAc (20 mL) and filtered through a pad of Celite using an Et$_2$O wash. Concentration of the filtrate under reduced pressure, followed by column chromatography (10 to 20% EtOAc/hexanes) of the residual solid afforded 675 mg (78%) of the title compound as an orange solid. $^1$H NMR (300 MHz, CDCl$_3$) δ: 9.20 (1H, d, J=1.0 Hz), 8.34 (1H, d, J=1.8 Hz), 8.29 (1H, dd, J=2.2, 8.2 Hz), 7.60 (2H, m), 7.25 (1H, d, J=8.4 Hz), 4.43 (2H, q, J=7.1 Hz), 2.90 (2H, s), 1.49 (6H, s), 1.43 (3H, t, J=7.1 Hz).

Ethyl 6-(2,2-dimethyl-4-trifluoromethanesulfonyloxy-(2H)-thiochromen-6-ylethynyl)-nicotinate (Compound 239)

A solution of sodium bis(trimethylsilyl)amide (284.2 mg, 1.55 mmol) in 3.6 mL of THF was cooled to −78° C. and a solution of ethyl 6-(2,2-dimethyl-4-oxo-thiochroman-6-ylethynyl)-nicotinate (Compound 238, 480.0 mg, 1.31 mmol) in 3.0 mL THF was added slowly. After 30 minutes a solution of 2-[N,N-bis(trifluoromethanesulfonyl)amino]-5-pyridine (608.0 mg, 1.55 mmol) in 3.0 mL of THF was added. After 5 minutes the solution was warmed to room temperature and stirred overnight. The reaction was quenched by the addition of saturated aqueous NH$_4$Cl and extracted with EtOAc. The combined organic layers were washed with 5% aqueous NaOH and H$_2$O before being dried (MgSO$_4$) and concentrated under reduced pressure. The title compound was isolated by column chromatography (20% EtOAc/hexanes) as a yellow solid, 566.0 mg (87%). $^1$H NMR (300 MHz, CDCl$_3$) δ: 9.21 (1H, d, J=2.0 Hz), 8.30 (1H, dd, J=2.0, 8.1 Hz), 7.68 (1H, d, J=1.5 Hz), 7.61 (1H, d, J=8.2 Hz), 7.49 (1H, dd, J=1.7, 8.1 Hz), 7.31 (1H, d, J=8.2 Hz), 5.92 (1H, s), 4.41 (2H, q, J=7.1 Hz), 1.53 (6H, s), 1.43 (3H, t, J=7.1 Hz).

Ethyl 6-[[4-(4-methylphenyl)-2,2-dimethyl-(2H)-thiochromen-6-yl]-ethynyl]nicotinate (Compound 240)

A solution of 4-methylbromobenzene (280.0 mg, 1.64 mmol) in 2.0 mL of THF was cooled to −78° C. and tert-butyllithium (209.5 mg, 3.27 mmol, 1.9 ml of a 1.7M solution in pentane) was added to give a yellow solution. After 30 minutes a solution of ZnCl$_2$ (680.0 mg, 5.0 mmol) in 4.0 mL THF was slowly added via cannula. The resulting solution was warmed to room temperature and transferred via cannula to a solution of ethyl 6-(2,2-dimethyl-4-trifluoromethanesulfonyloxy-(2H)-thiochromen-6-ylethynyl)-nicotinate (Compound 239, 120.0 mg, 0.24 mmol) and tetrakis(triphenylphosphine)palladium(0) (20.0 mg, 0.02 mmol) in 2.0 mL THF. This solution was heated to 50° C. for 2 hours, cooled to room temperature, and the reaction quenched by the addition of saturated aqueous NH$_4$Cl. The solution was extracted with EtOAc and the combined organic layers were washed with H$_2$O and saturated aqueous NaCl before being dried (MgSO$_4$) and concentrated under reduced pressure. The title compound, 80.0 mg (76%), was isolated by column chromatography (10 to 15% EtOAc/hexanes) as a colorless solid. $^1$H NMR (300 MHz, CDCl$_3$) δ: 9.15 (1H, d, J=2.2 Hz), 8.23 (1H, dd, J=2.1, 8.0 Hz), 7.51 (1H, d, J=8.1 Hz), 7.40–7.32 (3H, m), 7.18 (4H, m), 5.83 (1H, s), 4.40 (2H, q, J=7.1 Hz), 2.40 (3H, s), 1.47 (6H, s), 1.40 (3H, t, J=7.1 Hz).

Ethyl 6-[[4-(4-ethylphenyl)-2,2-dimethyl-(2H)-thiochromen-6-yl]-ethynyl]-nicotinate (Compound 241)

A solution of 4-ethylbromobenzene (300.0 mg, 1.62 mmol) in 2.0 mL of THF was cooled to −78° C. and tert-butyllithium (207.6 mg, 3.24 mmol, 1.9 mL of a 1.7M solution in pentane) was added to give a yellow solution. After 30 minutes a solution of ZnCl$_2$ (408.0 mg, 3.0 mmol) in 4.0 mL THF was slowly added via cannula. The resulting solution was warmed to room temperature and transferred via cannula to a solution of ethyl 6-(2,2-dimethyl-4-trifluoromethanesulfonyloxy-(2H)-thiochromen-6-ylethynyl) nicotinate (Compound 239, 178.0 mg, 0.36 mmol) and tetrakis(triphenylphosphine)palladium(0) (24 mg, 0.02 mmol) in 2.0 mL THF. This solution was heated to 50° C. for 1 hour, cooled to room temperature, and the reaction quenched by the addition of saturated aqueous NH$_4$Cl. This solution was extracted with EtOAc and the combined organic layers were washed with H$_2$O and saturated aqueous NaCl before being dried (MgSO$_4$) and concentrated under reduced pressure. The title compound was isolated by column chromatography (10 to 15% EtOAc/ hexanes) and recrystalization from CH$_3$CN to give 136.0 mg (83%) of pale yellow crystals. $^1$H NMR (300 MHz, CDCl$_3$) δ: 9.15 (1H, s), 8.23 (1H, dd, J=2.2, 8.2 Hz), 7.51 (1H, d, J=8.1 Hz), 7.49–7.34 (3H, m), 7.24–7.17 (4H, m), 5.83 (1H, s), 4.40 (2H, q, J=7.1 Hz), 2.70 (2H, q, J=7.6 Hz), 1.47 (6H, s), 1.40 (3H, t, J=7.1 Hz), 1.29 (3H, t, J=7.1 Hz).

4-[[4-phenyl-2,2-dimethyl-(2H)-thiochromen-6-yl]-ethynl]-benzoic acid (Compound 242)

To a solution of ethyl 4-[[4-phenyl-2,2-dimethyl-(2H)-thiochromen-6-yl]-ethynyl]-benzoate (Compound 225, 105.0 mg, 0.247 mmol) in 3.0 mL THF and 3.0 mL EtOH was added NaOH (120.0 mg, 3.0 mmol, 3.0 mL of a 1M aqueous solution). The resulting solution was heated to 45° C. and stirred overnight. Upon cooling to room temperature the reaction mixture was acidified with 10% aqueous HCl and extracted with EtOAc. The combined organic layers were washed with H$_2$O, saturated aqueous NaCl, and dried (Na$_2$SO$_4$) before removing the solvent under reduced pressure. The residual solid was recrystallized from CH$_3$CN to give the title compound as a pale-yellow solid. $^1$H NMR (300 MHz, d$_6$-acetone) δ: 8.00 (2H, d, J=8.4 Hz), 7.57 (2H, d, J=8.4 Hz), 7.48–7.29 (7H, m), 7.18 (1H, d, J=1.3 Hz), 5.96 (1H, s), 1.48 (6H, s).

4-[[4-(4-methylphenyl)-2,2-dimethyl-(2H)-thiochromen-6-yl]-ethyl]-benzoic acid (Compound 243)

To a solution of ethyl 4-[[4-(4-methylphenyl)-2,2-dimethyl-(2H)thiochromen-6-yl]-ethynyl]-benzoate (Compound 226, 126.0 mg, 0.287 mmol) in 3.0 mL THF and 3.0 mL EtOH was added NaOH (160.0 mg, 4.0 mmol, 2.0 mL of a 2M aqueous solution). The resulting solution was heated to 45° C. and stirred overnight. Upon cooling to room temperature the reaction mixture was acidified with 10% aqueous HCl and extracted with EtOAc. The combined organic layers were washed with H$_2$O, saturated aqueous NaCl, and dried (Na$_2$SO$_4$) before removing the solvent under reduced pressure. The residual solid was recrystallized from CH$_3$CN to give 85.0 mg (72%) of the title compound as a pale-yellow solid. $^1$H NMR (300 MHz, d$_6$-acetone) δ: 8.00 (2H, d, J=8.3 Hz), 7.58 (2H, d, J=8.3 Hz), 7.45–7.38 (2H, m), 7.28–7.17 (5H, m), 5.92 (1H, s), 2.37 (3H, s), 1.47 (6H, s).

4-[[4-(4-ethylphenyl)-2,2-dimethyl-(2H)-thiochromen-6-yl]-ethyl]-benzoic acid (Compound 244)

To a solution of ethyl 4-[[4-(4-ethylphenyl)-2,2-dimethyl-(2H)-thiochromen-6-yl]-ethynyl]-benzoate (Compound 227, 940.0 mg, 2.08 mmol) in 10.0 mL THF and 5.0 mL EtOH was added NaOH (416.0 mg, 10.4 mmol, 5.2 mL of a 2M aqueous solution). The resulting solution was stirred overnight at room temperature. The reaction mixture was acidified with 10% aqueous HCl and extracted with EtOAc. The combined organic layers were washed with H$_2$O, saturated aqueous NaCl, and dried (Na$_2$SO$_4$) before removing the solvent under reduced pressure. The residual solid was recrystallized from CH$_3$CN to give 786.0 mg (89%) of the title compound as a colorless solid. $^1$H NMR (300 MHz, d$_6$-acetone) δ: 8.01 (2H, d, J=8.3 Hz), 7.60 (2H, d, J=8.5 Hz), 7.42 (2H, m), 7.29 (2H, m), 7.22 (3H, m), 5.94 (1H, s), 2.69 (2H, q, J=7.7 Hz), 1.47 (6H, s), 1.25 (3H, t, J=7.7 Hz).

4-[[4-(4-isopropylhenyl)-2,2-dimethyl-(2H)-thiochromen-6-yl]-ethynyl]-benzoic acid Compound 245)

To a solution of ethyl 4-[[4-(4-isopropylphenyl)-2,2-dimethyl-(2H)-thiochromen-6-yl]-ethynyl]-benzoate (Compound 228, 89.0 mg, 0.19 mmol) in 3.0 mL THF and 3.0 mL EtOH was added NaOH (80.0 mg, 2.0 mmol, 2.0 mL of a 1M aqueous solution). The resulting solution was heated to 45° C. and stirred overnight. Upon cooling to room temperature the reaction mixture was acidified with 10% aqueous HCl and extracted with EtOAc. The combined organic layers were washed with H$_2$O, saturated aqueous NaCl, and dried (Na$_2$SO$_4$) before removing the solvent under reduced pressure. The residual solid was recrystallized from CH$_3$CN to give 78.0 mg (93%) of the title compound as a pale-yellow solid. $^1$H NMR (300 MHz, d$_6$-acetone) δ: 8.00 (2H, d, J=8.4 Hz), 7.58 (2H, d, J=8.4 Hz), 7.45–7.21 (7H, m), 5.93 (1H, s), 2.95 (1H, hept, J=7.0 Hz), 1.47 (6H, s), 1.25 (6H, d, J=7.0 Hz).

4-[[4-(4-tert-butylphenyl)-2,2-dimethyl-(2H)-thiochromen-6-yl]-ethynyl]-benzoic acid (Compound 246)

To a solution of ethyl 4-[[4-(4-tert-butylphenyl)-2,2-dimethyl-(2H)-thiochromen-6-yl]-ethynyl]-benzoate (Compound 229, 65.0 mg, 0.135 mmol) in 2.0 mL THF and 2.0 mL EtOH was added NaOH (80.0 mg, 2.0 mmol, 2.0 mL of a 1M aqueous solution). The resulting solution was heated to 45° C. and stirred overnight. Upon cooling to room temperature the reaction mixture was acidified with 10% aqueous HCl and extracted with EtOAc. The combined organic layers were washed with $H_2O$, saturated aqueous NaCl, and dried ($Na_2SO_4$) before removing the solvent under reduced pressure. The residual solid was recrystallized from $CH_3CN$ to give 33.0 mg (54%) of the title compound as a pale-yellow solid. $^1H$ NMR (300 MHz, $d_6$-acetone) δ: 8.01 (2H, d, J=8.4 Hz), 7.57 (2H, d, J=8.4 Hz), 7.45 (4H, m), 7.24 (3H, m), 5.93 (1H, s), 1.47 (6H, s), 1.34 (9H, s).

4-[[4-(5-methyl-thiophen-2-yl)-2,2-dimethyl-(2H)-thiochromen-6-yl]-ethynyl]-benzoic acid (Compound 247)

To a solution of ethyl 4-[[4-(5-methylthiophen-2-yl)-2,2-dimethyl-(2H)-thiochromen-6-yl]-ethynyl]-benzoate (Compound 230, 143.0 mg, 0.322 mmol) in 3.0 mL THF and 3.0 mL EtOH was added NaOH (160.0 mg, 4.0 mmol, 4.0 mL of a 1M aqueous solution). The resulting solution was stirred overnight at room temperature. The reaction mixture was acidified with 10% aqueous HCl and extracted with EtOAc. The combined organic layers were washed with $H_2O$, saturated aqueous NaCl, and dried ($Na_2SO_4$) before removing the solvent under reduced pressure. The residual solid was recrystallized from $CH_3CN$ to give 110.0 mg (82%) of the title compound as a pale-yellow solid. $^1H$ NMR (300 MHz, $d_6$-acetone) δ: 8.03 (2H, d, J=8.4 Hz), 7.63 (2H, d, J=8.3 Hz), 7.60 (1H, s), 7.44 (2H, s), 6.87 (1H, d, J=3.5 Hz), 6.79 (1H, m), 6.10 (1H, s), 2.49 (3H, s), 1.45 (6H, s).

4-[[4-(5-methyl-thiophen-2-yl)-2,2-dimethyl-(2H)-thiochromen-6-yl]-ethyl]benzoic acid (Compound 248)

To a solution of ethyl 4-[[4-(5-ethylthiophen-2-yl)-2,2-dimethyl-(2H)-thiochromen-6-yl]-ethynyl]-benzoate (Compound 231, 23.0 mg, 0.05 mmol) in 1.0 mL THF and 1.0 mL EtOH was added NaOH (40.0 mg, 1.0 mmol, 1.0 mL of a 1M aqueous solution). The resulting solution was stirred overnight at room temperature. The reaction mixture was acidified with 10% aqueous HCl and extracted with EtOAc. The combined organic layers were washed with $H_2O$, saturated aqueous NaCl, and dried ($Na_2SO_4$) before removing the solvent under reduced pressure. The residual solid was recrystallized from $CH_3CN$ to give 15.5 mg (72%) of the title compound as an orange solid. $^1H$ NMR (300 MHz, $d_6$-acetone) δ: 8.03 (2H, d, J=8.3 Hz), 7.63 (2H, d, J=8.3 Hz), 7.61 (1H, s), 7.44 (2H, s), 6.90 (1H, d, J=3.5 Hz), 6.83 (1H, d, J=3.5 Hz), 6.10 (1H, s), 2.86 (2H, q, J=7.6 Hz), 1.45 (6H, s), 1.30 (3H, t, J=7.6 Hz).

4-[[4-(5-tert-butylthiopen-2-yl)-2,2-dimethyl-(2H)-thiochromen-6-yl]-ethyl]benzoic acid (Compound 249)

To a solution of ethyl 4-[[4-(5-tert-butylthiophen-2-yl)-2,2-dimethyl(2H)-thiochromen-6-yl]-ethynyl]-benzoate (Compound 232, 88.0 mg, 0.181 mmol) in 2.0 mL THF and 2.0 mL EtOH was added NaOH (160.0 mg, 4.0 mmol, 4.0 mL of a 1M aqueous solution). The resulting solution was stirred overnight at room temperature. The reaction mixture was acidified with 10% aqueous HCl and extracted with EtOAc. The combined organic layers were washed with $H_2O$, saturated aqueous NaCl, and dried ($Na_2SO_4$) before removing the solvent under reduced pressure. The residual solid was recrystallized from $CH_3CN$ to give 68.0 mg (82%) of the title compound as a pale-yellow solid. $^1H$ NMR (300 MHz, $d_6$-acetone) δ: 8.03 (2H, d, J=8.3 Hz), 7.63 (2H, d, J=8.3 Hz), 7.62 (1H, s), 7.44 (2H, d, J=1.2 Hz), 6.87 (2H, s), 6.11 (1H, s), 1.45 (6H, s), 1.39 (9H, s).

4-[[4-(6-methylpyridin-3-yl)-2,2-dimethyl-(2H)-thiochromen-6-yl]-ethynyl]-benzoic acid (Compound 250)

To a solution of ethyl 4-[[4-(6-methylpyridin-3-yl)-2,2-dimethyl-(2H)-thiochromen-6-yl]-ethynyl]-benzoate (Compound 233, 70.0 mg, 0.159 mmol) in 3.0 mL THF and 3.0 mL EtOH was added NaOH (120.0 mg, 3.0 mmol, 3.0 mL of a 1M aqueous solution). The resulting solution was stirred overnight at 35° C. Upon cooling to room temperature, the reaction mixture was acidified with 10% aqueous HCl and extracted with EtOAc. The combined organic layers were washed with $H_2O$, saturated aqueous NaCl, and dried ($Na_2SO_4$) before removing the solvent under reduced pressure. The residual solid was recrystallized from acetone to give 60.0 mg (92%) of the title compound as a colorless solid. $^1H$ NMR (300 MHz, $d_6$-acetone) δ: 8.36 (1H, d, J=2.1 Hz), 7.91 (2H, d, J=8.3 Hz), 7.60 (2H, d, J=8.3 Hz), 7.56 (1H, dd, J=2.1 8.0 Hz), 7.45 (2H, m), 7.31 (1H, d, J=8.0 Hz), 7.06 (1H, s), 6.06 (1H, s), 2.51 (3H, s), 1.44 (6H, s).

4-[[4-(4-methylphenyl)-2,2-dimethyl-(2H)-thiochromen-6-yl]-ethynyl]-2-fluorobenzoic acid (Compound 251)

To a solution of ethyl 4-[[4-(4-methylphenyl)-2,2-dimethyl-(2H)-thiochromen-6-yl]-ethynyl]-2-fluorobenzoate (Compound 236, 100.0 mg, 0.219 mmol) in 3.0 mL THF and 3.0 mL EtOH was added NaOH (80.0 mg, 2.0 mmol, 2.0 mL of a 1M aqueous solution). The resulting solution was heated to 40° C. and stirred overnight. Upon cooling to room temperature the reaction mixture was acidified with 10% aqueous HCl and extracted with EtOAc. The combined organic layers were washed with $H_2O$, saturated aqueous NaCl, and dried ($Na_2SO_4$) before removing the solvent under reduced pressure. The residual solid was recrystallized from $CH_3CN$ to give 78.0 mg (83%) of the title compound as a pale-yellow solid. $^1H$ NMR (300 MHz, $d_6$-acetone) δ: 7.94 (1H, d, J=7.8 Hz), 7.43–7.17 (9H, m), 5.93 (1H, s), 2.38 (3H, s), 1.47 (6H, s).

4-[[4-(4-ethylphenyl)-2,2-dimethyl-(2H)-thiochromen-6-yl]-ethynyl]-2-fluorobenzoic acid (Compound 252)

To a solution of ethyl 4-[[4-(4-ethylphenyl)-2,2-dimethyl-(2H)-thiochromen-6-yl]-ethynyl]-2-fluorobenzoate (Compound 237, 125.0 mg, 0.266 mmol) in 3.0 mL THF and 3.0 mL EtOH was added NaOH (120.0 mg, 3.0 mmol, 3.0 mL of a 1M aqueous solution). The resulting solution was stirred overnight at room temperature. The reaction mixture was acidified with 10% aqueous HCl and extracted with EtOAc. The combined organic layers were washed with $H_2O$, saturated aqueous NaCl, and dried ($Na_2SO_4$) before removing the solvent under reduced pressure. The residual solid was recrystallized from $CH_3CN$ to give 100.0 mg (86%) of the title compound as a pale-yellow solid. $^1H$ NMR (300 MHz, $d_6$-acetone) δ: 7.94 (1H, d J=7.8 Hz), 7.43–7.20 (9H, m), 5.93 (1H, s), 2.68 (2H, q, J=7.6 Hz), 1.47 (6H, s), 1.24 (3H, t, J=7.6 Hz).

6-[[4-(4-methylhexyl)-2,2-dimethyl-(2H)-thiochromen-6-yl]-ethyl]-nicotinic acid (Compound 253)

To a solution of ethyl 6-[[4-(4-methylphenyl)-2,2-dimethyl-(2H)-thiochromen-6-yl]-ethynyl]-nicotinate (Compound 240, 66.0 mg, 0.15 mmol) in 2.0 mL THF and 2.0 mL EtOH was added NaOH (80.0 mg, 2.0 mmol, 2.0 mL of a 1M aqueous solution). The resulting solution was heated to 45° C. and stirred overnight. Upon cooling to room temperature the reaction mixture was acidified with 10% aqueous HCl and extracted with EtOAc. The combined organic layers were washed with $H_2O$, saturated aqueous NaCl, and dried (Na$_2$SO$_4$) before removing the solvent under reduced pressure to give the title compound as a yellow solid, 50.0 mg (81%). $^1$H NMR (300 MHz, d$_6$-acetone) δ: 9.09 (1H, d, J=1.4 Hz), 8.30 (1H, dd, J=2.0, 8.1 Hz), 7.65 (1H, d, J=8.1 Hz), 7.46 (2H, s), 7.24 (5H, m), 5.94 (1H, s), 2.37 (3H, s), 1.48 (6H, s).

6-[[4-(4-ethylphenyl)-2,2-dimethyl-(2H)-thiochromen-6-yl]-ethyl]-nicotinic acid (Compound 254)

To a solution of ethyl 6-[[4-(4-ethylphenyl)-2,2-dimethyl-(2H)-thiochromen-6-yl]-ethynyl]-nicotinate (Compound 241, 110.0 mg, 0.24 mmol) in 3.0 mL THF and 3.0 mL EtOH was added NaOH (120.0 mg, 3.0 mmol, 3.0 mL of a 1M aqueous solution). This mixture was heated to 40° C. for 1 hour, cooled to room temperature, and the resulting solution was stirred overnight. The reaction mixture was acidified with 10% aqueous HCl and extracted with EtOAc. The combined organic layers were washed with H$_2$O, saturated aqueous NaCl, and dried (Na$_2$SO$_4$) before removing the solvent under reduced pressure to give 100 mg (96%) of the title compound as a colorless solid. $^1$H NMR (300 MHz, d$_6$-acetone) δ: 9.08 (1H, d, J=2.0 Hz), 8.30 (1H, dd, J=2.2, 8.2 Hz), 7.66 (1H, d, J=8.2 Hz), 7.46 (2H, s), 7.31–7.21 (5H, m), 5.95 (1H, s), 2.69 (2H, q, J=7.6 Hz), 1.48 (6H, s), 1.25 (3H, t, J=7.6 Hz).

4-[[4-(4-methylphenyl)-2,2-dimethyl-7-fluoro-(2H)-thiochromen-6-yl]-ethynyl]benzoic acid (Compound 255)

To a solution of ethyl 4-[[4-(4-methylphenyl)-2,2-dimethyl-7-fluoro-(2H)-thiochromen-6-yl]-ethynyl]-benzoate (Compound 213, 108.0 mg, 0.236 mmol) in 2.0 mL THF and 2.0 mL EtOH was added NaOH (120.0 mg, 3.0 mmol, 3.0 mL of a 1M aqueous solution). The resulting solution was heated to 45° C. and stirred overnight. Upon cooling to room temperature the reaction mixture was acidified with 10% aqueous HCl and extracted with EtOAc. The combined organic layers were washed with H$_2$O, saturated aqueous NaCl, and dried (Na$_2$SO$_4$) before removing the solvent under reduced pressure. The residual solid was recrystallized from CH$_3$CN to give 85 mg (80%) of the title compound as a pale-yellow solid. $^1$H NMR (300 MHz, d$_6$-acetone) δ: 8.03 (2H, d, J=8.3 Hz), 7.61 (2H, d, J=8.3 Hz), 7.31–7.18 (6H, m), 5.90 (1H, s), 2.37 (3H, s), 1.48 (6H, s).

4-[[4-(4-methylphenyl)-2,2-dimethyl-7-methoxy-(2H)-thiochromen-6-yl]-ethynyl]-benzoic acid (Compound 256)

To a solution of ethyl 4-[[4-(4-methylphenyl)-2,2-dimethyl- 7-methoxy-(2H)-thiochromen-6-yl]-ethynyl]-benzoate (Compound 215, 64.0 mg, 0.113 mmol) in 2.0 mL THF and 2.0 mL EtOH was added NaOH (80.0 mg, 2.0 mmol, 2.0 mL of a 1M aqueous solution). The resulting solution was heated to 45° C. and stirred overnight. Upon cooling to room temperature the reaction mixture was acidified with 10% aqueous HCl and extracted with EtOAc. The combined organic layers were washed with H$_2$O, saturated aqueous NaCl, and dried (Na$_2$SO$_4$) before removing the solvent under reduced pressure. The residual solid was recrystallized from CH$_3$CN to give 50 mg (83%) of the title compound as a colorless solid. $^1$H NMR (300 MHz, d$_6$-acetone) δ: 8.00 (2H, d, J=8.2 Hz), 7.56 (2H, d, J=8.2 Hz), 7.28–7.14 (5H, m), 7.06 (1H, s), 5.76 (1H, s), 3.96 (3H, s), 2.36 (3H, s), 1.47 (6H, s).

4-[[4-(5-methyl-2-thienyl)-2,2-dimethyl-7-fluoro-(2H)-thiochromen-6-yl]-ethynyl]-benzoic acid (Compound 257)

To a solution of ethyl 4-[[4-(5-methyl-2-thienyl)-2,2-dimethyl-7-fluoro(2H)-thiochromen-6-yl]-ethynyl]-benzoate (Compound 214, 58.0 mg, 0.125 mmol) in 2.0 mL THF and 2.0 mL EtOH was added NaOH (80.0 mg, 2.0 mmol, 2.0 mL of a 1M aqueous solution). The resulting solution was heated to 45° C. and stirred overnight. Upon cooling to room temperature the reaction mixture was acidified with 10% aqueous HCl and extracted with EtOAc. The combined organic layers were washed with H$_2$O, saturated aqueous NaCl, and dried (Na$_2$SO$_4$) before removing the solvent under reduced pressure. The residual solid was recrystallized from CH$_3$CN to give 50 mg (90%) of the title compound as a pale-yellow solid. $^1$H NMR (300 MHz, d$_6$-acetone) δ: 8.05 (2H, d, J=8.3 Hz), 7.56 (2H, d, J=8.3 Hz), 7.61 (1H, d, J=7.4 Hz), 7.31 (1H, d, J=9.6 Hz), 6.89 (1H, d, J=3.5 Hz), 6.79 (1H, d, J=3.5 Hz), 6.06 (1H, s), 2.49 (3H, s), 1.46 (6H, s).

4-Bromophenylacetate (Compound 258)

To a solution of 4-bromophenol (20.0 g, 0.121 mol) in 200 mL CH$_2$Cl$_2$ was added triethylamine (14.0 g, 0.139 mol) followed by acetyl chloride (9.53 g, 0.121 mol) in small portions at room temperature. After stirring for 21 hours the mixture was poured into 200 mL H$_2$O. The organic layer was washed with 5% aqueous NaOH, H$_2$O, and dried over MgSO$_4$. Removal of the solvent under reduced pressure and distillation of the residue afforded 20.6 g (83%) of the product as a colorless oil, bp 93–95° C./2 mm.

2-Hydroxy-5-bromo-acetophenone (Compound 259)

A mixture of AlCl$_3$ (6.20 g, 46.50 mmol) and 4-bromophenylacetate (Compound 258, 10.0 g, 46.50 mmol) was heated to 150° C. for 30 minutes while a stream of argon was passed over the molten solid. Upon cooling to room temperature the orange solid was carefully treated with 100 mL of H$_2$O and 100 mL of 10% aqueous HCl. The resulting mixture was extracted with EtOAc and the combined organic layers were washed with H$_2$O and saturated aqueous NaCl before being dried over Na$_2$SO$_4$. Concentration of the solution under reduced pressure afforded a tan solid which after recrystallization from i-PrOH provided 7.18 g (72%) of the title compound as an off-white crystalline solid. $^1$H NMR (300 MHz, CDCl$_3$) δ: 12.17 (1H, s), 7.84 (1H, d, J=2.6 Hz), 7.55 (1H, dd, J=2.5, 9.0 Hz), 6.90 (1H, d, J=8.9 Hz), 2.64 (3H, s).

2,2-Dimethyl-6-bromo-chroman-4-one (Compound 260)

To a solution of piperidine (2,83 g, 33.25 mmol) in 45 mL benzene was added trifluoroacetic acid (344.6 mg, 3.02 mmol) as a solution in 4.0 mL of benzene. Acetone (8.78 g, 151.3 mmol) was added followed by 2-hydroxy-5-bromoacetophenone (Compound 259, 6.50 g, 30.23 mmol). The resulting solution was heated to reflux in a flask fitted with a Dean-Stark trap. After 24 hours, an additional 2.5 equivalents of acetone and 0.1 equivalents of trifluoroacetic acid were added. After a total of 43 hours the reaction was cooled to room temperature and diluted with EtOAc. The solution was washed with 1M aqueous HCl, H$_2$O, and saturated aqueous NaCl before being dried (MgSO$_4$) and concentrated under reduced pressure. Distillation of the residual oil (bulb-to-bulb) afforded 4.80 g (62%) of the title compound as a clear yellow oil, bp 105–115° C./5 mm. The reaction conditions here are a moderate modification of the synthesis of the title compound described by Buckle et al. in J. Med. Chem. 1990 3028–3034. $^1$H NMR (300 MHz, CDCl$_3$) δ: 7.97 (1H, d, J=2.6 Hz), 7.54 (1H, dd, J=2.6, 8.7 Hz), 6.84 (1H, d, J=8.8 Hz), 2.72 (2H, s), 1.46 (6H, s).

2,2-Dimethyl-6-trimethylsilanylethynyl-chroman-4-one (Compound 261)

A solution of 2,2-dimethyl-6-bromo-chroman-4-one (Compound 260, 4.30 g, 16.85 mmol) and copper (I) iodide (321 mg, 0.17 mmol) in 55.0 mL Et$_3$N was sparged with argon for 30 minutes. To this solution were added trimethylsilylacetylene (4.66 g, 50.56 mmol) and bis (triphenylphosphine)-palladium(II) chloride (1.18 g, 0.17 mmol). The mixture was heated to 70° C. for 26 hours, cooled to room temperature, and diluted with Et$_2$O (100 mL). The resulting mixture was filtered through a pad of Celite using an Et$_2$O wash and the filtrate washed with H$_2$O, a solution of NH$_4$OH/saturated aqueous NH$_4$Cl (9:1), H$_2$O, 1M aqueous HCl, H$_2$O and saturated aqueous NaCl before being dried (Na$_2$SO$_4$) and concentrated under reduced pressure. Column chromatography (5% EtOAc-hexanes) of the residual oil afforded 4.09 g (89%) of the product as a yellow waxy solid. $^1$H NMR (300 MHz, CDCl$_3$) δ: 7.99 (1H, d, J=2.1 Hz), 7.53 (1H, dd, J=2.2, 8.6 Hz), 6.86 (1H, d, J=8.6 Hz), 2.72 (2H, s), 1.45 (6H, s), 0.24 (9H, s).

2,2-Dimethyl-6-ethynyl-chroman-4-one (Compound 262)

To a solution of 2,2-dimethyl-6-trimethylsilanylethynyl-chroman-4-one (Compound 261, 4.05 g, 14.87 mmol) in 60.0 mL of MeOH was added K$_2$CO$_3$ (410.9 mg, 2.97 mmol) The resulting mixture was stirred at room temperature for 24 hours, diluted with EtOAc (100 mL) and washed with H$_2$O and saturated aqueous NaCl, and dried over Na$_2$SO$_4$. Concentration of this solution under reduced pressure afforded 2.71 g (91%) of the product as a tan solid. $^1$H NMR (300 MHz, CDCl$_3$) δ: 8.01 (1H, d, J=2.2 Hz), 7.56 (1H, dd, J=2.2, 8.6 Hz), 6.90 (1H, d, J=8.6 Hz), 3.02 (1H, s), 2.74 (2H, s), 1.47 (6H, s).

Ethyl 4-[(2,2-dimethyl-4-oxo-chroman-6-yl)ethynyl]-benzoate (Compound 263)

A solution of 6-ethynyl-2,2-dimethylchroman-4-one (Compound 262, 2.60 g, 13.0 mmol) and ethyl 4-iodobenzoate (3.6 g, 13.0 mmol) in 50.0 mL Et$_3$N was purged with argon for 15 minutes. To this solution was added bis(triphenylphosphine)-palladium(II) chloride (1.82 g, 2.6 mmol) and copper(I) iodide (496 mg, 2.6 mmol). After sparging for an additional 10 minutes with argon, the solution was stirred overnight at room temperature. The reaction mixture was filtered through a pad of Celite using an Et$_2$O wash. Concentration of the filtrate under reduced pressure, followed by column chromatography (2–5% EtOAc-hexanes) of the residual solid afforded 2.28 g (50%) the title compound as an orange solid. $^1$H NMR (300 MHz, CDCl$_3$) δ: 8.06 (1H, d, J=2.2 Hz), 8.02 (2H, d, J=8.5 Hz), 2.61 (1H, dd, J=2.2, 8.6 Hz), 7.55 (2H, d, J=8.5 Hz), 6.93 (1H, d, J=8.6 Hz), 4.39 (2H, q, J=7.1 Hz), 2.75 (3H, s), 1.48 (6H, s), 1.41 (t, J=7.1 Hz).

Ethyl 4-(2,2-dimethyl-4-trifluoromethanesulfonyloxy-(2H)-chromen-6-ylethynyl)-benzoate (Compound 264)

A solution of sodium bis(trimethylsilyl)amide (1.56 g, 8.5 mmol) in 18.0 mL of THF was cooled to −78° C. and a solution of ethyl 4-((2,2-dimethyl-4-oxo-chroman-6-yl)ethynyl)-benzoate (Compound 263, 2.26 g, 6.49 mmol) in 15.0 mL was added slowly. After 30 minutes a solution of 2-[N,N-bis(trifluoromethanesulfonyl)amino]-5-pyridine (3.10 g, 7.79 mmol) in 10 mL of THF was added slowly. After 5 minutes the solution was warmed to room temperature and stirred overnight. The reaction was quenched by the addition of saturated aqueous NH$_4$Cl and extracted with EtOAc. The combined organic layers were washed with 5% aqueous NaOH and H$_2$O before being dried (MgSO$_4$) and concentrated under reduced pressure. The title compound, 2.0 g (64%), was isolated by column chromatography (5% EtOAc-hexanes) as a colorless solid. $^1$H NMR (300 MHz, CDCl$_3$) δ: 8.03 (2H, d, J=8.3 Hz), 7.57 (2H, d, J=8.3 Hz), 7.45–7.21 (2H, m), 6.85 (1H, d, J=8.4 Hz), 5.69 (1H, s), 4.40 (2H, q, J=7.1 Hz), 1.55 (6H, s), 1.4 (3H, t, J=7.1 Hz).

Ethyl 4-[[4-phenyl-2,2-dimethyl-(2H)-chromen-6-yl]-ethynyl]-benzoate (Compound 265)

A solution of bromobenzene (250.0 mg, 1.59 mmol) in 3.0 mL of THF was cooled to −78° C. and tert-butyllithium (203.7 mg, 3.18 mmol, 1.9 ml of a 1.7M solution in pentane) was added to give a yellow solution. After 30 minutes a solution of ZnCl$_2$ (440.0 mg, 3.18 mmol) in 5.0 mL THF was slowly added via cannula. The resulting solution was warmed to room temperature and transferred via cannula to a solution of ethyl 4-(2,2-dimethyl-4-trifluoromethanesulfonyloxy-(2H)-chromen-6-ylethynyl)-benzoate (Compound 264, 150.0 mg, 0.31 mmol) and tetrakis(triphenylphosphine)palladium(0) (24.0 mg, 0.02 mmol) in 2.0 mL THF. This solution was heated to 50° C. for 2 hours, cooled to room temperature, and the reaction quenched by the addition of saturated aqueous NH$_4$Cl. This solution was extracted with EtOAc and the combined organic layers were washed with H$_2$O and saturated aqueous NaCl before being dried (MgSO$_4$) and concentrated under reduced pressure. The title compound, 110.0 mg (87%), was isolated by column chromatography (2.5% EtOAc/hexanes) as a colorless solid. $^1$H NMR (300 MHz, CDCl$_3$) δ: 7.99 (2H, d, J=8.3 Hz), 7.51 (2H, d, J=8.3 Hz), 7.47–7.35 (6H, m), 7.21 (1H, d, J=2.0 Hz), 6.88 (1H, d, J=8.4 Hz), 5.66 (1H, s), 4.38 (2H, q, J=7.1 Hz), 1.52 (6H, s), 1.40 (3H, t, J=7.1 Hz).

Ethyl 4-[[4-(4-methylphenyl)-2,2-dimethyl-(2H)-chromen-6-yl]-ethynyl]-benzoate (Compound 266)

A solution of 4-methylbromobenzene (237.0 mg, 1.38 mmol) in 3.0 mL of THF was cooled to −78° C. and tert-butyllithium (177.5 mg, 2.77 mmol, 1.6 ml of a 1.7M solution in pentane) was added to give a yellow solution. After 30 minutes a solution of ZnCl$_2$ (377.0 mg, 2.77 mmol) in 5.0 mL THF was slowly added via cannula. The resulting solution was warmed to room temperature and transferred via cannula to a solution of ethyl 4-(2,2-dimethyl-4-trifluoromethanesulfonyloxy-(2H)-chromen-6-ylethynyl)-benzoate (Compound 264, 150.0 mg, 0.31 mmol) and tetrakis(triphenylphosphine)palladium(0) (24.0 mg, 0.02 mmol) in 2.0 mL THF. This solution was heated to 50° C. for 2 hours, cooled to room temperature, and the reaction quenched by the addition of saturated aqueous NH$_4$Cl. This solution was extracted with EtOAc and the combined organic layers were washed with H$_2$O and saturated aqueous NaCl before being dried (MgSO$_4$) and concentrated under reduced pressure. The title compound, 120.0 mg (92%), was isolated by column chromatography (2.5% EtOAc/hexanes) as a colorless solid. $^1$H NMR (300 MHz, CDCl$_3$) δ: 7.98 (2H, d, J=8.5 Hz), 7.50 (2H, d, J=8.5 Hz), 7.34 (1H, dd, J=2.1, 8.3 Hz), 7.25–7.21 (5H, m), 6.85 (1H, d, J=8.3 Hz), 5.62 (1H, s), 4.36 (2H, q, J=7.1 Hz), 2.41 (3H, s), 1.49 (6H, s), 1.39 (3H, t, J=7.1 Hz).

Ethyl 4-[[4-(4-ethylphenyl)-2,2-dimethyl-(2H)-chromen-6-yl]-ethynyl]-benzoate (Compound 267)

A solution of 4-ethylbromobenzene (280.0 mg, 1.51 mmol) in 3.0 mL of THF was cooled to −78° C. and tert-butyllithium (198.6 mg, 3.10 mmol, 1.9 ml of a 1.7M solution in pentane) was added to give a yellow solution. After 30 minutes a solution of ZnCl$_2$ (408.0 mg, 3.10 mmol) in 5.0 mL THF was slowly added via cannula. The resulting solution was warmed to room temperature and transferred via cannula to a solution of ethyl 4-(2,2-dimethyl-4-trifluoromethanesulfonyloxy-(2H)-chromen-6-ylethynyl)-benzoate (Compound 264, 150.0 mg, 0.31 mmol) and tetrakis(triphenylphosphine)palladium(0) (24.0 mg, 0.02 mmol) in 2.0 mL THF. This solution was heated to 50° C. for 2 hours, cooled to room temperature, and the reaction quenched by the addition of saturated aqueous NH$_4$Cl. This solution was extracted with EtOAc and the combined organic layers were washed with H$_2$O and saturated aqueous NaCl before being dried (MgSO$_4$) and concentrated under reduced pressure. The title compound, 123.0 mg (91%), was isolated by column chromatography (2.5% EtOAc/hexanes) as a pale-yellow solid. $^1$H NMR (300 MHz, CDCl$_3$) δ: 8.00 (2H, d, J=8.4 Hz), 7.52 (2H, d, J=8.4 Hz), 7.36 (1H, dd, J=2.0, 8.3 Hz), 7.31–7.25 (5H, m), 6.88 (1H, d, J=8.3 Hz), 5.65 (1H, s), 4.38 (2H, q, J=7.1 Hz), 2.73 (2H, q, J=7.6 Hz), 1.52 (6H, s), 1.41 (3H, t, J=7.1 Hz), 1.31 (2H, t, J=7.6 Hz).

Ethyl 4-[[4-(4-(1-methylethyl)phenyl)-2,2-dimethyl-(2H)-chromen-6-yl]-ethynyl]-benzoate (Compound 268)

A solution of 4-iso-propylbromobenzene (250.0 mg, 1.25 mmol) in 3.0 mL of THF was cooled to −78° C. and tert-butyllithium (160.8 mg, 2.51 mmol, 1.5 ml of a 1.7M solution in pentane) was added to give a yellow solution. After 30 minutes a solution of ZnCl$_2$ (345.0 mg, 2.53 mmol) in 5.0 mL THF was slowly added via cannula. The resulting solution was warmed to room temperature and transferred via cannula to a solution of ethyl 4-((2,2-dimethyl-4-trifluoromethanesulfonyloxy-(2H)-chromen-6-yl)ethynyl)-benzoate (Compound 264, 150.0 mg, 0.31 mmol) and tetrakis(triphenylphosphine) palladium(0) (24.0 mg, 0.02 mmol) in 2.0 mL THF. This solution was heated to 50° C. for 2 hours, cooled to room temperature, and the reaction quenched by the addition of saturated aqueous NH$_4$Cl. This solution was extracted with EtOAc and the combined organic layers were washed with H$_2$O and saturated aqueous NaCl before being dried (MgSO$_4$) and concentrated under reduced pressure. The title compound, 100.0 mg (72%), was isolated by column chromatography (2.5% EtOAc/hexanes) as a colorless solid. $^1$H NMR (300 MHz, CDCl$_3$) δ: 7.99 (2H, d, J=8.3 Hz), 7.52 (2H, d, J=8.3 Hz), 7.36 (1H, dd, J=2.1, 8.3 Hz), 7.30–7.26 (5H, m), 6.88 (1H, d, J=8.3 Hz), 5.64 (1H, s), 4.38 (2H, q, J=7.1 Hz), 2.98 (1H, hept, J=7.0 Hz), 1.51 (6H, s), 1.40 (3H, t, J=7.1 Hz), 1.31 (6H, d, J=7.0 Hz).

Ethyl 4-[[4-(4-(1.1-dimethylethyl)phenyl)-2,2-dimethyl-(2H)-chromen-6-yl]-ethynyl]-benzoate (Compound 269)

A solution of 4-tert-butylbromobenzene (280.0 mg, 1.61 mmol) in 3.0 mL of THF was cooled to −78° C. and tert-butyllithium (206.3 mg, 3.22 mmol, 1.7 ml of a 1.7M solution in pentane) was added to give a yellow solution. After 30 minutes a solution of ZnCl$_2$ (380.0 mg, 3.22 mmol) in 5.0 mL THF was slowly added via cannula. The resulting solution was warmed to room temperature and transferred via cannula to a solution of ethyl 4-((2,2-dimethyl-4-trifluoromethanesulfonyloxy-(2H)-chromen-6-yl)ethynyl)-benzoate (Compound 264, 150.0 mg, 0.31 mmol) and tetrakis(triphenylphosphine) palladium(0) (24.0 mg, 0.02 mmol) in 2.0 mL THF. This solution was heated to 50° C. for 2 hours, cooled to room temperature, and the reaction quenched by the addition of saturated aqueous NH$_4$Cl. This solution was extracted with EtOAc and the combined organic layers were washed with H$_2$O and saturated aqueous NaCl before being dried (MgSO$_4$) and concentrated under reduced pressure. The title compound, 85.0 mg (59%), was isolated by column chromatography (2.5% EtOAc/hexanes) as a colorless solid. $^1$H NMR (300 MHz, CDCl$_3$) δ: 7.99 (2H, d, J=8.3 Hz), 7.53 (2H, d, J=8.3 Hz), 7.45 (1H, d, J=8.4 Hz), 7.37 (1H, dd, J=2.0, 8.3 Hz), 7.32–7.28 (3H, m), 6.89 (1H, d, J=8.3 Hz), 5.66 (1H, s), 4.39 (2H, q, J=7.1 Hz), 1.52 (6H, s), 1.40 (3H, t, J=7.1 Hz), 1.39 (9H, s).

Ethyl 2-fluoro-4-[(2,2-dimethyl-4-oxo-chroman-6-yl)ethynyl]-benzoate (Compound 270)

A solution of 6-ethynyl-2,2-dimethylchroman-4-one (Compound 262, 314.0 mg, 1.57 mmol) and ethyl 2-fluoro-4-iodobenzoate (440.0 mg, 1.50 mmol) in 10.0 mL Et$_3$N was purged with argon for 15 minutes. To this solution was added bis(triphenylphosphine)-palladium(II) chloride (275.0 mg, 0.39 mmol) and copper(I) iodide (75.0 mg, 0.39 mmol). After sparging for an additional 10 minutes with argon, the solution was stirred overnight at room temperature. The reaction mixture was filtered through a pad of Celite using an Et$_2$O wash. Concentration of the filtrate under reduced pressure, followed by column chromatography (3–5% EtOAc-hexanes) of the residual solid afforded 400.0 mg (69%) the title compound as an orange solid. $^1$H NMR (300 MHz, CDCl$_3$) δ: 8.05 (1H, d, J=2.1 Hz), 7.90 (1H, d, J=7.8 Hz), 7.60 (1H, dd, J=2.2 8.5 Hz), 7.29 (1H, dd, J=1.5, 8.2 Hz), 7.25 (1H, d, J=11.4 Hz), 6.93 (1H, d, J=8.5 Hz), 4.39 (2H, q, J=7.1 Hz), 2.75 (2H, s), 1.48 (6H, s), 1.40 (3H, t, J=7.1 Hz).

Ethyl 2-fluoro-4-((2,2-dimethyl-4-trifluoromethanesulfonyloxy-(2H)-chromen- 6-yl)ethynyl)-benzoate (Compound 271)

A solution of sodium bis(trimethylsilyl)amide (238.0 mg, 1.30 mmol) in 3.0 mL of THF was cooled to −78° C. and a solution of ethyl 2-fluoro-4-((2,2-dimethyl-4-oxo-chroman-6-yl)ethynyl)-benzoate (Compound 270, 400.0 mg, 1.09 mmol) in 2.0 mL was added slowly. After 30 minutes a solution of 2-[N,N-bis(trifluoromethanesulfonyl)amino]-5-pyridine (510.0 mg, 1.30 mmol) in 1.0 mL of THF was added. After 5 minutes the solution was warmed to room temperature and stirred overnight. The reaction was quenched by the addition of saturated aqueous NH$_4$Cl and extracted with EtOAc. The combined organic layers were washed with 5% aqueous NaOH and H$_2$O before being dried (MgSO$_4$) and concentrated under reduced pressure. The title compound, 315.0 mg (58%), was isolated by column chromatography (5% EtOAc/hexanes) as a colorless solid. $^1$H NMR (300 MHz, CDCl$_3$) δ: 7.92 (1H, d, J=7.8 Hz), 7.44–7.26 (4H, m), 6.85 (1H, d, J=8.7 Hz), 5.70 (1H, s), 4.31 (2H, q, J=7.1 Hz), 1.55 (6H, s), 1.41 (3H, t, J=7.1 Hz).

Ethyl 2-fluoro-4-[[4-(4-methylphenyl)-2,2-dimethyl-(2H)-chromen-6-yl]-ethynyl]-benzoate (Compound 272)

A solution of 4-methylbromobenzene (140.0 mg, 0.80 mmol) in 3.0 mL of THF was cooled to −78° C. and tert-butyllithium (102.5 mg, 1.60 mmol, 0.94 ml of a 1.7M solution in pentane) was added to give a yellow solution. After 30 minutes a solution of ZnCl$_2$ (174.0 mg, 1.28 mmol) in 5.0 mL THF was slowly added via cannula. The resulting solution was warmed to room temperature and transferred via cannula to a solution of ethyl 2-fluoro-4-(2,2-dimethyl-4-trifluoromethanesulfonyloxy-(2H)-chromen-6-ylethynyl)-benzoate (Compound 271, 150.0 mg, 0.31 mmol) and tetrakis(triphenylphosphine)palladium(0) (20.0 mg, 0.02 mmol) in 2.0 mL THF. This solution was heated to 50° C. for 2 hours, cooled to room temperature, and the reaction quenched by the addition of saturated aqueous NH$_4$Cl. This solution was extracted with EtOAc and the combined organic layers were washed with H$_2$O and saturated aqueous NaCl before being dried (MgSO$_4$) and concentrated under reduced pressure. The title compound, 86.0 mg (62%), was isolated by column chromatography (5% EtOAc/hexanes) as a colorless solid. $^1$H NMR (300 MHz, CDCl$_3$) δ: 7.88 (1H, d, J=7.8 Hz), 7.35 (1H, d, J=7.8 Hz), 7.35 (1H, dd, J=2.0, 8.4 Hz), 7.28–7.19 (7H, m), 6.88 (1H, d, J=8.3 Hz), 5.64 (1H, s), 4.40 (2H, q, J=7.1 Hz), 2.43 (3H, s), 1.51 (6H, s), 1.41 (3H, t, J=7.1 Hz).

Ethyl 2-fluoro-4-[[4-(4-ethylphenyl)-2,2-dimethyl-(2H)-chromen-6-yl]-ethynyl]benzoate (Compound 273)

A solution of 4-ethylbromobenzene (150.0 mg, 0.80 mmol) in 3.0 mL of THF was cooled to −78° C. and tert-butyllithium (102.5 mg, 1.60 mmol, 0.94 ml of a 1.7M solution in pentane) was added to give a yellow solution. After 30 minutes a solution of ZnCl$_2$ (218.0 mg, 1.60 mmol)

in 5.0 mL THF was slowly added via cannula. The resulting solution was warmed to room temperature and transferred via cannula to a solution of ethyl 2-fluoro-4-(2,2-dimethyl-4-trifluoromethanesulfonyloxy-(2H)-chromen-6-ylethynyl)-benzoate (Compound 271, 160.0 mg, 0.32 mmol) and tetrakis(triphenylphosphine)palladium(0) (20.0 mg, 0.02 mmol) in 2.0 mL THF. This solution was heated to 50° C. for 2 hours, cooled to room temperature, and the reaction quenched by the addition of saturated aqueous $NH_4Cl$. This solution was extracted with EtOAc and the combined organic layers were washed with $H_2O$ and saturated aqueous NaCl before being dried ($MgSO_4$) and concentrated under reduced pressure. The title compound, 115.0 mg (79%), was isolated by column chromatography (5% EtOAc/hexanes) as a colorless solid. $^1H$ NMR (300 MHz, $CDCl_3$) δ: 7.88 (1H, d, J=7.8 Hz), 7.35 (1H, dd, J=2.0, 8.3 Hz), 7.28–7.20 (7H, m), 6.88 (1H, d, J=8.3 Hz), 5.65 (1H, s), 4.39 (2H, q, J=7.1 Hz), 2.73 (2H, q, J=7.6 Hz), 1.52 (6H, s), 1.40 (3H, t, J=7.1 Hz), 1.31 (3H, t, J=7.6 Hz).

4-[[4-phenyl-2,2-dimethyl-(2H)-chromen-6-yl]-ethynyl]-benzoic acid (Compound 274)

To a solution of ethyl 4-[[4-phenyl-2,2-dimethyl-(2H)-chromen-6-yl]-ethynyl]-benzoate (Compound 265, 70.0 mg, 0.171 mmol) in 3.0 mL THF and 3.0 mL EtOH was added NaOH (120.0 mg, 3.0 mmol, 3.0 mL of a 1M aqueous solution). The resulting solution was heated to 35° C., cooled to room temperature and stirred overnight. The reaction was acidified with 10% aqueous HCl and extracted with EtOAc. The combined organic layers were washed with $H_2O$, saturated aqueous NaCl, and dried ($Na_2SO_4$) before the solvent was removed under reduced pressure. The residual solid was recrystallized from $CH_3CN$ to give 48.0 mg (74%) of the title compound as a colorless solid. $^1H$ NMR (300 MHz, $d_6$-acetone) δ: 8.00 (2H, d, J=8.2 Hz), 7.57 (2H, d, J=8.2 Hz), 7.51–7.37 (6H, d), 7.14 (1H, d, J=2.0 Hz), 6.91 (1H, d, J=8.3 Hz), 5.80 (1H, s), 1.50 (6H, s), 4-[[4-(4-methylphenyl)-2,2-dimethyl-(2H)-chromen-6-yl]-ethynyl]-benzoic acid (Compound 275)

To a solution of ethyl 4-[[4-(4-methylphenyl)-2,2-dimethyl-(2H)chromen-6-yl]-ethynyl]-benzoate (Compound 266, 90.0 mg, 0.213 mmol) in 3.0 mL THF and 3.0 mL EtOH was added NaOH (120.0 mg, 3.0 mmol, 3.0 mL of a 1M aqueous solution). The resulting solution was heated to 35° C., cooled to room temperature and stirred overnight. The reaction mixture was acidified with 10% aqueous HCl and extracted with EtOAc. The combined organic layers were washed with $H_2O$, saturated aqueous NaCl, and dried ($Na_2SO_4$) before the solvent was removed under reduced pressure. The residual solid was recrystallized from $CH_3CN$ to give 70.0 mg (83%) the title compound as a colorless solid. $^1H$ NMR (300 MHz, $d_6$-acetone) δ: 8.01 (2H, d, J=8.3 Hz), 7.57 (2H, d, J=8.3 Hz), 7.40 (1H, dd, J=2.1, 8.3 Hz), 7.30–7.20 (4H, m), 7.16 (1H, d, J=2.0 Hz), 6.90 (1H, d, J=8.3 Hz), 5.67 (1H, s), 2.38 (3H, s), 1.49 (6H, s).

4-[[4-(4-ethylphenyl)-2,2-dimethyl-(2H)-chromen-6-yl]-ethynyl]-benzoic acid (Compound 276)

To a solution of ethyl 4-[[4-(4-ethylphenyl)-2,2-dimethyl-(2H)-chromen-6-yl]-ethynyl]-benzoate (Compound 267, 82.0 mg, 0.188 mmol) in 3.0 mL THF and 3.0 mL EtOH was added NaOH (120.0 mg, 3.0 mmol, 3.0 mL of a 1M aqueous solution). The resulting solution was heated to 35° C., cooled to room temperature and stirred overnight. The reaction mixture was acidified with 10% aqueous HCl and extracted with EtOAc. The combined organic layers were washed with $H_2O$, saturated aqueous NaCl, and dried ($Na_2SO_4$) before the solvent was removed under reduced pressure. The residual solid was recrystallized from $CH_3CN$ to give 65.0 mg (85%) the title compound as a colorless solid. $^1H$ NMR (300 MHz, $d_6$-acetone) δ: 8.01 (2H, d, J=8.4 Hz), 7.57 (2H, d, J=8.4 Hz), 7.40 (1H, dd, J=2.0, 8.3 Hz), 7.35–7.25 (4H, m), 7.17 (1H, d, J=2.0 Hz), 6.90 (1H, d, J=8.3 Hz), 5.77 (1H,s), 2.69 (2H, q, J=7.6 Hz), 1.49 (6H, s), 1.24 (2H, t, J=7.6 Hz).

4-[[4-(4-(1-methylethyl)phenyl)-2,2-dimethyl-(2H)-chromen-6-yl]-ethynyl]benzoic acid (Compound 277)

To a solution of ethyl 4-[[4-(4-(1-methylethyl)phenyl)-2,2-dimethyl-(2H)-chromen-6-yl]-ethynyl]-benzoate (Compound 268, 95.0 mg, 0.210 mmol) in 3.0 mL THF and 3.0 mL EtOH was added NaOH (120.0 mg, 3.0 mmol, 3.0 mL of a 1M aqueous solution). The resulting solution was heated to 35° C., cooled to room temperature and stirred overnight. The reaction mixture was acidified with 10% aqueous HCl and extracted with EtOAc. The combined organic layers were washed with $H_2O$, saturated aqueous NaCl, and dried ($Na_2SO_4$) before the solvent was removed under reduced pressure. The residual solid was recrystallized from $CH_3CN$ to give 75.0 mg (84%) the title compound as a colorless solid. $^1H$ NMR (300 MHz, $CDCl_3$) δ: 8.05 (2H, d, J=8.4 Hz), 7.55 (2H, d, J=8.4 Hz), 7.36 (1H, dd, J=2.0, 8.3 Hz), 7.30–7.26 (5H, m), 6.88 (1H, d, J=8.3 Hz), 5.64 (1H, s), 2.98 (1H, hept, J=6.9 Hz), 1.51 (6H, s), 1.31 (6H, d, J=6.9 Hz).

4-[[4-(4-(1,1-dimethylethyl)phenyl)-2,2-dimethyl-(2H)-chromen-6-yl]-ethynyl]benzoic acid (Compound 278)

To a solution of ethyl 4-[[4-(4-(1,1-dimethylethyl)phenyl)-2,2-dimethyl(2H)-chromen-6-yl]-ethynyl]-benzoate (Compound 269, 72.0 mg, 0.155 mmol) in 3.0 mL THF and 3.0 mL EtOH was added NaOH (120.0 mg, 3.0 mmol, 3.0 mL of a 1M aqueous solution). The resulting solution was heated to 35° C., cooled to room temperature and stirred overnight. The reaction mixture was acidified with 10% aqueous HCl and extracted with EtOAc. The combined organic layers were washed with $H_2O$, saturated aqueous NaCl, and dried ($Na_2SO_4$) before the solvent was removed under reduced pressure. The residual solid was recrystallized from $CH_3CN$ to give 50.0 mg (74%) the title compound as a colorless solid. $^1H$ NMR (300 MHz, $d_6$-acetone) δ: 8.00 (2H, d, J=8.3 Hz), 7.57 (2H, d, J=8.3 hz), 7.51 (2H, d, J=8.3 Hz), 7.41 (1H, dd, J=2.0, 8.3 Hz), 7.31 (2H, d, J=8.3 Hz), 7.19 (1H, d, J=2.0 Hz), 6.91 (1H, d, J=8.3 Hz), 5.78 (1H, s), 1.49 (6H, s), 1.35 (9H, s).

2-Fluoro-4-[[4-(4-methylphenyl)-2,2-dimethyl-(2H)-chromen-6-yl]-ethynyl]-benzoic acid (Compound 279)

To a solution of ethyl 2-fluoro-4-[[4-(4-methylphenyl)-2,2-dimethyl-(2H)-chromen-6-yl]-ethynyl]-benzoate (Compound 272, 60.0 mg, 0.136 mmol) in 2.0 mL THF and 1.0 mL EtOH was added NaOH (120.0 mg, 3.0 mmol, 3.0 mL of a 1M aqueous solution). The resulting solution was heated to 35° C., cooled to room temperature and stirred overnight. The reaction mixture was acidified with 10% aqueous HCl and extracted with EtOAc. The combined organic layers were washed with $H_2O$, saturated aqueous NaCl, and dried ($Na_2SO_4$) before the solvent was removed under reduced pressure. The residual solid was recrystallized from $CH_3CN$ to give 53.0 mg (94%) the title compound as a colorless solid. $^1H$ NMR (300 MHz, $d_6$-acetone) δ: 7.93 (1H, d, J=7.8 Hz), 7.43–7.16 (8H, m), 6.91 (1H, d, J=8.3 Hz), 5.77 (1H, s), 2.38 (3H, s), 1.49 (6H, s).

2-Fluoro-4-[[4-(4-ethylphenyl)-2,2-dimethyl-(2H)-chromen-6-yl]-ethynyl]-benzoic acid (Compound 280)

To a solution of ethyl 2-fluoro-4-[[4-(4-ethylphenyl)-2,2-dimethyl-(2H)chromen-6-yl]-ethynyl]-benzoate (Compound 273, 82.0 mg, 0.180 mmol) in 2.0 mL THF and 2.0 mL EtOH was added NaOH (120.0 mg, 3.0 mmol, 3.0 mL of a 1M aqueous solution). The resulting solution was heated to 35° C., cooled to room temperature and stirred overnight. The reaction mixture was acidified with 10% aqueous HCl and extracted with EtOAc. The combined organic layers were washed with $H_2O$, saturated aqueous NaCl, and dried ($Na_2SO_4$) before the solvent was removed under reduced pressure. The residual solid was recrystallized from $CH_3CN$ to give 70.0 mg (91%) the title compound as a pale-yellow solid. $^1H$ NMR (300 MHz, $d_6$-acetone) δ: 7.93 (1H, d, J=7.8 Hz), 7.41 (1H, dd, J=2.1, 8.3 Hz), 7.37–7.25 (6H, m), 7.18 (1H, d, J=2.0 Hz), 6.91 (1H, d, J=8.3 Hz), 5.77 (1H, s), 2.69 (2H, q, J=7.6 Hz), 1.49 (6H, s), 1.24 (3H, t, J=7.6 Hz).

Method of Potentiating Nuclear Receptor Agonists
Overview and Introduction We have discovered that a subset of retinoid antagonists which exhibit negative hormone activity can be used for potentiating the biological activities of other retinoids and steroid receptor superfamily hormones. These other retinoids and steroid receptor superfamily hormones can be either endogenous hormones or pharmaceutical agents. Thus, for example, when used in combination with a retinoid negative hormone, certain activities of pharmaceutical retinoid agonists can be rendered more active in eliciting specific biological effects. Advantageously, this combination approach to drug administration can minimize undesirable side effects of pharmaceutical retinoids because lower dosages of the pharmaceutical retinoids can be used with improved effectiveness.

More particularly, we have discovered that AGN 193109, a synthetic retinoid having the structure shown in FIG. 1, exhibits unique and unexpected pharmacologic activities. AGN 193109 exhibits high affinity for the RAR subclass of nuclear receptors without activating these receptors or stimulating transcription of retinoid responsive genes. Instead, AGN 193109 inhibits the activation of RARs by retinoid agonists and therefore behaves as a retinoid antagonist.

Additionally, we have discovered that retinoid negative hormones can be used without coadministration of a retinoid agonist or steroid hormone to control certain disease symptoms. More specifically, the retinoid negative hormone disclosed herein can down-regulate the high level basal transcription of genes that are responsive to unliganded RARs. If, for example, uncontrolled cellular proliferation results from the activity of genes responsive to unliganded RARs, then that gene activity can be reduced by the administration of a retinoid negative hormone that inactivates RARs. Consequently, cellular proliferation dependent on the activity of unliganded RARs can be inhibited by the negative hormone. Inhibition of unliganded RARs cannot be achieved using conventional antagonists.

Significantly, we have discovered that AGN 193109 can both repress RAR basal activity and can sometimes potentiate the activities of other retinoid and steroid receptor superfamily hormone agonists. In the context of the invention, a hormone agonist is said to be potentiated by a negative hormone such as AGN 193109 if, in the presence of the negative hormone, a reduced concentration of the agonist elicits substantially the same quantitative response as that obtainable with the agonist alone. The quantitative response can, for example, be measured in a reporter gene assay in vitro. Thus, a therapeutic retinoid that elicits a desired response when used at a particular dosage or concentration is potentiated by AGN 193109 if, in combination with AGN 193109, a lower dosage or concentration of the therapeutic retinoid can be used to produce substantially the same effect as a higher dosage or concentration of the therapeutic retinoid when that therapeutic retinoid is used alone. The list of agonists that can be potentiated by coadministration with AGN 193109 includes RAR agonists, vitamin D receptor agonists, glucocorticoid receptor agonists and thyroid hormone receptor agonists. More particularly, specific agonists that can be potentiated by coadministration include: ATRA, 13-cis retinoic acid, the synthetic RAR agonist AGN 191183, 1,25-dihydroxyvitamin $D_3$, dexamethasone and thyroid hormone (3,3',5-triiodothyronine). Also disclosed herein is a method that can be used to identify other hormones that can be potentiated by coadministration with AGN 193109.

Thus, AGN 193109 behaves in a manner not anticipated for a simple retinoid antagonist, but as a negative hormone that can potentiate the activities of various members of the family of nuclear receptors. We also disclose a possible mechanism that can account for both negative hormone activity and the ability of AGN 193109 to potentiate the activities of other nuclear receptor ligands. This mechanism incorporates elements known to participate in retinoid-dependent signalling pathways and additionally incorporates a novel negative regulatory component.

Those having ordinary skill in the art will appreciate that RARs, which are high affinity targets of AGN 193109 binding, are transcription factors that regulate the expression of a variety of retinoid responsive genes. Cis-regulatory DNA binding sites for the RARs have been identified nearby genes that are transcriptionally regulated in a retinoid-dependent fashion. RAR binding to such DNA sites, known as retinoic acid response elements (RAREs), has been well defined. Importantly, the RAREs bind heterodimers consisting of one RAR and one RXR. The RXR component of the heterodimer functions to promote a high affinity interaction between the RAR/RXR heterodimer and the RARE (Mangelsdorf et al. The Retinoid Receptors in *The Retinoids: Biology, Chemistry and Medicine*, 2nd edition, eds. Sporn et al., Raven Press, Ltd., New York 1994, the disclosure of which is hereby incorporated by reference).

As detailed below, our findings related to the negative hormone activity of AGN 193109 are consistent with a mechanism involving the interaction of a putative Negative Coactivator Protein (NCP) with the RAR. According to the proposed mechanism, this interaction is stabilized by AGN 193109.

Our results further indicated that AGN 193109 can modulate intracellular availability of NCP for interaction with nuclear receptors other than RARs that are occupied by AGN 193109. It follows that AGN 193109 can potentiate transcriptional regulatory pathways involving nuclear receptors that share with the RARs the ability to bind the NCP. In this regard, AGN 193109 exhibits the ability to modulate a variety of nuclear receptor pathways, an activity that would not be predicted for a conventional retinoid antagonist. Accordingly, AGN 193109 is useful as an agent for potentiating the activity of nuclear receptor ligands, including both endogenous hormones and prescribed therapeutics. This specific embodiment illustrates the more general principle that any nuclear receptor negative hormone will potentiate the activity of other nuclear receptors that competitively bind the NCP.

Although other materials and methods similar or equivalent to those described herein can be used in the practice or testing of the present invention, the preferred methods and materials are now described. General references for methods that can be used to perform the various nucleic acid manipulations and procedures described herein can be found in *Molecular Cloning: A Laboratory Manual* (Sambrook et al. eds. Cold Spring Harbor Lab Publ. 1989) and *Current Protocols in Molecular Biology* (Ausubel et al. eds., Greene Publishing Associates and Wiley-Interscience 1987). The disclosures contained in these references are hereby incorporated by reference. A description of the experiments and results that led to the creation of the present invention follows.

Example 6 describes the methods used to demonstrate that AGN 193109 bound each of three RARs with high affinity but failed to activate retinoid dependent gene expression.

EXAMPLE 6

AGN 193109 Binds RARs With High Affinity But Does Not Transactivate Retinoid-Dependent Gene Expression Human RAR-α, RAR-β and RAR-γ receptors were separately expressed as recombinant proteins using a baculovirus expression system essentially according to the method described by Allegretto et al. in *J. Biol. Chem.* 268:26625 (1993). The recombinant receptor proteins were separately employed for determining AGN 193109 binding affinities using the [$^3$H]-ATRA displacement assay described by Heyman et al. in Cell 68:397 (1992). Dissociation constants (Kds) were determined according to the procedure described by Cheng et al. *in Biochemical Pharmacology* 22:3099 (1973).

AGN 193109 was also tested for its ability to transactivate RARs in CV-1 cells transiently cotransfected with RAR expression vectors and a retinoid responsive reporter gene construct. Receptor expression vectors pRShRAR-α (Giguere et al. *Nature* 330:624 (1987)), pRShRAR-β (Benbrook et al. Nature 333:669 (1988)) and pRShRAR-γ (Ishikawa et al. *Mol. Endocnnol.* 4:837 (1990)) were separately cotransfected with the ΔMTV-TREp-Luc reporter plasmid. Use of this luciferase reporter plasmid has been disclosed by Heyman et al. in *Cell* 68:397 (1992). The ΔMTV-TREp-Luc plasmid is essentially identical to the ΔMTV-TREp-CAT reporter construct described by Umesono et al. in *Nature* 336:262 (1988), except that the chloramphenicol acetyltransferase (CAT) reporter gene was substituted by a polynucleotide sequence encoding firefly luciferase. Transfection of green monkey CV-1 cells was carried out using the calcium phosphate coprecipitation method described in *Molecular Cloning: A Laboratory Manual* (Sambrook et al. eds. Cold Spring Harbor Lab Publ. 1989). CV-1 cells were plated at a density of $4 \times 10^4$/well in 12 well multiwell plates and transiently transfected with a calcium phosphate precipitate containing 0.7 µg of reporter plasmid and 0.1 µg of receptor plasmid according to standard laboratory procedures. Cells were washed after 18 hours to remove the precipitate and refed with Dulbecco's modified Eagle's medium (DMEM) (Gibco), containing 10% activated charcoal extracted fetal bovine serum (Gemini Bio-Products). Cells were treated with vehicle alone (ethanol) or AGN 193109 ($10^{-9}$ to $10^6$M) for 18 hours. Cell lysates were prepared in 0.1M KPO$_4$ (pH 7.8), 1.0% TRITON X-100, 1.0 mM DTT, 2 mM EDTA. Luciferase activity was measured as described by de Wet et al. in *Mol. Cell. Biol.* 7:725 (1987), using firefly luciferin (Analytical Luminescence Laboratory) and an EG&G Berthold 96-well plate luminometer. Reported luciferase values represented the mean ±SEM of triplicate determinations.

The results presented in Table 11 indicated that AGN 193109 bound each of RAR-α, RAR-β and RAR-γ with high affinity, but did not activate retinoid-dependent gene expression. More specifically, AGN 193109 bound each of the three receptors with Kd values in the 2–3 nM range. Despite this tight binding, AGN 193109 failed to activate gene expression when compared with inductions stimulated by ATRA. Accordingly, the half-maximal effective concentration of AGN 193109 ($EC_{50}$) was unmeasurable. Although not presented in the Table, we also found that AGN 193109 had no measurable affinity for the RXRs.

TABLE 11

AGN 193109 Binding and Transactivation of the RARs

|  | RAR-α | RAR-β | RAR-γ |
| --- | --- | --- | --- |
| $EC_{50}$ (nM) | No Activity | No Activity | No Activity |
| $K_d$ (nM) | 2 | 2 | 3 |

Example 7 describes the methods used to demonstrate that AGN 193109 is an antagonist of ATRA dependent gene expression.

EXAMPLE 7

AGN 193109-Dependent Inhibition of RAR Transactivation by ATRA

The ability of AGN 193109 to antagonize ATRA mediated RAR activation was investigated in CV-1 cells cotransfected by the calcium phosphate coprecipitation method of Sambrook et al. (*Molecular Cloning: A Laboratory Manual* Cold Spring Harbor Lab Publ. 1989). Eukaryotic expression vectors pRShRAR-α (Giguere et al. *Nature* 330:624 (1987)), pRShRAR-β (Benbrook et al. *Nature* 333:669 (1988)) and pRShRAR-γ (Ishikawa et al. *Mol. Endoctinol.* 4:837 (1990)) were cotransfected with the ΔMTV-Luc reporter plasmid described by Hollenberg et al. (Cell 55:899 (1988)). Notably, the reporter plasmid contained two copies of the TRE-palindromic response element. Calcium phosphate transfections were carried out exactly as described in Example 6. Cells were dosed with vehicle alone (ethanol), ATRA ($10^{-9}$ to $10^{-6}$M), AGN 193109 ($10^{-9}$ to $10^{-6}$M), or $10^{-8}$M ATRA in combination with AGN 193109 ($10^{-9}$ to $10^{-6}$M) for 18 hours. Cell lysates and luciferase activity measurements were also performed as in Example 6.

The results of these procedures are presented in FIGS. 2A through 2F where luciferase values represent the mean ±SEM of triplicate determinations. More specifically, the results presented in FIGS. 2A, 2C and 2E indicated that stimulation of transfected cells with ATRA led to dose responsive increases in luciferase activity. This confirmed that ATRA activated each of the three RARs in the experimental system and provided a comparative basis for detecting the activity of an antagonist. The graphic results presented in FIGS. 2B, 2D and 2F indicated that cotreatment of transfected cells with 10 nM ATRA and increasing concentrations of AGN 193109 led to an inhibition of luciferase activity. In particular, equal doses of AGN 193109 and ATRA gave greater than 50% inhibition relative to ATRA alone for all three RAR subtypes. Comparison of the ATRA dose response in the presence of different concentrations of AGN 193109 indicated that ATRA was competitively inhibited by AGN 193109. Notably, the horizontal axes on all of the graphs shown in FIG. 2 represents the log of the retinoid concentration. These results proved that AGN 193109 was a potent RAR antagonist.

We next performed experiments to elucidate the mechanism underlying the antagonist activity of AGN 193109. Those having ordinary skill in the art will appreciate that nuclear receptor activation is believed to involve a conformational change of the receptor that is induced by ligand binding. Indeed, the results of protease protection assays have confirmed that nuclear hormone agonists and antagonists cause receptor proteins to adopt different conformations (Keidel et al. *Mol. Cell Biol.* 14:287 (1994); Allan et al. *J. Biol. Chem.* 267:19513 (1992)). We used such an assay to determine if AGN 193109 and ATRA caused RAR-α to adopt different conformations. AGN 193583, an RAR-α-selective antagonist, was included as a positive control that is known to confer an antagonist-specific pattern of protease sensitivity.

Example 8 describes one method that was used to detect conformational changes in RAR-α resulting from AGN 193109 binding. As presented below, the results of this procedure unexpectedly indicated that AGN 193109 led to a pattern of trypsin sensitivity that was substantially identical to that induced by ATRA, an RAR agonist, and unlike that induced by a model RAR antagonist. This finding suggested that AGN 193109 possessed properties distinct from other retinoid antagonists.

EXAMPLE 8

Protease Protection Analysis

A plasmid constructed in the vector pGEM3Z (Pharmacia) and containing the RAR-α cDNA (Giguere et al. *Nature* 330:624 (1987)), was used in connection with the TNT-coupled reticulocyte lysate in vitro transcription-translation system (Promega) to prepare [$^{35}$S]-methionine labeled RAR-α. Limited proteolytic digestion of the labeled protein RAR-α was carried out according to the method described by Keidel et al. in *Mol. Cell. Biol.* 14:287 (1994). Aliquots of reticulocyte lysate containing [$^{35}$S]-methionine labeled RAR-α were incubated with either ATRA, AGN 193583 or AGN 193109 on ice for 45 minutes in a total volume of 9 μl. The retinoid final concentration for all trials was 100 nM for ATRA and AGN 193109, and 1000 nM for AGN 193583. The difference between the final concentrations of the retinoids was based on the approximate 10-fold difference in relative affinities of ATRA and AGN 193109 (having Kd at RAR-α of 2 and 10 nM, respectively) and AGN 193583 (having Kd at RAR-α of ≧100 nM). After ligand binding, 1 μl of appropriately concentrated trypsin was added to the mixture to give final concentrations of 25, 50 or 100 μg/ml. Samples were incubated at room temperature for 10 minutes and trypsin digestion stopped by addition of SDS-sample buffer. Samples were subjected to polyacrylamide gel electrophoresis and autoradiographed according to standard procedures.

Both the agonist and antagonist led to distinct patterns of trypsin sensitivity that were different from the result obtained by digestion of the unliganded receptor. Autoradiographic results indicated that trypsin concentrations of 25, 50 and 100 μg/ml completely digested the radiolabeled RAR-α in 10 minutes at room temperature in the absence of added retinoid. Prebinding of ATRA led to the appearance of two major protease resistant species. Prebinding of the RAR-α-selective antagonist AGN 193583 gave rise to a protease resistant species that was of lower molecular weight than that resulting from ATRA prebinding. This result demonstrated that a retinoid agonist and antagonist led to conformational changes detectable by virtue of altered trypsin sensitivities. Surprisingly, prebinding of AGN 193109 gave rise to a protease protection pattern that was indistinguishable from that produced by prebinding of ATRA.

The results presented above confirmed that AGN 193109 bound the RAR-α and altered its conformation. Interestingly, the nature of this conformational change more closely resembled that which resulted from binding of an agonist (ATRA) than the alteration produced by antagonist (AGN 193583) binding. Clearly, the mechanism of AGN 193109 dependent antagonism was unique.

We considered possible mechanisms that could account for the antagonist activity of AGN 193109. In particular, we used a standard gel shift assay to test whether AGN 193109 perturbed RAR/RXR heterodimer formation or inhibited the interaction between RAR and its cognate DNA binding site.

Example 9 describes a gel electrophoretic mobility-shift assay used to demonstrate that AGN 193109 neither inhibited RAR/RXR dimerization nor inhibited binding of dimers to a target DNA.

EXAMPLE 9

Gel Shift Analysis

In vitro translated RAR-α was produced essentially as described under Example 8, except that $^{35}$S-labeled methoinine was omitted. In vitro translated RXR-α was similarly produced using a pBluescript(II)(SK)-based vector containing the RXR-α cDNA described by Mangelsdorf, et al. in *Nature* 345:224–229 (1990) as the template for generating in vitro transcripts. The labeled RAR-α and RXR-α, alone or in combination, or prebound with AGN 193109 ($10^{-6}$M) either alone or in combination, were allowed to interact with an end-labeled DR-5 RARE double-stranded probe having the sequence 5'-TCAGGTCACCAGGAGGTCAGA-3' (SEQ ID NO:1). The binding mixture was electrophoresed on a non-denaturing polyacrylamide gel and autoradiographed according to standard laboratory procedures. A single retarded species appearing on the autoradiograph that was common to all the lanes on the gel represented an undefined probe-binding factor present in the reticulocyte lysate. Only the RAR/RXR combination gave rise to a retinoid receptor-specific retarded species. Neither RAR alone nor RXR alone bound the probe to produce this shifted species. The presence of AGN 193109 did not diminish this interaction.

These results indicated that AGN 193109 did not substantially alter either the homo- or hetero-dimerization properties of RAR-α. Further, AGN 193109 did not inhibit the interaction of receptor dimers with a DNA segment containing the cognate binding site.

In view of the unique properties which characterized AGN 193109, we proceeded to investigate whether this antagonist could additionally inhibit the activity of unliganded RARs. The receptor/reporter system used to make this determination advantageously exhibited high level constitutive activity in the absence of added retinoid agonist. More specifically, these procedures employed the ER-RAR chimeric receptor and ERE-tk-Luc reporter system. The ERE-tk-Luc plasmid includes the region –397 to –87 of the estrogen responsive 5'-flanking region of the Xenopus vitellogenin A2 gene, described by Klein-Hitpass, et al. in *Cell* 46:1053–1061 (1986), ligated upstream of the HSV thymidine kinase promoter and luciferase reporter gene of plasmid tk-Luc. The ER-RAR chimeric receptors consisted of the estrogen receptor DNA binding domain fused to the "D-E-F" domain of the RARs. Those having ordinary skill in the art appreciate this "D-E-F" domain functions to bind retinoid, to provide a retinoid inducible transactivation function and to provide a contact site for heterodimerization with RXR. Thus, luciferase expression in this reporter system was dependent on activation of the transfected chimeric receptor construct.

Example 10 describes the method used to demonstrate that AGN 193109 inhibited basal gene activity attributable to unliganded RARs. These procedures were performed in the absence of added retinoid agonist. The results presented below provided the first indication that AGN 193109 exhibited negative hormone activity.

EXAMPLE 10

Repression of Basal Gene Activity of a Retinoid-Regulated Reporter in Transiently Cotransfected Cell Lines CV-1 cells were co-transfected with the ERE-tk-Luc reporter plasmid and either ER-RAR-α, ER-RAR-β or ER-RAR-γ expression plasmids. The ERE-tk-Luc plasmid contained the estrogen-responsive promoter element of the *Xenopus laevis* vitellogenin A2 gene and was substantially identical to the reporter plasmid described by Klein-Hitpass et al. in *Cell* 46:1053 (1986), except that the CAT reporter gene was substituted by a polynucleotide sequence encoding luciferase. The ER-RAR-α, ER-RAR-β and ER-RAR-γ chimeric receptor-encoding polynucleotides employed in the co-transfection have been described by Graupner et al. in *Biochem. Biophys. Res. Comm.* 179:1554 (1991). These polynucleotides were ligated into the pECE expression vector described by Ellis et al. in *Cell* 45:721 (1986) and expressed under transcriptional control of the SV-40 promoter. Calcium phosphate transfections were carried out exactly as described in Example 6 using 0.5 μg/well of reporter plasmid and either 0.05 μg, 0.10 μg or 0.2 μg/well of receptor plasmid. Cells were dosed with vehicle alone (ethanol), ATRA ($10^{-9}$ to $10^{-6}$M), or AGN 193109 ($10^{-9}$ to $10^{-6}$M) for 18 hours. Cell lysates and luciferase activity measurements were performed as described in Example 6.

Figure 3A:
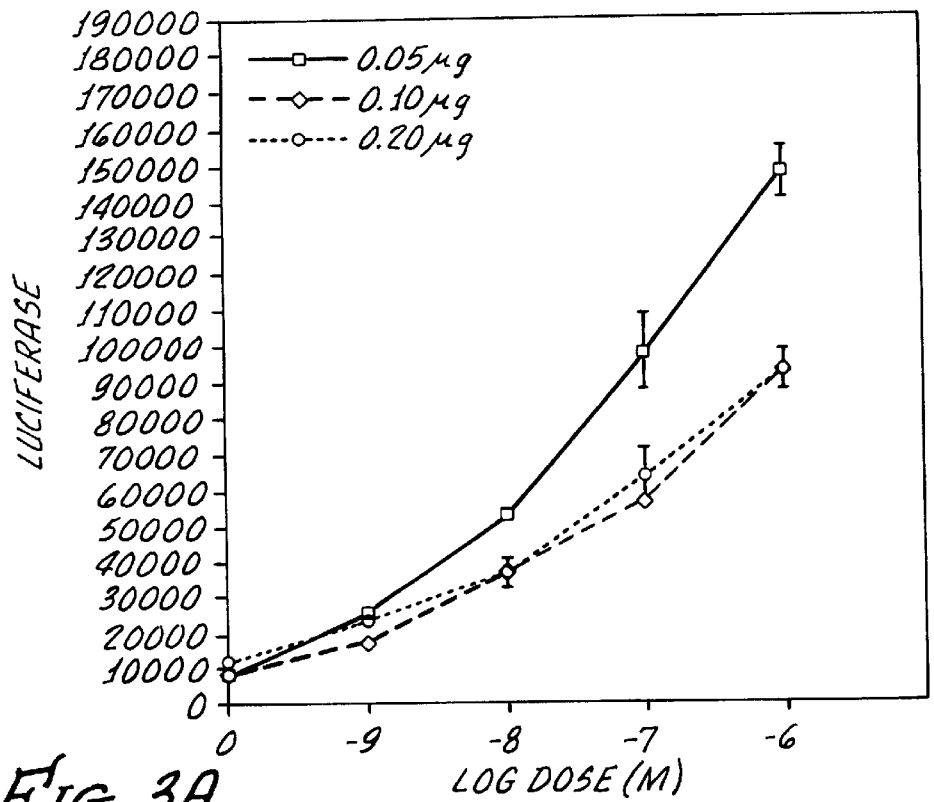
FIGS. 3A and 3B are line graphs representing luciferase activity detected in CV-1 cells transfected with reporter plasmid ERE-tk-Luc and expression plasmid ER-RAR-α and stimulated with ATRA (FIG. 3A) or AGN 193109 (FIG. 3B) at various concentrations. Data points represent the mean ±SEM of three independent luciferase determinations. The results of transfections carried out using different amounts of co-transfected ER-RAR-α (0.05, 0.1 and 0.2 μg/well) are indicated in each figure.
Figure 4A:
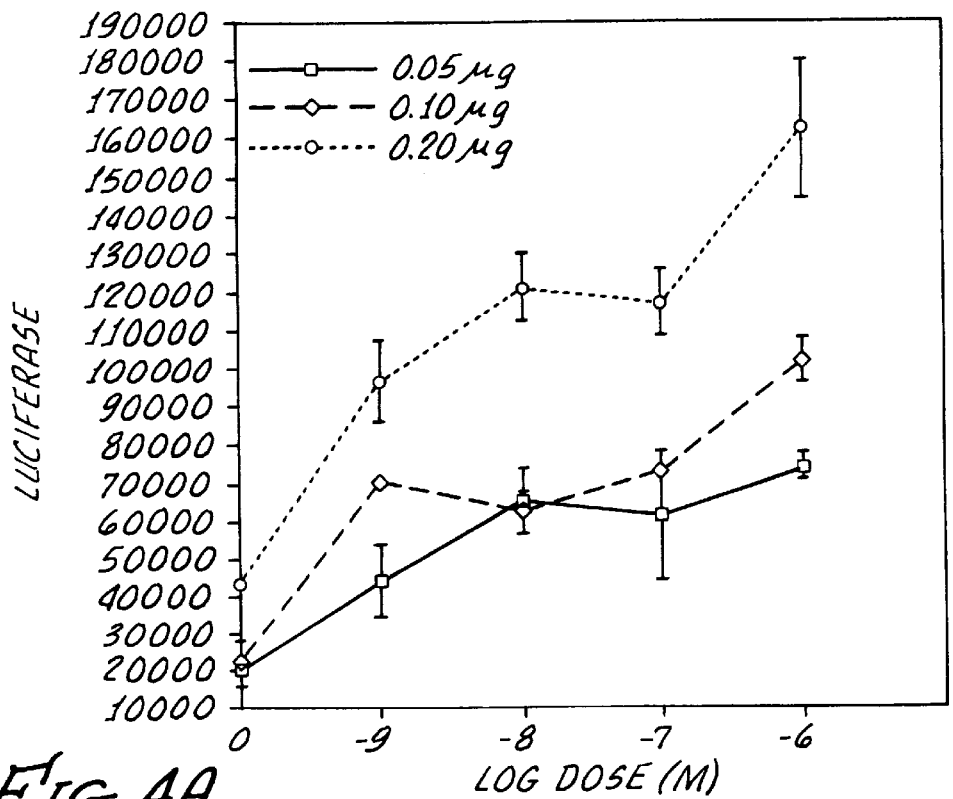
FIGS. 4A and 4B are line graphs representing luciferase activity in CV-1 cells transfected with reporter plasmid ERE-tk-Luc and expression plasmid ER-RAR-β and stimulated with ATRA (FIG. 4A) or AGN 193109 (FIG. 4B) at various concentrations. Data points represent the mean ±SEM of three independent luciferase determinations. The results of transfections carried out using different amounts of co-transfected ER-RAR-β (0.05, 0.1 and 0.2 μg/well) are indicated in each figure.
Figure 5A:
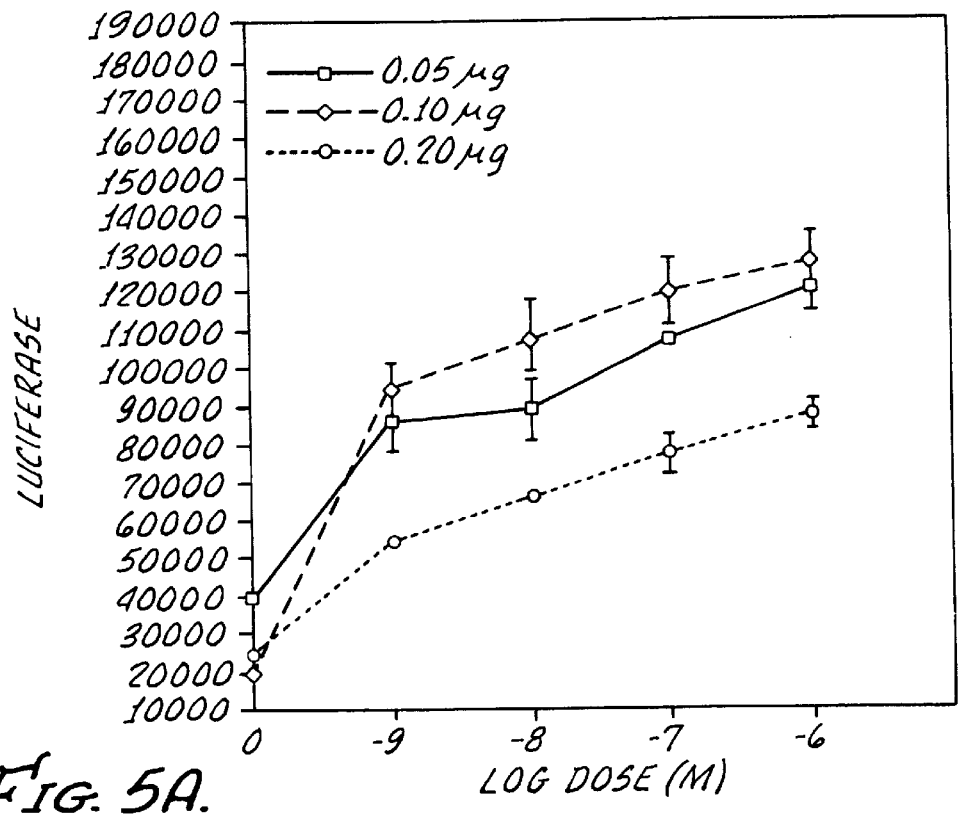
FIGS. 5A and 5B are line graphs representing luciferase activity detected in CV-1 cells transfected with reporter plasmid ERE-tk-Luc and expression plasmid ER-RAR-γ and stimulated with ATRA (FIG. 5A) or AGN 193109 (FIG. 5B) at various concentrations. Data points represent the mean ±SEM of three independent luciferase determinations. The results of transfections carried out using different amounts of co-transfected ER-RAR-γ (0.05, 0.1 and 0.2 μg/well) are indicated in each figure.

The results presented in FIGS. 3A, 4A and 5A confirmed that ATRA strongly induced luciferase expression in all transfectants. Basal level expression of luciferase for the three transfected chimeric RAR isoforms ranged from approximately 7,000 to 40,000 relative light units (rlu) and was somewhat dependent on the amount of receptor plasmid used in the transfection. Thus, the three chimeric receptors were activatable by ATRA, as expected. More specifically, all three receptors bound ATRA and activated transcription of the luciferase reporter gene harbored on the ERE-tk-Luc plasmid.

Figure 3B:
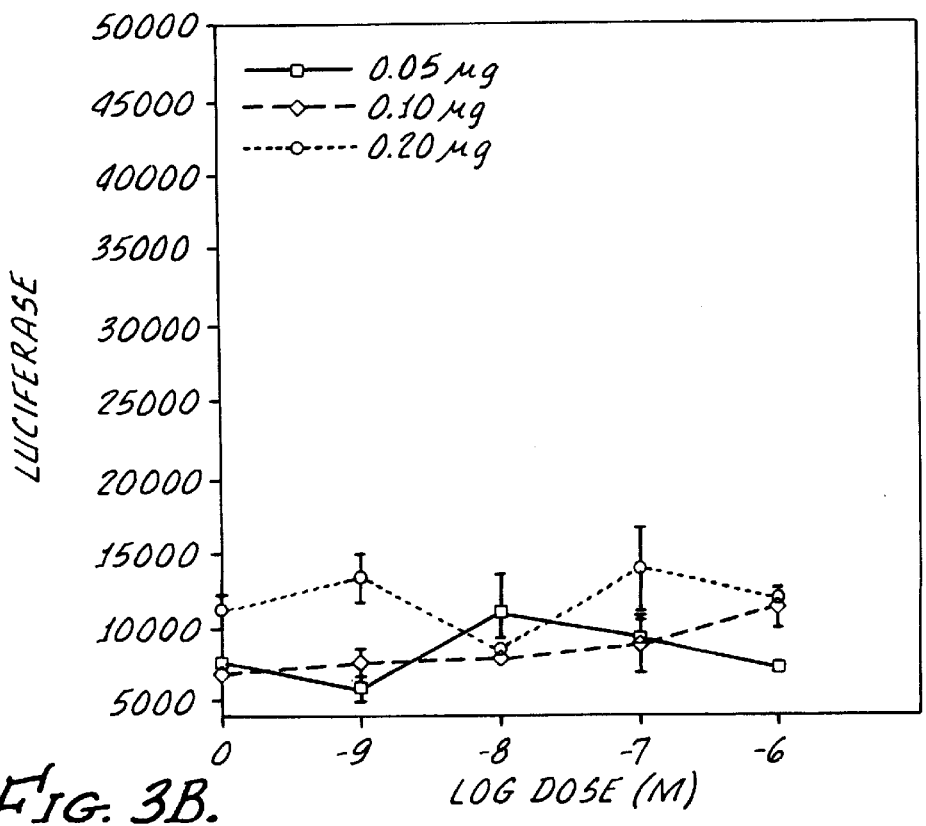
Figure 4B:
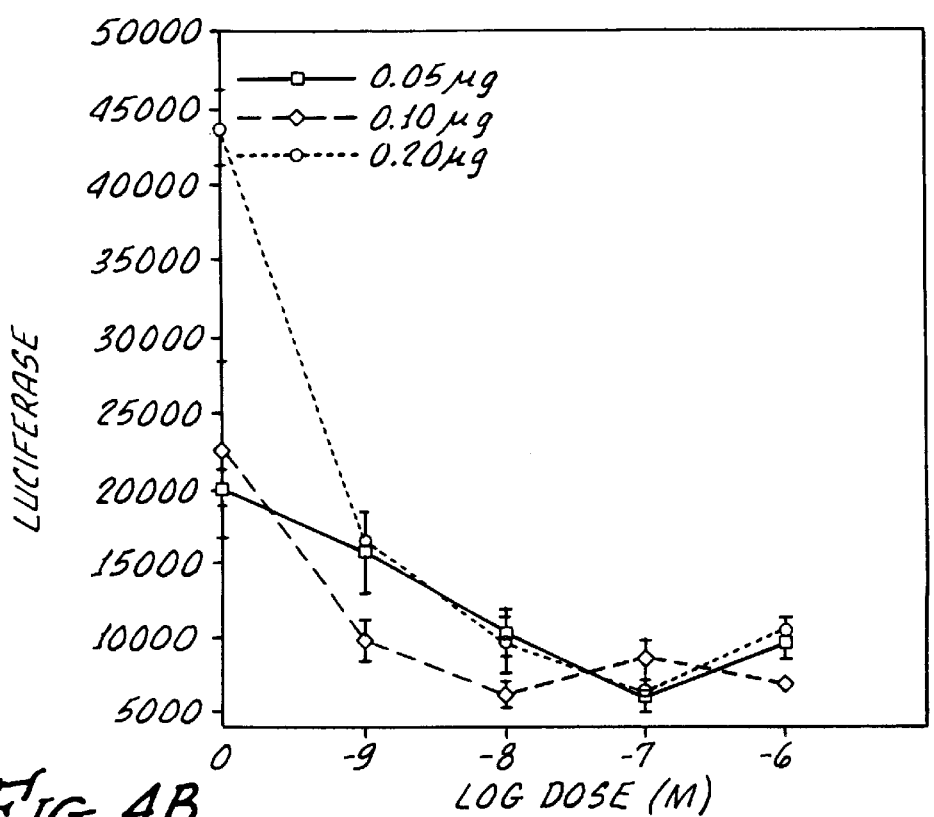
Figure 5B:
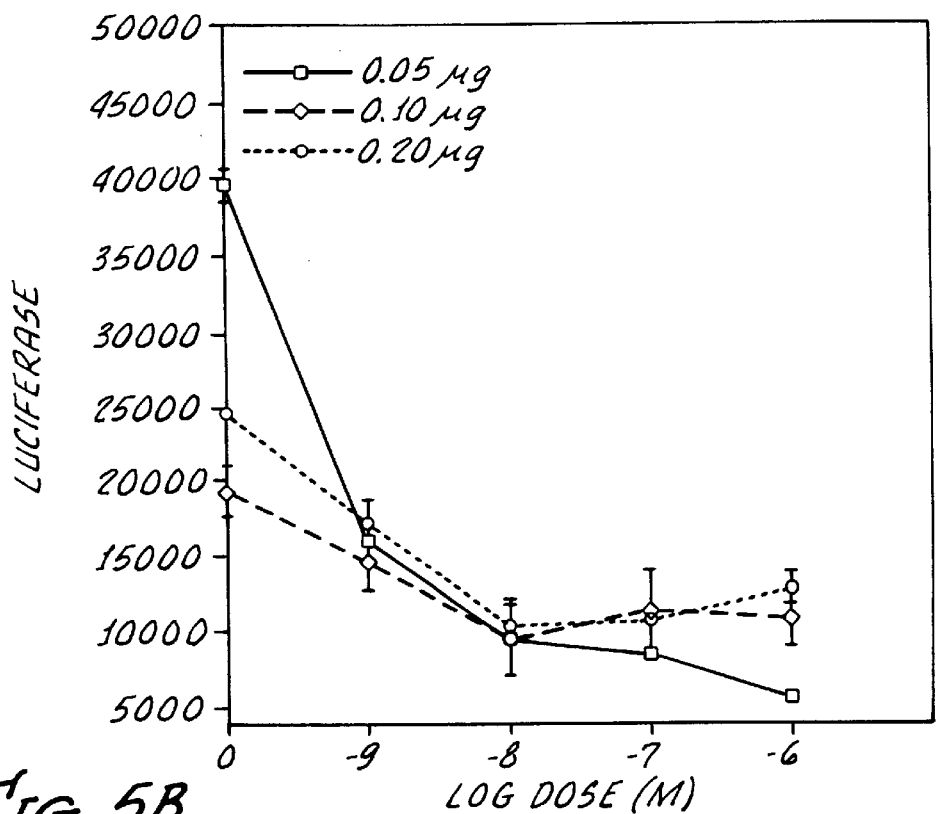

FIGS. 3B, 4B and 5B present AGN 193109 dose response curves obtained in the absence of any exogenous retinoid agonist. Interestingly, ER-RAR-α (FIG. 3B) was substantially unaffected by AGN 193109, while the ER-RAR-β and ER-RAR-γ chimeric receptors (FIGS. 4B and 5B, respectively) exhibited an AGN 193109 dose responsive decrease in luciferase reporter activity.

We further investigated the negative hormone activity of AGN 193109 by testing its ability to repress gene expression mediated by a chimeric RAR-γ receptor engineered to possess a constitutive transcription activator domain. More specifically, we used a constitutively active RAR-γ chimeric receptor fused to the acidic activator domain of HSV VP-16, called RAR-γ-VP-16, in two types of luciferase reporter systems. The first consisted of the ERE-tk-Luc reporter cotransfected with ER-RARs and ER-RXR-α. The second utilized the ΔMTV-TREp-Luc reporter instead of the ERE-tk-Luc reporter.

Example 11 describes the method used to demonstrate that AGN 193109 could suppress the activity of a transcription activator domain of an RAR. The results presented below proved that AGN 193109 could suppress RAR-dependent gene expression in the absence of an agonist and confirmed that AGN 193109 exhibited negative hormone activity.

EXAMPLE 11

Repression of RAR-VP-16 Activity in Transiently Transfected Cells

CV-1 cells were transiently cotransfected according to the calcium phosphate coprecipitation technique described under Example 6 using 0.5 μg/well of the ERE-tk-Luc luciferase reporter plasmid, 0.1 μg/well of the ER-RXR-α chimeric reporter expression plasmid, and either 0 μg or 0.1 μg/well of the RAR-γ-VP-16 expression plasmid. The chimeric receptor ER-RXR-α consisted of the hormone binding domain (amino acids 181 to 458) of RXR-α (Mangelsdorf, et al. *Nature* 345:224–229 (1990)) fused to the estrogen receptor DNA binding domain (Graupner, et al. *Biochem. Biophys. Res. Comm.* 179:1554 (1991)) and was expressed from the SV-40 based expression vector pECE described by Ellis, et al. in *Cell* 45:721 (1986). RAR-γ-VP-16 is identical to the VP16RAR-γ1 expression plasmid described by Nagpal et al. in *EMBO J.* 12:2349 (1993), the disclosure of which is hereby incorporated by reference, and encodes a chimeric protein having the activation domain of the VP-16 protein of HSV fused to the amino-terminus of full length RAR-γ. At eighteen hours post-transfection, cells were rinsed with phosphate buffered saline (PBS) and fed with DMEM (Gibco-BRL) containing 10% FBS (Gemini Bio-Products) that had been extracted with charcoal to remove retinoids. Cells were dosed with an appropriate dilution of AGN 193109 or ATRA in ethanol vehicle or ethanol alone for 18 hours, then rinsed with PBS and lysed using 0.1M KPO4 (pH 7.8), 1.0% TRITON X-100, 1.0 mM DTT, 2 mM EDTA. Luciferase activity was measured according to the method described by de Wet, et al. in *Mol. Cell. Biol.* 7:725 (1987), using firefly luciferin (Analytical Luminescence Laboratory) and an EG&G Berthold 96-well plate luminometer. Luciferase values represented the mean ±SEM of triplicate determinations.

Figure 6:
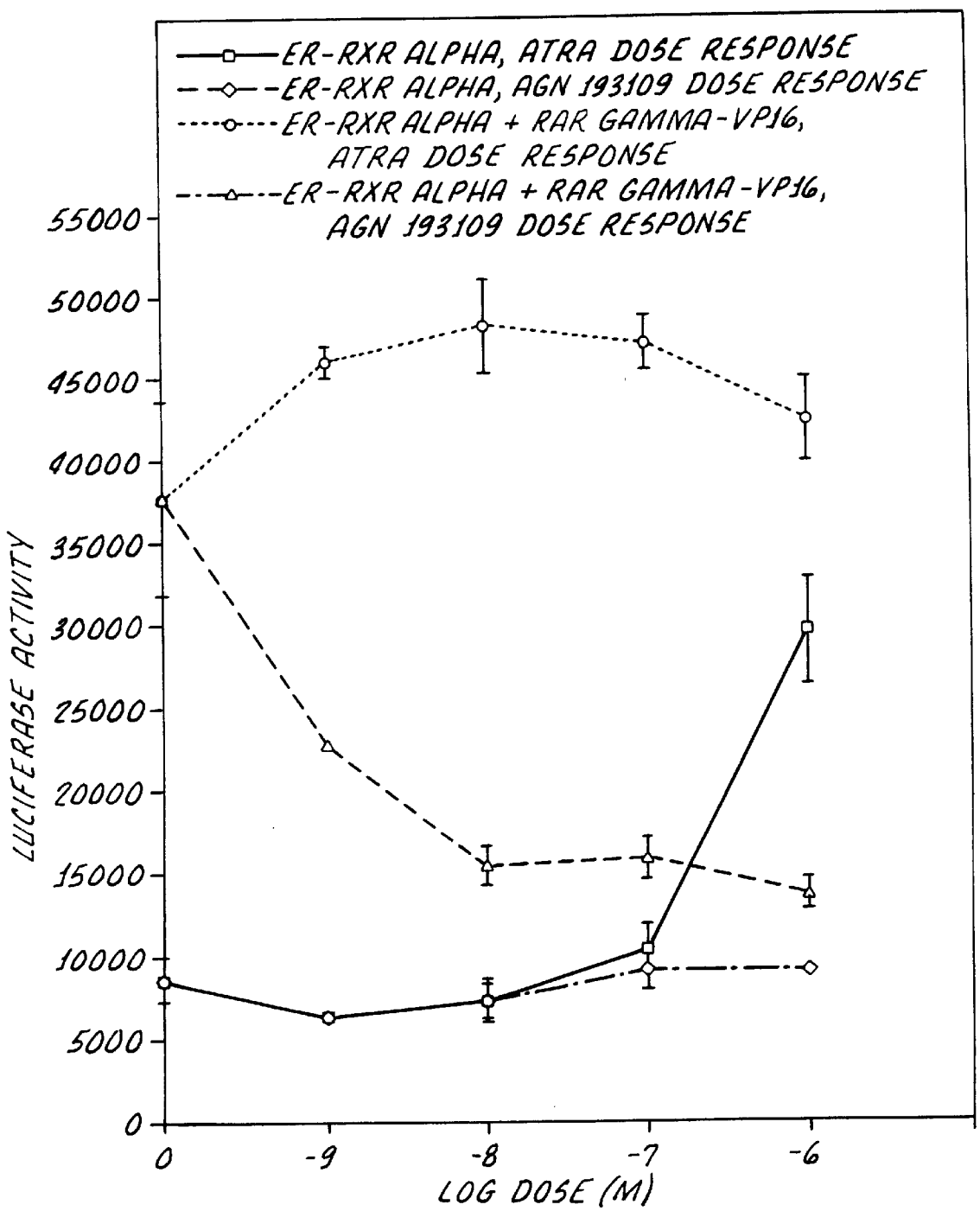
FIG. 6 shows ATRA and AGN 193109 dose responses of CV-1 cells cotransfected with the ERE-tk-Luc reporter plasmid and either the ER-RXR-α chimeric receptor expression plasmid alone, or in combination with the RAR-γ-VP-16 expression plasmid. ER-RXR-α cotransfected cells were treated with ATRA (square) and AGN 193109 (diamond). Cells cotransfected with the combination of ER-RXR-α and RAR-γ-VP-16 were treated with ATRA (circle) or AGN 193109 (triangle).

As shown in FIG. 6, CV-1 cells transfected with the ERE-tk-Luc reporter construct and the ER-RAR-α chimeric expression plasmid exhibited a weak activation of luciferase activity by ATRA, likely due to isomerization of ATRA to 9C-RA, the natural ligand for the RXRs (Heyman et al. *Cell* 68:397 (1992). Cells transfected with the same mixture of reporter and chimeric receptor plasmids but treated with AGN 193109 did not exhibit any effect on luciferase activity. As AGN 193109 does not bind to the RXRs, this latter result was expected. CV-1 cells similarly transfected with the ERE-tk-Luc reporter but with substitution of an ER-RAR chimeric receptor expression plasmid for ER-RXR-α exhibited a robust induction of luciferase activity following ATRA treatment.

In contrast, inclusion of the RAR-γ-VP-16 expression plasmid with the ER-RXR-α and ERE-tk-Luc plasmids in the transfection mixture resulted in a significant increase in the basal luciferase activity as measured in the absence of any added retinoid. This increase in basal luciferase activity observed for the ER-RXR-α/RAR-γ-VP-16 cotransfectants, when compared to the result obtained using cells transfected with ER-RXR-α alone, indicated that recombinant ER-RXR-α and RAR-γ-VP-16 proteins could heterodimerize. Interaction of the heterodimer with the cis-regulatory estrogen responsive element led to a targeting of the VP-16 activation domain to the promoter region of the ERE-tk-Luc reporter. Treatment of such triply transfected cells with ATRA led to a modest increase of luciferase activity over the high basal level. However, treatment of the triple transfectants with AGN 193109 resulted in a dose dependent decrease in luciferase activity. Importantly, FIG. 6 shows that AGN 193109 treatment of cells cotransfected with ER-RXR-α and RAR-γ-VP-16 led to repression of luciferase activity with maximal inhibition occurring at approximately $10^{-8}$M AGN 193109.

Our observation that AGN 193109 repressed the constitutive transcriptional activation function of RAR-γ-VP-16 in the presence of an RXR was explained by a model wherein binding of AGN 193109 to the RAR induced a conformational change in the RAR which stabilizes a negative conformation that facilitates the binding of a trans-acting negative coactivator protein. When the AGN 193109/RAR complex is bound by the NCP, the RAR is incapable of upregulating transcription of genes that are ordinarily responsive to activated RARs. Our model further proposes that the intracellular reservoir of NCP is in limiting concentration in certain contexts and can be depleted by virtue of AGN 193109 stimulated complexation with RARs.

The results presented in FIG. 6 additionally indicated that even at $10^{-6}$M AGN 193109, the ER-RXR-α and RAR-γ-VP-16 proteins could interact to form heterodimers competent for activating transcription of the reporter gene. More specifically, cells transfected with ER-RXR-α and RAR-γ-VP-16 and treated with AGN 193109 at a concentration ($10^{-8}$–$10^{-6}$M) sufficient to provide maximal inhibition, gave luciferase activity readings of approximately 16,000 rlu. Conversely, cells transfected only with ER-RXR-α and then treated with AGN 193109 at a concentration as high as $10^{-6}$M exhibited luciferase expression levels of only approximately 8,000 rlu. The fact that a higher level of luciferase activity was obtained in cells that expressed both ER-RXR-α and RAR-γ-VP-16, even in the presence of $10^{-6}$M AGN 193109 demonstrated the persistence of an interaction between the two recombinant receptors. The repression of RAR-γ-VP-16 activity by AGN 193109 suggested that modulation of NCP interaction can be codominate with VP-16 activation. Accordingly, we realized that it may be possible to modulate the expression of genes which are not ordinarily regulated by retinoids in an AGN 193109 dependent manner.

Candidates for AGN 193109 regulatable genes include those that are activated by transcription factor complexes which consist of non-RAR factors that associate or heterodimerize with RARs, wherein the non-RAR factor does not require an RAR agonist for activation. While stimulation with an RAR agonist may have substantially no effect on the expression of such genes, administration with AGN 193109 can promote formation of inactive transcription complexes comprising AGN 193109/RAR/NCP. Consequently, addition of the AGN 193109 retinoid negative hormone can down-regulate transcription of an otherwise retinoid-insensitive gene.

This same mechanism can account for the observation that AGN 193109 can repress the activity of the tissue transglutaminase (TGase) gene in HL-60 cells. A retinoid response element consisting of three canonical retinoid half sites spaced by 5 and 7 base pairs has been identified in the transcription control region of this gene. While TGase can be induced by RXR-selective agonists, it is not responsive to RAR-selective agonists. The TGase retinoid response element is bound by an RAR/RXR heterodimer (Davies et al. in Press). Interestingly, AGN 193109 is able to repress TGase activity induced by RXR agonists. This AGN 193109 mediated repression can be accounted for by the ability of this negative hormone to sequester NCPs to the RAR component of the heterodimer, thereby repressing the activity of the associated RXR.

We have also obtained results which support conclusions identical to those presented under Example 11 by employing RAR-γ-VP-16 and expression constructs and the ΔMTV-TREp-Luc reporter plasmid instead of the RAR-γ-VP-16 and ER-RXR-α expression constructs in combination with the ERE-tk-Luc reporter plasmid. Consistent with the results presented above, we found that RAR-γ-VP-16 activity at the ΔMTV-TREp-Luc reporter was inhibited by AGN 193109. Therefore, AGN 193109 repressed RAR-γ-VP-16 activity when this chimeric receptor was directly bound to a retinoic acid receptor response element instead of indirectly bound to an estrogen response element in the promoter region of the reporter plasmid. These findings demonstrated that an assay for identifying agents having negative hormone activity need not be limited by the use of a particular reporter plasmid. Instead, the critical feature embodied by an experimental system useful for identifying retinoid negative hormones involves detecting the ability of a compound to repress the activity of an RAR engineered to contain a constitutive transcription activation domain.

Generally, retinoid negative hormones can be identified as the subset of retinoid compounds that repress within a transfected cell the basal level expression of a reporter gene that is transcriptionally responsive to direct or indirect binding by a retinoid receptor or a chimeric receptor that includes at least the domains of the retinoid receptor located C-terminal to the DNA binding domain of that receptor. This approach has been adapted to a screening method useful for identifying retinoid negative hormones. In the various embodiments of the invented screening method, the structure of the receptor for which a negative hormone is sought is variable. More specifically, the retinoid receptor can be either of the RAR or the RXR subtype. The receptor can optionally be engineered to include a constitutive transcription activator domain. The retinoid receptor used to screen for negative hormones optionally contains a heterologous DNA binding domain as a substitute for the DNA binding domain endogenous to the native receptor. However, when a second receptor is used in the screening method, and where the second receptor can dimerize with the retinoid receptor for which a negative hormone is sought, then that retinoid receptor may not require a DNA binding domain because it can be linked to the transcription control region of the reporter gene indirectly through dimerization with the second receptor which is itself bound to the transcription control region.

In the practice of the screening method, the ability of a compound to repress the basal expression of a reporter is typically measured in an in vitro assay. Basal expression represents the baseline level of reporter expression in transfected cells under conditions where no exogenously added retinoid agonist is present. Optionally, steps may be taken to remove endogenous retinoid ligands from the environment of the transfected cells via procedures such as charcoal extraction of the serum that is used to culture cells in vitro.

Examples of reporter genes useful in connection with the screening method include those encoding luciferase, beta galactosidase, chloramphenicol acetyl transferase or cell surface antigens that can be detected by immunochemical means. In practice, the nature of the reporter gene is not expected to be critical for the operability of the method. However, the transcriptional regulatory region of the reporter construct must include one or more cis-regulatory elements that are targets of transcription factors for which negative hormones are being sought. For example, if one desires to identify RAR negative hormones, then the transcriptional regulatory region of the reporter construct could contain a cis-regulatory element that can be bound by an RAR-containing protein. In this example, there should be correspondence between the DNA binding domain of the RAR and the cis-regulatory element of the transcriptional regulatory region of the reporter construct. Thus, if a chimeric RAR having a constitutive transcription activator domain and a DNA binding domain that can bind cis-regulatory estrogen responsive elements is employed in the screening method, then the transcriptional regulatory region of the reporter construct should contain an estrogen responsive element.

Examples of cis-regulatory elements that directly bind retinoid receptors (RAREs) useful in connection with the reporter assay are disclosed by Mangelsdorf et al. in The Retinoid Receptors in *The Retinoids: Biology, Chemistry and Medicine*, 2nd edition, eds. Sporn et al., Raven Press, Ltd., New York (1994), the disclosure of which has been incorporated by reference hereinabove. Examples of cis-regulatory elements that indirectly bind chimeric receptors include DNA binding sites for any DNA binding protein for which the DNA binding domain of the protein can be incorporated into a chimeric receptor consisting of this DNA binding domain attached to a retinoid receptor. Specific examples of heterologous DNA binding domains that can be engineered into chimeric receptors and that will recognize heterologous cis-regulatory elements include those recognizing estrogen responsive elements. Thus, the retinoid receptor portion of a chimeric receptor useful in connection with the screening method need not contain the DNA binding of the retinoid receptor but must contain at least the ligand binding domain of the retinoid receptor.

A further example of indirect retinoid receptor binding to the cis-regulatory element includes the use of a protein that can bind the cis-regulatory element and dimerize with a retinoid receptor. In this case, the retinoid. receptor associates with the cis-regulatory element only by association with the protein responsible for DNA binding. An example of such a system would include the use of a fusion protein consisting of a heterologous DNA binding domain fused to an RXR, containing at least the domain of the RXR responsible for dimerization with RARs. Cointroduced RARs can dimerize with such a fusion protein bound to the cis-regulatory element. We anticipate that any cis-regulatory element-binding protein that dimerizes with RARs to result in an indirect association of the RAR with the cis-regulatory element will also be suitable for use with the negative hormone screening method.

In a preferred embodiment of the screening method, retinoid negative hormones are identified as those retinoids that repress basal expression of an engineered RAR transcription factor having increased basal activity. Although not essential for operability of the screening method, the engineered RAR employed in the following Example included a constitutive transcription activating domain. Use of this chimeric receptor advantageously provided a means by which the basal expression of a reporter gene could be elevated in the absence of any retinoid. Although we have employed transient transfection in the procedures detailed above, stably transfected cell lines constitutively expressing the chimeric receptor would also be useful in connection with the screening method.

As disclosed in the following Example, a chimeric retinoid receptor having a constitutive transcription activator domain was heterodimerizable with a second receptor engineered to contain a DNA binding domain specific for an estrogen responsive cis-regulatory element. In this case the chimeric retinoid receptor having a constitutive transcription activator domain associates with the cis-regulatory region controlling reporter gene expression indirectly via binding to a second receptor that binds a DNA target sequence. More particularly, the second receptor was engineered to contain a DNA binding domain that recognized an estrogen responsive element. Advantageously, the reporter gene having an estrogen responsive element in the upstream promoter region was unresponsive to retinoid agonists in the absence of the transfected chimeric receptor having the constitutive transcription activator domain. Accordingly, all reporter gene activity was attributed to the transfected receptors. The combination use of the estrogen responsive element DNA binding domain and the estrogen responsive element cis-regulatory element are intended to be illustrative only. Those having ordinary skill in the art will realize that other combinations of engineered receptors having specificity for non-RARE cis-regulatory elements will also be useful in the practice of the invented screening method.

Cells useful in connection with the screening method will be eukaryotic cells that can be transfected. The cells may be animal cells such as human, primate or rodent cells. We have achieved very good results using CV-1 cells, but reasonably expect that other cultured cell lines could also be used successfully. Any of a number of conventional transfection methods known in the art can be used to introduce an expression construct encoding the chimeric retinoid receptor having a constitutive transcription activator domain.

The constitutive transcription activator domain will consist of a plurality of amino acids which will likely have an overall acidic character as represented by a negative charge under neutral pH conditions. For example, the constitutive transcription activator domain may have an amino acid sequence which is also found in viral transcription factors. One example of a viral transcription factor having a constitutive transcription activator domain is the herpes simplex virus 16. However, other viral or synthetic transcription activator domains would also be useful in the construction of expression constructs encoding the chimeric retinoid receptor having a constitutive transcription activator domain.

As described below, we have developed a generalized screening method useful for identifying retinoid negative hormones. This screening method provides a means for distinguishing simple antagonists from negative hormones. Table 12 lists several retinoid compounds which exhibit potent affinity for RAR-$\gamma$ yet, with the exception of ATRA, did not transactivate this receptor in a transient cotransfection transactivation assay. We therefore tested these compounds to determine which were RAR-$\gamma$ antagonists and which, if any, of these antagonists exhibited negative hormone activity.

Example 12 describes the method used to identify retinoid compounds that were antagonists, and the subset of antagonists that exhibited negative hormone activity.

EXAMPLE 12

Assay for Retinoid Negative Hormones $4 \times 10^4$ CV-1 cells were transfected by the calcium phosphate coprecipitation procedure described in *Molecular Cloning: A Laboratory Manual* (Sambrook et al. eds. Cold Spring Harbor Lab Publ. 1989) using 0.5 $\mu$g ERE-tk-Luc reporter plasmid and 0.1 $\mu$g ER-RAR-$\gamma$ (Graupner et al. *Biochem. Biophys. Res. Comm.* 179:1554 (1991)) chimeric expression plasmid. After 18 hours, cells were rinsed with PBS and fed with DMEM (Gibco-BRL) containing 10% activated charcoal extracted FBS (Gemini Bio-Products). Cells were treated with $10^{-8}$M ATRA in ethanol or ethanol alone. In addition, ATRA treated cells were treated with $10^{-9}$, $10^{-8}$, $10^{-7}$ or $10^{-6}$M of the compounds listed in Table 12. After 18 hours, cells were rinsed in PBS and lysed in 0.1M KPO$_4$ (pH 7.8), 1.0% TRITON X-100, 1.0 mM DTT, 2 mM EDTA. Luciferase activities were measured as described by deWet et al. in *Mol. Cell. Biol.* 7:725 (1987).

TABLE 12

| Compound | Kd (nM) @ RAR-$\gamma^a$ | EC$_{50}$ (nM) @ RAR-$\gamma^b$ |
|---|---|---|
| ATRA | 12 | 17 |
| AGN 193109 (Compound 60) | 6 | na |
| AGN 193174 (Compound 34a) | 52 | na |

TABLE 12-continued

| Compound | Kd (nM) @ RAR-γ[a] | EC$_{50}$ (nM) @ RAR-γ[b] |
|---|---|---|
| AGN 193199 | 30 | na |
| AGN 193385 (Compound 23) | 25 | na |
| AGN 193389 (Compound 25) | 13 | na |
| AGN 193840 | 40 | na |
| AGN 193871 (Compound 50) | 30 | na |

[a]Relative affinity (Kd) determined by competition of $^3$H-ATRA binding to baculovirus expressed RAR-γ and application of the Cheng-Prussof equation.
[b]EC$_{50}$ measured in CV-1 cells transiently cotransfected with ΔMTV-TREp-Luc and RS-RAR-γ. "na" denotes no activity.

Figure 7:
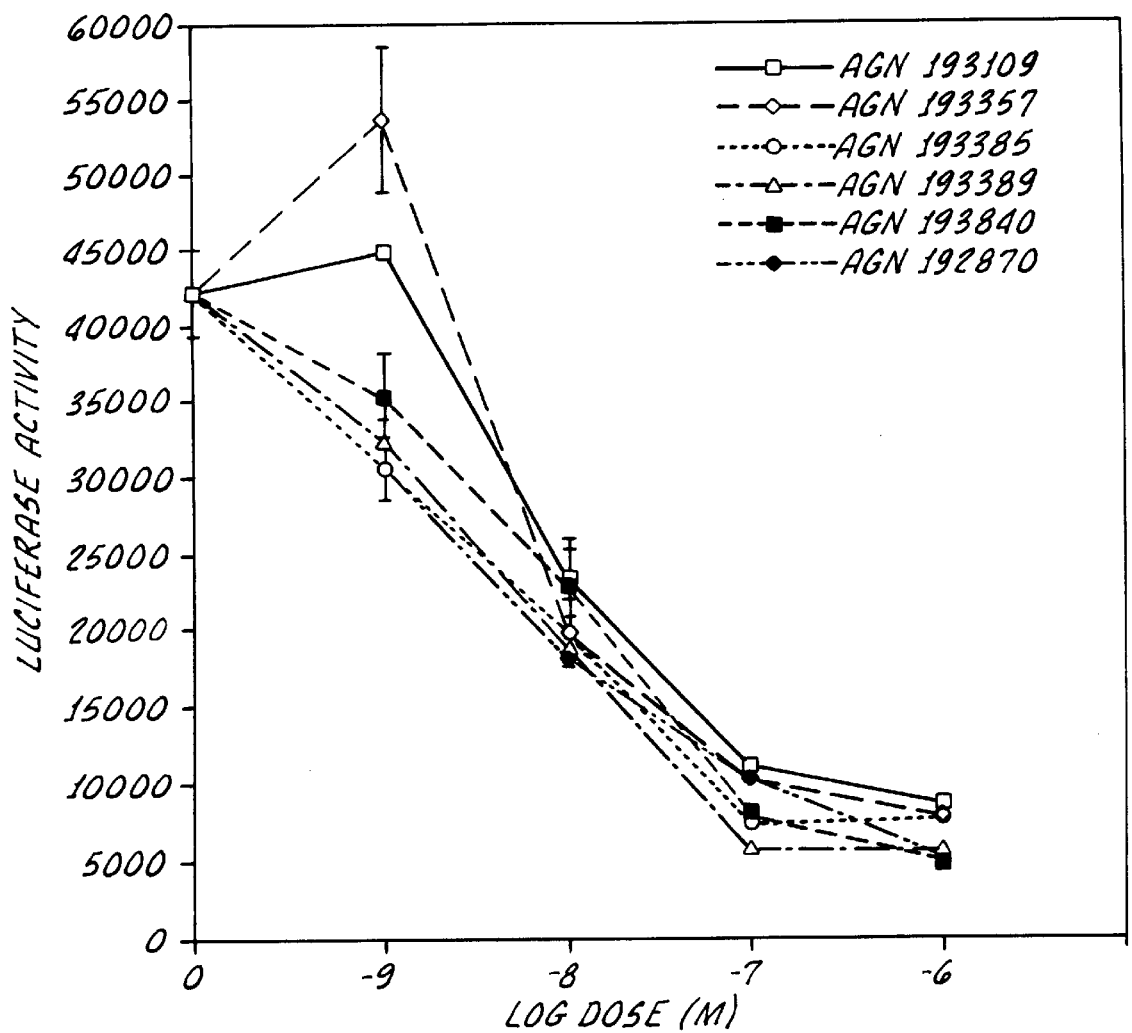
FIG. 7 shows a line graph representing luciferase activity measurements recorded in lysates of CV-1 cells transfected with the ERE-tk-Luc reporter and ER-RAR-γ expression construct and then treated with ATRA at $10^{-8}$M and the test compounds at the concentrations indicated on the horizontal axis. The test compounds were AGN 193109 (square), AGN 193357 (open diamond), AGN 193385 (circle), AGN 193389 (triangle), AGN 193840 (hatched square) and AGN 192870 (filled diamond).

As indicated by the results presented in part in FIG. 7 and in Table 12, with the exception of ATRA, all of the compounds listed in Table 12 were retinoid antagonists at RAR-γ.

The RAR-γ antagonists identified in Table 12 were next screened to determine which, if any, were also retinoid negative hormones. 4×10$^4$ CV-1 cells were transfected according to the calcium phosphate procedure described in *Molecular Cloning: A Laboratory Manual* (Sambrook et al. eds. Cold Spring Harbor Lab Publ. 1989) using 0.5 μg ERE-tk-Luc reporter plasmid and 0.1 μg ER-RXR-α (Graupner et al. *Biochem. Biophys. Res. Comm.* 179:1554 (1991)) and 0.2 μg RAR-γ-VP-16 (Nagpal et al. *EMBO J.* 12:2349 (1993)) chimeric expression plasmids. After 18 hours, cells were rinsed with PBS and fed with DMEM (Gibco-BRL) containing 10% activated charcoal extracted FBS (Gemini Bio-Products). Cells were treated with 10$^{-9}$, 10$^{-8}$, 10$^{-7}$ or 10$^{-6}$M of each of the compounds listed in Table 12. Treatment with ethanol vehicle alone served as the negative control. After 18 hours, cells were rinsed in PBS and lysed in 0.1M KPO$_4$ (pH 7.8), 1.0% TRITON X-100, 1.0 mM DTT, 2 mM EDTA. Luciferase activities were measured as previously by deWet et al. in *Mol Cell. Biol.* 7:725 (1987).

Figure 8:
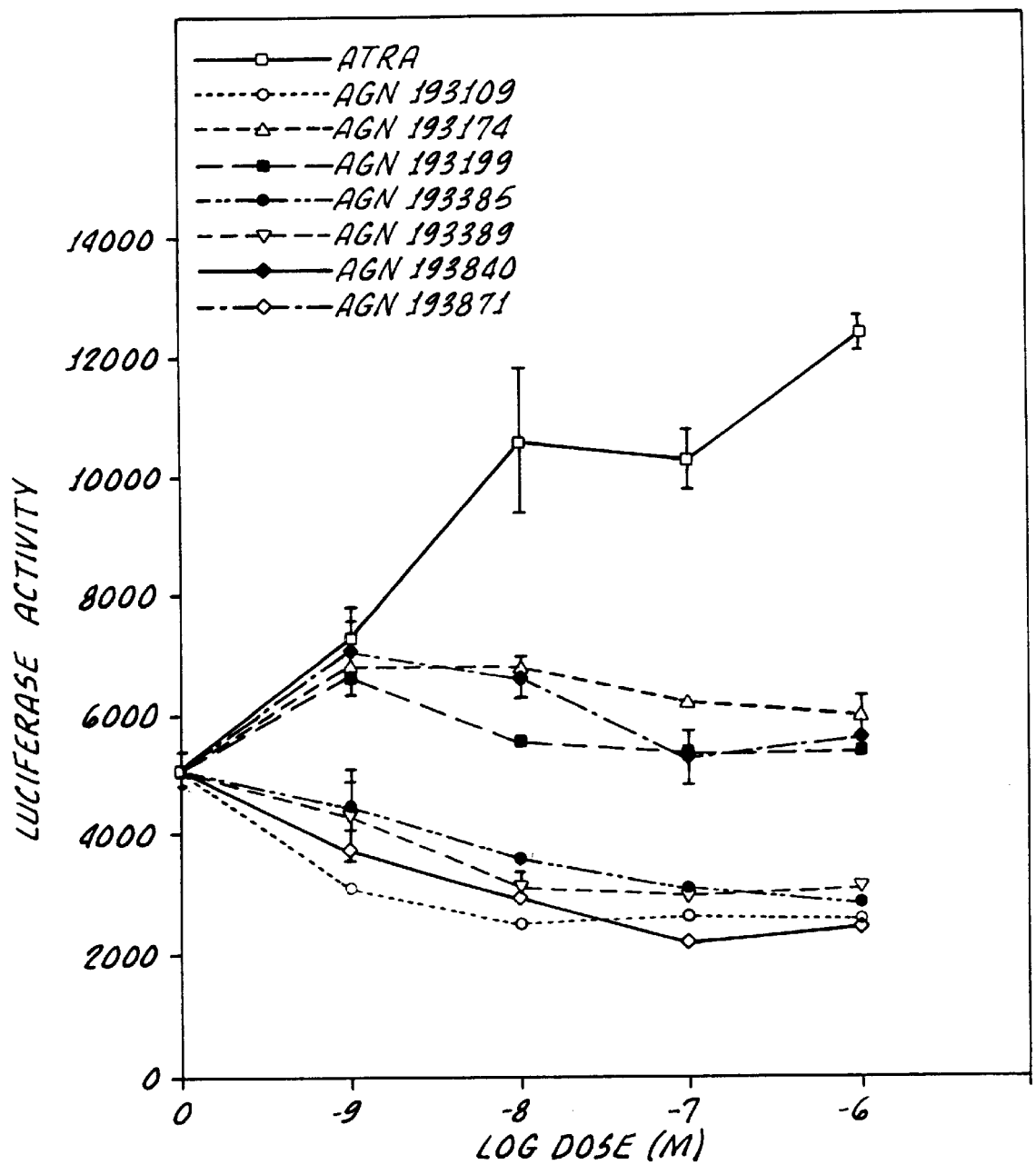
FIG. 8 shows a line graph representing luciferase activity measurements recorded in lysates of CV-1 cells transfected with the ERE-tk-Luc reporter and RAR-γ-VP-16 and ER-RXR-α expression constructs and then treated with the test compounds at the concentrations indicated on the horizontal axis. The test compounds were ATRA (open square), AGN 193109 (open circle), AGN 193174 (open triangle), AGN 193199 (hatched square), AGN 193385 (hatched circle), AGN 193389 (inverted triangle), AGN 193840 (diagonally filled square) and AGN 193871 (half-filled diamond).

As shown in FIG. 8, the retinoid antagonists of Table 12 could be separated into two classes by virtue of their effect on the constitutive transcription activation function of the RAR-γ-VP-16 chimeric retinoid receptor. One group, which included AGN 193174, AGN 193199 and AGN 193840, did not repress RAR-γ-VP-16 activity even though they were ATRA antagonists. In contrast AGN 193109, AGN 193385, AGN 193389 and AGN 193871 exhibited a dose dependent repression of RAR-γ-VP-16 constitutive activity. Therefore, while the compounds of both groups were RAR-γ antagonists, only those of the second group exhibited negative hormone activity. This assay advantageously distinguished retinoid negative hormones from simple retinoid antagonists.

Figure 9A:
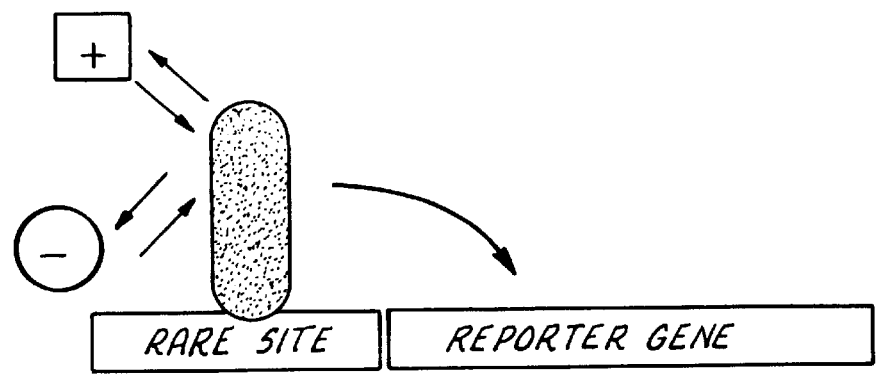
FIGS. 9A, 9B and 9C schematically diagram a mechanism whereby AGN 193109 can modulate the interaction between the RAR (shaded box) and negative coactivator proteins (−) illustrated in the context of a transactivation assay.
Figure 9B:
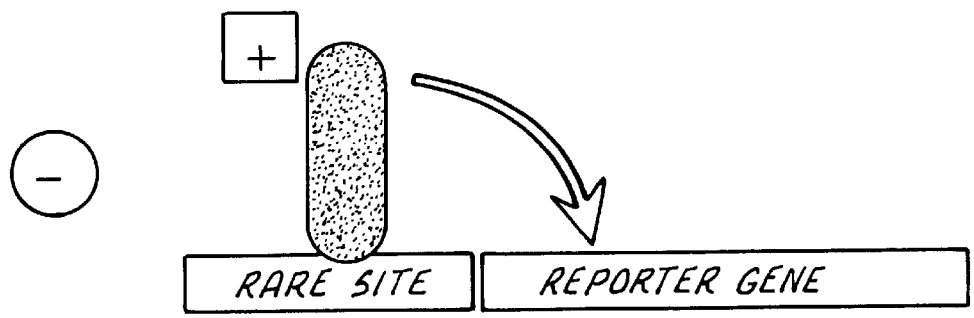
Figure 9C:
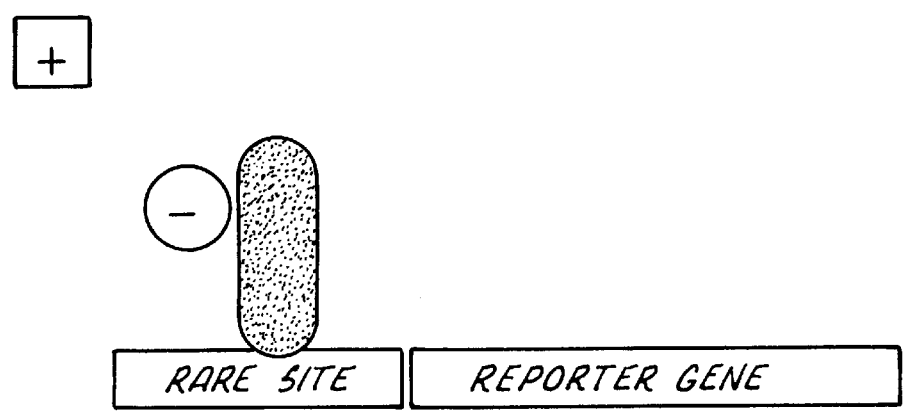

The foregoing experimental results proved that AGN 193109 met the criteria that define a negative hormone. More specifically, the results presented under Example 11 demonstrated that AGN 193109 had the capacity to exert inhibitory activity at the RARs even in the absence of exogenously added retinoid ligands. As such, this compound possessed biological activities that did not depend upon blockade of the interaction between the RARs and agonists such as ATRA and AGN 191183. These findings led us to conclude that AGN 193109 stabilized interactions between RARs and NCPs. As diagrammed in FIG. 9, NCP/RAR/PCP interactions exist in an equilibrium state. An agonist serves to increase PCP interactions and decrease NCP interactions, while an inverse agonist or negative hormone stabilizes NCP and decreases PCP interactions. As indicated previously, our experimental results suggested that the intracellular availability of NCP for other receptors can be modulated by AGN 193109 administration. More specifically, we discovered that AGN 193109 can promote complexation of NCP with RARs, thereby reducing the intracellular reservoir of NCP available for interaction with transcription factors other than the RARs.

We next examined the effect of AGN 193109 on agonist-mediated inhibition of AP-1 dependent gene expression. In *Endocr. Rev.* 14:651 (1993), Pfhal disclosed that retinoid agonists can down-regulate gene expression by a mechanism that involved inhibition of AP-1 activity. We postulated that AGN 193109 could have had either of two effects when used in combination with a retinoid agonist in a model system designed to measure AP-1 activity. First, AGN 193109 could conceivably have antagonized the effect of the agonist, thereby relieving the agonist-dependent inhibition of AP-1 activity. Alternatively, AGN 193109 could have potentiated the agonist's activity, thereby exaggerating the agonist-dependent inhibition of AP-1 activity.

Example 13 describes the methods used to demonstrate that AGN 193109 potentiated the anti-AP-1 activity of a retinoid agonist. As disclosed below, the AGN 191183 retinoid agonist weakly inhibited AP-1 dependent gene expression. The combination of AGN 193109 and the retinoid agonist strongly inhibited AP-1 dependent gene expression. By itself, AGN 193109 had substantially no anti-AP-1 activity.

EXAMPLE 13

AGN 193109 Potentiates the Anti-AP-1 Activity of a Retinoid Agonist

HeLa cells were transfected with 1 μg of the Str-AP1-CAT reporter gene construct and 0.2 μg of plasmid pRS-hRARα, described by Giguere et al. in *Nature* 33:624 (1987), using LIPOFECTAMINE (Life Technologies, Inc.). Str-AP1-CAT was prepared by cloning a DNA fragment corresponding to positions −84 to +1 of the rat stromelysin-1 promoter (Matrisian et al., *Mol. Cell. Biol.* 6:1679 (1986)) between the HindIII-BamHI sites of pBLCAT3 (Luckow et al., *Nucl. Acids Res.* 15:5490 (1987)). This sequence of the stromelysin-1 promoter contains an AP1 motif as its sole enhancer element (Nicholson et al., *EMBO J.* 9:4443 (1990). The promoter sequence was prepared by annealing two synthetic oligonucleotides having sequences:

5'-AGAAGCTTATGGAAGCAATTATGAGTCAGTTTGCGGGTGACTCTG    (SEQ ID NO:2),

CAAATACTGCCACTCTATAAAAGTTGGGCTCAGAAAGGTGGACCTCGAGGATCCAG-3' and

5'-CTGGATCCTCGAGGTCCACCTTTCTGAGCCCAACTTTTATAGAGTG    (SEQ ID NO:3)

GCAGTATTTGCAGAGTCACCCGCAAACTGACTCATAATTGCTTCCATAAGCTTCT-3'.

Procedures involving transfection, treatment with appropriate compounds and measurement of CAT activity were carried out as described by Nagpal et al. in *J. Biol. Chem.*

270:923 (1995), the disclosure of which is hereby incorporated by reference.

Figure 10:
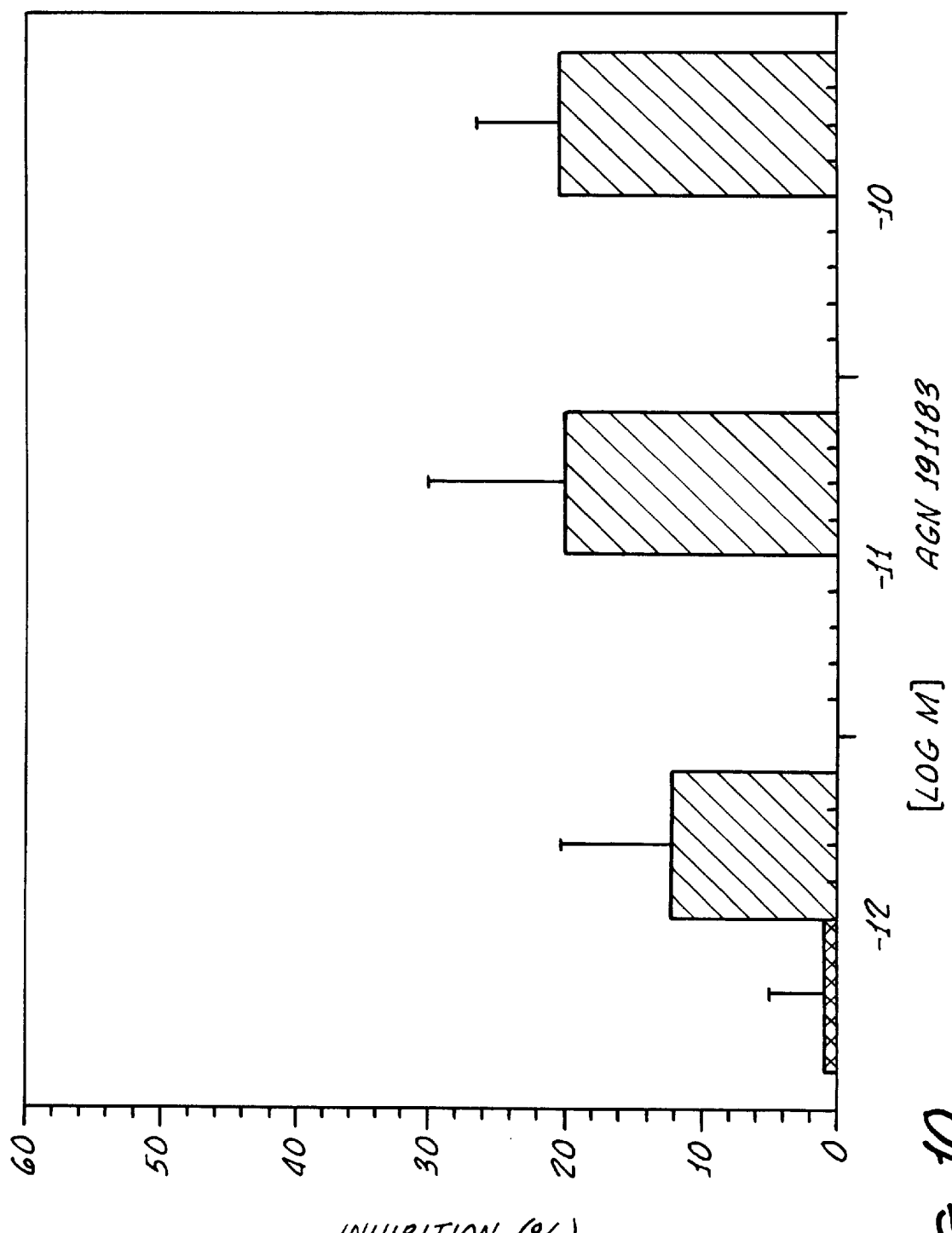
FIG. 10 is a bar graph showing the inhibition of TPA-induced Str-AP1-CAT expression as a function of AGN 191183 concentration ($10^{-10}$ to $10^{-12}$M) with the AGN 193109 concentration held constant at $10^{-8}$M. Results from trials conducted with AGN 191183 alone are shown as hatched bars while stripped bars represent the results from treatment with the combination of AGN 193109 and AGN 191183.

The results of these procedures indicated that AGN 193109 potentiated the anti-AP-1 activity of the retinoid agonist, AGN 191183. More specifically, in the concentration range of from $10^{-12}$ to $10^{-10}$M, AGN 191183 did not inhibit the TPA-induced Str-AP1-CAT expression. Treatment with AGN 193109 in the concentration range of from $10^{-10}$ to $10^{-8}$M did not substantially inhibit AP-1 mediated reporter activity. However, the results presented in FIG. 10 indicated that stimulation of the transfectants with the combination of AGN 193109 ($10^{-8}$M) and AGN 191183 in the concentration range of from $10^{-12}$ to $10^{-10}$M substantially inhibited TPA-induced Str-AP1-CAT expression by an amount of from 12% to 21%. Therefore, AGN 193109 potentiated the anti-AP-1 activity of AGN 191183 under conditions where this retinoid agonist ordinarily did not inhibit AP-1 activity.

We reasoned that AGN 193109 potentiated the agonist-mediated repression of AP-1 activity by a mechanism that likely involved AGN 193109-dependent sequestration of NCPs onto RARs. RARs belong to a superfamily of nuclear receptors that also includes receptors for 1,25-dihydroxyvitamin $D_3$, glucocorticoid, thyroid hormone, estrogen and progesterone. It was a reasonable assumption that the ability to bind NCPs may be shared among different members of the nuclear receptor superfamily. This led us to speculate that AGN 193109 could potentiate the anti-AP-1 activity of one or more of the ligands that interact with this superfamily of nuclear receptors.

The results presented in the preceding Example clearly indicated that AGN 193109 potentiated the anti-AP-1 activity of a retinoid agonist. More specifically, AGN 193109 lowered the threshold dose at which the anti-AP-1 activity of AGN 191183 could be detected. Since AGN 193109 has substantially no anti-AP-1 activity by itself, its effect on nuclear receptor agonists was synergistic. We also found that the AGN 193109 negative hormone potentiated the anti-AP-1 activity of 1,25-dihydroxyvitamin $D_3$, the natural ligand for the vitamin $D_3$ receptor.

The observed synergy between AGN 193109 and AGN 191183 in the preceding Example necessarily implied that the anti-AP-1 activity of the retinoid agonist and the AGN 193109-mediated potentiation of that activity must result from different mechanisms. If the mechanisms of action of the two agents were identical, then it follows that the effectiveness of the combination of AGN 193109 and the agonist would have been additive. Instead, the combination was shown to be more effective than either agent alone, an effect that could not have been predicted in advance of this finding.

Significantly, the AGN 193109 -mediated potentiation of the RAR agonist was performed using an approximately 100-fold molar excess of AGN 193109 over that of the retinoid agonist. Accordingly, the majority of RARs should have been bound by AGN 193109 leaving very few RARs available for agonist binding. In spite of this fact, the population of RARs that were not bound by AGN 193109 were able to bind retinoid agonist and vigorously stimulate an agonist-dependent response measurable as an inhibition of reporter gene expression. Thus, our data suggested possible heterogeneity of RARs that are induced by AGN 193109.

The negative hormone activity of AGN 193109, attributed to its ability to promote the interaction of RARs and NCPs, provided a basis for understanding the synergy between AGN 193109 and retinoid agonists. Our results were fully consistent with a model in which AGN 193109 treatment of cells promoted binding of RARs and NCPs, thereby reducing the number of free NCP and free RAR within the cell. This results in the generation of two populations of RARs that are functionally distinct. The first population is represented by RARs associated with NCPs. Such AGN 193109/RAR/NCP complexes cannot be activated by retinoid agonists. The second population consists of RARs that are not bound by NCP, and that remain available for interaction with agonists. This latter population is designated "RAR*" to indicate free RARs in an environment substantially depleted of NCP.

Figure 11:
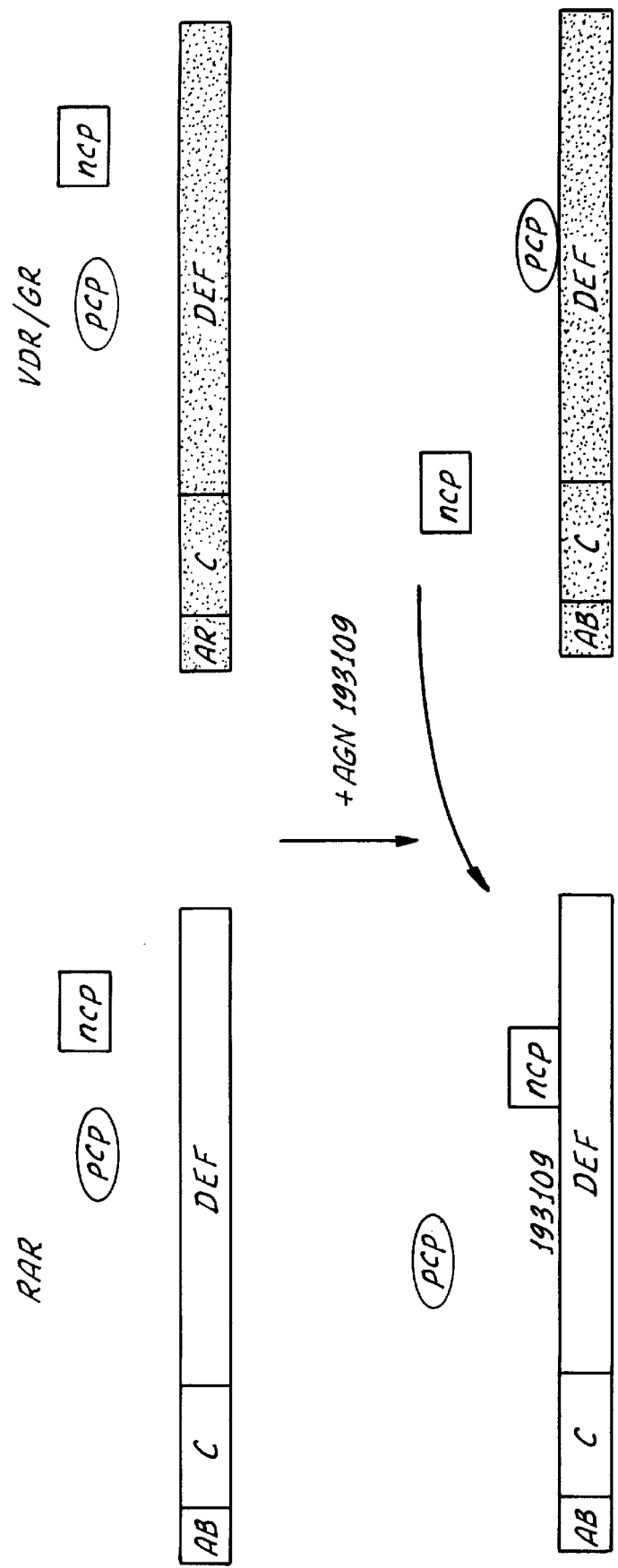
FIG. 11 schematically diagrams a mechanism whereby AGN 193109 can potentiate the activities of RARs and other nuclear receptor family members. As illustrated in the diagram, introduced RARs (open rectangles having AB-C-DEF domains) have increased sensitivity to RAR ligands in the anti-AP1 assay because the negative coactivator protein (ncp), present in limiting supply, is sequestered onto RARs thereby leading to two populations: RAR+ncp and RAR−ncp. RAR−ncp has increased sensitivity to ligands. Non-RAR nuclear factors (shaded rectangles having AB-C-DEF domains) have increased sensitivity to cognate ligands because ncp has been sequestered to the RAR by the activity of AGN 193109. The modular domains of the nuclear receptors are designated using standard nomenclature as "AB" (ligand independent transactivation domain), "C" (DNA binding domain), and "DEF" (ligand regulated transactivation domain and dimerization domain.

The RAR*s have decreased probabilities of association with NCP through equilibrium binding and have an increased sensitivity to retinoid agonists measurable, for example, as anti-AP-1 activity. This is so because, while the intracellular reservoir of NCP is depleted by virtue of AGN 193109 administration, the reservoir of PCP has not been depleted. Accordingly, free RAR*s can bind a retinoid agonist and interact with PCP factors in an environment substantially depleted of NCP. The ability of AGN 193109 to increase the sensitivity of other nuclear receptors to their respective agonists can be attributed to the ability of these different nuclear receptors to interact with the same NCPs that interact with AGN 193109/RAR complexes. This model of AGN 193109-mediated modulation of NCP availability for nuclear receptor family members is schematically represented in FIG. 11.

This mechanistic model led us to predict that AGN 193109 could modulate the activities of nuclear receptor ligands other than retinoid agonists. As illustrated in the following Example, we confirmed that AGN 193109 potentiated the activity of 1,25-dihydroxyvitamin $D_3$ in an in vitro transactivation assay.

Example 14 describes the methods used to demonstrate that AGN 193109 enhanced the activity of 1,25-dihydroxyvitamin $D_3$ in a transactivation assay.

EXAMPLE 14

AGN 193109 Potentiates 1,25-Dihydroxyvitamin $D_3$ Activity

Hela cells were transfected using the cationic liposome-mediated transfection procedure described by Felgner et al. in Proc. Natl. Acad. Sci. USA 84:7413 (1987). 5×10⁴ cells were plated in 12-well multiwell plates and grown in DMEM supplemented with 10% FBS. Cells were cotransfected in serum-free medium using 2 µg/well of LIPOFECTAMINE reagent (Life Technologies, Inc.) with 0.7 µg of the reporter plasmid MTV-VDRE-Luc, containing two copies of the 1,25-dihydroxyvitamin $D_3$ response element 5'-GTACAAGGTTCACGAGGTTCACGTCTTA-3' (SEQ ID NO:4) from the mouse osteopontin gene (Ferrara et al. J. Biol. Chem. 269:2971 (1994)) ligated into the reporter plasmid ΔMTV-Luc (Heyman et al. in Cell 68:397 (1992)), and 0.3 µg of the plasmid pGEM3Z (Pharmacia, Inc.) as carrier DNA to bring the final concentration of DNA to 1.0 µg per well. After six hours of transfection, cells were fed with growth medium containing charcoal extracted FBS at a final concentration of 10%. Eighteen hours after transfection cells were treated with vehicle alone (ethanol) or AGN 193109 in ethanol at a final concentration of either $10^{-8}$ or $10^{-7}$M. Six hours later 1,25-dihydroxyvitamin $D_3$ was added in ethanol to a final concentration of from $10^{-10}$ to $10^{-7}$M. Cells were lysed and harvested eighteen hours following 1,25-dihydroxyvitamin $D_3$ treatment. Luciferase activity was measured as described above. This experimental system allowed a convenient method of monitoring and quantitating 1,25-dihydroxyvitamin $D_3$-dependent gene expression.

Figure 12:
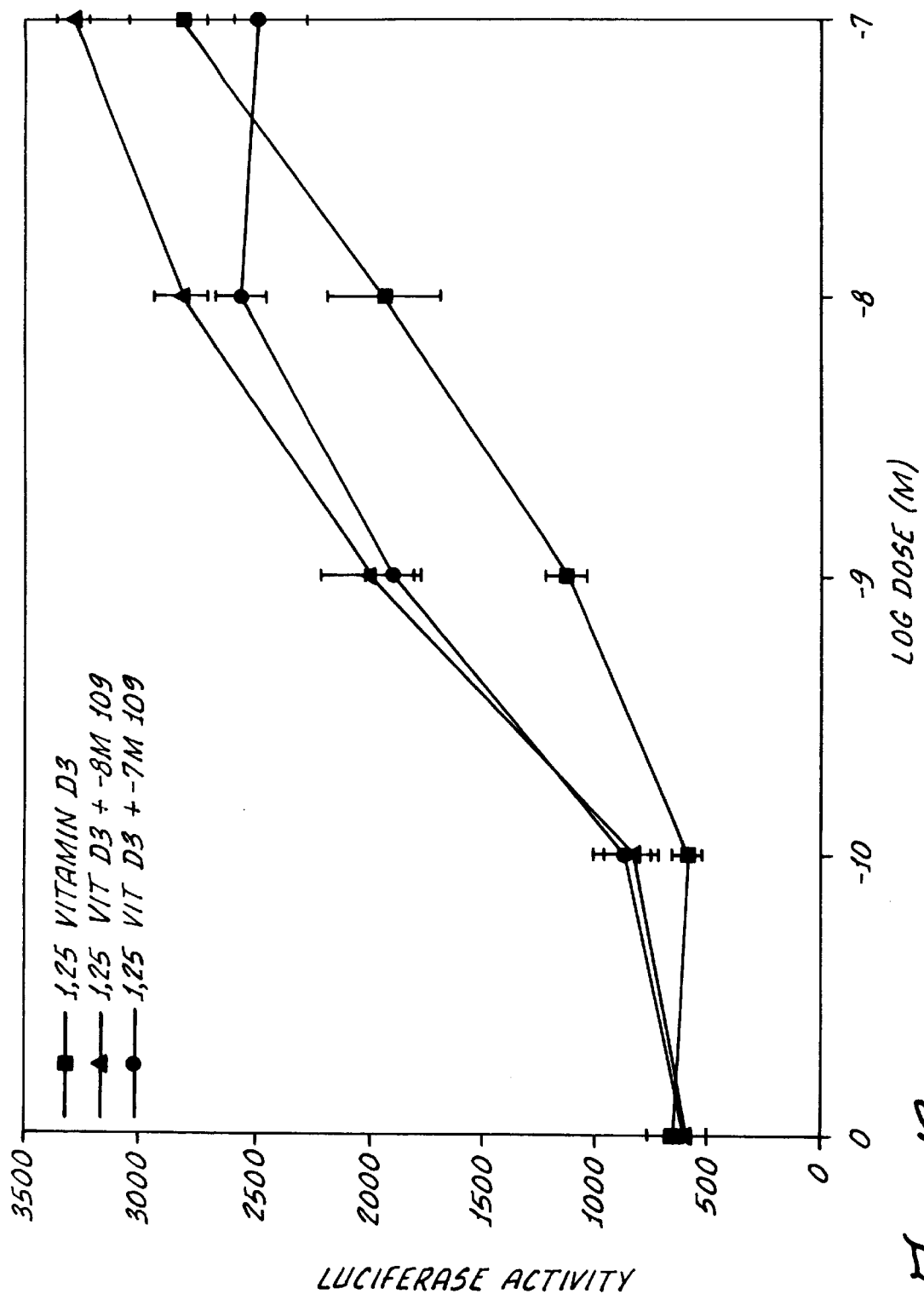
FIG. 12 is a line graph showing the effect of AGN 193109 on the 1,25-dihydroxyvitamin $D_3$ dose response in CV-1 cells transfected with the MTV-DR3-Luc reporter plasmid. Transfectants were treated with 1,25-dihydroxyvitamin $D_3$ (filled square), 1,25-dihydroxyvitamin $D_3$ and $10^{-8}$M AGN 193109 (filled triangle), and 1,25-dihydroxyvitamin $D_3$ and $10^{-7}$M AGN 193109 (filled circle).

The results presented in FIG. 12 indicated that, when compared with the result obtained using 1,25-dihydroxyvitamin $D_3$ alone, AGN 193109 coadministered with 1,25-dihydroxyvitamin $D_3$ shifted the dose response curve to the left. This confirmed that AGN 193109 potentiated the effectiveness of 1,25-dihydroxyvitamin $D_3$ in the in vitro transactivation assay. More specifically, FIG. 12 graphically illustrates that an AGN 193109 concentration as low as 10–100 nM rendered the 1,25-dihydroxyvitamin $D_3$ approximately 10 fold more active. While a 1,25-dihydroxyvitamin $D_3$ concentration of $10^{-8}$M was required to produce a luciferase expression of approximately 2,000 rlu, only one-tenth as much 1,25-dihydroxyvitamin $D_3$ was required to produce the same luciferase output when the vitamin was coadministered with AGN 193109 at a concentration of $10^{-8}$–$10^{-7}$M. Although not shown on the graph in FIG. 12, substantially identical results were obtained using AGN 193109 concentrations of $10^{-9}$M and $10^{-8}$M. Thus, coadministration with AGN 193109 substantially reduced the amount of 1,25-dihydroxyvitamin $D_3$ that was required to produce a similar effect in the absence of the negative hormone.

Interestingly, when the above procedure was repeated with cotransfection of a vitamin D receptor (VDR) expression plasmid, there was a coincident decrease in the ability of AGN 193109 to potentiate the activity of 1,25-dihydroxyvitamin $D_3$. We interpreted this result as indicating that over-expression of VDRs could affect the ability of AGN 193109 to potentiate the activity of 1,25-dihydroxyvitamin $D_3$. Thus, the intracellular concentration of a ligand receptor, which may differ in a tissue-specific fashion, can influence the ability of AGN 193109 to potentiate the activity of a ligand that binds the receptor. This was again consistent with a model in which titratable NCPs contributed to the regulation of the Vitamin $D_3$ response, and supported the model set forth above.

As illustrated in the following Example, we also confirmed that AGN 193109 potentiated the anti-AP-1 activity of 1,25-dihydroxyvitamin $D_3$. Our model for the activity of AGN 193109 action explains this observation by invoking that NCPs avidly associate with RARs in the presence of this drug. Endogenous vitamin D receptors present in HeLa cells likely were rendered more sensitive to the 1,25-dihydroxyvitamin $D_3$ ligand, with the consequence of exaggerating the ability of this ligand to inhibit expression from the Str-AP1-CAT reporter.

Example 15 describes the methods used to demonstrate that AGN 193109 potentiated the anti-AP-1 activity of 1,25-dihydroxyvitamin $D_3$.

EXAMPLE 15

AGN 193109 Potentiates the Anti-AP-1 Activity of 1,25-Dihydroxyvitamin $D_3$

HeLa cells were transfected with 1 μg of Str-AP1-CAT using LIPOFECTAMINE according to the method described by Nagpal et al. in *J. Biol. Chem.* 270:923 (1995). Transfected cells were treated with AGN 193109 alone ($10^{-9}$ to $10^{-7}$M), 1,25-dihydroxyvitamin $D_3$ alone ($10^{-12}$ to $10^{-7}$M) or 1,25-dihydroxyvitamin $D_3$ ($10^{-12}$ to $10^{-7}$M) in the presence of $10^{-8}$M AGN 193109.

Figure 13:
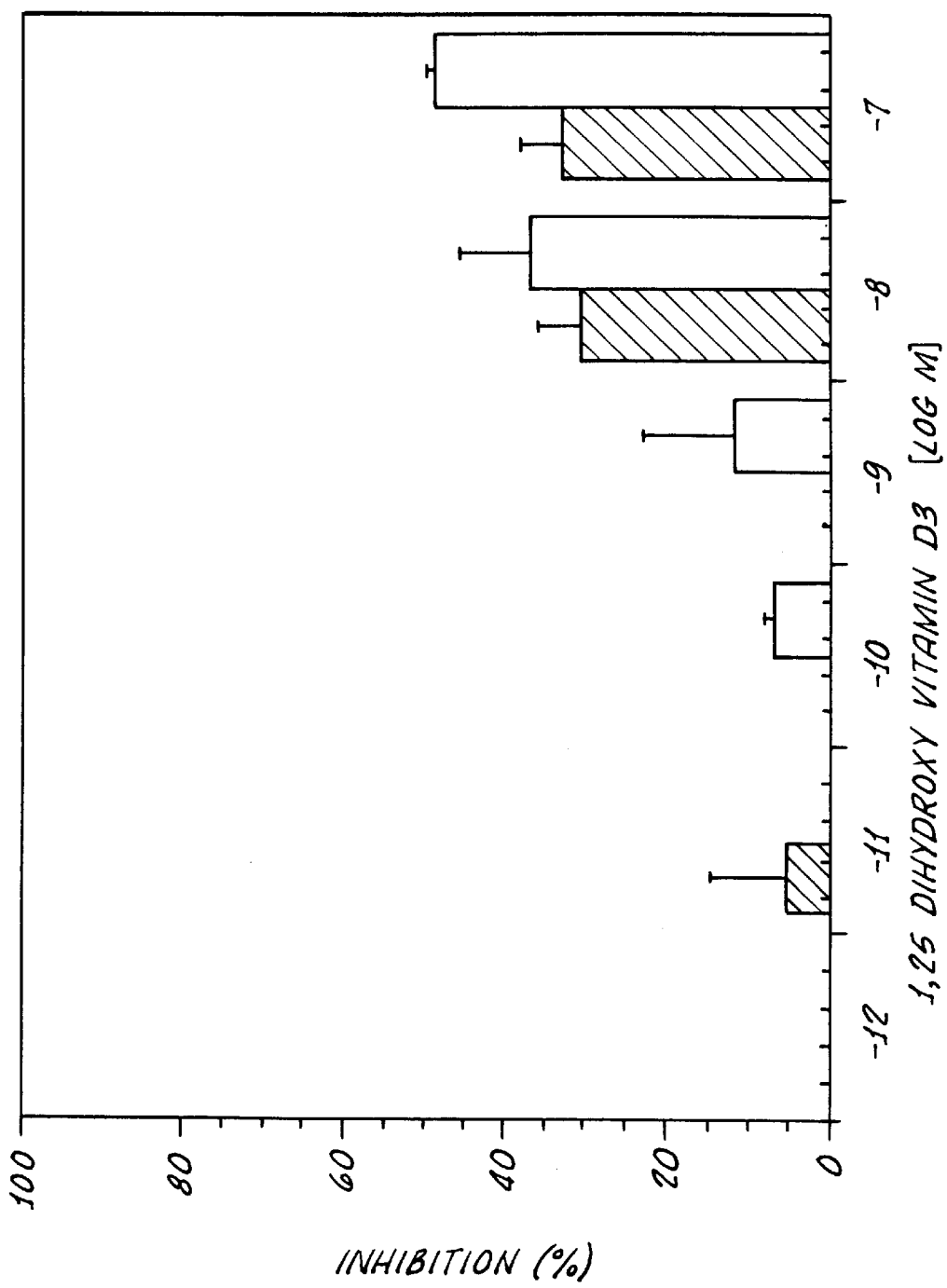
FIG. 13 is a bar graph showing the effect of AGN 193109 (10 nM) coadministration on 1,25-dihydroxyvitamin $D_3$-mediated inhibition of TPA induced Str-AP1-CAT activity. Filled bars represent inhibition of CAT activity in transfected cells treated with 1,25-dihydroxyvitamin $D_3$ alone. Open bars represent inhibition of CAT activity in transfected cells treated with the combination of 1,25-dihydroxyvitamin $D_3$ and AGN 193109.

The results of these procedures indicated that AGN 193109 potentiated the ability of 1,25-dihydroxyvitamin $D_3$ to inhibit TPA-induced AP-1 activity. When used alone in the concentration range of from $10^{-9}$ to $10^{-7}$M, AGN 193109 had no detectable anti-AP-1 activity. The results presented in FIG. 13 indicated that 1,25-dihydroxyvitamin $D_3$ repressed TPA-stimulated activity only in the $10^{-8}$ and $10^{-7}$M concentration range. Analysis of 1,25-dihydroxyvitamin $D_3$ mediated repression of TPA stimulated CAT activity in the presence of $10^{-8}$M AGN 193109 indicated that anti-AP-1 activity was detectable at $10^{-10}$ and $10^{-9}$M 1,25-dihydroxyvitamin $D_3$ and an increase in activity at $10^{-8}$ and $10^{-7}$M doses compared to 1,25-dihydroxyvitamin $D_3$ treatment alone. This AGN 193109 dependent modulation of 1,25-dihydroxyvitamin $D_3$ mediated anti-AP-1 activity was consistent with our model in which NCP sequestration to RARs made the NCP unavailable for interaction with other nuclear receptor family members. Accordingly, the receptors were rendered more sensitive to the 1,25-dihydroxyvitamin $D_3$ treatment.

The mechanisms underlying RAR mediated transactivation and anti-AP-1 activity are likely different. This conclusion was based on our observation that high doses of AGN 193109 completely inhibited transactivation without substantially inhibiting anti-AP1 activity. We therefore wished to gain additional evidence to support our model for RAR* formation mediated by AGN 193109 treatment. To accomplish this, we investigated whether AGN 193109 could potentiate the activity of the RAR specific agonist AGN 191183 in an in vitro transactivation assay.

Example 16 describes the methods used to demonstrate that AGN 193109 potentiated the activity of the RAR specific agonist, AGN 191183. The results of this procedure indicated that, under particular circumstances, AGN 193109 enhanced the potency of the RAR specific retinoid, and provided strong evidence that AGN 193109 promoted RAR* formation.

EXAMPLE 16

Potentiation of Retinoid Effectiveness by AGN 193109 Coadministration

Hela cells were transfected using the cationic liposome-mediated transfection procedure described by Felgner et al. in *Proc. Natl. Acad. Sci. USA* 84:7413 (1987). $5 \times 10^4$ cells were plated in 12 well multiwell plates and grown in DMEM supplemented with 10% FBS. Cells were cotransfected in serum free medium using LIPOFECTAMINE reagent (2 ug/well, Life Technologies, Inc.) with 0.7 μg of the reporter plasmid MTV-TREp-Luc, containing two copies of the TREpal response element 5'-TCAGGTCATGACCTGA-3' (SEQ ID NO:5) inserted into the reporter plasmid ΔMTV-Luc (Heyman et al. in *Cell* 68:397 (1992)), and 0.1 μg of the RAR-γ expression plasmid pRShRAR-γ (Ishikawa et al. *Mol. Endocrinol.* 4:837 (1990)). After six hours of transfection, cells were fed with growth medium containing charcoal extracted FBS at a final concentration of 10%. Eighteen hours after transfection, cells were treated with vehicle alone (ethanol) or AGN 193109 in ethanol at a final concentration of from $10^{-11}$ to $10^{-8}$M. Six hours later, AGN 191183 was added in ethanol to a final concentration of either 0, $10^{-10}$ or $10^{-9}$M. Cells were harvested after eighteen hours of AGN 191183 treatment and luciferase activity was measured as described above.

Preliminary experiments indicated that $10^{-9}$M AGN 193109 was relatively ineffective at inhibiting the response to of $10^{-9}$M AGN 191183 in HeLa cells. This contrasted with the ability of $10^{-9}$M AGN 193109 to inhibit $10^{-8}$M ATRA in CV-1 cells (FIG. 2).

Figure 14:
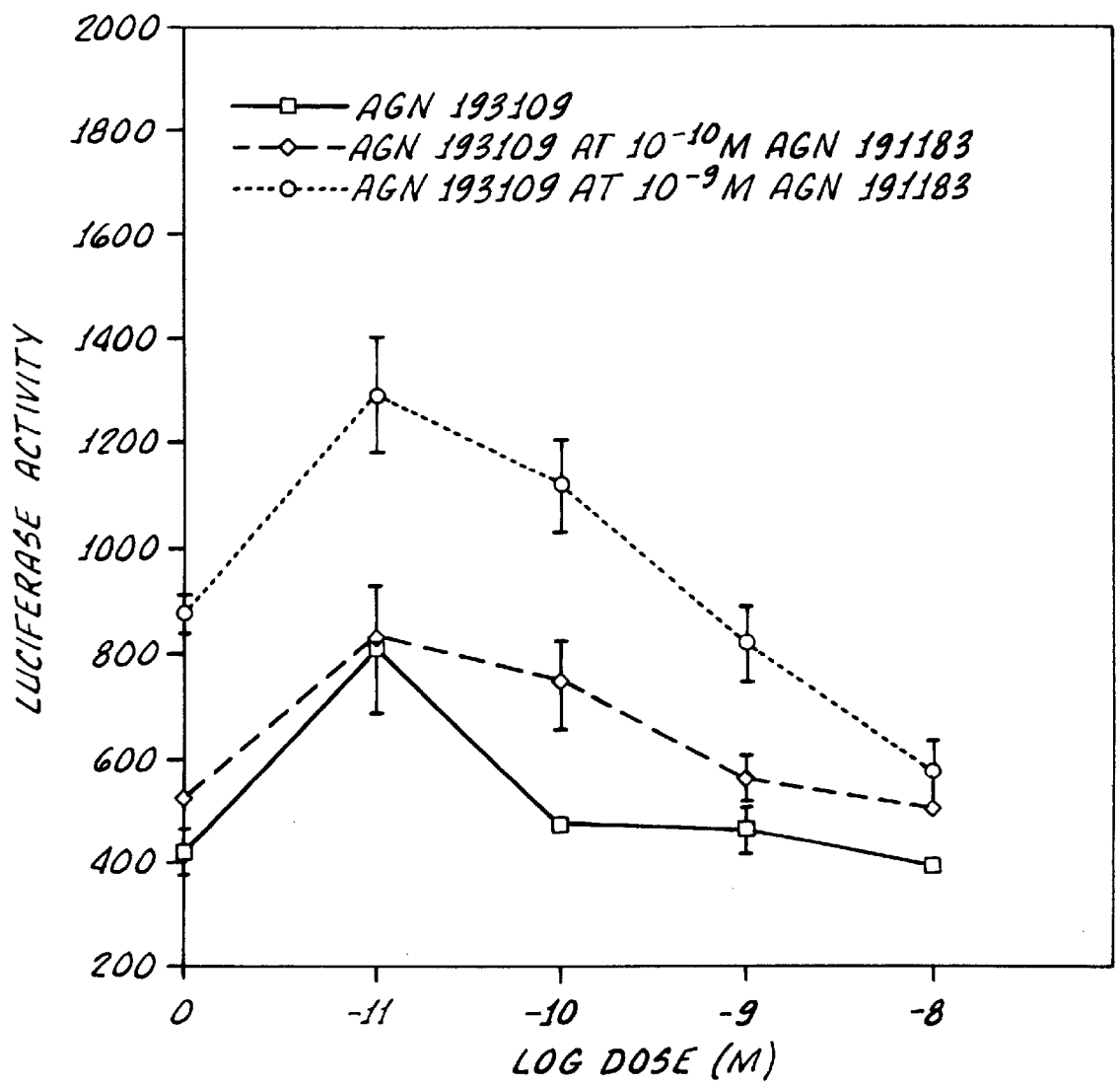
FIG. 14 is a line graph showing the effect of AGN 193109 alone and in combination with AGN 191183 on HeLa cells cotransfected with RAR-γ and the RAR responsive MTV-TREp-Luc reporter construct. Drug treatments illustrated in the graph are: AGN 193109 alone (square), AGN 193109 in combination with AGN 191183 at $10^{-10}$M (diamond) and AGN 193109 in combination with AGN 191183 at $10^{-9}$M.

The results presented in FIG. 14 supported the prediction that AGN 193109 stimulated the formation of RAR*. Consistent with our characterization of the antagonist and negative hormone activities of AGN 193109, treatment with AGN 193109 resulted in a biphasic dose response curve. The lowest doses of AGN 193109 ($10^{-11}$ and $10^{-10}$M) resulted in a stimulation of luciferase activity over that of AGN 191183 alone. This effect suggests that RAR*s are generated by AGN 193109. Curiously, this was also seen for AGN 193109 treatment alone, suggesting that RAR*'s can respond to an endogenous ligand. AGN 191183 is a synthetic retinoid agonist and, like ATRA, activates transcription through the RARs. Substitution of AGN 191183 for ATRA in Example 7 would give qualitatively similar results (i.e., AGN 193109 would antagonize the effect of 10 nM AGN 191183). Example 16 illustrates that, while AGN 193109 can function as an antagonist of RAR agonists, dosing conditions could easily be identified wherein AGN 193109 coadministration potentiated activation mediated by an RAR agonist. It is important to note that the doses of the compounds used in Example 16 are substantially lower than the doses employed in the procedure described under Example 7. We proposed that AGN 193109 treatment could lead to RAR heterogeneity RARs versus RAR*s. The apparent heterogeneity (i.e., ability to potentiate) appears to have different windows in transactivation versus AP-1 repression. The reason that the curves are biphasic is because, with increasing amounts of AGN 193109, there is proportionately less RAR available to bind the agonist. This doesn't appear to be the case for AP-1 repression and we are left to speculate that this difference must reflect two distinct mechanisms for transactivation and AP-1 repression by the same receptor species.

Clinical results have confirmed that some retinoids are useful for inhibiting the growth of premalignant and malignant cervical lesions. Exemplary studies supporting this conclusion have been published by Graham et al. in *West. J. Med.* 145: 192 (1986), by Lippman et al. in *J. Natl. Cancer Inst.* 84:241 (1992), and by Weiner et al. in *Invest. New Drugs* 4:241 (1986)).

Similar conclusions are supported by the results of in vitro studies that used cultured cells to quantitate the antiproliferative effects of various retinoids. More specifically, Agarwal et al. in *Cancer Res.* 51:3982 (1991) employed the ECE16-1 cell line to model the early stages of cervical dysplasia and demonstrated that retinoic acid could inhibit epidermal growth factor (EGF) dependent cellular proliferation.

Example 17 describes the methods used to demonstrate that AGN 193109 can antagonize the activity of the AGN 191183 retinoid agonist which inhibited proliferation of the ECE16-1 cell line.

EXAMPLE 17

AGN 193109 Antagonizes the Antiproliferative Effect of Retinoids in ECE16-1 Cells ECE16-1 cells were seeded at a density of $1\times10^4$ cells per cm$^2$ in complete medium containing DMEM:F12 (3:1), nonessential amino acids, 5% FBS, 5 µg/ml transferrin, 2 nM of 3,3',5 triiodothyronine (thyroid hormone or "T$_3$"), 0.1 nM cholera toxin, 2 mM L-glutamine, $1.8\times10^{-4}$M adenine and 10 ng/ml EGF. Cells were allowed to attach to plates overnight and then shifted to defined medium containing DMEM:F12 (3:1), 2 mM L-glutamine, nonessential amino acids, 0.1% bovine serum albumin, $1.8\times10^{-4}$M adenine, 5 µg/ml transferrin, 2 nM T$_3$, 50 µg/ml ascorbic acid, 100 ug/ml streptomycin, 100 units/ml penicillin and 50 µg/ml gentamicin. Defined medium (DM) was supplemented with 10 ng/ml EGF. EGF treated cells received 10 nM of the AGN 191183 retinoid agonist in combination with either 0, 0.1, 1.0, 10, 100 or 1000 nM AGN 193109 or 1000 nM AGN 193109 alone. After three days of treatment, cells were harvested as described by Hembree et al. in *Cancer Res.* 54:3160 (1994) and cell numbers determined using a COULTER counter.

Figure 15:
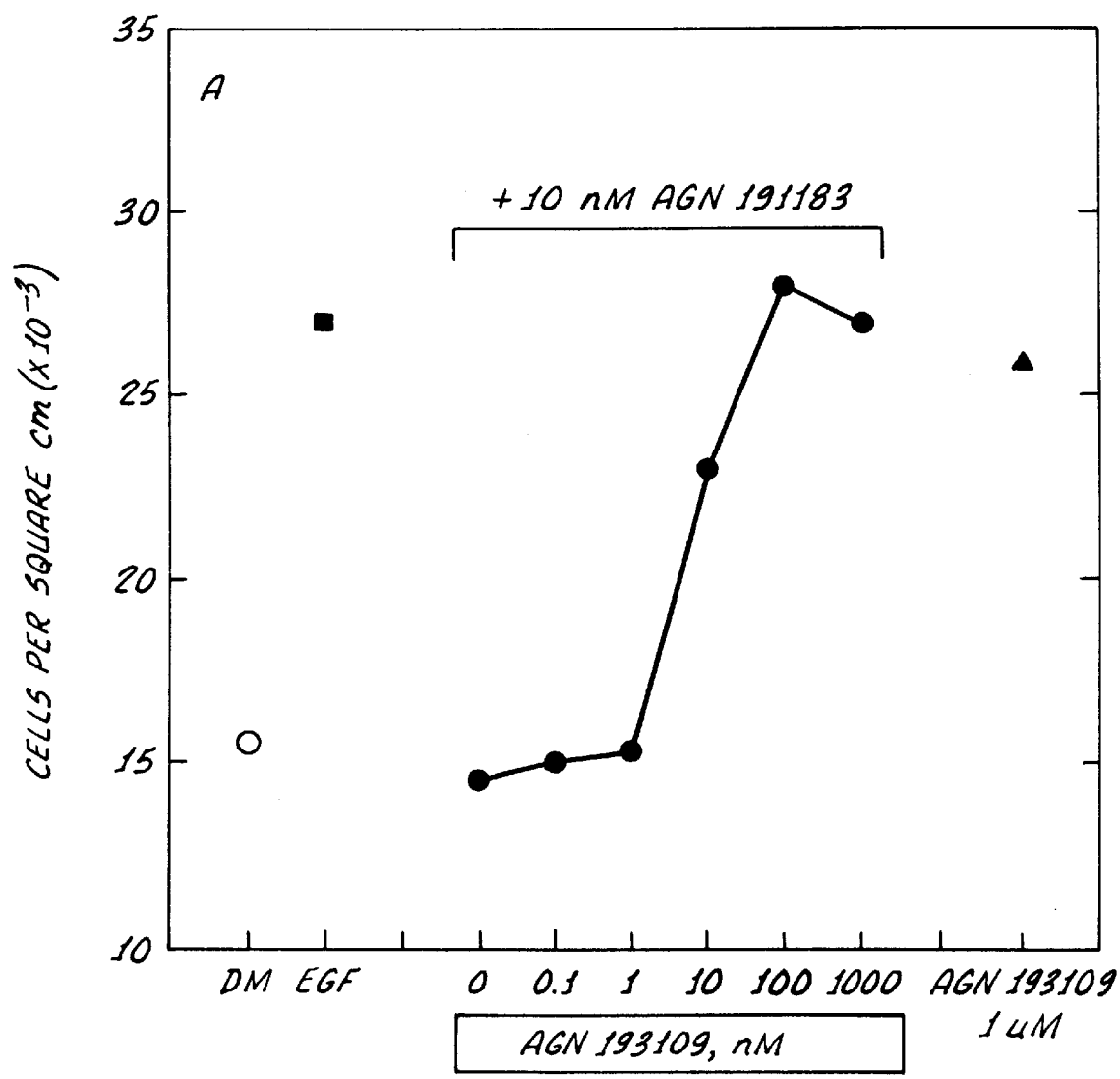
FIG. 15 is a line graph showing that ECE16-1 cells proliferated in response to EGF (filled square) but not in response to defined medium alone (open circle). Cells treated with AGN 193109 alone are represented by the filled triangle. The filled circles represent results obtained for cells treated with 10 nM AGN 191183 and 0–1000 nM AGN 193109.

The results presented in FIG. 15 demonstrated that ECE16-1 cells proliferated in response to EGF but not in defined medium alone. This confirmed the findings published by Andreatta-van Leyen et al. in *J. Cell. Physio.* 160:265 (1994), and by Hembree et al. in *Cancer Res.* 54:3160 (1994). Addition of 10 nM AGN 191183 and 0 nM AGN 193109 completely inhibited EGF mediated proliferation. Thus, AGN 191183 was a potent antiproliferative retinoid. Increasing the AGN 193109 concentration from 0 nM to 10 nM antagonized the AGN 191183 mediated growth inhibition by approximately 50%. A ten-fold molar excess of AGN 193109 completely reversed the antiproliferative effect of AGN 191183. Treatment of cells with 1000 nM AGN 193109 alone had no effect on the EGF mediated proliferation increase. These results proved that AGN 193109 antagonized the antiproliferative effect of a retinoid but had substantially no antiproliferative activity of its own when used to treat cells representing cervical epithelium that is sensitive to growth inhibition by retinoids such as AGN 191183. Notably, there was no evidence that AGN 193109 potentiated the antiproliferative activity of the AGN 191183 agonist using the ECE16-1 model system.

In contrast to the model system represented by the ECE16-1 cell line, there are other examples where cellular proliferation associated with cervical dysplasia cannot be inhibited by retinoid agonists. For example, Agarwal et al. in *Cancer Res.* 54:2108 (1994) described the use of CaSki cells as a model for cervical tumors that are unresponsive to retinoid therapy. As disclosed below, rather than inhibiting cell proliferation, retinoid treatment had substantially no effect on the growth rate of CaSki cells. The following Example addressed the effect of the AGN 193109 negative hormone on the proliferation rates of this cell line. The results unexpectedly proved that AGN 193109 can inhibit the proliferation of cervical tumor cells that are unresponsive to the antiproliferative effects of retinoid agonists.

Example 18 describes the methods used to demonstrate that AGN 193109 inhibited the growth of a cervical tumor cell line that did not respond to the antiproliferative effects of other retinoids such as AGN 191183. Significantly, AGN 193109 displayed antiproliferative activity in the absence of added retinoid.

EXAMPLE 18

AGN 193109 Inhibits the Proliferation Rate of CaSki Cervical Carcinoma-Derived Cell Line We tested the effect of EGF on CaSki cell proliferation, either alone or in combination with the AGN 191183 retinoid agonist and/or the AGN 193109 negative hormone at a concentration of $10^{-6}$M. Cell proliferation assays were performed as described above for studies involving ECE16-1 cells. EGF was added to the retinoid treated cultures to give a final concentration of 20 ng/ml. Cells were treated with AGN 191183 ($10^{-10}$ to $10^{-6}$M) in the presence or absence of $10^{-6}$M AGN 193109 for a total of three days. The media was replaced with fresh media and each of the two retinoid compounds, as appropriate, every day. Cell numbers were determined using a COULTER counter as described above.

Figure 16:
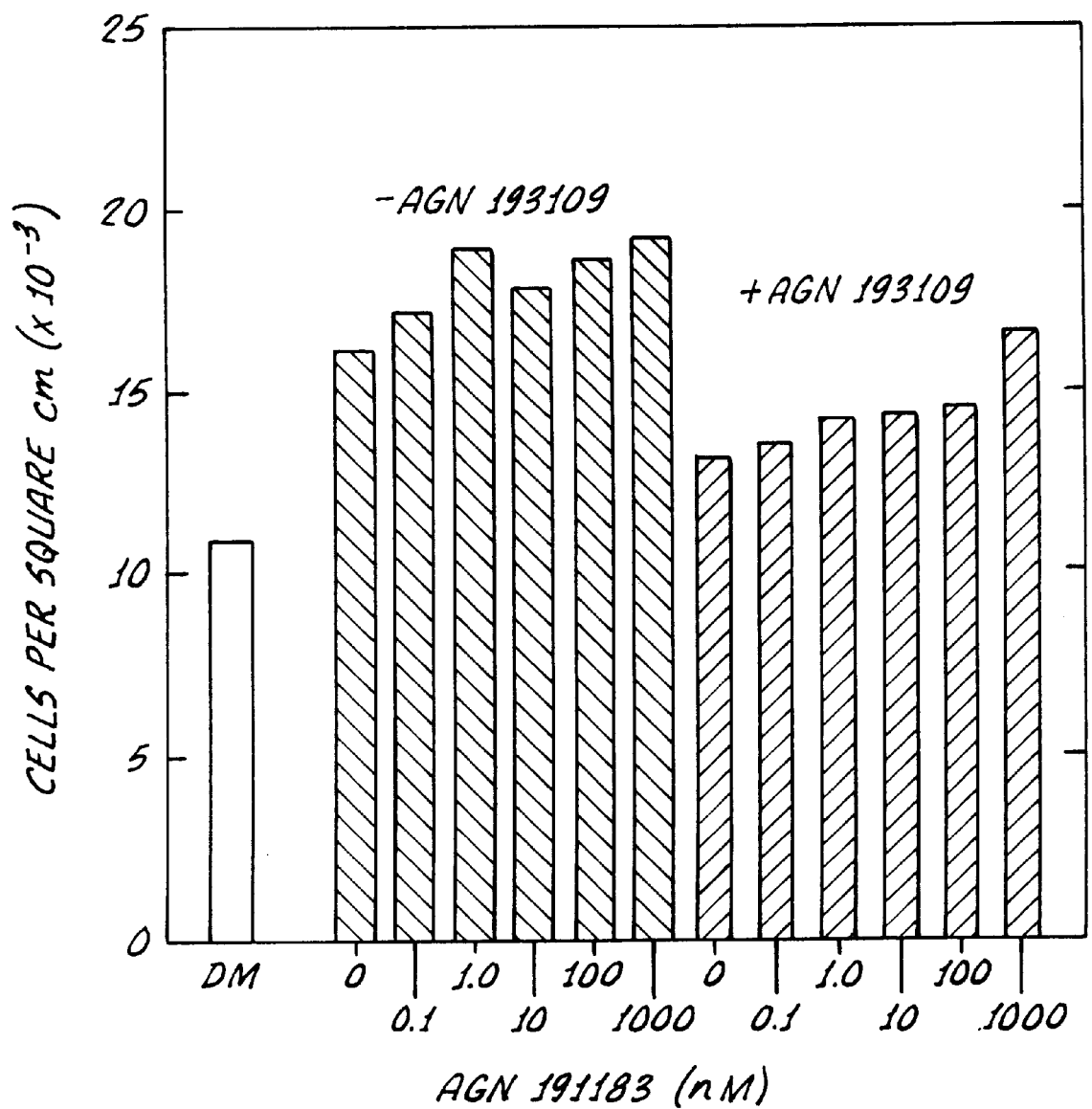
FIG. 16 is a bar graph showing the effect of AGN 193109 on the proliferation of CaSki cells in the presence or absence of the AGN 191183 retinoid agonist. All sample groups received 20 ng/ml of epidermal growth factor (EGF) with the exception of the sample propagated in defined medium (DM) alone (open bar). Stripped bars represent samples propagated in the absence of AGN 193109. Filled bars represent samples propagated in the presence of 1000 nM AGN 193109. The concentrations of AGN 191183 used in the procedure are shown on the horizontal axis.

The results presented in FIG. 16 indicated that CaSki cells were substantially refractory to the effects of a retinoid agonist and that AGN 193109 exhibited antiproliferative activity in the absence of added retinoid. The presence of EGF in the culture media stimulated CaSki cell growth. This conclusion was based on comparison of the stripped bar representing no AGN 191183 and the open bar representing defined growth media ("DM") alone. AGN 191183 treatment had no antiproliferative activity on the CaSki tumor cell line. We discounted any slight increase in the cellular proliferation rate associated with the retinoid agonist, because a ten thousand fold increase in the retinoid agonist concentration was associated with only roughly a 20% increase in the proliferation rate. Thus, the AGN 191183 agonist had substantially no effect on the proliferation rate of CaSki cells.

The results presented in FIG. 16 also indicated that AGN 193109 inhibited proliferation of the CaSki cervical epithelial cell line. This conclusion was based on comparison of the measurements appearing as the "0" AGN 191183 black bar and the "0" AGN 191183 stripped bar. Thus, AGN 193109 was capable of stimulating a biological response in the absence of added retinoid agonist when used to treat cervical tumor cells that were not growth inhibited by retinoid agonists such as AGN 191183.

Our discovery that the AGN 193109 negative hormone could inhibit cellular proliferation was consistent with a model in which unliganded RAR mediated the expression of genes that were required for proliferation. While an RAR agonist such as AGN 191183 had substantially no effect, or perhaps promoted cellular proliferation slightly, AGN 193109 had an antiproliferative effect. The AGN 193109 negative hormone likely bound RARs thereby promoting NCP association and causing the RARs to adopt an inactive conformation. According to our model, this repressed gene activity that was positively regulated by unliganded RARs. This ability of AGN 193109 to down-regulate the activity of unliganded RARs likely resulted from its ability to promote the association of RARs and NCPs.

Those having ordinary skill in the art will appreciate that some retinoid agonists are useful for controlling the undesirable consequences of cell growth that follows retinal detachment. After retinal detachment the retinal pigment epithelium (RPE) dedifferentiates, proliferates and migrates into the subretinal space. This process can negatively impact the success of surgical procedures aimed at retinal reattachment. Campochiaro et al. in *Invest. Opthal & Vis. Sci.* 32:65 (1991) have demonstrated that RAR agonists such as ATRA exhibited an antiproliferative effect on the growth of primary human RPE cultures. Retinoid agonists have also been shown to decrease the incidence of retinal detachment following retinal reattachment surgery (Fekrat et al. *Opthamology* 102:412 (1994)). As disclosed in the following Example, we analyzed the ability of the AGN 193109 negative hormone to suppress growth in primary human RPE cultures.

Example 19 describes the methods used to demonstrate that AGN 193109 potentiated the antiproliferative effect of a retinoid antagonist in a primary culture of human retinal pigment epithelium.

EXAMPLE 19

AGN 193109 Potentiates the Antiproliferative Activity of ATRA

Primary cultures of human retinal pigment epithelium (RPE) were established according to the method described by Campochiaro et al. in *Invest. Opthal & Vis. Sci.* 32:65 (1991). $5 \times 10^4$ cells were plated in 16-mm wells of 24-well multiwell plates in DMEM (Gibco) containing 5% FBS. Cells were mock treated with ethanol vehicle alone, ATRA ($10^{-10}$ to $10^{-6}$M) in ethanol, AGN 193109 ($10^{-10}$ to $10^{-6}$M) in ethanol, or ATRA ($10^{-10}$ to $10^{-6}$ M) and $10^{-6}$M AGN 193109. Cells were fed with fresh media containing the appropriate concentrations of these compounds every two days for a total of five days of treatment. Cells were removed from the plates by gentle digestion with trypsin and the number of cells was counted with an electronic cell counter.

The results presented in FIG. 17 indicated that AGN 193109 dramatically potentiated the antiproliferative activity of ATRA on RPE cells. Treatment of primary RPE cells with ATRA led to a dose dependent decrease in RPE cell proliferation with an approximately 40% decrease at $10^{-6}$M ATRA relative to control cultures. AGN 193109 treatment did not substantially alter the growth rate of the RPE cells at any concentration tested in the procedure. Unexpectedly, the combination of ATRA ($10^{-11}$ to $10^{-6}$M) and $10^{-6}$M AGN 193109 had a stronger antiproliferative activity than ATRA alone. Thus, AGN 193109 cotreatment potentiated the antiproliferative effect of ATRA. More specifically, the results shown in the Figure indicated that the antiproliferative effect of $10^{-8}$M ATRA was obtainable using only $10^{-10}$M ATRA in combination with $10^{-7}$M AGN 193109. Thus, the AGN 193109 negative hormone advantageously enhanced the antiproliferative activity of ATRA by approximately 100 fold.

In an independent experiment, comparison of the antiproliferative effect of ATRA ($10^{-11}$ to $10^{-6}$M) with that of ATRA and $10^{-6}$M AGN 193109 again demonstrated the apparent increase in sensitivity of primary RPE cells to ATRA in the presence of AGN 193109. In this system, AGN 193109 neither functioned as a retinoid antagonist nor exhibited an antiproliferative effect when used alone. However, AGN 193109 coadministration potentiated the antiproliferative activity of the retinoid agonist.

AGN 193109 was tested for its ability to potentiate the antiproliferative effect of 13-cis retinoic acid (13-cis RA) in primary RPE cultures using conditions and techniques to measure RPE cell proliferation described above. Notably, 13-cis RA is clinically significant. More particularly, 13-cis RA is useful in the treatment of several disease states, including acne (Peck et al. *N. Engl. J. Med.* 300:329 (1977); Jones et al. *Br. J. Dennatol.* 108:333 (1980)), and squamous cell carcinoma of the skin and cervix in combination treatment with interferon 2α (Lippman et al. *J. Natl. Cancer Inst.* 84:241 (1992); Moore et al. *Seminars in Hematology* 31:31 (1994)).

The results presented in FIG. 18 indicated that both 13-cis RA($10^{-12}$ to $10^{-6}$M) and ATRA ($10^{-12}$ to $10^{-6}$M) effectively inhibited RPE cell growth. Notably, the 13-cis isomer was approximately two orders of magnitude less effective in this assay when compared with ATRA. Similar to the results obtained using coadministration of AGN 193109 and ATRA (above), coadministration of AGN 193109 (either $10^{-8}$ or 10–6M) with 13-cis RA ($10^{-12}$ to $10^{-6}$M) dramatically increased the potency of 13-cis RA in mediating repression of RPE cell proliferation. In contrast to treatment with 13-cis RA alone, coadministration of AGN 193109 enhanced the potency of 13-cis RA. Thus, AGN 193109 potentiated the antiproliferative activity of 13-cis RA.

We next tested the ability of AGN 193109 to potentiate the activities of other nuclear receptor hormones in primary RPE cell cultures. Dexamethasone, a synthetic glucocorticoid receptor agonist, is one member of a class of compounds that have been used clinically for their potent anti-inflammatory and immunosuppressive properties. Thyroid hormone (T3; 3,3',5'-Triiodothyronine) is a natural thyroid hormone receptor agonist used primarily for hormone replacement therapy in the treatment of hypothyroidism. Methods used in these experiments were identical to those described above for procedures employing ATRA and 13-cis RA.

The results of these procedures indicated that coadministration of AGN 193109 and the nuclear receptor agonists potentiated the antiproliferative activities of the nuclear receptor agonists. More specifically, the results presented in FIG. 19 showed that single-agent treatment of RPE cells with either dexamethasone ($10^{-11}$ to $10^{-6}$M) or ATRA ($10^{-12}$ to $10^{-6}$M) was substantially unable to inhibit RPE cell proliferation. However, treatment of RPE cells with dexamethasone ($10^{-11}$ to $10^{-6}$M) and either $10^{-8}$ or $10^{-6}$M AGN 193109 repressed RPE cell proliferation to an extent that approximated the inhibition caused by treatment with ATRA. Similarly, the results presented in FIG. 20 indicated that AGN 193109 potentiated the antiproliferative activity of thyroid hormone. Similar to the results obtained using dexamethasone, the proliferation of RPE cells was refractory to single-agent treatment with thyroid hormone ($10^{-11}$ to $10^{-6}$M). However, co-treatment of RPE cells with thyroid hormone ($10^{-11}$ to $10^{-6}$M) and AGN 193109 (either $10^{-8}$ or $10^{-6}$M) inhibited RPE cell proliferation in a thyroid hormone dependent manner. We concluded that AGN 193109 rendered primary RPE cultures sensitive to the antiproliferative effects of these nuclear receptor agonists. The mechanism by which AGN 193109 mediated these effects likely involved modulation of NCP/RAR interactions.

We additionally examined the effect of AGN 193109 on the expression of marker genes in other experimental systems that were sensitive to retinoid agonists. Both the MRP8 and stromelysin genes are known to be inhibited by retinoid agonists in a variety of biological systems. For example, Wilkinson et al. in *J. Cell Sci.* 91:221 (1988) and Madsen et al. in *J. Invest. Dermatol.* 99:299 (1992) have disclosed that MRP8 gene expression was elevated in psoriasis. Conversely, MRP8 gene expression was repressed by the retinoid agonist AGN 190168 in human psoriatic skin (Nagpal et al., submitted 1995), in human keratinocyte raft cultures (Chandraratna et al. *J. Invest. Dermatol.* 102:625 (1994)) and in cultured human newborn foreskin keratinocytes (Thacher et al. *J. Invest. Dermatol.* 104:594 (1995)). Nagpal et al. in *J. Biol. Chem.* 270:923 (1995) have disclosed that stromelysin mRNA levels were repressed by retinoid agonists such as AGN 190168 in cultured human newborn foreskin keratinocytes. We analyzed the regulated expression of these genes following treatment of cultured human newborn foreskin keratinocytes with either the AGN 191183 retinoid agonist or AGN 193109.

Example 20 describes the methods used to demonstrate that AGN 193109 inhibited MRP-8 expression in cultured keratinocytes.

EXAMPLE 20

AGN 193109 Inhibits MRP-8 Expression in Keratinocytes

Primary foreskin keratinocytes were isolated according to the procedure described by Nagpal et al. in *J. Biol. Chem.* 270:923 (1995) and cultured in keratinocyte growth medium (KGM) that was purchased from Clonetics. After 3 days of treatment with AGN 191183 ($10^{-7}$M) or AGN 193109 ($10^{-6}$M), total cellular RNA was isolated from treated and control keratinocytes according to standard methods. The mRNA was reverse transcribed into cDNA which then served as the template in a PCR amplification protocol using primers specific for either the glyceraldehyde phosphate dehydrogenase (GAPDH) housekeeping gene or MRP-8. The GAPDH primers had the sequences 5'-CCACCCATGGCAAATTCCATGGCA-3' (SEQ ID NO:6) and 5'-TCTAGACGGCAGGTCAGGTCCACC-3' (SEQ ID NO:7). The MRP-8 primers had the sequences 5'-ACGCGTCCGGAAGACCIGGT-3' (SEQ ID NO:8) and 5'-ATTCTGCAGGTACATGTCCA-3' (SEQ ID NO:9). An aliquot from the MRP-8 amplification reaction (10 $\mu$l) was removed after every cycle of PCR amplification starting from 12 cycles and ending at 21 cycles. Similarly, an aliquot of the GAPDH amplification reaction was removed after every PCR cycle starting at 15 cycles and ending at 24 cycles. The samples were electrophoresed on 2% agarose gels and the separated amplification products detected by ethidium bromide staining. The staining intensity of the amplification products served as a quantitative measure of the amount of starting mRNA specific for the given primer set.

The results of this procedure indicated that both AGN 191183 and AGN 193109 independently inhibited MRP-8 expression in keratinocytes. The intensity of the stained GAPDH amplification product was substantially equivalent in the lanes of the gel representing starting material isolated from control, AGN 191183, and AGN 193109 treated keratinocytes. Weak bands representing the GAPDH amplification product were first detectable in lanes corresponding to samples removed after 18 cycles of PCR amplification. The equivalent staining intensities among the various lanes of the gel indicated that equivalent masses of starting material were used for all samples. Accordingly, differences in the intensities of stained bands representing MRP-8 amplification products were indicative of differences in MRP-8 mRNA expression among the various starting samples. As expected, the MRP-8 amplified signal was inhibited in AGN 191183 ($10^{-7}$M) treated cultures relative to an untreated control. AGN 193109 ($10^{-6}$M) treatment of cultured keratinocytes also repressed MRP8 expression as judged by lower intensity of stained amplification product.

As illustrated in the following Example, AGN 193109 also inhibited expression of a second marker gene in keratinocytes. Nagpal et al. in *J Biol. Chem.* 270:923 (1995) disclosed that stromelysin mRNA expression was down-regulated by RAR specific agonists in cultured newborn human foreskin keratinocytes. Nicholson et al. (*EMBO J.* 9:4443 (1990)) disclosed that an AP-1 promoter element played a role in the retinoid-dependent negative regulation of the stromelysin-1 gene. Thus, it was of interest to determine whether AGN 193109 could alter the expression of this gene.

Example 21 describes the methods used to demonstrate that AGN 193109 inhibited stromelysin-1 gene expression in the absence of an exogenously added retinoid agonist.

EXAMPLE 21

AGN 193109 Inhibits Stromelysin-1 Expression in Cultured Keratinocytes

Primary foreskin keratinocytes were either mock treated or treated for 24 hours with the RAR agonist AGN 191183 ($10^{-7}$M), or AGN 193109 ($10^{-6}$M). Total RNA prepared from mock-treated and retinoid-treated keratinocytes was reverse transcribed and the resulting cDNA was PCR amplified using β-actin or stromelysin-1 oligo primers exactly as described by Nagpal et al. in *J. Biol. Chem.* 270:923 (1995)), the disclosure of which has been incorporated by reference. A sample (10 μl) from the PCR amplification reaction was removed after every three cycles starting from 18 cycles of PCR amplification. The sample was electrophoresed on a 2% agarose gel and detected after ethidium bromide staining.

Results of these procedures indicated that AGN 193109 inhibited stromelysin-1 gene expression in the absence of an exogenously added retinoid agonist. More specifically, ethidium-stained bands representing β-actin amplification products were easily detectable the agarose gels after 18 cycles of PCR. While all band intensities increased with additional cycles of the amplification reaction, stained bands were somewhat less intense in samples representing AGN 191183 treated cells. This indicated that a slightly lesser amount of RNA must have been present in the starting samples corresponding to cells treated with AGN 191183. The results also indicated that stromelysin-1 mRNA was detectable in mock-treated keratinocytes starting at 33 cycles of PCR amplification. As expected, stromelysin-1 mRNA expression was inhibited after AGN 191183 ($10^{-7}$M) treatment as judged by the weaker band intensity on when compared with samples derived from mock-treated samples. When normalized to the intensities of the β-actin amplification products, and consistent with the results obtained in measurements of MRP-8 expression, AGN 193109 ($10^{-6}$M) treatment of keratinocytes resulted in down-regulation of stromelysin-1 mRNA levels. Indeed, the down-regulation stimulated by AGN 193109 treatment was indistinguishable from the down-regulation caused by treatment of keratinocytes with the RAR agonist AGN 191183.

As disclosed herein, AGN 193109 can have any of three possible effects with respect to modulating the activity of a coadministered steroid superfamily agonist. First, AGN 193109 may have no effect. Second, AGN 193109 may antagonize the effect of the agonist, thereby leading to a decrease in the activity of the agonist. Finally, AGN 193109 may potentiate the activity of the agonist, thereby leading to a stimulation of the measured effect produced by the agonist.

Compounds having activities that can be modulated by AGN 193109 include retinoid receptor agonists and agonists which bind to other members of the steroid receptor superfamily. This latter category of agonists includes vitamin D receptor agonists, glucocorticoid receptor agonists and thyroid hormone receptor agonists. Peroxisome proliferator-activated receptors, estrogen receptor and orphan receptors having presently unknown ligands may also be potentiated by AGN 193109. In the case where the steroid superfamily agonist is an RAR agonist, AGN 193109 may either antagonize or potentiate the activity of that agonist. In the case where the agonist used in combination with AGN 193109 is a compound that can bind to a nuclear receptor other than an RAR, coadministration of AGN 193109 will either have no effect or will sensitize of the system to the agonist so that the activity of the agonist is potentiated.

A generalized exemplary procedure for determining which of the three possible activities AGN 193109 will have in a particular system follows. This description illustrates each of the possible outcomes for AGN 193109 coadministration with a steroid receptor superfamily agonist. Biological systems useful for assessing the ability of AGN 193109 to modulate the activity of a nuclear receptor agonist include but are not limited to: established tissue culture cell lines, virally transformed cell lines, ex-vivo primary culture cells and in vivo studies utilizing living organisms. Measurement of the biological effect of AGN 193109 in such systems could include determination of any of a variety of biological endpoints. These endpoints include: analysis of cellular proliferation, analysis of programmed cell death (apoptosis), analysis of the differentiation state of cells via gene expression assays, analysis of the ability of cells to form tumors in nude mice and analysis of gene expression after transient or stable introduction of reporter gene constructs.

For illustrative purposes, an mRNA species designated as mRNA "X" is expressed from gene "X" in primary cultured "Y" cells isolated from the organ "Z." Under standard culture conditions, where several "Y" cell genetic markers are maintained, including expression of gene "X", addition of a retinoid agonist leads to a decrease in the abundance of "X" mRNA. Analysis of gene X expression can be assessed via isolation of cellular mRNA and measurement of the abundance of X mRNA levels via polymerase chain reaction, ribonuclease protection or RNA blotting procedures such as Northern analyses. After isolation from organ Z, primary Y cells are cultured in an appropriate growth medium. The primary cultures are then plated into tissue culture plates for expansion of the cell population. This step facilitates separation of the cells into four sample groups so that various doses of the retinoid agonist and AGN 193109 can be delivered. The first group will be a control, receiving vehicle only. The second group will receive the RAR agonist, retinoic acid, delivered in ethanol, in amounts sufficient to provide final concentrations in the range of from $10^{-11}$ to $10^{-6}$M. The lowest dose may need to be empirically determined depending on the sensitivity of the system. Such determinations fall within the scope of routine experimentation for one having ordinary skill in the art. The third group will receive both the nuclear receptor agonist at the same doses used for treating the cells of group 2, and a constant dose of AGN 193109. The dose of AGN 193109 used for treating the cells of group 3 will also need to be determined empirically, but should approximate the affinity constant (Kd) of AGN 193109 for the RAR subtypes (i.e., at least $10^{-8}$M). The fourth group will receive AGN 193109 at doses minimally including that used for agonist coadministration in group 3. An alternative to this dosing regimen would substitute AGN 193109 for the retinoid agonist described in the foregoing example, as specified in group 2, and a constant dose of retinoid agonist in place of AGN 193109, as specified in groups 3 and 4. After a suitable incubation period, cells should be harvested in a manner suitable for determination of the biological endpoint being measured as an indicator of agonist activity.

For example, analysis of the effect of AGN 193109 on retinoic acid dependent regulation of gene expression would involve comparison of the abundance of the mRNA species X in the mRNA pool harvested from cells treated according to each of the four protocols described above. RNA derived from control cells will serve to determine the baseline expression of X mRNA and will represent a condition corresponding to no repression. Comparison of this level with that measured in the mRNA pool derived from cells treated with retinoic acid will allow for determination of the effect of this agonist on gene expression. Quantitated levels of the repression of specific mRNAs resulting from retinoic acid treatment can then be compared with mRNA abundances from cells treated in parallel with either AGN 193109 alone or AGN 193109 in combination with retinoic acid. While this generalized example illustrates an analysis of the effect of coadministered AGN 193109 on the expression of a gene repressed by a retinoid agonist, the example could alternatively have described analysis of the effect of coadministered AGN 193109 on a gene that was induced by a retinoid agonist. The critical feature for determining whether AGN 193109 will behave as an agonist, as a negative hormone or have no effect in a particular system will involve quantitative comparison of the magnitude of the effect in the presence and absence of AGN 193109.

An example in which AGN 193109 potentiated the activity of a coadministered agonist would be a case in which AGN 193109 cotreatment with retinoic acid resulted in a level of X mRNA expression that is further repressed relative to the level measured in cells treated with retinoic acid alone. More specifically, comparison of the dose response curve of the biological effect (i.e., repression of X mRNA abundance) plotted on the Y-axis versus the dose of the agonist (logarithmic scale) on the X-axis would allow comparison of agonist-mediated repression of X mRNA abundance in the presence and absence of AGN 193109 cotreatment. The ability of AGN 193109 to sensitize the biological response to the agonist, thereby potentiating the activity of the agonist, will be indicated by a leftward shift in the dose response curve. More specifically, in the presence of AGN 193109 less agonist would be required to obtain the same biological effect obtainable using the agonist alone.

An example of AGN 193109 mediating antagonism of a coadministered agonist would be a case in which AGN 193109 cotreatment with retinoic acid resulted in a level of X mRNA expression that is less repressed compared to that measured in cells treated with retinoic acid alone. Comparison of dose response curves of X mRNA repression versus log dose of agonist in the presence and absence of AGN 193109 will demonstrate a shift to the right in the dose response curve. More specifically, in the presence of AGN 193109, more agonist will be necessary to obtain the same biological effect obtainable with single agent treatment with the agonist alone.

The above examples wherein AGN 193109 mediates either antagonism or potentiation describe experimental outcomes for coadministration of AGN 193109 with a retinoid agonist. If, however, the agonist coadministered with AGN 193109 is an agonist capable of binding and activating a member of the steroid receptor superfamily other than an RAR, then instead of antagonizing the agonist, it becomes possible that AGN 193109 would have no effect on the activity of the agonist. If AGN 193109 cotreatment with such an agonist results in a level of mRNA expression which is equal to that measured in cells treated with agonist alone, then AGN 193109's ability to affect the availability of NCPs via promotion of RAR:NCP associations will be silent in this system. This would be an example wherein AGN 193109 has no effect on a coadministered agonist.

Example of Antagonism

The method disclosed in the above generalized example for determining the effect of AGN 193109 coadministered with a retinoid agonist is exemplified by the procedure described under Example 7. CV-1 cells cotransfected with one of the three retinoic acid receptors and the retinoid agonist inducible MTV-TREp-Luc reporter construct were dosed with either ethanol (control, group 1), AGN 193109 at final concentrations of from $10^{-9}$ to $10^{-6}$M (group 2), AGN 193109 at final concentrations of from $10^{-9}$ to $10^{-6}$M coadministered with retinoic acid at $10^{-8}$M (group 3), or retinoic acid ($10^{-8}$M, group 4). Comparison of the luciferase activity of group 1 with that of group 4 allowed determination of the level of retinoid agonist induced expression of the luciferase reporter gene in the absence of added AGN 193109. Comparison of luciferase reporter gene expression in cells of group 3 with that measured in cells of group 4 indicated that AGN 193109 behaved as an antagonist of the retinoid agonist in this system.

Example of Antagonism

The method disclosed in the generalized example for determining the effect of AGN 193109 coadministered with a retinoid agonist was similarly used to determine in Example 17 that AGN 193109 functioned as an antagonist of a retinoid agonist-mediated repression of EGF-stimulated cellular proliferation in ECE-16-1 transformed cervical epithelial cells. In this procedure, treatments of ECE-16-1 cells included a control sample treated with EGF alone (group 1), a sample treated with the combination of EGF and AGN 193109 at a final concentration of $10^{-6}$M (group 2), a sample treated with the combination of EGF and AGN 193109 at final concentrations of from $10^{-10}$ to $10^{-6}$M coadministered with a single dose of the retinoid agonist AGN 191183 at $10^{-8}$M (group 3), and a sample treated with the combination of EGF and AGN 191183 at $10^{-8}$M (group 4). After three days of treatment, cellular proliferation rates were determined. Determination that the cells had been stimulated to proliferate by EGF was possible because an additional control treatment was included wherein cells were exposed to defined medium that did not contain EGF. Comparison of the number of cells in group 1 with the number of cells in group 4 allowed for determination that RAR agonist AGN 191183 repressed the EGF-stimulated proliferation of ECE-16-1 cells. Comparison of group 3 with group 4 indicated that AGN 193109 antagonized the activity of the RAR agonist in this system.

Example of Potentiation

The method disclosed in the generalized example for determining the effect of AGN 193109 coadministered with a retinoid agonist was also used in Example 14 to determine that AGN 193109 potentiated the activity of a nuclear receptor agonist in HeLa cells transfected with the 1,25-dihydroxyvitamin $D_3$ inducible MTV-VDRE-Luc reporter gene. Treatments of transfected cells included vehicle alone (control, group 1), 1,25-dihydroxyvitamin $D_3$ at final concentrations of from $10^{-10}$ to $10^{-7}$M (group 2), 1,25-dihydroxyvitamin $D_3$ at final concentrations of from $10^{-10}$ to $10^{-7}$M coadministered with AGN 193109 at a final concentration of either $10^{-8}$ or $10^{-7}$M (group 3), and AGN 193109 as a single agent treatment at a final concentration of either $10^{-8}$ or $10^{-7}$M (group 4). Comparison of the luciferase activity measured in group 1 (control) cells with that of group 2 cells allowed for determination that 1,25-dihydroxyvitamin $D_3$ stimulated luciferase activity was dose-dependent. Comparison of luciferase activity measured in cells of group 4 (AGN 193109 single agent treatment) with that measured in cells of group 3 (AGN 193109 coadministration) similarly allowed for determination of dose-dependent 1,25-dihydroxyvitamin $D_3$ stimulated luciferase activity in the presence of a given concentration of AGN 193109. In this instance, the zero value represented the luciferase activity in cells treated with AGN 193109 alone (group 4). Such a dosing regimen allowed for comparison of three 1,25-dihydroxyvitamin $D_3$ dose response curves. Comparison of the dose response curve of 1,25-dihydroxyvitamin $D_3$ in the absence of AGN 193109 with the curve representing coadministration of AGN 193109 (either $10^{-8}$ or $10^{-7}$M) demonstrated potentiation of the agonist activity as evidenced by a leftward shift in the half-maximal response.

Example of Potentiation

The method disclosed in the generalized example for determining the effect of AGN 193109 coadministered with a retinoid agonist was further used to determine in Example 19 that AGN 193109 potentiated the antiproliferative activity of an RAR agonist in primary cultures of human retinal pigment epithelium cells. Treatments of cells included: ethanol vehicle alone (group 1), retinoic acid at final concentrations of from $10^{-10}$ to $10^{-6}$M (group 2), retinoic acid at final concentrations of from $10^{-10}$ to $10^{-6}$M coadministered with $10^{-6}$M AGN 193109 (group 3), and AGN 193109 alone at final concentrations of from $10^{-10}$ to $10^{-6}$M (group 4). Comparison of assay results obtained using cells of groups 1 and 2 allowed for determination of the dose dependent inhibition of proliferation of these cells by retinoic acid. Similarly, comparison of results obtained using cells of group 3 with those of group 1 allowed for determination of the dose dependent inhibition of proliferation of these cells by retinoic acid in the presence of coadministered AGN 193109. Group 4 demonstrated the inability of AGN 193109 to substantially alter the proliferation rate of these cells when used as a single treatment agent. Comparison of the dose response curves of retinoic acid mediated repression of cellular proliferation generated in groups 2 and 3 provided the basis for the conclusion that AGN 193109 sensitized primary RPE cells to the antiproliferative effects of the RAR agonist, thereby potentiating the activity of the RAR agonist.

As indicated above, Agarwal et al., in *Cancer Res.* 54:2108 (1994)), showed that CaSki cell growth, unlike the growth of HPV immortalized ECE-16-1 cells, was not inhibited by treatment with retinoid agonists. As disclosed herein, we unexpectedly found that CaSki cell growth was inhibited by AGN 193109 in the absence of a retinoid agonist. The following Example illustrates how AGN 193109 can be used to inhibit the growth of CaSki cell tumors in vivo.

EXAMPLE 22

Inhibition of CaSki Cell Tumor Growth in Nude Mice Following Administration of AGN 193109

$1\times10^6$ CaSki cells are injected into each of a panel of nude mice. Tumor formation is assessed using techniques that will be familiar to one having ordinary skill in the art. After injection, mice are randomly divided into control and test groups. The control group receives a placebo. The test group is administered with AGN 193109. Animals administered with the placebo receive intragastric intubation of corn oil. The test animals receive 20 $\mu$Mol/kg AGN 193109 in corn oil daily for the period of the treatment. Tumor volume is measured in cubic milliliters using graduated calipers. Tumor volume is plotted as function of time. Mice receiving AGN 193109 exhibit tumors which are significantly reduced in their growth rate as compared to tumors in control mice as judged by tumor size and number over the period of the study. This result provides an in vivo demonstration that AGN 193109 inhibits the growth of an advanced cervical carcinoma that is resistant to therapy comprising administration of a retinoid agonist.

As indicated above, CaSki cells are a model of cervical tumors that are not responsive to retinoid agonist therapy. However, herein we have disclosed that CaSki cell growth was inhibited by AGN 193109 in the absence of treatment with a retinoid agonist. The ability of AGN 193109 to inhibit the proliferation of CaSki cells suggested that AGN 193109 could be used to therapeutically treat cervical carcinomas that are insensitive to retinoid agonist therapy. The following Example illustrates one method that can be used to assess the therapeutic potential of AGN 193109 in the treatment of a cervical carcinoma.

EXAMPLE 23

Assessing the Therapeutic Potential of AGN 193109 in Patients Having Cervical Carcinoma A patient presenting with an advanced cervical carcinoma is first identified. A cervical biopsy is obtained according to methods that will be familiar to one having ordinary skill in the art. Cells from the explanted tumor are propagated in tissue culture according to standard techniques to provide cell numbers sufficient to allow division into three sample groups. Culture conditions described by Agarwal et al. in *Cancer Res.* 54:2108 (1994) are employed for this purpose. The first group is reserved as a control and receives vehicle alone (ethanol). The second group is treated with the RAR agonist retinoic acid at a concentration of from $10^{-10}$ to $10^{-6}$M. The third group is treated with AGN 193109 at doses ranging from $10^{-10}$ to $10^{-6}$M. Cells are fed with fresh growth medium daily and are provided with the retinoids described above as appropriate for each sample group. Cells are counted after three days using an electric cell counter. Comparison of the number of cells in control cultures with the number of cells in retinoic acid treated cultures indicates the RAR agonist does not substantially inhibit the growth rate of the cultured cervical carcinoma cells. In contrast, cells treated with AGN 193109 exhibit a dose-dependent decrease in cell number when compared with cell counts in the control group. This result, wherein AGN 193109 treatment inhibits cultured cervical carcinoma cell proliferation, indicates that AGN 193109 will be a useful therapeutic agent for treating cervical carcinoma patients having metastatic disease.

Cervical carcinoma patients having undergone surgery for the removal of primary tumors and who present with metastatic disease are enlisted in a randomized clinical study seeking to demonstrate the therapeutic benefit of AGN 193109 in this indication. Patients are divided into two groups. The first group is a control group while members of the second group are treated with AGN 193109. AGN 193109 is combined with a pharmaceutically acceptable excipient to produce a composition suitable for systemic administration, all according to techniques that will be familiar to one having ordinary skill in the art. The control group is administered a placebo formulation and the experimental group is administered with the formulation containing the AGN 193109 negative hormone. Dosing of patients is at the maximum tolerated dose and is performed every other day for a period of from three months to one year. The outcome of the study is quantified via measurement of disease-free survival over time. Individuals receiving AGN 193109 display a significant increase in disease-free survival, including a disproportionate number of patients displaying complete remission of their metastatic disease. This result indicates that AGN 193109 has therapeutic utility for in vivo treatment of cervical carcinomas that are unresponsive to the antiproliferative effects of retinoid agonists, such as retinoic acid.

As disclosed above, AGN 193109 potentiated the antiproliferative activity of RAR agonists in primary cultures of human retinal pigment epithelium cells. Accordingly, coadministration of AGN 193109 with an RAR agonist in vivo is reasonably expected to increase the therapeutic index of the agonist because a lesser amount of the RAR agonist will be required to obtain the same therapeutic endpoint. Additionally, AGN 193109 has been demonstrated to sensitize primary cultures of human retinal pigment epithelium cells to the antiproliferative effects of glucocorticoid and thyroid hormone receptor agonists. The following rabbit model of PVR will be utilized in two separate studies to demonstrate the increased therapeutic index obtained via coadministration of AGN 193109 with an RAR agonist (13-cis retinoic acid) or a thyroid hormone receptor agonist, respectively. Notably, the rabbit model of retinal redetachment published by Sen et al. in *Arch. Opthalmol.* 106:1291 (1988), has been used to demonstrate that retinoid agonists which inhibit proliferation of primary RPE cells in vitro also inhibit the frequency of retinal detachment in vivo (Araiz et al. *Invest. Opthalmol.* 34:522 (1993)). Thus, with respect to their use as therapeutics in the prevention of retinal detachment, a correlation between the in vitro and in vivo activities of retinoid agonists has already been established. The following Examples illustrate how AGN 193109 can be used in therapeutic applications directed at preventing retinal detachment.

EXAMPLE 24

Use of AGN 193109 to Increase the Therapeutic Potential of Steroid Superfamily Receptor Agonists in the Treatment of Proliferative Vitreoretinopathy (PVR)

In a first study, human RPE cells are injected into the vitreous cavity of rabbit eyes according to the method described by Sen et al. in *Arch. Opthalmol.* 106:1291 (1988). After intravitreal injection, the rabbits are divided into five groups. The first group (control) will receive vehicle alone by intravitreal injection. The second group receives retinoic acid as single agent treatment (100 μg) by intravitreal injection. The third group receives AGN 193109 as a single agent treatment (100 μg) by intravitreal injection. The fourth group receives by intravitreal injection the RAR agonist (retinoic acid) at a dose one-tenth the amount administered to group 2 (10 μg). The fifth group receives the combination of AGN 193109 (100 μg) and retinoic acid (10 μg) by intravitreal injection. Animals receive a single intravitreal injection of the appropriate treatment one day after intravitreal injection of human RPE cells. Rabbits are examined by indirect ophthalmoscopy on days 7, 14 and 28, and are graded for the frequency and severity of tractional retinal detachment. Rabbits from the group injected with 100 μg retinoic acid exhibit a significantly reduced frequency and severity of retinal detachment compared to control rabbits or rabbits receiving either AGN 193109 or retinoic acid (10 μg) alone. Rabbits in the group administered with the combination of AGN 193109 and retinoic acid (10 μg) exhibit significantly reduced frequency and severity of retinal detachment as compared to those in groups either control, AGN 193109 or retinoic acid (10 μg). This result demonstrates that AGN 193109 improves the therapeutic index of the RAR agonist retinoic acid in an in vivo model of PVR.

In a second study, rabbits are first provided with an injection of human RPE cells into the vitreous cavity of the eye, and then divided into four groups. The first group (control) receives vehicle alone by intravitreal injection. The second group receives thyroid hormone as single agent treatment (100 μg) by intravitreal injection. The third group is administered with AGN 193109 as a single agent treatment (100 μg) by intravitreal injection. The fourth group is administered with the combination of AGN 193109 (100 μg) and thyroid hormone (100 μg). Rabbits are examined by indirect ophthalmoscopy on days 7, 14 and 28, and graded for the frequency and severity of tractional retinal detachment. Comparison of the frequency and severity of retinal detachment in the four groups demonstrates that single agent treatment with either AGN 193109 or thyroid hormone does not inhibit retinal detachment when compared with control rabbits. In contrast, the group of rabbits administered with the combination of AGN 193109 and thyroid hormone exhibit significantly reduced incidence and severity of retinal detachment. This result demonstrates that AGN 193109 improves the therapeutic index of thyroid hormone in an in vivo model of PVR.

The following Example illustrates how AGN 193109 can be used to enhance the therapeutic index of an RAR agonist used to treat human patients following retinal reattachment surgery.

EXAMPLE 25

Increasing the Therapeutic Index of RAR Agonist 13-cis Retinoic Acid

A population of adult volunteers having retinal detachment resulting from PVR is first identified. Individuals undergo surgical repair of the detachments using techniques that are standard in the art. The patients are then divided into five groups. The control group consists of patients who undergo surgical repair of the retinal detachment and do not receive any retinoid compound. The second group receives 40 mg oral 13-cis retinoic acid twice daily for four weeks postoperatively. The third group receives 40 mg oral AGN 103109 twice daily for four weeks postoperatively. The fourth group receives 4 mg oral 13-cis retinoic acid twice daily for four weeks postoperatively. The fifth group receives 40 mg oral AGN 193109 in combination with 4 mg oral 13-cis retinoic acid twice daily for four weeks postoperatively. The treatment protocol and assessment of drug efficacy is performed essentially as described by Fekrat et al. in *Ophthalmology* 102:412 (1995).

The frequency and severity of retinal redetachment in postoperative patients in all five groups is monitored over a period of nine months using ophthalmologic examination techniques that will be familiar to those of ordinary skill in the art. Patients receiving 40 mg oral 13-cis retinoic acid exhibit significantly reduced incidence of retinal redetachment when compared with control patients, patients receiving 4 mg oral 13-cis retinoic acid twice daily or patients receiving 40 mg oral AGN 193109 twice daily. Examination of the patient group receiving the combination of 40 mg oral AGN 193109 and 4 mg oral 13-cis retinoic acid twice daily for four weeks postoperatively demonstrates the therapeutic outcome in this patient group is equal to or better than those patients receiving 40 mg oral 13-cis retinoic acid twice daily for four weeks postoperatively. This result demonstrates that the AGN 193109 negative hormone improves the therapeutic index of an RAR agonist by virtue of decreasing the frequency and severity of retinal redetachment in PVR patients.

Generalized Assay for Identifying Nuclear Receptor Negative Hormones

We have demonstrated above that AGN 193109 can function as a negative hormone capable of repressing the basal transcriptional activity of RAR nuclear receptors. Further, we have described an assay using CV-1 cells co-transfected with the ERE-tk-Luc luciferase reporter plasmid and the ER-RXR-α and RAR-γ-VP-16 receptor expression plasmids for distinguishing RAR ligands that are simple antagonists from those having negative hormone activity.

We have concluded that RAR negative hormones mediate repression of RAR-mediated transcriptional activity by promoting increased interaction between the RAR and NCPs. Further, we have demonstrated that AGN 193109 can potentiate the effects of agonists of other nuclear receptors in a manner consistent with the mutual sharing of NCPs between members of the steroid superfamily of nuclear receptors. As such, ligands can be designed and screened to identify compounds having negative hormone activity at these non-RAR nuclear receptors.

Our method of RAR negative hormone screening based on the use of CV-1 cells co-transfected with the ERE-tk-Luc luciferase reporter plasmid and the ER-RXR-A and RAR-γ-VP-16 receptor expression plasmids can be adapted generally such that the RAR-γ moiety of the RAR-γ-VP-16 plasmid is converted to that of peroxisome proliferator-activated receptors (PPAR), vitamin D receptor (VDR), thyroid hormone receptor (T3R) or any other steroid superfamily nuclear receptor capable of heterodimerizing with RXR. CV-1 cells co-transfected with such plasmids would express high basal levels of luciferase activity. Ligands capable of binding the ligand binding domain of the receptor substituted for the RAR-γ moiety can be easily screened for negative hormone activity by measuring their ability to repress luciferase activity.

For steroid superfamily nuclear receptors that do not heterodimerize with RXR (e.g., glucocorticoid and estrogen receptors) the same end result can be achieved using GR-VP-16 or ER-VP-16 receptors and a luciferase reporter plasmid consisting of the appropriate glucocorticoid or estrogen response element fused to a heterologous promoter element and luciferase or other reporter gene. An essential feature of a generalized negative hormone screening assay is the inclusion of at least the ligand binding domain of the particular nuclear receptor for which inverse agonists are to be screened and a method for localizing the nuclear receptor ligand binding domain to the promoter of a reporter gene. This could be achieved using the receptors's natural DNA binding site, or alternatively by construction of a chimeric receptor having a heterologous DNA binding domain and corresponding use of a reporter gene which is under control of a DNA regulatory element which is recognized by the heterologous DNA binding domain. In a preferred embodiment, the plasmid expressing the nuclear receptor for which inverse agonists are to be screened would express this nuclear receptor as a fusion protein containing a constitutive activation domain, such as the HSV VP-16 activation domain, in order to provide allow high basal activity. This high basal activity would effectively increase assay sensitivity, thereby allowing analysis of nuclear receptor ligands which repress basal transcriptional activity in the absence of added nuclear receptor agonist.

The following Example illustrates one method that can be used to screen for compounds having negative hormone activity at the thyroid hormone receptor.

EXAMPLE 26

Method of Identifying Thyroid Hormone Receptor Negative Hormones

CV-1 cells are co-transfected with the luciferase reporter plasmid ERE-tk-Luc and the plasmids ER-RXR-α and T3R-VP-16. T3R-VP-16 is identical to the plasmid RAR-γ-VP-16, except the RAR-γ moiety of RAR-γ-VP-16 has been substituted by the thyroid hormone receptor cDNA. As such, T3R-VP-16 expresses a fusion protein containing the activation domain of HSV VP-16 in frame with the N-terminus of the thyroid hormone receptor. Standard transfection and cell culture methods are employed for this purpose. After transfection, cells are rinsed and fed with growth medium containing 10% fetal calf serum which has been extracted with activated charcoal. Cells are treated with vehicle alone (ethanol), thyroid hormone ($10^{-9}$ to $10^{-10}$M), or compound TR-1 ($10^{-9}$ to $10^{-6}$M). TR-1 is a synthetic thyroid hormone receptor ligand which exhibits strong affinity for the thyroid hormone receptor in competition binding studies, but which does not activate transfected thyroid hormone receptor in transient cotransfection transactivation assays using a thyroid hormone responsive reporter gene and a thyroid hormone receptor expression plasmid. Further, TR-1 is capable of antagonizing thyroid hormone mediated transactivation and as such is a thyroid receptor antagonist.

Analysis of luciferase activity from CV-1 cell transfected with ERE-tk-Luc, ER-RXRα and T3R-VP-16 demonstrates a high basal level of luciferase reporter activity in vehicle-treated cells. Cells treated with thyroid hormone show a slight increase of luciferase activity in a dose dependent manner. Cells treated with TR-1 exhibit a dose dependent decrease in luciferase activity. This indicates that TR-1 exhibits thyroid receptor inverse agonist activity, presumably due to the increased interaction of a NCP with the thyroid hormone receptor.

The proliferation rate of human primary retinal pigment epithelium cells is repressed by treatment with RAR agonists. The therapeutic value of this observation has been demonstrated in post-operative use retinoid therapy after retinal reattachment surgery. We have above demonstrated the AGN 193109 RAR negative hormone can sensitize primary RPE cells to the antiproliferative effect of ATRA and 13-cis retinoic acid in coadministration procedures. Further, AGN 193109 was also shown to sensitize RPE cells to the antiproliferative effects of other nuclear receptor agonists. More specifically, AGN 193109 sensitized RPE cells to the antiproliferative effects of the glucocorticoid agonist, dexamethasone, and the thyroid hormone agonist 3,3',5-triiodothyronine, T3. This data was consistent with our working model wherein AGN 193109 modulated the availability of NCPs that were shared between the members of the nuclear receptor family. Treatment of RPE cells with the thyroid hormone receptor inverse agonist TR-1 will similarly alter the availability of shared NCPs such that coadministration with a non-thyroid receptor agonist, such as the RAR agonist 13-cis retinoic acid will lead to an increased antiproliferative effect upon the RPE cultures as compared to 13-cis retinoic acid as a single agent treatment.

The following Example illustrates one method that can be used to render primary RPE cells more sensitive to the antiproliferative activity of an RAR agonist. Notably, this Example further illustrates how the activity of RAR agonists can be potentiated by coadministration with a negative hormone.

EXAMPLE 27

Sensitizing Primary Retinal Pigment Epithelium Cells to the Antiproliferative Effects of RAR Agonists by Coadministration of the TR-1 Thyroid Hormone Inverse Agonist Human primary RPE cells are obtained and cultured according to standard methods. The cultured cells are divided into four groups and treated as follows. Group 1 receives vehicle alone (ethanol). Group 2 is treated with 13-cis retinoic acid at concentrations ranging from $10^{-11}$ to $10^{-6}$M. Group 3 is treated with the thyroid hormone inverse agonist TR-1 at concentrations ranging from $10^{-11}$ to $10^{-1}$M. Group 4 is co-treated with 13-cis retinoic acid at concentrations ranging from $10^{-11}$ to $10^{-6}$M TR-1. Cells are refed with fresh growth medium and re-treated with the appropriate compound every two days for a total of five days of treatment. The proliferation rate over the duration of the experiment is quantitated via measurement of the cell number in the cultures using an electric cell counter.

TR-1 treated cells (Group 3) exhibits rates of cellular proliferation which are essentially the same as control (Group 1) cells and there is no effect of this inverse agonist upon the measured growth rate of the cultures. Cells treated with 13-cis retinoic acid (Group 2) exhibit a dose dependent decrease in cell number. Comparison of the dose dependent decrease in cellular proliferation of Group 4 cells (13-cis RA and TR-1 coadministration) with that obtained in Group 3 demonstrates the ability of TR-1 thyroid hormone receptor inverse agonist coadministration to sensitize RPE cultures to the antiproliferative effect of 13-cis retinoic acid as measured by the shift in the dose response curve of this RAR agonist to the left in Group 4 as compared to Group 2 cells.

What is claimed is:
1. A compound of the formula

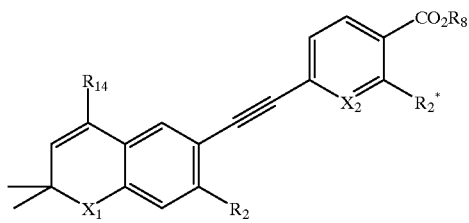

where
X$_1$ is S or O;
X$_2$ is CH or N;
R$_2$ is H, F, CF$_3$ or alkoxy of 1 to 6 carbons;
R$_2$* H, F, or CF$_3$;
R$_8$ is H, or lower alkyl of 1 to 6 carbons;
R$_{14}$ is unsubstituted phenyl, thienyl or pyridyl, or phenyl, thienyl or pyridyl substituted with one to three R$_{15}$ groups, where R$_{15}$ is lower alkyl of 1 to 6 carbons, chlorine, CF$_3$, or alkoxy of 1 to 6 carbons, or a pharmaceutically acceptable salt of said compound.

2. A compound in accordance with claim 1 where X$_1$ is S.
3. A compound in accordance with claim 2 where X$_2$ is CH.
4. A compound in accordance with claim 2 where R$_{14}$ is phenyl, 2-thienyl, or 3-pyridyl unsubstituted or substituted with one lower alkyl group having 1 to 6 carbons.
5. A compound in accordance with claim 2 where R$_2$ is H or F.
6. A compound in accordance with claim 2 where R$_2$* is H or F.
7. A compound in accordance with claim 2 where X$_2$ is N.
8. A compound in accordance with claim 1 where X$_1$ is O.
9. A compound in accordance with claim 8 where X$_2$ is CH.
10. A compound in accordance with claim 8 where R$_{14}$ is phenyl, 2-thienyl, or 3-pyridyl unsubstituted or substituted with one lower alkyl group having 1 to 6 carbons.
11. A compound in accordance with claim 8 where R$_2$ is H or F.
12. A compound in accordance with claim 8 where R$_2$* is H or F.
13. A method of treating a pathological condition in a mammal, said condition associated with a retinoic acid receptor activity, said method comprising administering to said mammal a retinoid antagonist or negative hormone capable of binding to a retinoic acid receptor subtype selected from the group consisting of RAR$_\alpha$, RAR$_\beta$ and RAR$_\gamma$, said antagonist or negative hormone being administered in an amount pharmaceutically effective to provide a therapeutic benefit against said pathological condition in said mammal and wherein said antagonist or negative hormone is a compound in accordance with claim 1.
14. The method of claim 13 wherein the pathological condition is the toxicity or undesired side effects resulting from administration of a retinoid compound to said mammal, and wherein said therapeutic benefit is the prevention or amelioration of said toxicity or undesired side effects.
15. The method of claim 13 wherein the retinoid antagonist or negative hormone is administered in order to cure or ameliorate a preexisting pathological condition caused by intake of a retinoid drug or vitamin A or vitamin A precursors by the mammal.

16. The method of claim 13 wherein the retinoid antagonist or negative hormone is administered topically to block or ameliorate undesired topical side effects of a retinoid drug administered for a therapeutic purpose.
17. The method of claim 13 wherein the retinoid antagonist or negative hormone is administered topically to block or ameliorate undesired topical side effects of a retinoid drug administered systemically for a therapeutic purpose.
18. The method of claim 13 wherein the retinoid antagonist or negative hormone is administered topically to treat a pre-existing condition or side effect caused by a retinoid drug or vitamin A.
19. The method of claim 13 wherein the retinoid antagonist or negative hormone is administered systemically to treat a pre-existing condition or side effect caused by a retinoid drug or vitamin A.
20. The method of claim 13 wherein the retinoid antagonist or negative hormone is administered systemically to block or ameliorate bone toxicity caused by coadministration of a retinoid drug or vitamin A.
21. A compound of the formula

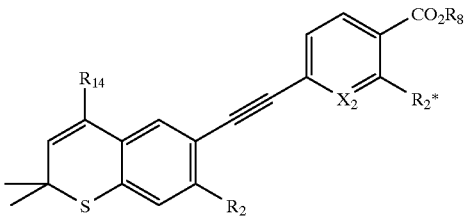

wherein
X$_2$ is CH or N;
R$_2$ is H,F or OCH$_3$;
R$_2$* is H or F;
R$_8$ is H, or lower alkyl of 1 to 6 carbons, and
R$_{14}$ is selected from the group consisting of phenyl, 4-(lower-alkyl) phenyl, 5-(lower alkyl)-2-thienyl, and 6-(lower alkyl)-3-pyridyl where lower alkyl has 1 to 6 carbons, or a pharmaceutically acceptable salt of said compound.

22. A compound in accordance with claim 21 where X$_2$ is CH.
23. A compound in accordance with claim 22 where R$_2$ is H.
24. A compound in accordance with claim 23 where R$_2$* is H.
25. A compound in accordance with claim 24 where the R$_{14}$ group is selected from phenyl, 4-methylphenyl, 4-ethylphenyl, 4-i-propylphenyl, 4-t-butylphenyl, 5-methyl-2-thienyl, 5-ethyl-2-thienyl, 5-t-butyl-2-thienyl and 6-methyl-3-pyridyl.
26. A compound in accordance with claim 25 where R$_8$ is ethyl or H, or a pharmaceutically acceptable salt of said compound.
27. A compound in accordance with claim 23 where R$_2$* is F.
28. A compound in accordance with claim 27 where the R$_{14}$ group is selected from 4-methylphenyl and 4-ethylphenyl.
29. A compound in accordance with claim 28 where R$_8$ is ethyl or H, or a pharmaceutically acceptable salt of said compound.
30. A compound in accordance with claim 22 where R$_2$ is F and R$_2$* is H.
31. A compound in accordance with claim 30 where the R$_{14}$ group is selected from 4-methylphenyl and 5-methyl-2-thienyl.

32. A compound in accordance with claim 30 where $R_8$ is ethyl or H, or a pharmaceutically acceptable salt of said compound.

33. A compound in accordance with claim 22 where $R_2$ is $OCH_3$, $R_2^*$ is H and $R_{14}$ is 4-methylphenyl.

34. A compound in accordance with claim 33 where $R_8$ is ethyl or H, or a pharmaceutically acceptable salt of said compound.

35. A compound in accordance with with claim 21 where $X_2$ is N, $R_2$ is H, $R_2^*$ is H, and $R_{14}$ is selected from the group consisting of 4-methylphenyl and 4-ethylphenyl.

36. A compound in accordance with claim 35 where $R_8$ is ethyl or H, or a pharmaceutically acceptable salt of said compound.

37. A compound of the formula

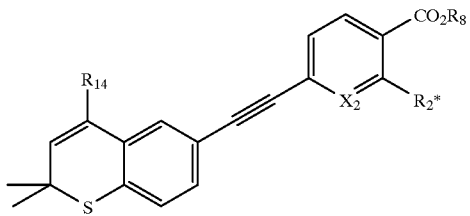

where $R_2^*$ is H or F;

$R_8$ is H, or lower alkyl of 1 to 6 carbons, and $R_{14}$ is selected from the group consisting of phenyl, and 4-(lower-alkyl)phenyl, where lower alkyl has 1 to 6 carbons, or a pharmaceutically acceptable salt of said compound.

38. A compound in accordance with claim 37 where $R_2^*$ is H.

39. A compound in accordance with claim 38 where the $R_{14}$ group is selected from phenyl, 4-methylphenyl, 4-ethylphenyl, 4-i-propylphenyl, and 4-tbutylphenyl.

40. A compound in accordance with claim 39 where $R_8$ is ethyl or H, or a pharmaceutically acceptable salt of said compound.

41. A compound in accordance with claim 37 where $R_2^*$ is F.

42. A compound in accordance with with claim 41 where $R_{14}$ is selected from the group consisting of 4-methylphenyl and 4-ethylphenyl.

43. A compound in accordance with claim 42 where $R_8$ is ethyl or H, or a pharmaceutically acceptable salt of said compound.

44. A compound of the formula

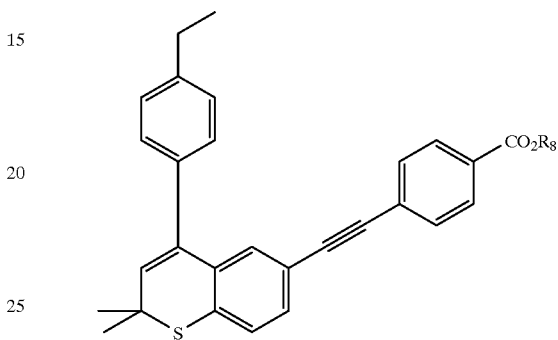

where $R_8$ is H, lower alkyl of 1 to 6 carbons, or a pharmaceutically acceptable salt of said compound.

45. A compound in accordance with claim 44 where $R_8$ is H, or a pharmaceutically acceptable salt of said compound.

46. A compound in accordance with claim 44 where $R_8$ is ethyl.

* * * * *

UNITED STATES PATENT AND TRADEMARK OFFICE
CERTIFICATE OF CORRECTION

PATENT NO. : 5,958,954
DATED : September 28, 1999
INVENTOR(S) : Klein et al.

It is certified that error appears in the above-identified patent and that said Letters Patent is hereby corrected as shown below:

Column 1,
Lines 15, 17 and 19, after "filed", insert -- on --.

Column 2,
Line 51, "RXB-β" should be -- RXR- β --.

Column 15,
TABLE 1, Compound #17, "thiazoly" should be -- thiazolyl --.

Column 19,
Line 1, "co-tranfection" should be -- co-transfection --.

Column 20,
Lines 11, 13, 14 and 32, "ug/well" should be -- $\mu$g/well --.

Column 24,
Line 29, "admistered" should be -- administered --.

Column 29,
Lines 10 and 64, "Incuded" should be -- Induced --.

Column 30,
Line 13, delete the second occurrence of "was".
Line 63, "fluor" should be -- fluoro --.

Column 32,
Reaction Scheme 1, below Formula 7, "PdCl$_2$(PPH$_3$)$_2$" should be -- PdCl$_2$(PPh$_3$)$_2$ --.

Column 34,
Line 66, "tetrahydronaphtalene" should be -- tetra-hydronaphthalene --.

Column 44,
Line 67, delete the second occurrence of "is".

Column 47,
Line 25, delete the second occurrence of "is".

Column 51,
Line 46, "dihydronaphtalene" should be -- dihydronaphthalene --.

UNITED STATES PATENT AND TRADEMARK OFFICE
CERTIFICATE OF CORRECTION

PATENT NO. : 5,958,954
DATED : September 28, 1999
INVENTOR(S) : Klein et al.

It is certified that error appears in the above-identified patent and that said Letters Patent is hereby corrected as shown below:

Column 55,
Line 32, "substitituted" should be -- substituted --.

Column 58,
Line 16, "examplary" should be -- exemplary --.

Column 60,
Line 32, delete the second occurrence of "to".

Column 68,
Line 16, "hydroxyde" should be -- hydroxide --.

Column 71,
Lines 47 and 63, after "layers", insert -- were --.
Line 51, "1H" should be -- $^1$H --.

Column 72,
Lines 1, 18 and 41, "1H NMR" should be -- $^1$H NMR --.
Line 18, after "Hg", insert -- . --.
Line 36, after "layers", insert -- were --.
Line 53, "canula" should be -- cannula --.

Column 73,
Lines 8, 9 after "solution", insert -- was --.
Line 14, "1H NMR" should be -- $^1$H NMR --.

Column 74,
Lines 3, 18 and 59, "1H" should be -- $^1$H --.
Line 3, "d6" should be -- $d_6$ --.

Column 75,
Lines 18 and 53, "1H" should be -- $^1$H --.
Line 18, "d6" should be -- $d_6$ --.

Column 76,
Lines 5, 25, 46 and 64, "1H" should be -- $^1$H --.

Column 77,
Lines 15, 35 and 55, "1H" should be -- $^1$H --.

UNITED STATES PATENT AND TRADEMARK OFFICE
CERTIFICATE OF CORRECTION

PATENT NO.  : 5,958,954
DATED       : September 28, 1999
INVENTOR(S) : Klein et al.

It is certified that error appears in the above-identified patent and that said Letters Patent is hereby corrected as shown below:

Column 78,
Lines 5, 24, 43 and 67, "1H" should be -- $^1$H --.
Line 5, "d6" should be -- $d_6$ --.
Line 10, "hz" should be -- Hz --.
Line 25, after "7.99", insert -- ( --.
Line 34, "methylphenlyl" should be -- methylphenyl --.

Column 79,
Lines 22, 39 and 57, "1H" should be -- $^1$H --.
Line 42, after "6.01", insert -- ( --.
Line 51, "tetrabutylamonium" should be -- tetrabutylammonium --.

Column 80,
Lines 9 and 57, "1H" should be -- $^1$H --.

Column 81,
Lines 10 and 58, "1H" should be -- $^1$H --.
Line 13, after "7.33", "9" should be -- ( --.
Lines 27 and 43, "1H NMR" should be -- $^1$H NMR --.
Lines 27 and 43, "d6" should be -- $d_6$ --.

Column 82,
Lines 6, 20, 49 and 63 "1H" should be -- $^1$H --.
Line 35, "1H" should be -- $^1$H_ --.

Column 83,
Lines 11, 26, 42 and 57, "1H" should be -- $^1$H --.
Lines 42 and 57, "d6" should be -- $d_6$ --.

Column 84,
Lines 5, 37 and 54, after "solvents", insert -- were --.
Lines 6, 38 and 55,"1H" should be -- $^1$H --.
Lines 6, 39 and 55,"d6" should be -- $d_6$ --.

Column 85,
Line 8, "1H NMR" should be -- $^1$H NMR --.
Line 42,"1H" should be -- $^1$H --.
Line 42,"d6" should be -- $d_6$ --.
Line 66, "though" should be -- through --.

UNITED STATES PATENT AND TRADEMARK OFFICE
CERTIFICATE OF CORRECTION

PATENT NO. : 5,958,954
DATED : September 28, 1999
INVENTOR(S) : Klein et al.

It is certified that error appears in the above-identified patent and that said Letters Patent is hereby corrected as shown below:

Column 86,
Lines 7 and 41, "1H NMR" should be -- $^1$H NMR --.
Lines 19 and 53, after "solution", insert -- was --.
Lines 24 and 58, "1H" should be -- $^1$H --.

Column 87,
Lines 7, 24 and 44, after "solution", insert -- was --.
Lines 11, 28 and 67, "1H" should be -- $^1$H --.
Lines 28 and 67, "d6" should be -- $d_6$ --.
Line 49, "1H NMR" should be -- $^1$H NMR --.

Column 88,
Lines 16, 34, 67, "1H NMR" should be -- $^1$H NMR --.
Line 34, "d6" should be -- $d_6$ --.
Line 49, "1H" should be -- $^1$H --.
Line 65, after "phase", insert -- was --.

Column 89,
Line 11, after "layers", insert -- were --.
Line 15, "1H NMR" should be -- $^1$H NMR --.
Lines 30 and 53, "1H" should be -- $^1$H --.
Line 51, after "solvents", insert -- were --.

Column 90,
Line 2, "canula" should be -- cannula --.
Lines 15, 36, 63, "1H" should be -- $^1$H --.
Line 22, "Compound 45" should be -- (Compound 45) --.
Line 36, "d6" should be -- $d_6$ --.

Column 91,
Lines 9 and 25, after "mixture", insert -- was --.
Lines 12, 33, 47, and 64, "1H" should be -- $^1$H --.
Line 27, after "filtrate", insert -- was --.
Line 48, after "7.48", insert -- ( --.

Column 92,
Lines 10 and 47, "1H" should be -- $^1$H --.
Line 26, "1H NMR" should be -- $^1$H NMR --.
Line 59, after "solution", insert -- was --.

UNITED STATES PATENT AND TRADEMARK OFFICE
CERTIFICATE OF CORRECTION

PATENT NO. : 5,958,954
DATED : September 28, 1999
INVENTOR(S) : Klein et al.

It is certified that error appears in the above-identified patent and that said Letters Patent is hereby corrected as shown below:

Column 93,
Lines 5, 23, 59 and 62, "1H" should be -- $^1$H --.
Line 36, "temparature" should be -- temperature --.
Line 37, after "mixture", insert -- was --.
Line 39, after "phase", insert -- was --.

Column 94,
Lines 11, 44 and 60, "1H NMR" should be -- $^1$H NMR --.
Line 27, "1H" should be -- $^1$H --.
Line 60, "J=1H" should be -- J=lHz --.

Column 95,
Line 9, after "solvent", insert -- was --.
Line 10, "1H NMR" should be -- $^1$H NMR --.
Lines 30, 50, 67, "1H" should be -- $^1$H --.
Line 30, "d6" should be -- $d_6$ --.
Line 63, after "mixture", insert -- was --.

Column 96,
Line 11, after "filtrate", insert -- was --.
Lines 12 and 46, "1H" should be -- $^1$H --.
Line 25, "1H NMR" should be -- $^1$H NMR --.

Column 97,
Line 2, after "compound", insert -- was --.
Lines 3, 54 and 20, "1H" should be -- $^1$H --.
Line 21, "hz" should be -- Hz --.
Line 37, "finaly" should be -- finally --.
Line 41, "1H NMR" should be -- $^1$H NMR --.
Line 50, "though" should be -- through --.
Line 51, after "filtrate", insert -- was --.

Column 98,
Lines 5, 27 and 42, "1H" should be -- $^1$H --.
Lines 6 and 27, "d6" should be -- $d_6$ --.
Line 23, after "layers", insert -- were --.
Line 37, after "fraction", insert -- was --.
Line 65, after "layer", insert -- was --.

UNITED STATES PATENT AND TRADEMARK OFFICE
CERTIFICATE OF CORRECTION

PATENT NO.    : 5,958,954
DATED         : September 28, 1999
INVENTOR(S)   : Klein et al.

It is certified that error appears in the above-identified patent and that said Letters Patent is hereby corrected as shown below:

Column 99,
Lines 2, 17 and 37, "1H" should be -- $^1$H --.
Line 15, after "filtrate", insert -- was --.
Line 31, after "reaction", insert -- was --.
Line 55, "naphthalinecarboxylate" should be -- naphthalenecarboxylate --.
Line 61, after "solution", insert -- was --.

Column 100,
Lines 3 and 25, after "solvent", insert -- was --.
Line 4, "crystalized" should be -- crystallized --.
Line 9, "1H NMR" should be -- $^1$H NMR --.
Line 24, after "layers", insert -- were --.
Line 26, "recrystalized" should be -- recrystallized --.
Line 28, after "residue", insert -- was --.
Line 31, "1H" should be -- $^1$H --.

Column 101,
Line 9, "temparature" should be -- temperature --.
Line 10, after "mixture", insert -- was --.
Line 33, "1H" should be -- $^1$H --.
Lines 37 and 52, "1H NMR" should be -- $^1$H NMR --.

Column 102,
Lines 2, 20, 38 and 56, "1H NMR" should be -- $^1$H NMR --.
Line 38, "d6" should be -- $d_6$ --.
Line 54, after "compound", insert -- was --.

Column 103,
Line 4, "compounds" should be -- compound --.
Line 5, "1H" should be -- $^1$H --.

Column 104,
Line 62, "fluror" should be -- fluoro --.

Column 105,
Line 49, after "Ethyl 4-", insert -- [ --.
Lines 50 and 55, after "6-yl", insert -- ) --.
Lines 50 and 55, after "ethynyl", ")" should be -- ] --.
Line 54, after "ethyl 4-", insert -- [ --.

UNITED STATES PATENT AND TRADEMARK OFFICE
CERTIFICATE OF CORRECTION

PATENT NO. : 5,958,954
DATED : September 28, 1999
INVENTOR(S) : Klein et al.

It is certified that error appears in the above-identified patent and that said Letters Patent is hereby corrected as shown below:

Column 106,
Line 4, after "Ethyl 4-", insert -- [ --.
Lines 5, 10 and 36-37, after "6-yl", insert -- ) --.
Lines 5, 10 and 37, after "ethynyl", ")" should be -- ] --.
Lines 9 and 35, after "ethyl 4-", insert -- [ --.
Lines 40 and 67, after "reaction", insert -- was --.
Line 43, after "layers", insert -- were --.

Column 107,
Line 1, "Thei" should be -- The --.
Line 2, after "layers", insert -- were --.
Line 9, after "6.73", insert -- ( --.
Line 20, after "ethyl 4-", insert -- [ --.
Line 22, after "6-yl", insert -- ) --.
Line 22, after "ethynyl", ")" should be -- ] --.
Line 26, after "reaction", insert -- was --.

Column 108,
Line 29, "recrystalization" should be -- recrystallization --.

Column 109,
Lines 35 and 61, after "ethyl 4-", insert -- [ --.
Lines 35-36 and 62-63, after "6-yl", insert -- ) --.
Line 36 and 63, after "ethynyl", ")" should be -- ] --.
Line 66, after "reaction", insert -- was --.

Column 110,
Lines 19 and 44, after "ethyl 4-", insert -- [ --.
Lines 20-21 and 45-46, after "6-yl", insert -- ) --.
Lines 21 and 46, after "ethynyl", ")" should be -- ] --.
Line 49, after "reaction", insert -- was --.
Line 54, "compounds" should be -- compound --.

Column 111,
Lines 2 and 26, after "ethyl 4-", insert -- [ --.
Lines 3-4, 27-8, after "6-yl", insert -- ) --.
Lines 4 and 28, after "ethynyl", ")" should be -- ] --.
Lines 7, 31 and 57, after "reaction", insert -- was --.

Column 112,
Line 16 and 43, after "reaction", insert -- was --.
Line 27, "," should be -- . --.

UNITED STATES PATENT AND TRADEMARK OFFICE
CERTIFICATE OF CORRECTION

PATENT NO. : 5,958,954
DATED : September 28, 1999
INVENTOR(S) : Klein et al.

It is certified that error appears in the above-identified patent and that said Letters Patent is hereby corrected as shown below:

Column 113,
Line 2, after "reaction", insert -- was --.
Line 17, "fluro" should be -- fluoro --.
Line 32, after "Ethyl 4-", insert -- [ --.
Lines 33 and 64-65, after "6-yl", insert -- ) --.
Lines 33 and 65, after "ethynyl", ")" should be -- ] --.
Line 63, after "ethyl 4-", insert -- [ --.

Column 114,
Line 2, after "reaction", insert -- was --.
Line 22, after "ethyl 4-', insert -- [ --.
Lines 23-24, after "6-yl", insert -- ) --.
Line 24, after "ethynyl", ")" should be -- ] --.
Line 28, after "reaction", insert -- was --.

Column 115,
Line 22, after "ethyl 6-", insert -- [ --.
Lines 23-24, after "6-yl", insert -- ) --.
Line 24, after "ethynyl", ")" should be -- ] --.
Lines 28 and 54, after "reaction", insert -- was --.
Lines 60, "recrystalization" should be -- recrystallization --.

Column 117,
Line 54, "butylthiopen" should be -- butylthiophen --.

Column 121,
Line 4, after "filtrate", insert -- was --.

Column 122,
Lines 11, 37 and 63, after "reaction", insert -- was --.

Column 123,
Lines 22 and 49, after "reaction", insert -- was --.

Column 124,
Line 49, after "reaction", insert -- was --.

Column 125,
Line 8, after "reaction", insert -- was --.
Line 36, after "(6H, s)", "," should be -- . --.

UNITED STATES PATENT AND TRADEMARK OFFICE
CERTIFICATE OF CORRECTION

PATENT NO. : 5,958,954
DATED : September 28, 1999
INVENTOR(S) : Klein et al.

It is certified that error appears in the above-identified patent and that said Letters Patent is hereby corrected as shown below:

Column 126,
Line 42, "hz" should be -- Hz --.

Column 169,
Line 9, delete the second occurrence of "with".

Signed and Sealed this

Twenty-second Day of March, 2005

JON W. DUDAS
*Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

TCAGGTCACC AGGAGGTCAG A                                                                   21

(2) INFORMATION FOR SEQ ID NO:2:

(i) SEQUENCE CHARACTERISTICS:
      (A) LENGTH: 101 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

AGAAGCTTAT GGAAGCAATT ATGAGTCAGT TTGCGGGTGA CTCTGCAAAT ACTGCCACTC   60

TATAAAAGTT GGGCTCAGAA AGGTGGACCT CGAGGATCCA G                    101

(2) INFORMATION FOR SEQ ID NO:3:

(i) SEQUENCE CHARACTERISTICS:
      (A) LENGTH: 101 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

CTGGATCCTC GAGGTCCACC TTTCTGAGCC CAACTTTTAT AGAGTGGCAG TATTTGCAGA    60

GTCACCCGCA AACTGACTCA TAATTGCTTC CATAAGCTTC T                      101

(2) INFORMATION FOR SEQ ID NO:4:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

GTACAAGGTT CACGAGGTTC ACGTCTTA                                      28

(2) INFORMATION FOR SEQ ID NO:5:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

TCAGGTCATG ACCTGA                                                   16

(2) INFORMATION FOR SEQ ID NO:6:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

-continued (xi) SEQUENCE DESCRIPTION: SEQ ID NO:6:

CCACCCATGG CAAATTCCAT GGCA                                              24

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

TCTAGACGGC AGGTCAGGTC CACC                                              24

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

ACGCGTCCGG AAGACCTGGT                                                   20

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

ATTCTGCAGG TACATGTCCA                                                   20